US011620533B2

(12) United States Patent
Johnson et al.

(10) Patent No.: US 11,620,533 B2
(45) Date of Patent: Apr. 4, 2023

(54) CYPHERGENICS-BASED DECODING AND ENCODING OF PROGRAM DATA

(71) Applicant: Quantum Digital Solutions Corporation, Marina Del Rey, CA (US)

(72) Inventors: William C. Johnson, Marina Del Rey, CA (US); Karen Ispiryan, Santa Monica, CA (US); Gurgen Khachatryan, Marina Del Rey, CA (US)

(73) Assignee: Quantum Digital Solutions Corporation, Marina Del Rey, CA (US)

( * ) Notice: Subject to any disclaimer, the term of this patent is extended or adjusted under 35 U.S.C. 154(b) by 0 days.

(21) Appl. No.: 17/668,965

(22) Filed: Feb. 10, 2022

(65) Prior Publication Data

US 2022/0245239 A1 Aug. 4, 2022

Related U.S. Application Data

(63) Continuation of application No. PCT/US2022/015109, filed on Feb. 3, 2022.
(Continued)

(51) Int. Cl.
*G06F 21/53* (2013.01)
*G06N 3/126* (2023.01)
(Continued)

(52) U.S. Cl.
CPC ............. *G06N 3/126* (2013.01); *G06F 21/53* (2013.01); *G16B 30/00* (2019.02); *G16B 30/20* (2019.02);
(Continued)

(58) Field of Classification Search
CPC .......................... G06F 21/53; G06F 2221/2149
See application file for complete search history.

(56) References Cited

U.S. PATENT DOCUMENTS 3,094,817 A1 1/2012 Blom et al.
8,633,797 B2 1/2014 Farris et al.
(Continued)

FOREIGN PATENT DOCUMENTS

AU 2019201785 A1 2/2020
CN 102075931 B 4/2013
(Continued)

OTHER PUBLICATIONS

Briscoe, G. et al., "Digital Ecosystems: Ecosystem-Oriented Architectures," Dec. 2011, arXiv preprint arXiv:1112.0204v1, 39 pages.
(Continued)

*Primary Examiner* — Beemnet W Dada
(74) *Attorney, Agent, or Firm* — RMCK Law Group, PLC

(57) ABSTRACT

A method for executing computer programs in a trusted execution environment of a device is disclosed. The method includes retrieving a genomic differentiation object corresponding a computer program; modifying the genomic differentiation object based on genomic regulation instructions (GRI) to obtain a modified genomic differentiation object; and executing a first executable instruction of the computer program. Executing the first executable instruction includes: retrieving first encoded data that is input to the first executable instruction; extracting a sequence from metadata associated with the encoded data; generating a first genomic engagement factor (GEF) based on the first sequence, the GRI and, and the modified genomic differentiation object; decoding the first encoded data based on the first GEF to obtain first decoded data; and executing the first executable instruction using the first decoded data.

29 Claims, 26 Drawing Sheets

Related U.S. Application Data

(60) Provisional application No. 63/229,348, filed on Aug. 4, 2021, provisional application No. 63/145,860, filed on Feb. 4, 2021.

(51) Int. Cl.
*G16B 30/20* (2019.01)
*G16B 50/30* (2019.01)
*H04L 9/06* (2006.01)
*H04L 9/32* (2006.01)
*H04L 9/00* (2022.01)
*G16B 99/00* (2019.01)
*G16B 50/50* (2019.01)
*G16B 30/00* (2019.01)
*H03M 7/00* (2006.01)

(52) U.S. Cl.
CPC .............. *G16B 50/30* (2019.02); *G16B 50/50* (2019.02); *G16B 99/00* (2019.02); *H03M 7/00* (2013.01); *H04L 9/002* (2013.01); *H04L 9/0643* (2013.01); *H04L 9/3247* (2013.01); *H04L 9/50* (2022.05); *G06F 2221/2149* (2013.01)

(56) References Cited

U.S. PATENT DOCUMENTS

| | | | |
|---|---|---|---|
| 8,832,808 B2 | 9/2014 | Liu et al. | |
| 8,898,479 B2 | 11/2014 | Shaw | |
| 8,903,090 B2 | 12/2014 | Bikel et al. | |
| 9,043,596 B2 | 5/2015 | Jung et al. | |
| 9,449,191 B2 | 9/2016 | MacCarthy et al. | |
| 9,548,860 B2 | 1/2017 | Zhang et al. | |
| 9,596,220 B2 | 3/2017 | Hassan et al. | |
| 9,807,570 B1 | 10/2017 | Lazarini et al. | |
| 9,922,320 B2 | 3/2018 | Bonalle et al. | |
| 10,007,660 B2 | 6/2018 | Sarikaya et al. | |
| 10,031,679 B2 | 7/2018 | O'Hare et al. | |
| 10,131,280 B2 | 11/2018 | Wind et al. | |
| 10,169,574 B2 | 1/2019 | Nesher et al. | |
| 10,419,215 B2 | 9/2019 | Hassan | |
| 10,469,260 B2 | 11/2019 | Hassan | |
| 10,552,620 B2 | 2/2020 | Desai et al. | |
| 10,601,596 B2 | 3/2020 | Costa et al. | |
| 10,615,967 B2 | 4/2020 | Basmov et al. | |
| 10,630,467 B1 | 4/2020 | Gilbert et al. | |
| 10,652,743 B2 | 5/2020 | Fitzgibbon | |
| 10,664,583 B2 | 5/2020 | Proulx et al. | |
| 10,700,865 B1 | 6/2020 | Hendrick et al. | |
| 10,708,046 B1 | 7/2020 | Ashrafi | |
| 10,769,615 B2 | 9/2020 | Li et al. | |
| 10,777,605 B2 | 9/2020 | Freedman et al. | |
| 10,817,590 B1 | 10/2020 | Daly et al. | |
| 10,826,877 B2 | 11/2020 | Nayshtut et al. | |
| 10,832,072 B1 | 11/2020 | Fraser | |
| 10,860,302 B2 | 12/2020 | Nightingale et al. | |
| 10,862,870 B2 | 12/2020 | Maier et al. | |
| 10,875,420 B2 | 12/2020 | Grimm et al. | |
| 10,880,340 B2 * | 12/2020 | Harrison | H04L 67/02 |
| 10,891,849 B1 | 1/2021 | Kumar et al. | |
| 10,903,541 B2 | 1/2021 | Abdo et al. | |
| 10,903,868 B2 | 1/2021 | Perthuis et al. | |
| 10,904,256 B2 | 1/2021 | Brickell | |
| 10,910,087 B2 | 2/2021 | Cho et al. | |
| 10,934,748 B2 | 3/2021 | Harajli et al. | |
| 10,936,303 B2 | 3/2021 | Bonar et al. | |
| 10,936,731 B2 | 3/2021 | Linton et al. | |
| 10,944,559 B2 | 3/2021 | Fitzgibbon et al. | |
| 10,951,578 B1 | 3/2021 | Nainar et al. | |
| 10,951,609 B2 | 3/2021 | Komperla et al. | |
| 10,956,609 B2 | 3/2021 | Kochura et al. | |
| 10,956,828 B2 | 3/2021 | Chow et al. | |
| 10,957,420 B2 | 3/2021 | Agrawal et al. | |
| 10,972,452 B2 | 4/2021 | Mathaiyan et al. | |
| 10,972,538 B2 | 4/2021 | Chen et al. | |
| 10,977,372 B2 | 4/2021 | Sood et al. | |
| 10,992,338 B1 | 4/2021 | Priyantha et al. | |
| 11,000,213 B2 | 5/2021 | Kamath et al. | |
| 11,005,810 B2 | 5/2021 | Souhrada et al. | |
| 11,019,048 B2 | 5/2021 | Callaghan | |
| 11,022,625 B2 | 6/2021 | Tanaka | |
| 11,023,558 B1 | 6/2021 | Kurien et al. | |
| 11,023,622 B2 | 6/2021 | Rozas et al. | |
| 11,343,318 B2 | 5/2022 | Lee et al. | |
| 11,424,009 B2 | 8/2022 | Philippe et al. | |
| 2002/0029280 A1 | 3/2002 | Holden et al. | |
| 2002/0078352 A1 | 6/2002 | Angwin et al. | |
| 2003/0217165 A1 | 11/2003 | Buch et al. | |
| 2005/0026117 A1* | 2/2005 | Judson | G16H 70/40 434/154 |
| 2009/0070281 A1 | 3/2009 | Solomon | |
| 2010/0318800 A1 | 12/2010 | Simon et al. | |
| 2011/0016318 A1 | 1/2011 | Syngkon et al. | |
| 2012/0124387 A1 | 5/2012 | Skocic | |
| 2013/0185806 A1 | 7/2013 | Hatakeyama | |
| 2013/0254255 A1* | 9/2013 | Nilsson | G06F 9/5011 709/201 |
| 2014/0298461 A1 | 10/2014 | Hohndel et al. | |
| 2016/0024556 A1 | 1/2016 | Zhang | |
| 2016/0085916 A1* | 3/2016 | Smith | G16H 50/70 705/3 |
| 2017/0236520 A1 | 8/2017 | Borgstrom et al. | |
| 2017/0242961 A1* | 8/2017 | Shukla | G16B 50/00 |
| 2017/0261518 A1 | 9/2017 | Paczesny | |
| 2018/0046766 A1 | 2/2018 | Deonarine et al. | |
| 2018/0068000 A1 | 3/2018 | Messaoud et al. | |
| 2018/0201998 A1 | 7/2018 | Kiang et al. | |
| 2019/0289038 A1 | 9/2019 | Li et al. | |
| 2019/0318816 A1 | 10/2019 | Witchey | |
| 2019/0394243 A1 | 12/2019 | Wiig et al. | |
| 2020/0007345 A1 | 1/2020 | Barry et al. | |
| 2020/0184489 A1 | 6/2020 | Negi et al. | |
| 2020/0311816 A1 | 10/2020 | Calvin | |
| 2021/0050995 A1 | 2/2021 | Ragan et al. | |
| 2022/0103529 A1* | 3/2022 | Johnson | G06F 21/577 |

FOREIGN PATENT DOCUMENTS

| | | |
|---|---|---|
| CN | 105046636 B | 5/2017 |
| CN | 110971403 A | 4/2020 |
| CN | 108847932 B | 7/2020 |
| CN | 108599934 B | 9/2020 |
| CN | 108134772 B | 11/2020 |
| DE | 102019108328 A1 | 10/2020 |
| WO | 2018007525 A2 | 1/2018 |
| WO | 2018096559 A1 | 5/2018 |
| WO | 2019107129 A1 | 6/2019 |
| WO | 2020209988 A2 | 10/2020 |
| WO | 2021013736 A1 | 1/2021 |
| WO | 2021158791 A1 | 8/2021 |

OTHER PUBLICATIONS

Briscoe, G. et al., "Digital Ecosystems: Self-Organisation of Evolving Agent Populations," Oct. 2009, arXiv preprint arXiv:0803. 2675v4, 5 pages.

Carlini, F. et al.,"The Genesy Model for a Blockchain-Based Fair Ecosystem of Genomic Data," Frontiers in Blockchain, Technology and Code, vol. 3, Dec. 2020, 14 pages.

Hadzic, M. et al., "Methodology Framework for the Design of Digital Ecosystems," IEEE International Conference on Systems, Man and Cybernetics, 2007, pp. 7-12.

Hedin, Y. et al., "Security in Multi-Agent Systems," Procedia Computer Science, vol. 60, 2015, pp. 1604-1612.

Heesch, M.V. et al., "Towards Quantum-Safe VPNs and Internet," IACR Cryptol. ePrint Arch., 2019, 1277, 8 pages.

Lobo, L.M.R.J et al., "Use of Genetic Algorithm in Network Security," International Journal of Computer Applications (0975-8887), vol. 53, No. 8, Sep. 2012, pp. 1-7.

(56) References Cited

OTHER PUBLICATIONS

PCT International Search Report and Written Opinion dated Apr. 22, 2022 for International Application No. PCT/US2022/015109, 17 pages.
PCT International Search Report and Written Opinion dated May 17, 2021 for International Application No. PCT/US2021/016617, 17 pages.
Shaw, H., "A Cryptographic System Based upon the Principles of Gene Expression," 2017 Cryptography 1(3), 21, www.mdpi.com/journal/cryptography, 18 pages.
Paganini, P., "DNA Contains Instructions for Biological and Computer Viruses," Aug. 2017, https://securityaffairs.co/wordpress/61940/hacking/dna-contains-instructions-biological-computer-viruses.html, 6 pages.
Sharma, D et al., "Encoding Scheme For Data Storage And Retrieval On DNA Computers," IET Nanobiotechnology, E-Firston Sep. 2, 2020, vol. 14, Iss. 7, pp. 635-641.

\* cited by examiner

FIG. 1

CYPHERGENICS (CG) TECHNOLOGY ENABLES COMPREHENSIVE POST QUANTUM SECURITY.

| | PKI : POST QUANTUM | QKD : POST QUANTUM | CYPHERGENICS : POST QUANTUM |
|---|---|---|---|
| SECURITY COHORT ID ATTRIBUTES | | | |
| Authentication : Facilitation | Trusted Third Party | Trusted Third Party | Digital-Cohort to Digital-Cohort |
| Non-Repudiation : Facilitation | Trusted Third Party | Trusted Third Party | Digital-Cohort to Digital-Cohort |
| Integrity : Facilitation | Message | Message | Digital Object by Digital Object |
| SECURITY TECHNOLOGY ATTRIBUTES | | | |
| Key Mgmt. : Basis | Under Development | Quantum Phenomena | Virtual Binary Language Script (VBLS) |
| Encryption : Basis | Under Development | Quantum Phenomena | Virtual Binary Language Script (VBLS) |
| Engagement : Scalability | One to Many | One to One | Many to Many |
| SECURITY APPLICATION ATTRIBUTES | | | |
| Domain | Network | Optical Communications Networks | Global Digital Ecosystems |
| Function | Data Transport | Data Transport | Security-Instance by Security-Instances |
| Engagement | Device to Device | Photon Detector to Photon Detector | Digital-Cohort to Digital-Cohort |
| Primary Application | Session Managed Engagement | Session Managed Engagement | Security Architecture Generation |
| SECURITY ENGAGEMENT ATTRIBUTES | | | |
| Session Coordination | Per Engagement | Per Engagement | Obsoleted by VBLS |
| Secret Key Generation | Per Engagement | Per Engagement | Obsoleted by VBLS |
| Secret Key Exchange | Per Engagement | Per Engagement | Obsoleted by VBLS |
| Secret Key Retention | Per Engagement | Per Engagement | Obsoleted by VBLS |

FIG. 3

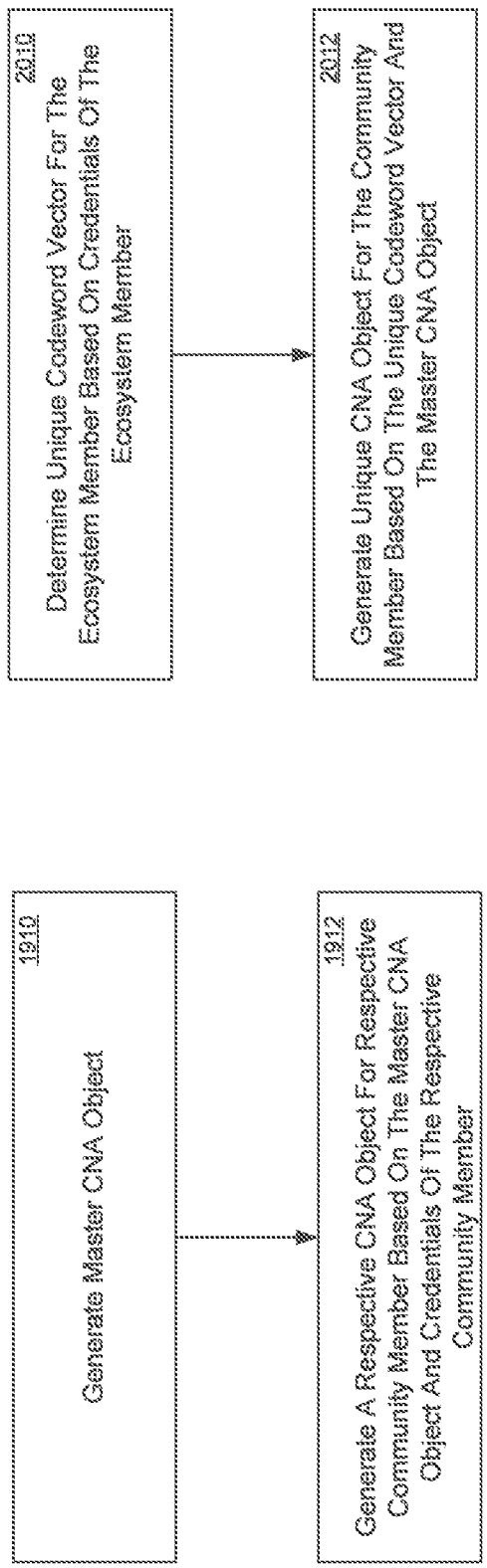

CYPHERGENICS-BASED DECODING AND ENCODING OF PROGRAM DATA

CROSS-REFERENCE TO RELATED APPLICATIONS

This application is a bypass continuation of PCT International Application No. PCT/US2022/015109, filed Feb. 3, 2022, which claims the benefit of U.S. Provisional Application Nos. 63/145,860, filed Feb. 4, 2021 and 63/229,348, filed Aug. 4, 2021. The entire disclosures of the above applications are incorporated by reference.

FIELD OF INVENTION

The present disclosure relates to Cyphergenics (CG)-enabled security platforms and corresponding digital genomic constructions that exhibit controlled entropy yet are subject to digital modification and reconstruction by computationally complex functions and processes without loss of genomic integrity. These constructions enable formation of comprehensively secure hyper-scalable digital ecosystems, enclaves, and/or digital cohorts having mutual identity of interests, and application specific security architectures based on genomic network topologies that are interoperable with contemporary application and networks stacks. In some implementations of the disclosure, the security platforms may be configured to facilitate secure data exchange between ecosystem members. In some aspects of the disclosure, the security platforms are configured to facilitate virtual trusted execution domains, whereby a processing environment is configured to perform CG-based encoding and decoding of instructions and program data. In some aspects of the disclosure, the security platforms are configured to facilitate material data chains (MDCs).

BACKGROUND

The requirement to distinguish the Noble from the Nefarious has grown in urgency as the ARPAnet community of adjunct-nodes breached their perimeter into a world-wide-web comprised of virtual digital ecosystems supported by an interoperable Digital Monoculture. By the time the material consequences faced by this new machine-connected-world became apparent, first responder technologies (e.g., Firewalls, Analytics, Forensics, PM, Proxies, and Monitoring) were already relegated to network perimeter patrol and rapid recovery services.

Experts broadly agree cryptography offers the only provable machine-connected-world security solution. Quantum, Homomorphic, and Obfuscation-based cryptographic research have garnered huge investment but no more than hoped for impact. Nevertheless, the most essential but indomitably complex of all cryptographic disciplines—hyper-scalability—remains unattended. Efforts to update PM to post quantum status abound, even as its linear scalability perseveres.

Applicant has developed and has disclosed herein, Cyphergenics (CG) technologies, which comprehensively resolves the heretofore intractable hyper-scalability dilemma, descriptions of which are disclosed in this document. As will be discussed, Cyphergenics enables unlimited deployment of cryptographic-based digital ecosystem security for di minimis overhead and bandwidth, while fully preserving interoperability. Importantly, hyper-scalability directly facilitates functional homomorphic cryptography and functional indistinguishable obfuscation.

SUMMARY

The artificial bifurcation of attacks on cyber infrastructure and assaults on privacy has been and remains misguided, as both leverage the same digital ecosystem (machine-connected-world) and digital monoculture (everything-interoperable-with-everything). Security solutions remain pedestrian kluges, expert at postmortem forensics and anemic at interdiction despite brilliant adaptations and extensions of vintage security technologies and methods. The limited capability of these technologies to thwart subversion, espionage, interloping, piracy, and assaults on privacy (whether covert or clandestine surveillance enabled) is well documented. Increasingly larger digital attack surfaces and powerful new variants of weaponized malware and processor exploits, and ultimately quantum computer assisted Cryptanalysis and artificial intelligence-informed subversive algorithms portend new levels of catastrophe.

Noble engagement has facilitated heretofore unimaginable virtualization of products, services, and knowledge, and redefined efficiency and efficacy. From within the same network centric campus, Nefarious engagement foments catastrophic cyber-attacks (e.g., subversion, espionage, interloping, and piracy) and pervasive assaults-on-privacy (e.g., covert and clandestine mass surveillance, profiling, and assimilation). It is substantially the common-machine-language and inherent hyper-scalability essential to their network centric missions that they share, which renders the noble and nefarious effectively indistinguishable.

Applicant submits that the most critical network centric competency is not the digital ecosystem comprised of various digital cohorts (e.g., networks, grids, clouds, systems, devices, appliances, sensors, IoT, applications, files, and data) nor its interoperable Digital Monoculture. It is the common-machine-language and hyper-scalability they share in order to scale their ubiquitous on-demand engagement (e.g., connection, communication, collaboration, and coordination) that accounts for hundreds of billions of unattended security instances: a huge permutation of billions of cohorts by millions of points-of-control by hundreds of billions of security instances per day.

It remains impractical to rebuild the digital ecosystem and Digital Monoculture, as well as interminably disruptive and financially imprudent. A technology capable of changing the common-machine-language based on computationally quantum-proof cryptography would offer highly effective security while eviscerating hyper-scalability essential to Digital Monoculture interoperability.

Cyphergenics (CG), a wholly new technology based on computationally complex genomic constructions, liberates modern cryptography from its intractably bounded but powerful computationally complex foundation. In embodiments, CG enables virtual unboundedness by generating information theory-constructed genomic constructions exhibiting computational complexity which can be directly regulated as are bio-chemical enabled constructions. Importantly, CG digital rendering preserves bio-chemical unbounded properties while vastly expanding the range of their inherent differences and correlation. CG preserves the ability of genomic constructions based on different Digital-DNA to be strategically regulated absent compromise of computational integrity. FIG. 1 illustrates attributes of Cyphergenics-based digital ecosystems in relation to related attributes of organic ecosystems and modern digital ecosystems, according to some embodiments of the present disclosure.

In embodiments, unique genomic and cryptographic properties amalgamated by information theory principles enable Cyphergenics-based technology to achieve highly functional hyper-scalability exhibiting unbounded differences (affiliation) and correlation (authentication). These properties in turn give rise to Virtual Affiliation, Virtual Authentication, Virtual Agility, Virtual Organic Engagement, and Virtual Trusted Execution Domains—powerful attributes whose applications far exceed security.

In embodiments, Cyphergenics enables hyper-scalability of specific digital ecosystems, enclaves, and cohorts, having mutual identity of interests (Digital-DNA related and regulated), which form the active basis of their engagement. These domain resident ecosystems, enclaves, and cohorts engage on the basis of hyper-scalable digital data objects and digital coder objects exhibiting unique, non-recurring, and computationally quantum-proof attributes reflecting their mutual identity of interest called Virtual Binary Language Script (VBLS) they share with impunity to nefarious intent.

While the Cyphergenics (CG) technology may be supported by a wide range of digital capable platforms and component configurations, some embodiments of the present disclosure are configured to ensure the orderly prosecution of critical computationally complex genomic construction and Digital-DNA regulation functions and processes. In embodiments, Cyphergenics Ecosystem security platform (CG-ESP) may be comprised of modules which control specific computational and genomic construction, and digital DNA regulation functions. In embodiments, this adaptability is critical given Cyphergenics functions may be rendered by ciphers, without any ciphers, or in combination.

In embodiments, Cyphergenics supports applications beyond network centric interests, such that its modules-based rendering may serve multiple purposes. For example, they allow individual genomic information theory enabled construction and regulation processes and functions to be re-imagined and incrementally improved or modified without compromising hyper-scalability, and they allow for computational and functional innovation among Cyphergenics application ready attributes.

Security applications with few exceptions must endure the network configurations over which they transact and the vulnerabilities these networks often induce, e.g., NAT circumvention of IP-SEC security to extend exhausted IP-IV addresses. Cyphergenics VBLS attribute enables powerful new, security application-centric genomic network topologies to operate simultaneously, interoperably, and on-demand over existing network configurations. Cyphergenics enables many security centric genomic network topologies to include Directed Architectures, Spontaneous Architectures, Ephemeral Architectures, Interledger Architecture, and others. FIG. 2 demonstrates an example of this adaptability and shows a Cyphergenics-enabled security stack that may be applied coextensively at various layers of commonly known application and network stacks and examples of Cyphergenics-facilitated genomic architectures of digital ecosystems that may result from such application, according to some embodiments of the present disclosure.

In embodiments, Cyphergenics's range of information theory-enabled genomic construction allows for digital-cohort to be spawned as progeny of a specific enterprise and/or enclave prior to their own conception. In embodiments, Cyphergenics-enabled digital ecosystems may be rendered gnomically flat or hierarchical, with or without orientation to order, e.g., time. In embodiments, a Cyphergenics cohort can serve the role of Cambrian Genome carrier—preserving instructions for subsequent construction of its own species-specific Ecosystem, Enclaves, and Progeny (reverse procreation), for which it must still undergo genomic regulation to achieve correlation and differentiation.

The differences between Cyphergenics—which implementation and practice are explained in the details of this patent—and the search for postmodern (quantum proof) cryptography technology is summarized below, examples of which may be observed in FIG. 3. Even if successful, contemporary efforts to defeat quantum computer enhanced cryptanalysis only stand to preserve the status quo, no matter that network centric security challenges continue to markedly and materially escalate.

In embodiments, Cyphergenics-based technology may displace the underlying approaches as opposed to developing variants of the existing technology and its inherent limitations.

The present disclosure relates to different implementations of Cyphergenics-based technologies and security platforms that are applied in myriad digital ecosystems having different and wide-ranging mutual identities of interest and topologies. In embodiments of the present disclosure, instances of Cyphergenics-based security platforms may be configured for the different types of digital ecosystems with different architectures to optimize different aspects of the respective ecosystem which they serve.

According to some embodiments of the present disclosure, a device is disclosed. In embodiments, the device includes a storage system including one or more computer-readable storage mediums, wherein the storage system stores: a computer program comprised of a set of encoded computer-executable instructions; a genomic data set that includes a genomic differentiation object that was used to encode the set of encoded computer-executable instructions; and genomic regulation instructions (GRI) corresponding to the computer program, wherein the genomic regulation instructions were used to encode the set of encoded computer-executable instructions. The device further includes a processing system comprising a VDAX and a set of processing cores. The VDAX is configured to: receive encoded instructions to be executed from the set of encoded computer-executable instructions and decode the encoded instructions into decoded executable instruction based on a modified genomic differentiation object and sequences extracted from metadata associated with the encoded instructions. In these embodiments, the modified genomic differentiation object is modified from the genomic differentiation object using the GRI. The set of processing cores are configured to receive the decoded executable instructions from the VDAX and to execute the decoded executable instructions. In some implementations, the genomic differentiation object is a ZNA object.

In implementations, the VDAX is configured to modify the genomic differentiation object based on the GRI using a set of computational functions to obtain the modified genomic differentiation object. For each respective encoded instruction that is to be executed by the processing device, the VDAX is further configured to: obtain a genomic engagement factor (GEF) corresponding to the respective encoded computer-executable instruction, decode the respective encoded instruction using the GEF corresponding to the respective encoded instruction to be executed to obtain a respective decoded executable instruction; and output the respective decoded instruction to a processing core of the set of processing cores. In these implementations, the GEF is generated based on a sequence that is extracted from metadata corresponding to the respective encoded computer-executable instruction, the GRI, and the modified genomic data object. In some of these implementations, decoding the respective encoded instruction using the GEF includes decrypting the respective encoded instruction using the GEF as a key to obtain the respective decoded instruction. In some implementations, decoding the respective encoded instruction using the GEF includes disambiguating the respective decoded instruction from the respective encoded instruction using the respective GEF. In some of these implementations, disambiguating the respective decoded instruction from the respective encoded instruction includes executing an XOR operation using the encoded instruction and the GEF as input to the XOR operation. In some implementations, wherein each respective encoded instruction was encoded with a different respective GEF, such that each respective GEF is determined based on a respective sequence extracted from respective metadata that uniquely corresponds to the respective encoded instruction. In some of these implementations, the respective metadata that uniquely corresponds to the respective encoded instruction includes one or more of random-access memory (RAM) metadata, application metadata, operating system-application metadata, and filesystem metadata. In some of these implementations, the respective sequence that is used to generate the respective GEF that is used to decode the respective encoded instruction is a set of bits extracted from a bit representation of the respective metadata. In some implementations, the set of encoded computer-executable instructions includes a plurality of sub-sets of instructions, such that each subset of plurality of subsets is decoded with a respective GEF that is generated based on a respective sequence extracted from metadata that respectively corresponds to the respective subset of computer-executable instructions. In some of these implementations, the respective metadata from which the respective sequence was extracted includes one or more of random-access memory (RAM) metadata corresponding to the subset, application metadata corresponding to the subset, operating system-application metadata corresponding to the subset, and filesystem metadata corresponding to the subset. In some implementations, obtaining the GEF corresponding to the respective encoded computer-executable instruction includes sequence mapping the sequence into the modified genomic data object to obtain the GEF. In some of these implementations, sequence mapping the sequence into the modified genomic data object includes: generating a sequence conversion vector (SCV) based on the sequence and the GRI; mapping the modified genomic differentiation object based on the SCV to obtain a mapped modified genomic differentiation object; and generating the GEF based on the mapped modified genomic differentiation object.

In implementations, the storage system stores a second computer program comprising a second set of encoded computer-executable instructions and second GRI corresponding to the second computer program that are used to decode the second set of encoded computer-executable instructions. In some of these implementations, the second GRI are different from the GRI used to decode the set of encoded computer-executable instructions. In some of these implementations, the storage device further stores a second genomic differentiation object that is used to encode and decode the second set of encoded computer-executable instructions and is different from the genomic differentiation object used to encode and decode the set of encoded computer-executable instructions. In some implementations, the genomic differentiation object is modified using the second GRI to obtain a second modified genomic differentiation object, such that the second modified genomic differentiation object is used to decode the second set of encoded computer-executable instructions.

In some implementations, the processing system is a processing device and the VDAX is a dedicated core of the processing device. In some implementations, the VDAX is a field programmable gate array that is in electrical communication with the set of processing cores. In some implementations, the VDAX is a microprocessor that is in electrical communication with the set of processing cores. In some implementations, the VDAX is included in an operating system that is executed by the set of processing cores.

In implementations, the device is one of a server computing device, a mobile computing device, a personal computing device, a vehicle, an internet of things device, a sensor device, a video recording device, a wearable computing device, a smart appliance, is a network router, a gaming device, or the like. In implementations, the computer program is a software application, a middleware application, a firmware application, and/or an operating system.

According to some embodiments of the present disclosure, a method for executing computer programs in a trusted execution environment of a device is disclosed. The method includes retrieving a genomic differentiation object corresponding to a set of one or more computer programs including a first computer program, wherein the first computer program comprises a first set of encoded computer-executable instructions and the genomic differentiation object comprises a binary vector of specific length. The method further includes modifying the genomic differentiation object based on first genomic regulation instructions (GRI) to obtain a first modified genomic differentiation object, wherein the first GRI were used to encode the first set of encoded executable instructions of the first computer program. The method also includes obtaining a first encoded instruction that is to be executed from the first set of encoded computer-executable instructions of the first computer program; obtaining a first sequence from first metadata associated with the first encoded instruction; generating a first genomic engagement factor (GEF) based on the first sequence and the first modified genomic differentiation object; decoding the first encoded instruction using the first GEF to obtain a first decoded instruction; and executing the first decoded instruction. In some implementations, the genomic differentiation object is a ZNA object.

In some implementations, the method further includes obtaining a second encoded instruction that is to be executed from the first set of encoded computer-executable instructions of the first computer program; obtaining a second sequence from second metadata associated with the second encoded instruction; generating a second GEF based on the second sequence and the modified genomic differentiation object; decoding the second encoded instruction using the second GEF to obtain a second decoded instruction; and executing the second decoded instruction.

In some implementations, the method further includes modifying the genomic differentiation object with second GRI corresponding to a second computer program of the set of computer programs to obtain a second modified genomic differentiation object, wherein the second computer program comprises a second set of encoded computer-executable instructions. In these implementations, the method further includes obtaining a third encoded instruction that is to be executed from the second set of encoded computer-executable instructions of the second computer program; obtaining a third sequence from third metadata associated with the third encoded instruction; generating a third GEF based on the third sequence and the second modified genomic differentiation object; decoding the third encoded instruction using the third GEF to obtain a third decoded instruction; and executing the third decoded instruction. In some of these implementations, the genomic differentiation object is assigned to both the first computer program and the second computer program. In some of these implementations, the first GRI corresponds only to the first computer program and the second GRI corresponds only to the second computer program. In some implementations, the first computer program and the second computer program and any other computer programs of the set of computer programs are distributed by the same entity. In some of these implementations, the entity assigns the genomic differentiation object to the first and second computer programs. In some implementations, a VDAX of the device assigns the genomic differentiation object to the first and second computer programs. In some of these implementations, the VDAX generates the first GRI and the second GRI.

In some implementations, the method further includes installing the first computer program prior to decoding the first encoded instruction and the second encoded instruction. In some of these implementations, installing the first computer program includes: obtaining a set of unencoded computer-executable instructions that comprise the first computer program; allocating memory on a computer-readable storage medium of the device to the first computer program; generating the first GRI and associating the first GRI with the first computer program; modifying the genomic differentiation object based on the first GRI to obtain the modified genomic differentiation object; and generating the first set of encoded computer-executable instructions. In generating the first set of encoded instructions, the method includes, for each respective unencoded instruction in the set of unencoded computer-executable instructions: determining a respective sequence from respective metadata associated with the respective unencoded instruction; generating a respective GEF based on the respective sequence and the modified genomic differentiation object; encoding the respective unencoded using the respective GEF to obtain a respective encoded instruction of the first set of encoded computer-executable instructions; and storing the respective encoded instruction at a memory location of the allocated memory. In some of these implementations, the respective metadata from which the respective sequence is extracted includes one or more of random-access memory (RAM) metadata, application metadata, operating system-application metadata, and filesystem metadata.

In some implementations, the execution environment is a processing device that includes an executable isolation components VDAX that is a dedicated core of the processing device that decodes encoded instructions and a set of processing cores that execute the decoded instructions.

In implementations, the device is one of a server computing device, a mobile computing device, a personal computing device, a vehicle, an internet of things device, a sensor device, a video recording device, a wearable computing device, a smart appliance, is a network router, a gaming device, or the like. In implementations, the first computer program is a software application, a middleware application, a firmware application, and/or an operating system.

According to some embodiments of the present disclosure, a method for executing computer programs in a trusted execution environment of a device is disclosed. The method includes retrieving a genomic differentiation object corresponding to a set of one or more computer programs including a computer program; modifying the genomic differentiation object based on genomic regulation instructions (GRI) to obtain a modified genomic differentiation object; and executing a first executable instruction of the computer program. In implementations, executing the first executable instruction includes: retrieving first encoded data that is input to the first executable instruction; extracting a first sequence from first metadata associated with the first encoded data; generating a first genomic engagement factor (GEF) based on the first sequence, the GRI and, and the modified genomic differentiation object; decoding the first encoded data based on the first GEF to obtain first decoded data; executing the first executable instruction using the first decoded data. The method further includes executing a second executable instruction of the computer program, wherein executing the second executable instruction includes: retrieving second encoded data that is input to the second executable instruction; extracting a second sequence from second metadata associated with the second encoded data; generating a second GEF based on the second sequence, the GRI and, and the modified genomic differentiation object; decoding the second encoded data based on the second GEF to obtain second decoded data; and executing the second executable instruction using the second decoded data. In some implementations, the genomic differentiation object is an ZNA object. In some of these implementations, ZNA object is an N×M binary matrix. In some of these implementations, a VDAX of the device generates and assigns the ZNA object to the computer program.

In some implementations, executing the first executable instruction further includes: obtaining output data resulting from execution of the first executable instruction; generating a third GEF based on a third sequence corresponding to the output data, the GRI, and the modified genomic differentiation object; and transforming the output data into third encoded data based on the third GEF. In some of these implementations, the method further includes writing the third encoded data to memory. In some of these implementations, the third sequence is extracted from metadata corresponding to the output data, wherein the metadata includes one or more of random-access memory (RAM) metadata, application metadata, operating system-application metadata, and filesystem metadata. In some implementations, the method further includes executing a third executable instruction of the computer program by: retrieving the third encoded data that is input to the third executable instruction; extracting the third sequence from a value representing the metadata corresponding to the output data; generating the third GEF based on the third sequence, the GRI and, and the modified genomic differentiation object; decoding the third encoded data based on the third GEF to obtain the output data; and executing the first executable instruction using the output data resulting from execution of the first executable instruction.

In some implementations, the first metadata from which the first sequence is extracted and the second metadata from which the second sequence is extracted includes one or more of random-access memory (RAM) metadata, application metadata, operating system-application metadata, and filesystem metadata.

In some implementations, generating the first GEF includes: generating a sequence conversion vector (SCV) based on the first sequence and the first GRI; mapping the modified genomic differentiation object based on the SCV to obtain a mapped modified genomic differentiation object; and generating the first GEF based on the mapped modified genomic differentiation object. In some of these implementations, generating the SCV includes combining the first sequence and the GRI. In some of these implementations, generating the SCV further includes applying one or more computational functions to the combination of the first sequence and the GRI to obtain the SCV.

In some implementations, decoding the first encoded data includes decrypting the first encoded data using the first GEF and decoding the second encoded data includes decrypting the second encoded data using the second GEF.

In some implementations, decoding the first encoded data includes disambiguating the first encoded data using the first GEF and disambiguating the second encoded data includes decrypting the second encoded data using the second GEF.

In implementations, the device is one of a server computing device, a mobile computing device, a personal computing device, a vehicle, an internet of things device, a sensor device, a video recording device, a wearable computing device, a smart appliance, is a network router, a gaming device, or the like. In implementations, the first computer program is a software application, a middleware application, a firmware application, and/or an operating system.

According to some embodiments of the present disclosure, a method for verifying an unverified portion of a material data chain (MDC) that is maintained by a creator cohort in a ledger-based digital ecosystem is disclosed. In embodiments, the method includes receiving, by a processing system of a verification cohort, the unverified portion of the MDC from the creator cohort, the unverified portion of the MDC including a set of consecutive material data blocks (MDBs) generated by the creator cohort. Each respective MDB includes respective material data that is stored in the respective MDB, respective metadata relating to the MDB, and a creator-generated verification value generated by the creator cohort with respect to the verification cohort. The method further includes retrieving, by the processing system of the verification cohort, a genomic differentiation object assigned to the verification cohort with respect to the ledger-based ecosystem and first genomic regulation instructions (GRI) used by the creator cohort to generate the creator-generated verification value. The method further includes modifying, by the processing system of the verification cohort, the genomic differentiation object based on the first GRI using a set of computational functions to obtain a modified differentiation object. For each MDB in the unverified portion of the MDC, the method further includes generating a genomic engagement factor (GEF) based on a sequence extracted with respect to the MDB, the modified genomic differentiation object, and the first GRI; determining a verifier-generated verification value based on the MDB, an MDB preceding the MDB in the MDC, and the GEF; determining whether the verifier-generated verification value matches the creator-generated verification value in the MDB; and in response to determining that the verifier-generated verification value matches the creator-generated verification value, generating a verification record corresponding to the MDB indicating that the MDB has been verified by the verification cohort. The unverified portion of the MDC is verified by the verification cohort when each of the MDBs in the unverified portion of the MDC have been verified by the verification cohort.

In some implementations, the creator-generated verification value of each MDB is generated by the creator cohort based on the MDB, an MDB preceding the MDB in the MDC, and a second modified genomic differentiation object that is derived by the creator cohort by modifying a second genomic differentiation object assigned to the creator cohort using second GRI, wherein the second GRI matches the first GRI.

In some of these implementations, the creator-generated verification value of a respective MDB matches the verifier-generated verification value generated by the verification cohort only if the genomic differentiation object assigned to the verification cohort is sufficiently correlated with the second genomic differentiation object assigned to the creator cohort. In some implementations, the creator-generated verification value of a respective MDB matches the verifier-generated verification value generated by the verification cohort only if the genomic differentiation object assigned to the verification cohort exactly matches the second genomic differentiation object assigned to the creator cohort. In some implementations, the genomic differentiation object is assigned to the verification cohort by an ecosystem VDAX that controls a genomic topology of the ledger-based ecosystem and the second genomic differentiation object is assigned to the creator cohort by the ecosystem VDAX.

In some implementations, wherein the first GRI was generated and provided by the creation cohort during a one-time link exchange process. In some implementations, the first GRI was generated by the verification cohort and provided to the creation cohort during a one-time link exchange process. In some implementations, the first GRI was generated by an enclave VDAX and provided to the creation cohort, the verification cohort, and one or more other verification cohorts, such that the first GRI is used by the verification cohort and the one or more other verification cohorts to verify the creator-generated verification value.

In some implementations, generating the GEF includes: generating a sequence conversion vector based on the sequence and the first GRI; and mapping the modified genomic differentiation object based on the sequence conversion vector to obtain a mapped genomic differentiation object; and generating the GEF based on the mapped genomic differentiation object.

In some implementations, the generating the verifier-generated verification value includes: generating a linking value based on the MDB and the preceding MDB in the MDC, the linking value being indicative of a combination of the MDB and the preceding MDB; and applying one or more computational functions to the linking value based on the GEF to obtain the verifier-generated verification value. In some of these implementations, generating the linking value includes: generating a first hash value of at least a portion of the MDB; generating a second hash value of at least a portion of the preceding MDB; and combining the first hash value and the second hash value to obtain the linking value. In some implementations, the one or more computational functions include one or more cipher-based functions that transform the linking value into the verifier-generated verification value using the GEF as a key. In some of these implementations, the one or more cipher-based functions include an encryption function. In some implementations, the one or more cipher-based functions include a disambiguation function. In some implementations, the one or more computational functions include one or more cipher-less functions that transform the linking value into the verifier-generated verification value using the GEF as an input parameter. In some of these implementations, the one or more cipherless functions include a hash function. In some implementations, the one or more computational functions include one or more cipherless functions and one or more cipher-based functions that in combination transform the linking value into the verifier-generated verification value using the GEF as an input parameter.

In some implementations, the method further includes transmitting the verification record to the creator cohort. In some of these implementations, the method further includes storing, by the processing system of the verification cohort, the verification record in a verification chain that is maintained by the verification cohort. In some of these implementations, storing the verification record includes: generating a verification block containing one or more verification records corresponding to one or more respective MDBs in the MDC; and adding the verification block to the verification chain. In some of these implementations, the verification chain is a sidechain of a second MDC maintained by the verification cohort. In some implementations, the creator cohort stores the verification record in a creator-cohort verification chain that maintains verification records provided by verification cohorts. In some of these implementations, the creator-cohort verification chain is a sidechain of the MDC.

According to some embodiments of the present disclosure, a method for maintaining a material data blockchain (MDC) is disclosed. The method includes receiving, by a first set of processors that executes a ledger-based application and a creator VDAX that corresponds to a creator cohort, an unnotarized material data block (MDB) from the ledger-based application, wherein the unnotarized MDB includes a metadata portion and a payload portion that contains substantive data being stored in the MDB. The method further includes extracting, by the creator VDAX, a first sequence of bits from the metadata portion of the MDB and generating, by the creator VDAX, a first genomic engagement factor (GEF) based on the first sequence, a first genomic differentiation object that is assigned to the creator VDAX, and first genomic regulation instructions (GRI) that are maintained by the creator VDAX. The method further includes applying, by the creator VDAX, one or more computational functions to the unnotarized MDB using the first GEF as input to obtain a creator-generated value corresponding to the unnotarized MBD. The method also includes updating, by the first set of processors, the unnotarized MBD by digitally signing the unnotarized MBD with the creator-generated value; providing, by the first set of processors, the unnotarized MDB to one or more notary cohorts; and receiving, by the first set of processors, a respective notary value from each of the one or more notary cohorts, wherein each respective notary value is generated by a respective notary cohort of the one or more notary cohorts using respective GRI that is held by the respective notary cohort and a respective genomic differentiation object that is assigned to the respective notary cohort. The method further includes updating, by the first set of processors, the unnotarized MDB with the respective notary values received from the one or more notary cohorts to obtain a notarized MDB and adding, by the first set of processors, the notarized MDB to the MDC.

In some implementations, the method further includes: receiving, by a second set of processors that executes a notary VDAX corresponding to a notary cohort of the one or more notary cohorts, the unnotarized MDB; extracting, by the notary VDAX, a second sequence of bits from the metadata portion of the MDB; generating, by the notary VDAX, a second genomic engagement factor (GEF) based on the second sequence, a second genomic differentiation object that is assigned to the notary VDAX, and second GRI that are maintained by the notary VDAX; applying, by the notary VDAX, one or more computational functions to the unnotarized MDB using the second GEF as input to obtain a notary value corresponding to the unnotarized MBD; and providing, by the second set of processors, the notary value to the creator cohort. In some of these implementations, the method further includes digitally signing, by the second set of processors, the unnotarized MDB with the notary value to obtain an at least partially notarized MDB and updating, by the second set of processors, a second MDC that is maintained by the notary cohort with the at least partially notarized MDB. In some of these implementations, providing the notary value to the creator cohort includes providing the at least partially notarized MDB to the creator cohort. In some implementations, generating the second GEF includes determining a sequence conversion vector (SCV) based on the second sequence and the second GRI. In some of these implementations, generating the second GEF includes: mapping the second genomic differentiation object based on the SCV to obtain a mapped genomic differentiation object; modifying the mapped genomic differentiation object based on at least one of the SCV and the second GRI to obtain a modified mapped genomic differentiation object; and determining the second GEF based on the modified mapped genomic differentiation object. In some of these implementations, generating the second GEF includes: modifying the second genomic differentiation object based on the second GRI to obtain a modified genomic differentiation object; mapping the modified genomic differentiation object based on the SCV to obtain a mapped modified genomic differentiation object; and determining the second GEF based on the mapped modified genomic differentiation object. In some of these implementations, the method further includes storing the modified genomic differentiation object, such that the modified genomic differentiation object is used to determine subsequent GEFs for other MDBs received from the creator cohort. In some implementations, the second sequence of bits is equal to the first sequence of bits. In other implementations, the second sequence is different than the first sequence of bits. In some implementations, the one or more computational functions include one or more cipher-based functions that transform at least a portion of the unnotarized MDB into the notary value using the second GEF as a key. In some of these implementations, the one or more cipher-based functions include an encryption function. In some implementations, the one or more cipher-based functions include a disambiguation function. In some implementations, the one or more computational functions include one or more cipherless functions that transform at least a portion of the unnotarized MDB into the notary value using the second GEF as an input parameter. In some of these implementations, the one or more cipherless functions include a hash function. In some implementations, the one or more computational functions include one or more cipherless functions and one or more cipher-based functions that in combination transform that transform at least a portion of the unnotarized MDB into the notary value using the second GEF as an input parameter. In some implementations, the second genomic differentiation object and the first genomic differentiation object are correlated genomic differentiation objects. In some implementations, the second genomic differentiation object and the first genomic differentiation object are uncorrelated genomic differentiation objects. In some implementations, the method further includes receiving, by the second set of processors, a confirmation request from a verifying cohort, the confirmation request including the notarized MDB and generating, by the notary VDAX, a recreated notary value based on the notarized MDB based on a third sequence of bits that is extracted from the notarized MDB, the second GRI, and the second genomic data object. In some implementations, the method further includes providing, by the second set of processors, a response to the verifying cohort indicating the recreated notary value, wherein the verifying cohort confirms an integrity of the notarized MDB in response to determining the recreated notary value matches the notary value used to notarize the notarized MDB. In some of these implementations, the method further includes determining, by the second set of processors, whether the recreated notary value matches the notary value used to notarize the notarized MDB, and in response to determining the recreated notary value matches the notary value used to notarize the notarized MDB, providing, by the second set of processors, a response to the verifying cohort confirming an integrity of the notarized MDB.

According to some implementations of the present disclosure, a device is disclosed. The device includes a VDAX having a genomic data set assigned thereto, the genomic data set corresponding to a digital ecosystem to which the device is a member and including a genomic eligibility object, a genomic correlation object, and a genomic differentiation object. The VDAX includes link spawning means for spawning a first link for a second device in the digital ecosystem, wherein the link includes first genomic regulation instructions (GRI) that are used by the second device to generate virtual binary language script (VBLS) that is decodable by the VDAX. The VDAX further includes VBLS decoding means for decoding VBLS generated by the second device for the device based on the first GRI and the genomic differentiation object to obtain decoded digital objects encoded in the VBLS.

In embodiments, the VDAX further includes link hosting means for decoding a second link received from the second device to obtain second GRI generated by the second device, the second link including second encoded GRI, second encoded link information for decoding the encoded GRI, and a second public sequence that is used to decode the second encoded link information. The VDAX also includes VBLS encoding means for encoding digital objects for the second device based on the second GRI and the genomic differentiation object. In some embodiments, the link hosting means includes: means for generating a correlation vector based on the genomic eligibility object, first credentials of the device, and second credentials of the second device; means for decoding the second encoded link information based on the correlation vector to obtain a set of zone references; means for generating a window vector based on the set of zone references and the genomic correlation object; means for generating a transformation value based on the public sequence, the window, and the genomic correlation object of the device; and means for decoding the second GRI using the transformation value to obtain the second GRI. In some of these implementations, the VBLS encoding means comprises: means for generating a genomic engagement factor (GEF) based on the first GRI, a sequence extracted from an unencoded portion of a digital object, and the genomic differentiation object; and means for encoding a digital object based on the GEF to obtain a VBLS object that is decodable by the second device. In some of these implementations, the means for encoding the digital object encrypts a payload of the digital object using the GEF as a key to obtain a VBLS object. In some implementations, the means for encoding the digital object XORs payload of the digital object and the GEF to obtain the VBLS object.

In some implementations, the first link includes encoded GRI that contains the first GRI, encoded link information that includes information that is used by the second device to decode the first GRI from the encoded GRI, and a public sequence that is used by the second device to decode the link information from the encoded link information. In some of these implementations, the link spawning means generates the first link based on the genomic eligibility object, the genomic correlation object, first credentials corresponding to the device, and second credentials corresponding to the second device. In some of these implementations, the link spawning means generates the first link by generating a correlation vector based on the genomic eligibility object assigned to the VDAX, the first credentials, and the second credentials, wherein the correlation vector is used to encode the link information. In some of these implementations, the genomic eligibility object is a first CNA object that is uniquely derived from a master CNA object using the first credentials. In some of these implementations, the link spawning means includes means for generating the correlation vector based on the first CNA object, the first credentials, and the second credentials. In some of these implementations, the means for generating the correlation vector is configured to: apply a code mapping function to the first credentials to obtain a first code word vector that uniquely corresponds to the first device and indicates respective portions of the master CNA object that were allocated to the first CNA object; apply the code mapping function to the second credentials to obtain a second code vector corresponding to that uniquely corresponds to the second device and indicates respective portions of the master CNA object that were allocated to a second CNA object that is assigned to the second device; determine an intersection vector that indicates an intersection of the first code vector and the second code vector; and determine the correlation vector from the first CNA object based on the intersection vector. In some of these implementations, the correlation vector represents a unique correlation between the first CNA object of the device and the second CNA object of the second device.

In some implementations, the genomic eligibility object is a PNA object that is uniquely derived from a master PNA object using the first credentials corresponding to the device, wherein the PNA object includes a secret ratio that is maintained in secret by the device, a public primitive polynomial assigned to the device, and a public component of the master PNA object.

In some of these implementations, the public component of the master PNA object includes a first master primitive polynomial of degree M, a second master primitive polynomial of degree M, and a public component that includes (N−1) respective pairs of M-bit values, wherein the first credentials and the second credentials are represented in N-bit vectors. In some implementations, the link spawning means includes means for generating the correlation vector based on the PNA object of the device and the engagement information of the second device. In some of these implementations, the engagement information of the second device includes credentials corresponding to the second device and a second public polynomial assigned to the second device.

In some implementations, the link spawning means includes: means for generating a correlation vector based on the genomic eligibility object, first credentials of the device, and second credentials of the second device; means for generating the first GRI; means for generating a set of zone references, wherein each zone reference indicates a respective portion of the genomic correlation object; means for generating a window vector based on the genomic correlation object and the set of zone references; means for generating the public sequence based on the window and the first GRI; means for generating transformation value based on the public sequence, the window, and the genomic correlation object of the device; means for encoding the first GRI using the transformation value to obtain the encoded GRI; and means for encoding the set of zone references using the correlation vector to obtain the encoded link information. In some of these implementations, the device provides the encoded link information, the public sequence, and the encoded GRI to the second device and the second device decodes the encoded GRI based on the encoded link information, the public sequence, a second genomic data set assigned to the second device, the first credentials, and the second credentials.

In some implementations, the means for decoding VBLS includes: means for generating a genomic engagement factor (GEF) based on the first GRI, a sequence extracted from an unencoded portion of a VBLS object, and the genomic differentiation object; means for decoding the VBLS object based on the GEF to obtain a decoded portion of a digital object. In some of these implementations, the means for decoding the VBLS object decrypts an encoded portion of the VBLS object using the GEF as a key to obtain a decoded portion of the digital object.

In some implementations, the means for decoding the VBLS object disambiguates an encoded portion of the VBLS object by XORing an unencoded portion of the VBLS object and the GEF to obtain the decoded digital object.

In some implementations, the digital object is a media frame. In some implementations, the digital object is a network packet. In some implementations, the digital object is a file.

A more complete understanding of the disclosure will be appreciated from the description and accompanying drawings and the claims, which follow.

BRIEF DESCRIPTION OF THE DRAWINGS

The accompanying drawings, which are included to provide a better understanding of the disclosure, illustrate embodiments of the disclosure and together with the description serve to explain the principle of the disclosure. In the drawings:

Figure 1:
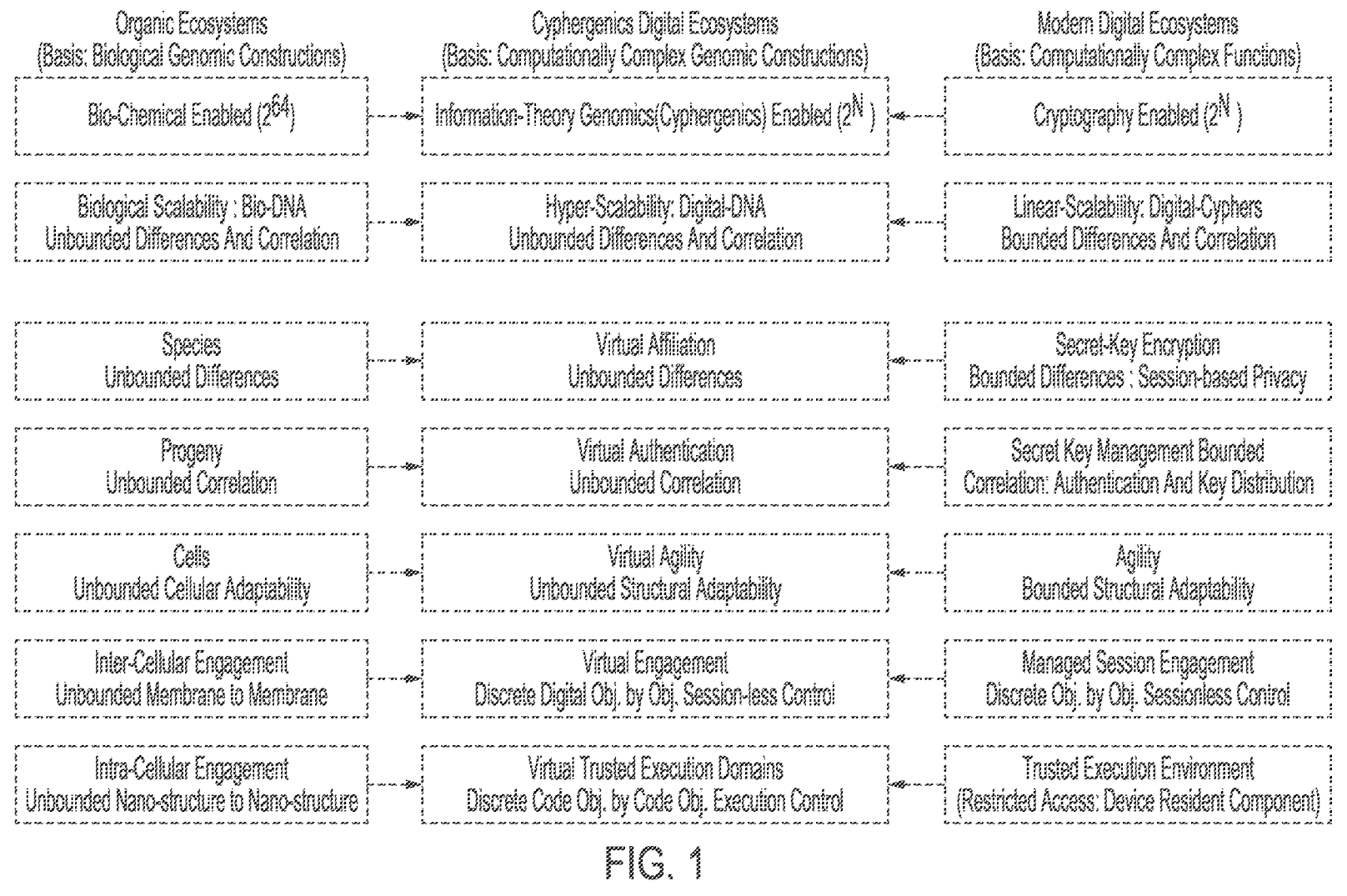

FIG. 1 is a schematic illustrating features of Cyphergenics-based digital ecosystems in relation to organic ecosystems and modern digital ecosystems, according to some embodiments of the present disclosure.

FIG. 3 illustrates attributes of Cyphergenics-based technologies in relation to the attributes (and potential shortcomings) of current and developing security-related technologies, according to some embodiments of the present disclosure.

FIG. 19 illustrates an example process for generating a master CNA object in accordance with some embodiments of the present disclosure.

FIG. 20 illustrates an example process for allocating CNA objects for ecosystem members based on a master CNA object in accordance with some embodiments of the present disclosure.

DETAILED DESCRIPTION

Introduction

Figure 2:
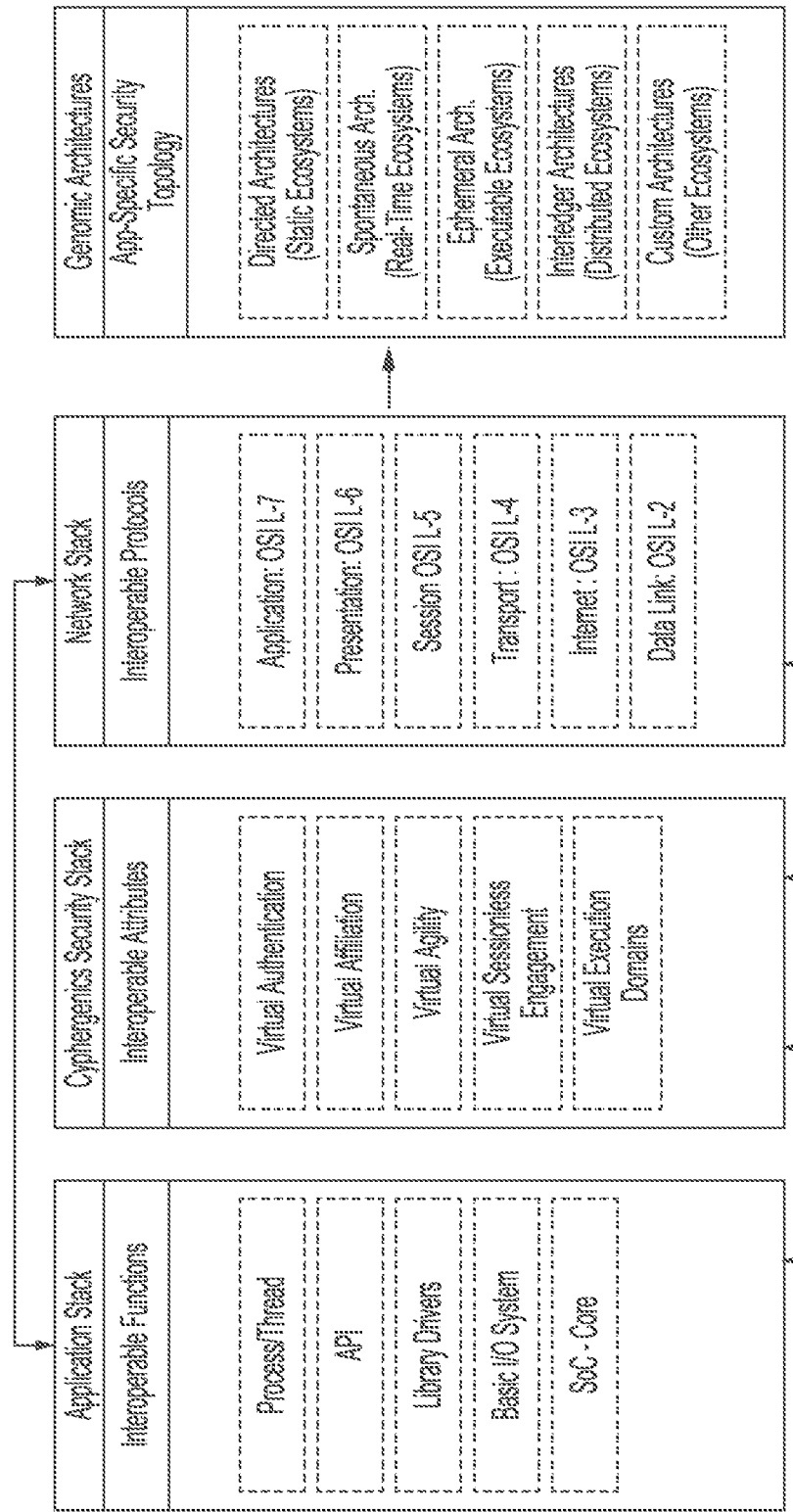
FIG. 2 illustrates a Cyphergenics-enabled security stack that may be applied coextensively with commonly known application and network stacks and examples of Cyphergenics-facilitated genomic architectures of digital ecosystems that may result from such application, according to some embodiments of the present disclosure.

It is submitted that hyper-scalability (e.g., where N digital cohorts have the ability to directly establish mutual identity of interest exhibiting high entropy with N different digital cohorts) is important to all things network-centric and the missing link to comprehensive security of dynamic-state-virtualization of digital ecosystems. Hyper-scalability (e.g., many-to-many) may facilitate wholly new network-centric virtualized products and services in addition to comprehensive security that prevailing linearly scalable technologies e.g., public key infrastructure (one-to-many) and quantum key distribution (one-to-one) cannot, no matter whether they achieve quantum resistant status or not.

As discussed herein, Cyphergenics-enabled hyper-scalability, which requires di minimis additional overhead or bandwidth, is equally effective and computationally undaunted across all Network and Application stack level although N×N engagement-instances might increase to increase to $N^X \times N^Y$. In embodiments, outcomes of hyper-scalable direct digital-cohort-to-digital-cohort virtual authentication and virtual affiliation are similar in outcome as hyper-scalable biological-progeny-to-biological-progeny virtual correlation and virtual differentiation, no matter the profoundly different base technologies by which each is accomplished. The same holds true for other digital attributes (e.g., virtual agility, virtual data objects, and virtual code objects), enabled by CG-based hyper-scalability.

Discussion of Cyphergenics, a wholly digitally fulfilled technology, is substantially assisted by adoption of corollary genomic terminology, having wholly bio-chemical fulfillment that is likely and hopefully more familiar to all but a few at this time. While the specific bio-chemical processes do not technically inform Cyphergenics, their ability to address similar challenges and levels of complexity added merit, after the fact, to Cyphergenics underlying propositions. Non-limiting examples of where Cyphergenics-based terms and computationally complex digital functions and processes and bio-chemical-based functions and processes share corollary genomic expression amongst others may include:

Genomic Information: numerical, narrative, or other such scripts, which elements in the aggregate exhibit little to no computationally discernable order or relationship.

Genomic Entropy: computationally assessable and confirmable degree to which recurring or predictable patterns are absent from the genomic information.

Genomic Construction: The ability to rearrange or reconfigure genomic information from its original sequence or relational basis to specific subsets without loss of relative entropy.

Genomic Modification: The ability to process genomic information based on computationally complex functions and processes, which computational properties remain provable if not observable, and consistent across the modified genomic information base.

Genomic Regulation: The ability to conditionally and temporarily modify a complete genomic information base or specific subset(s) in order to accomplish a specific objective (e.g., digital-cohort precision uncoordinated revocation), which requires pre-requisite knowledge of the then (i.e., modified) current base.

Genomic Revision: The ability to derive a subset of genomic information by re-construction, modification, or regulation, which enable unique, computationally quantum proof, non-recurring transformation of digital-data-objects and digital-code-objects that nevertheless retain specific genomic correlation and differentiation attributes.

The present disclosure relates to various embodiments of Cyphergenics ecosystem security platforms (also referred to as "CG-ESPs", "security platforms", or "genomic security platforms") and CG-facilitated processes and techniques. In embodiments, a CG-ESP provides the computational resources and process control with which genomic information, genomic entropy, genomic construction, genomic modification, genomic regulation, and genomic revision uniquely collaborate to render computationally complex hyper-scalability. In embodiments, hyper-scalability, in turn, enables digital ecosystems, enclaves, and digital cohorts to engage on a genomic basis in order to achieve virtual authentication, virtual affiliation, virtual agility, virtual sessionless engagement, and/or virtual execution domain attributes. In some embodiments, these attributes in turn facilitate application specific genomic network security topologies without replacement or reconfiguration of hardware connectivity.

In embodiments, instances of a CG-ESP may be parameterized with specific information theory-constructed genomic attributes (e.g., digital genomic data sets reflecting one or more mutual identities of interest of specific digital communities comprised in whole or in-part of ecosystem, enclaves, and/or digital cohorts (or "cohorts")). In embodiments, the parameterization of a CG-ESP instance with specific information theory-constructed genomic attributes configures a respective Virtual Anonymity Exchange controller (or "VDAX"), which may be executed by a processing system to enable the VDAX to perform a role within a respective digital community. As will be discussed, a VDAX may be embodied in different manners, depending on the type of device which the VDAX serves, the intended purpose of the VDAX, and/or the desired level of security. For example, in some implementations a VDAX may be embodied as software, firmware, or other computer-executable instructions that are executed by a processor. In some implementations, a VDAX may be embodied as hardware, such as a dedicated core of a processing device, a field-programmable gate array, a microprocessor, a system-on-chip (SoC), and/or the like. In some implementations, a VDAX may be a combination of hardware and software elements. In embodiments, a CG-ESP may enable multiple VDAXs no matter their having disparate or overlapping mutual identity of interests.

In embodiments, CG-ESPs may be configured to construct and manage digital correlation and differentiation functions on behalf of a digital ecosystem or components thereof. In embodiments, a digital ecosystem may refer to a digital community having one or more enclaves each having a mutual identity of interest. In embodiments, an enclave may refer to a set of one or more cohorts having a mutual identity of interest. In embodiments, the term "cohorts" may refer to independent cohorts and/or dependent cohorts. In some embodiments, independent cohorts may refer to a collection of one or more devices that operate as an independent entity. In some of these embodiments, independent cohorts may include, but are not limited to, grids, networks, cloud services, systems, computers, appliances, devices, and IoT devices (including IoT sensors). A dependent cohort may refer to an individual digital entity which is enabled by an independent cohort that acts as a surrogate on behalf of the individual digital entity. Examples of dependent cohorts include, but are not limited to, sensors, applications (apps), data, files, and content. As will be discussed, the designation of independent and dependent cohorts may vary across different types of architectures and ecosystems. For example, according to some embodiments of an ephemeral architectures (discussed below), certain device components (e.g., processors, processor cores, cameras, and the like) and software instances may be designated independent cohorts, while other device components and software instances may be designated dependent cohorts. It is noted that in some embodiments, these types of designations may be decided by a community owner associated with the digital ecosystem.

In example embodiments, a Cyphergenics-based ecosystem security platform ("CG-ESP") forms an ecosystem with one or more enclaves and manages membership of a collection of independent and dependent cohorts having a mutual identity of interest. In embodiments, a GC-ESP provides one or more core competences, such as a platform competence that controls and manages genomic functions and processes, and a link-exchange competence, which provides a means by which link data (e.g., genomic engagement cargo) is exchanged. In embodiments, a mutual identity of interest may be defined in accordance with any logical commonality between the cohorts within an enclave, which may be defined by or on behalf of a community owner. For example, mutual identities of interest may exist between user devices, servers, printers, documents, applications (e.g., cohorts) that form business units (e.g., enclaves) within an enterprise organization (e.g., digital ecosystem). In another example, mutual identities of interest may exist between the user devices, smart devices, gaming devices, sensors, wearable devices, files, and applications (e.g., cohorts) that operate on a home network (e.g., an ecosystem), such that the home network may have one or more enclaves (e.g., a work-related enclave used for a home office and a personal enclave for an individual or family's devices, applications, and files). In another example, mutual identity of interest may exist between autonomous vehicles (e.g., cohorts) that are driving on a particular grid (e.g., enclave) of a smart transportation system (ecosystem) managed by a regional authority (e.g., community owner). The foregoing are non-limiting examples of ecosystems, enclaves, cohorts, and identities of interest, and many other examples will be discussed throughout the document. Furthermore, it is noted that because a digital entity may be considered a cohort in a first ecosystem (e.g., a mobile device in an enterprise ecosystem), a digital entity may serve different roles within an ecosystem or across multiple ecosystems. For instance, a mobile device in an enterprise ecosystem may be considered an enterprise ecosystem cohort but may define an entire digital ecosystem in an executable ecosystem.

As will be discussed in greater detail, a configuration of CG-ESP may be defined by the community owner of a digital ecosystem. When referencing a "community owner" throughout the disclosure, the term may refer to the entity that administers, maintains, or owns the community (e.g., company, organization, government, individual human, or the like) and/or representatives thereof (e.g., network administrator, CIO, IT administrator, homeowner, consultant, security expert, artificial intelligence software acting on behalf of the community owner, or any other suitable representative). Furthermore, in some embodiments, a CG-ESP may be pre-configured and sold to the community owner, whereby the community owner may or may not be able to make decisions regarding community membership and/or decisions regarding the functionalities of the CG-ESP (e.g., which CG-ESP modules and configurations are used in the CG-ESP).

In the context of biology, core biological genomic competences, which include biological differentiation and correlation, provide a convenient corollary to describe formulation of CG-ESP digital processes. It is understood, however, that any reference to or derivations of "genomic" cohorts (e.g., genomic data sets, DNA, sequence mapping, mutating, cloning, and/or the like) in the context of Cyphergenics-related technologies is not intended to suggest that these processes mimic or inherent any or all specific properties of biological genomic constructions or processes. In embodiments, a CG-ESP executes genomic processes that may include digital generation, modification, corroboration, and/or allocation of specific types of genomic data. In embodiments, these genomic processes and data enable computation of differences and correlation exhibiting user-controlled entropy. In these embodiments, these digital genomic processes rely upon specific information theory-facilitated constructions. In some implementations, these constructions may be referred to as digital DNA (or genomic data). In embodiments, digital DNA may include one or more information theory-facilitated constructions, such as LNA (genomic correlation), CNA (genomic engagement-integrity), PNA (genomic engagement-eligibility), XNA (genomic differentiation), and/or ZNA (genomic code isolation/cloaking). As will be discussed, these Cyphergenics-based (or "CG-based") processes and constructions facilitate hyper-scalability across a wide array of digital ecosystems. Examples of CG-based processes may include, but are not limited to, CG-based link processes, CG-based sequence mapping, and/or CG-based transformations, example implementations of which are discussed throughout the disclosure.

In embodiments, genomic digital links (or "links") enable exchange of information necessary for a Virtual Digital Anonymity Exchange controller ("VDAX") (discussed further below) to perform higher level computationally complex genomic functions. In embodiments, CG-based genomic link processes may include link spawning, link hosting, and/or link updating, example implementations of which are described throughout the disclosure. These CG-based link processes provide attribute-specific genomic construction information, such as LNA (genomic correlation), CNA (genomic engagement-integrity), and PNA (genomic engagement-eligibility).

In embodiments, CG-based sequence mapping may refer to techniques used in the computational transformation of digital sequences (e.g., public or private protocol sequences) into genomic engagement factors. In embodiments, these genomic engagement factors may be unique and non-recurring. While different types of sequences may be broadly disparate, sequences may be processed in a manner that results in genomic engagement factors exhibiting specific levels of entropy. In embodiments, CG-based sequence mapping processes, compatible with a broad range of protocols and formats, may be initiated with respect to sequences exhibiting preexisting entropy, whereby sequences are respectively transformed by computationally complex CG-functions and processed into unique genomic engagement factors. These genomic engagement factors may then be used to encode digital objects into VBLS.

As will be discussed, embodiments of CG-ESPs may facilitate a number of hyper-scalable attributes that are not possible with modern cryptography and related security systems. These attributes may include, but are not limited to, virtual affiliation (unbounded differences), virtual authentication (unbounded correlation), virtual agility (unbounded structural adaptability), and Virtual Binary Language Script (VBLS), which enables virtual engagement (discrete data object-by-object session-less control), and virtual trusted execution domains (discrete code object by code object execution control). It is noted that the term "unbounded", as used herein implies unbounded in any practical sense of the word, while recognizing that it may be theoretically possible to describe a "bounded" scenario.

Hyper-Scalability: In some embodiments, hyper-scalability may refer to the ability to comprehensively associate N cohorts (or other community members) by M points of contact over T instances (M×N×T). Considering that there are billions of potential cohorts making countless points of contact and communicating over countless instances, hyper-scalability of such magnitude requires a fundamental breakthrough in modern cryptography. The CG-based systems described herein will create a significant reduction in computational expense and session states. In embodiments, these significant reductions come at the expense of relatively insignificant overhead and/or bandwidth.

Virtual Authentication: In embodiments, virtual authentication of ecosystem members (e.g., ecosystem, enclave, cohorts, etc.) may require hyper-scalability technologies. In embodiments, hyper-scalability technology enables ecosystem, enclave, and/or cohort engagement where precise and unique correlation (e.g., "who's who") may be required. In some of these embodiments, precise and unique correlation may refer to a specific set of information theory-facilitated genomic processes where a digital community (e.g., a cohort, enclave, ecosystem, or the like) to uniquely verify an identity of another member (e.g., another cohort, enclave, ecosystem, and/or the like). In embodiments, virtual authentication may refer to the ability to authenticate an unbounded number of ecosystem members (e.g., ecosystem, enclave, cohorts, and the like). As will be discussed, CG-enabled ecosystems may achieve unbounded correlation for the members of the ecosystem (e.g., enclaves, cohorts, dependent cohorts), which in turn provides for an unbounded amount of unique relationships to be formed. In some embodiments, of the present disclosure, cohorts from different ecosystems may also be configured to authenticate one another in an unbounded manner. As will be described, unbounded correlation may be achieved by genomic computationally complex constructions and processes (also referred to as "Cyphergenics-based" or "CG-based" or "CG-enabled" constructions and/or processes).

Virtual Affiliation: In embodiments, virtual differentiated engagement between ecosystems, enclaves, and cohorts may require hyper-scalability. Hyper-scalability technology enables ecosystem, enclave, and cohort engagement for most, if not all, scenarios where precise and unique differentiation ("what's what" and "we're alone") may be required. In embodiments, precise and unique differentiation may refer to a set of congruent or sufficiently congruent processes that are performed by a unique pair of community members to establish a unique engagement that differentiates the pair from any other community members. In some of these embodiments, such precise and unique differentiation ensures that unintended digital entities cannot participate in the uniquely established engagement (e.g., decode intercepted data or the like). In embodiments, hyper-scalable differentiation may refer to the ability for an ecosystem member to uniquely affiliate with an unbounded number of other ecosystem members (e.g., ecosystem, enclave, cohorts, and/or the like). Organic ecosystems evidence powerful, although bounded, differentiation across species, progeny, and siblings, derived from complex bio-chemical processes. Nevertheless, unbounded differentiation may be achieved by specific genomic information theory based digital constructions and processes. As will be discussed, CG-enabled ecosystems may achieve unbounded differentiation for the members of the ecosystem (e.g., enclaves, cohorts, dependent cohorts) which in turn provides for an unbounded amount of unique relationships to be formed. In some embodiments, of the present disclosure, cohorts from different ecosystems may also be configured to form unique engagements in an unbounded manner. As will be described, unbounded differentiation may be achieved by genomic information theory governed constructions and processes (also referred to as "Cyphergenics-based" or "CG-based" constructions and/or processes).

Virtual Agility: In embodiments, virtual agility within ecosystem, enclave, and/or cohort platform stack(s) may be enhanced by hyper-scalability. Hyper-scalability technology enables ecosystems, enclaves, and cohorts to agilely execute hyper-scalable-differentiation and hyper-scalable-correlation for software and hardware managed processes. In some embodiments, agile execution of software and/or hardware managed processes may refer to processes that can be applied at various levels of a respective protocol stack (e.g., OSI-networking stack, software stack, processing stack, and/or the like). Organic Ecosystems evidence powerful, although bounded, agility at the cellular level controlled by complex bio-chemical processes. Nevertheless, unbounded agility may be achieved by specific genomic information theory-facilitated digital constructions and processes.

Virtual Binary Languages Script (VBLS): Virtual Binary Language Scripts-enabled Ecosystem, Enclave, and/or Cohort engagement requires hyper-scalability. Hyper-scalability technology can enable ecosystems, enclaves, and cohorts to engage via unique, non-recurring, computationally quantum proof binary languages (or non-quantum-proof binary languages if the community owner so desires). Organic ecosystems evidence powerful, although bounded, unique cellular engagement, based on complex bio-chemical processes. Nevertheless, unbounded unique digital object engagement, may be achieved by specific genomic information theory governed digital constructions.

Virtual Trusted Execution Domain: In some embodiments, employing computationally complex genomic constructions and processes, a suitably configured CG-ESP enables processes for uniquely transforming engagement for components of executable ecosystems. In embodiments, executable ecosystems may refer to different software and hardware components of a device (or a system of interdependent devices acting as a single unit). In embodiments, executable ecosystem components may include, but are not limited to, e.g.: application components (APIs, libraries, threads), operating system components (e.g., kernel, services, drivers, libraries, and the like), and system-on-chip (Soc) components (Processing Units, e.g., Core), hardware components (e.g., disks, sensors, periphery devices, and/or the like), and/or other suitable types components. In some embodiments, these ecosystem components (e.g., specific designations and organizations such as ecosystems, enclaves, and cohorts) may prosecute (e.g., encode and/or decode) executable binaries collaboratively or independently.

Genomic Facilitated Virtual Network Architectures: In embodiments, the genomic processes and competences of CG-EPSs enable inversion of the application security and network architecture relationship protocol, regardless of the unique demands of a particular use case. In some embodiments, the disclosed "genomic network topology" technology enables creation of wholly new use case-specific security architectures. In some embodiments, a single physical network topology may simultaneously support multiple genomic topologies. As used herein, a genomic topology or genomic network topology may refer to a topology of a digital ecosystem that is defined using the genomic constructions of the respective members of a digital ecosystem.

In embodiments, ecosystems, and enclaves as well as membership thereto may be defined by the owner of a digital community. For example, a network administrator affiliated with a corporate entity may configure a security platform instance, which establishes respective enclaves for different units or projects of the corporate entity. In this example, the network administrator may configure the security platform instance to add cohorts to one or more enclaves based on the cohort's function. It is noted that in some embodiments, a cohort can be included in multiple enclaves and enclaves may have overlapping cohorts. Furthermore, in some embodiments, multiple cohorts may be associated with a single device, such as a computing device and various hardware (e.g., CPU, GPU, memory devices) and/or software components (operating system, file systems, applications, files). As will be discussed, CG-ESPs may be configured to form many different types of ecosystems, and membership eligibility may be configurable and defined by the community owner and/or CG-ESP provider. In embodiments, the security platform is configured to "genomically" construct disparate functions, systems, and/or theaters of operation that are "genomically" based on mutual identity of interests. Put another way, in these embodiments, a CG-ESP may be configured and operated to (e.g., by a community owner or similar party) control the genomic network topology of a digital ecosystem using the genomic constructions of the community members (e.g., enclaves, ecosystems, and/or cohorts) within a digital community. In this way, community members can be established, added to certain enclaves or ecosystems, revoked from certain enclaves or ecosystems, and the like by modifying the genomic constructions of one or more members within the digital community.

In some embodiments, a Cyphergenics-based ecosystem security platform (CG-ESP) may refer to a set of CG-enabled modules that perform various CG-based functions on a specific configuration of genomic data, and a CG-ESP instance may refer to an instance of the CG-ESP platform having a configuration of the CG-enabled modules that is dependent on the role that the CG-ESP instance is performing with respect to a community (e.g., ecosystem-level, enclave-level, cohort level, dependent cohort level). In some embodiments, a CG-ESP platform instance may be embodied as a VDAX. In these embodiments, a VDAX may execute a specific configuration of CG-enabled modules that are defined for the role of the VDAX. Examples of VDAX roles may include ecosystem VDAX, enclave VDAX, cohort VDAX, and/or dependent VDAX, whereby each of these VDAXs may be configured in accordance with the CG-ESP modules and the CG-enabled operations necessitated by the role. In embodiments, a CG-ESP instance may provide one or more core competences, which may include control and management of genomic constructions, functions, and processes (platform competence) and/or secure data exchange functions and processes (link exchange competence). In embodiments, an ecosystem VDAX may perform security related functions on behalf of the ecosystem and may be considered the "progenitor" of the ecosystem. In some of these embodiments, one or more corresponding enclave VDAXs may be configured to perform security related functions on behalf of a respective enclave. In embodiments, a cohort VDAX may perform genomic security related functions on behalf of respective independent cohorts within an ecosystem. In embodiments, a dependent VDAX may perform genomic security related functions on behalf of a respective dependent cohort within an ecosystem. It is noted that in some embodiments, an independent cohort may host one or more dependent VDAXs on behalf of one or more dependent cohorts that depended on the independent cohort. Furthermore, in some embodiments, a single cohort VDAX associated with an independent cohort may be configured to perform security related functions for the cohort across disparate enclaves and ecosystems. In these embodiments, a cohort VDAX may manage and leverage different genomic data sets on behalf of the cohort according to a respective configuration of the different ecosystems and/or enclaves. For example, a mobile device that a user uses for work and personal matters may be configured with a cohort VDAX that manages and leverages one or more genomic data sets pertaining to the user's work ecosystem and enclaves in accordance with the CG-ESP configurations of the organization that the user works for as well as one or more genomic data sets pertaining to ecosystems and enclaves in which the user participates in accordance with the platform configurations of those ecosystems and enclaves. In some embodiments, one or more enclave VDAXs and/or an ecosystem VDAX can be hosted by the same computing system. For example, the ecosystem and enclave VDAXs of a large digital ecosystem (e.g., a federal or state government, large corporations, military, autonomous vehicle grid, IoT grid, or the like) may be hosted on a distributed cloud computing system (e.g., AWS®, Azure®, Google Cloud Services®, privately owned server banks, and the like), whereas the ecosystem and enclave security controllers of a small digital ecosystem (e.g., a home network, a small office network, a grass roots non-profit, or the like) may be hosted on a single computing device (e.g., a central server, a router, a mobile device, or the like). It is also noted that in some example embodiments, a VDAX may be configured to perform different roles with respect to different ecosystems.

For purposes of explanation, the terms "progenitor" and "progeny" (e.g., "progenitor security controller" or "progenitor VDAX" and "progeny security controller" or "progeny VDAX") may be used to denote a relationship where a "progenitor" VDAX may generate, assign, and/or otherwise provide a genomic data set to a "progeny" VDAX. For example, in some embodiments, an ecosystem VDAX may modify its own digital genomic data set for one or more enclaves, such that for each enclave, the "progeny" enclave VDAX thereof is assigned a unique, but correlated genomic data set that was derived from the "progenitor" ecosystem VDAX. Similarly, in another example, an enclave VDAX may modify its own genomic data set to generate, assign, and/or otherwise provide unique and correlated genomic data sets for the cohorts in the enclave, such that for each cohort, the progeny cohort VDAX thereof is assigned its own genomic data set. In this way, the progeny (e.g., progeny VDAXs) of a progenitor VDAX may be able to exchange data in a cryptographically secure manner in part due to the high degree of correlation between their respective genomic data sets. It is noted that in some embodiments of a CG-ESP platform, an ecosystem VDAX may generate and assign the genomic data sets for the cohorts of the ecosystem, even if there exists enclave VDAXs. In embodiments, a progenitor VDAX (e.g., an ecosystem or enclave VDAX) may provide a role-based configuration of a CG-ESP platform to a progeny VDAX, such that the progeny VDAX is configured with the proper CG-ESP modules given a role of the progeny VDAX with respect to the VDAX. As will be discussed, the configurations may include respective modules configured with specific cypher-based, cipherless, and/or hybrid computationally complex functions that are used in the discussed CG-based processes. In embodiments, a cipher-based function may refer to executed functions where all stages (one or more stages) of the function are performed using key-based reversable transformations (e.g., symmetric ciphers). Examples of key-based reversable functions may include but are not limited to Advanced Encryption Standard (AES), SAFER+, SAFER++, TDES, and the like. In embodiments, cipherless functions may refer to executed functions where none of the stages of the function are performed using key-based reversable functions. In embodiments, hybrid functions may refer to executed functions that include at least one stage that is performed using a cipher-based function and at least one stage is performed using a cipherless function. For example, a hybrid function may include a first stage where a cipher-based function is used to determine an intermediate value and a second stage where a cipherless transforms the intermediate value to an output value, which may or may not be reversable.

In some embodiments, CG-ESPs are configurable by the ecosystem owner or on behalf of the ecosystem owner. As mentioned, a CG-ESP may include a set of interdependent modules that collectively perform one or more genomic security functions, such that any level VDAX includes instances of some or all of the interdependent modules. It is noted that these interdependent modules may be implemented as executable instructions that are executed by a traditional processing device (e.g., CPU or GPU and/or FPGA, microprocessors, or special purpose chipsets) that are specifically configured to perform certain genomic functions. Put another way, the interdependent modules of a particular security controller instance (e.g., an ecosystem VDAX, an enclave VDAX, a cohort VDAX, a dependent VDAX, and/or the like) may be individually embodied as software, middleware, firmware, and/or hardware. Reference to processors, execution, or the like is meant to apply to any of these configurations, unless context specifically provides otherwise. In embodiments, the individual modules of a particular CG-ESP instance may be configured to operate on specific set of different types of genomic data objects (e.g., CNA, LNA, XNA, PNA, ZNA, or the like) and/or to execute different types of functions and strategies. For examples, some modules may be configured to apply cipher-based computationally complex functions to the genomic data objects and/or digital data generated or leveraged in connection to a genomic security operation. Examples of cipher-based computationally complex functions may include, but are not limited to, Advanced Encryption Standard (AES) encryption/decryption, SAFER+ encryption/decryption operations, XOR operations, proprietary privately developed encryption/decryption operations, and/or the like. Additionally or alternatively, in some embodiments, some of the interdependent modules may be configured to apply cipher-less computationally complex functions to the genomic data objects and/or digital data generated or leveraged in connection to a genomic security operation. Examples of cipher-less computationally complex functions may include, but are not limited to, cryptographic hash functions, transformations based on parametrized linear equations, transformations based on multivariable equations, lattice-based transformations, parameterized cyclic shift operations, and/or the like. Additionally or alternatively, in some embodiments some modules may be configured to apply hybrid (e.g., cipher-based and cipherless) computationally complex functions to the genomic data objects and/or digital data generated or leveraged in connection to a genomic security operation. As discussed, a hybrid function may include some combination of cipher-based and cipherless functions. As will be discussed, a CG-ESP may be configured (e.g., by or on behalf of a community owner) in accordance with the needs and limitations of the digital community to which it serves. It is noted that a function may be referred to as "computationally complex" not necessarily because of the complexity of the function, but because of the computational complexity associated with reversing the function without a key or analogous information. For example, an XOR function that receives two input parameters and outputs an output value indicating the XOR of the two input parameters may be referred to as "computationally complex" because determining the input parameters given only the output value of the XOR operation requires a much greater degree of computational resources.

In embodiments, a CG-ESP is configured to provide secure end-to-end data exchanges between ecosystem members using specific genomic data sets containing one or more digitally generated genomic constructions which may be embodied in objects (e.g., binary matrices, binary vectors, primitive binary polynomials, and the like) that exhibit configurable entropy. In embodiments, these digitally generated mathematical objects are used to securely exchange digital objects between any pair of sufficiently correlated ecosystem members by leveraging the high degrees of correlation and differentiability between the respective genomic data sets of the ecosystem members using a series of CG-based processes. In embodiments, hyper scalable genomic correlation may provide the ability to have an unbounded community of genomic progeny that can be directly authenticated as fellow enclave or ecosystem members without the support of out of bound trusted services (e.g., Certificate Authority, Secret Key Exchange, and the like). In some embodiments, hyper scalable differentiation may refer to the ability for two sufficiently affiliated cohorts to generate and exchange virtual binary language script (VBLS) (individual instances of which may be referred to VBLS objects) based on links that are hosted with respect to the other community member. In embodiments, a link includes digitally encoded instructions (which may be referred to as "genomic regulation instructions" or "GRI") from one VDAX to another VDAX that define a manner by which the genomic data set (e.g., XNA or ZNA) of the second VDAX is to be modified in order to the second VDAX to generate VBLS that can be decoded by the VBLS (assuming that the link is securely kept by the second VDAX). In embodiments, the second VDAX may "host" a link that indicates GRI corresponding to the first VDAX, whereby the second VDAX may modify its genomic data set based on the GRI and may generate VBLS that is readable by the first cohort based on the modified genomic data and GRI. In embodiments, the second VDAX maps a sequence into the modified genomic data to obtain a genomic engagement factor, which is in turn used to encode a digital object (e.g., using disambiguation and/or encryption techniques) that is included in the VBLS object. In embodiments, VBLS objects may be data containers that include one or more encoded digital objects and metadata that is used to decode the encoded digital object(s). In embodiments, a first VDAX receives a VBLS object and decodes a digital object from the VBLS by modifying its own genomic data set using the GRI provided to the second VDAX, determining a genomic engagement factor based on its modified genomic data set, and decoding the encoded digital objects based on the genomic engagement factor. As will be discussed, only the first VDAX is able to decode digital objects from VBLS, while any other cohort (digital community member or otherwise) that does not have access to the GRI contained in the link information cannot decode the encoded digital objects in the VBLS.

As will be discussed, in embodiments, CG domain components (e.g., ecosystem, enclave, independent cohorts, and/or dependent cohorts) may be configured with digital genomic data sets, such that digital ecosystem CG-enabled components may achieve precision control of differences and correlation using computationally complex functions, which may be cypher-based, cipherless, and/or hybrid functions. In embodiments, CG-enabled methods may support CG-based genomic processes that enable dynamic specification of entropy. In embodiments, the CG domain components engage in accordance with information theory genomics (Cyphergenics) and may utilize information theory genomics that are capable of virtual authentication, virtual scalability, and/or virtual agility. In embodiments, the CG components are configured to generate VBLS, such that the CG-enabled processes enable two domain components to construct and engage via unique non-recurring digital languages (e.g., VBLS). In embodiments, the CG components provide the ability to establish and control differences and correlation between CG domain components, which may enable broad scalability (e.g., hyper-scalability). In embodiments, CG domain components engage via specific digital protocols comprised of digital objects, whereby the digital objects retain the information genomic attributes of their progenitor components (e.g., ecosystem or enclave). In embodiments, hyper-scalability, when exercised at the digital object level enables agile application of CG-based attributes beyond the component level (e.g., at the format and/or protocol level).

As mentioned, a genomic data set (also referred to as a "digital DNA set", "DNA set" or "DNA") may include one or more digitally generated mathematical constructions that exhibit specific levels of entropy, such that the levels of entropy is a configurable. As mentioned, for purposes of explanation, references to and derivations from biological genetic concepts are made. For example, terms such as DNA, "genomic data", "mutating", "genomic constructions", "progeny", "cloning", "sequence mapping" and the like are used throughout the disclosure. It should be understood that such references do not intend to ascribe any particular properties of biological genetic materials or processes to any of the terms used herein. Rather, the terminology is used to teach others how to practice various aspects of the disclosure. In embodiments, a genomic data set may include genomic eligibility object, a genomic correlation object, and/or a genomic differentiation object, which may generally be referred to as "genomic data objects".

In embodiments, genomic eligibility objects may refer to digital generated mathematical objects that allow a pair of cohorts to genomically confirm engagement eligibility, which may be performed in part of a "trustless" authentication process between two VDAXs. In embodiments, a progenitor VDAX (e.g., an ecosystem VDAX) may derive progeny genomic eligibility objects for its progeny from its genomic eligibility object (a "progenitor genomic eligibility object"), such that each progeny receives a unique but correlated genomic eligibility object. Upon being assigned a genomic eligibility object, a progeny VDAX may receive a genomic eligibility object. In some embodiments, a progeny VDAX may receive a genomic eligibility via a one-time trusted event (e.g., upon ecosystem admission to a particular ecosystem, when a device is manufactured, configured, or sold, or the like). After this single trusted event, sufficiently VDAXs can independently confirm engagement eligibility with one another using their respective genomic eligibility objects. In embodiments, genomic eligibility objects may include CNA objects, PNA objects, or other suitable types of mathematical objects exhibiting configurable entropy level, correlation, and differentiation, which are discussed in greater detail below.

In embodiments, genomic correlation objects may refer to digitally generated mathematical objects that allow VDAXs to exchange links, whereby a link provides instructions that allow a pair of sufficiently correlated VDAXs to sufficiently differentiate themselves from other sufficiently correlated VDAXs in a digital community. In embodiments, the genomic correlation object is used by VDAXs to confirm link exchange correlation, which allows two ecosystem components (e.g., enclave and/or cohorts) to establish a specific relationship and engage one another. In example implementations, the genomic correlation objects of the community members of a digital ecosystem are LNA objects or any other suitable types of mathematical objects exhibiting configurable entropy and correlation, which are discussed in greater detail below.

In embodiments, genomic differentiation objects may refer to digitally generated mathematical objects that allow a pair of VDAXs (e.g., enclaves or cohorts) to generate and decode VBLS objects generated by the other respective VDAXs, provided the VDAXs are successfully hosting links spawned by the other respective VDAXs. In some embodiments, a first VDAX generates VBLS for a second VDAX in part by modifying its genomic differentiation object in the manner defined in the instructions contained in a hosted link corresponding to the second VDAX and decodes VBLS from the second VDAX in part by modifying its genomic differentiation object in the manner defined in the instructions contained in a link hosted by the second VDAX with respect to the first VDAX. Examples of genomic differentiation objects may include, but are not limited to, XNA object, ZNA objects, or any other suitable types of mathematical objects exhibiting configurable entropy and correlation, which are discussed in greater detail below.

As will be discussed, different combinations and configurations of CG-ESP modules and genomic data sets can be used in different CG-ESPs. Contemporary network capabilities substantially reflect their underlying deployment architecture. VBLS-enabled genomic constructed architectures, operating at the bit level, may remain interoperable with the underlying deployment architecture. According to embodiments of the present disclosure, VBLS provides unprecedented facility and flexibility to uniquely tailored use cases—whether they be network, software, or hardware centric-architectures. Examples of different architectures include, but are not limited to: directed architectures that can be deployed in static ecosystems (e.g., large enterprises), free-form architectures that may be deployed in transient ecosystems (e.g., social networks, websites), spontaneous ecosystems that may be implemented for dynamic ecosystems (e.g., city-wide autonomous vehicles control system), ephemeral architectures that may be implemented for executable ecosystems (e.g., OS, browser), and/or Interledger architectures that may be implemented for affirmation ecosystems (e.g., Blockchains or other distributed ledgers). In embodiments, these architectures which overlay existing physical network topologies evidence genomic constructed topologies; multiple genomic constructed topologies may exist simultaneously and interoperably. Examples of different architectures and CG-enabled ecosystems are discussed throughout the disclosure.

Cyphergenics Ecosystem Security Platform

Figure 4:
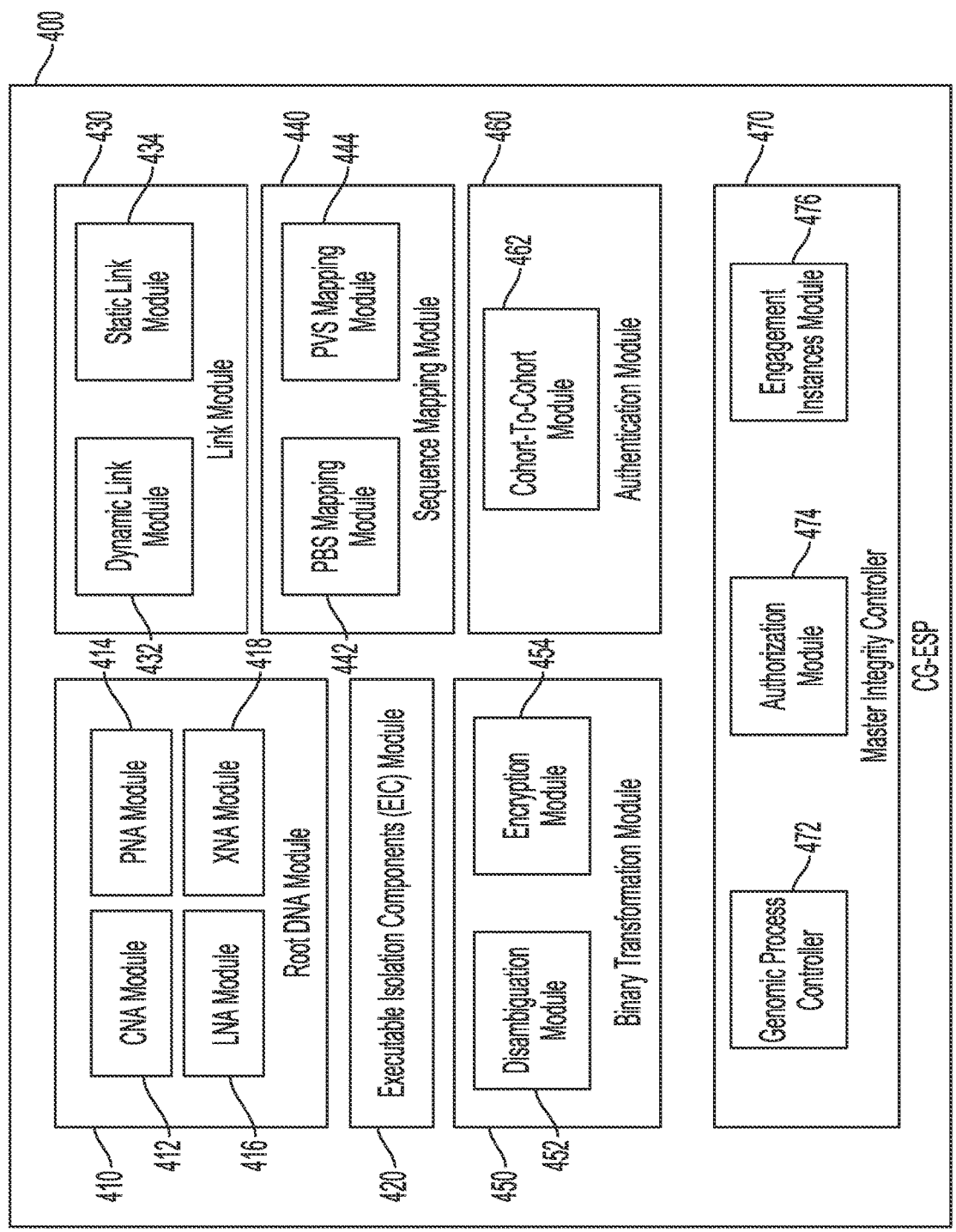
FIG. 4 illustrates an example configuration of a Cyphergenics-based ecosystem security platform, according to some embodiments of the present disclosure.

FIG. 4 illustrates an example of a CG-ESP 400 according to some embodiments of the present disclosure. In these embodiments, a CG-ESP 400 includes a set of CG-modules that are configured to perform a set of CG-processes and related computational methods with respect to a specific configuration of a genomic data set, such that different CG-ESPs 400 may include different CG-modules that perform different genomic functions and related computational methods that operate on a corresponding configuration of a genomic data set. In embodiments, a CG-ESP 400 is configured to be executed by ecosystem members having different roles (e.g., ecosystem VDAX, enclave VDAX, cohort VDAX, and/or dependent VDAX), such that different roles may execute some, all, or none of the CG-processes and computational methods defined in a respective CG-modules of the CG-ESP. In this way, all community members may participate in a CG-enabled digital ecosystem using a corresponding CG-ESP instance that is executed by the community member and/or on behalf of the community member (e.g., for dependent cohorts), such that the CG-ESP instance is configured for the role of the community member (e.g., ecosystem, enclave, cohort, or dependent cohort). For example, a community member serving as the ecosystem progenitor (e.g., ecosystem VDAX) may be configured with a CG-ESP instance that includes a CG module that defines CG-functions and related computational methods to generate genomic data sets (digital DNA sets) having one or more specific types of genomic data (e.g., CNA, PNA, LNA, XNA, and/or ZNA), whereas a community member that is an independent cohort (e.g., principal VDAX) within the ecosystem may be configured with a CG-ESP instance that includes CG modules that define CG-processes and computational methods for mutating its genomic data, exchanging links, sequence mapping, transforming digital objects, and the like. In this way, different community members of a CG-enabled ecosystem may execute different instances of a certain CG-ESP 400. It is noted that in some embodiments, the modules of an instance of a CG-ESP 400 executed by the VDAXs of the digital ecosystem which the CG-ESP instance supports. Furthermore, as the different types of VDAXs within a particular digital ecosystem may perform different roles within the digital ecosystem, the different classes of VDAXs of a CG-enabled ecosystem may execute some or all of the modules of the CG-ESP, and with respect to the individual modules, different classes of VDAXs of the CG-ESP instance may be configured to perform some or all of the genomic functions of the CG module. It is also noted that while different classes of VDAXs within a digital ecosystem may be configured to perform different respective roles within the digital ecosystem, all VDAXs that are configured to perform a certain CG-process with respect to the digital ecosystem (e.g., XNA and LNA modification, link exchange processes, VBLS generation/decoding, and/or the like) are configured with CG-ESP modules that include functionally identical functions that perform the certain CG-process (e.g., the same cipher-based, cipherless, or hybrid functions, functions that extract the same sequences, and the like). In this way, the sufficiently related VDAXs are able to perform certain CG-operations in a functionally congruent manner, which enables the sufficiently related VDAXs to, for example, confirm engagement eligibility and/or integrity, spawn and host links, and/or generate and decode VBLS objects.

In embodiments, the CG-modules of a CG-ESP 400 may include a root DNA module 410, an executable isolation components (EIC) module 420, a link module 430, a sequence mapping module 440, a binary transformation module 450, an authentication module 460, and/or a master integrity controller 470. As mentioned, in some embodiments, a CG-enabled digital ecosystem includes a set of VDAXs, whereby the set of VDAXs include two or more classes of VDAXs (e.g., ecosystem VDAX(s), enclave VDAX(s), cohorts VDAX(s), and/or dependent VDAX(s)). In some of these embodiments, the VDAXs of each class may execute respective instances of some or all of the CG-ESP modules (e.g., a root DNA module 410, EIC module 420, link module 430, sequence mapping module 440, binary transformation module 450, authentication module 460, and/or a master integrity controller 470). In embodiments, individual modules may be cypher-based, cipherless, and/or hybrid (e.g., include functions that are cypher-based and cipherless).

In embodiments, respective CG-ESP instances may be executed by respective processing systems that may include one or more CPUs, GPUs, microcontrollers, FPGAs, microprocessors, special-purpose hardware, and/or the like. Furthermore, in some embodiments, the modules of a CG-ESP instance may be executed in by a virtual machine or a container (e.g., a Docker container).

Root DNA Module(s)

In embodiments, the CG-ESP 400 includes a root DNA module 410. In embodiments, the root DNA module 410 manages ecosystem specific data and genomic processes from which the root DNA module 410 formulates specific and highly rigorous difference and correlation enabling genomic constructions (e.g., DNA sets). In some embodiments, the root DNA module 410 may include a CNA module 412, a PNA module 414, an LNA module 416, and/or an XNA module 418.

In embodiments, a root DNA module 410 manages ecosystem specific data and CG genomic processes from which the root DNA module 410 formulates specific and highly rigorous difference and correlation-enabling CNA. In embodiments, CG-enabled ecosystem component eligibility-correlation is enabled by CG-genomic processes that formulate and construct CNA objects. In embodiments, the CNA module 412 may define CG-genomic processes and related methods that are configured to establish specific relationships between individual ecosystem components (ecosystems, enclaves, cohorts, and/or dependent cohorts). In embodiments, CNA may enable VDAXs of the same ecosystem to confirm eligibility for engagement. In embodiments, CNA enables ecosystem VDAXs and sub-ecosystem VDAXs to retain unique confirmation of eligibility for engagement. In embodiments, the CNA module 412 may be configured to prosecute genomic-based eligibility correlation using a wide range of information theory-facilitated computationally complex functions. In embodiments, these information theory-facilitated functions may be cypher-based, cipherless, or hybrid computationally complex functions. Non-limiting examples of CNA generation and CNA-based eligibility correlation are discussed later in the disclosure.

In embodiments, a root DNA module 410 manages ecosystem specific data and CG genomic processes from which the root DNA module 410 formulates specific and highly rigorous difference and correlation-enabling PNA. In embodiments, CG-enabled ecosystem component eligibility-synchronization is enabled by CG-genomic processes that formulate and construct PNA objects. In some embodiments, the PNA module 414 defines CG-processes that employ CG-genomic processes and related computational methods to establish specific relationships between individual ecosystem components. In this way, PNA may enable ecosystem components (e.g., enclaves, cohorts, and/or dependent cohorts) of the same ecosystem to confirm eligibility for engagement. In embodiments, PNA enables ecosystem VDAX and descendant VDAXs sub-ecosystems to nevertheless retain unique confirmation of eligibility for engagement. In embodiments, a PNA root module 414 may be configured to prosecute genomic based eligibility-synchronization, which may be computed in accordance with a wide range of information theory-facilitated computationally complex functions. In embodiments, these information theory-facilitated functions may include be cypher-based, cipherless, or hybrid computationally complex functions. Non-limiting examples of PNA generation and PNA-based eligibility correlation are discussed later in the disclosure.

In embodiments, a root DNA module 410 manages ecosystem specific data and CG genomic processes from which the root DNA module 410 formulates specific and highly rigorous difference and correlation-enabling LNA. In some embodiments, CG ecosystem component link-exchange-correlation is enabled by CG-genomic processes which formulate and construct LNA objects. In embodiments, the LNA module 416 defines CG-processes and related computational methods to establish specific relationships between individual ecosystem components. In this way, LNA may enable certain VDAXs within an ecosystem (e.g., members of the same enclave) to confirm link-exchange-correlation. In embodiments, LNA enables VDAXs in a digital ecosystem to exchange information ("link exchange") which allows each to engage the other, whereby link-exchange bears corresponding computational complexity. In some embodiments, CG-based LNA-enabled link exchange is predicated on two sets of information, each unique to one of the parties such that the link-exchange between the parties (e.g., a first VDAX and a second VDAX) is unique (e.g., di-symmetric). In embodiments, LNA root modules 416 prosecute genomic based link-exchange-correlation, which may be computed in accordance with a wide range of information theory-facilitated computationally complex functions. In embodiments, these information theory-facilitated functions may be cypher-based, cipherless, or hybrid computationally complex functions. Non-limiting examples of LNA generation and LNA-based link exchange are discussed later in the disclosure.

In embodiments, a root DNA module 410 manages ecosystem specific data and CG genomic processes from which the root DNA module 410 formulates specific and highly rigorous difference enabling XNA. In these embodiments, ecosystem member engagement-differentiation may be enabled by CG-genomic processes that formulate and construct XNA objects. In embodiments, the root XNA module 418 employs XNA-specific CG-processes and related computational methods to establish specific relationships between individual ecosystem components. In embodiments, XNA enables VDAXs of the same ecosystem to confirm engagement-differentiation. In some embodiments, XNA enables VDAX (e.g., ecosystem VDAX, enclave VDAX, cohort VDAX, and/or dependent VDAX) of different ecosystems to confirm engagement-differentiation. Engagement-differentiation allows a pair of VDAXs to sufficiently differentiate themselves from other sufficiently correlated VDAXs for purposes of securely exchanging data, whereby the engagement bears corresponding computational complexity. In some embodiments, XNA-enabled engagement may be predicated on two sets of information, each unique to one of the parties, such that the engagement between the two VDAXs (e.g., a first VDAX and a second VDAX) is unique (e.g., di-symmetric). In embodiments, an XNA module 418 prosecutes genomic-based engagement differentiation, which may be computed in accordance with a wide range of information theory-facilitated computationally complex functions. In embodiments, the information theory-facilitated functions may be cypher-based, cipherless, or hybrid computationally complex functions Non-limiting examples of XNA generation and XNA-based genomic differentiation are discussed later in the disclosure.

In embodiments, an CG-ESP may include an EIC module 420 that manages ecosystem specific data and CG-genomic processes from which the EIC modules 420 formulate specific and highly rigorous difference enabling constructions called ZNA. In embodiments, ecosystem EIC engagement-differentiation is enabled by CG-genomic processes which formulate and construct ZNA objects. In embodiments, ZNA enables VDAXs of the same ecosystem to directly control genomic-enabled differentiation processes absent participation by other VDAX components. For example, in embodiments an EIC VDAX (e.g., core and memory) may employ ZNA-specific genomic processes and other related computational methods to establish differentiation with other specific EIC VDAXs. In embodiments, an EIC module 420 may define CG-processes for prosecuting genomic-based engagement differentiation, which may be computed in accordance with a wide range of information theory-facilitated computationally complex functions. In embodiments, the information theory-facilitated functions may be cypher-based, cipherless, or hybrid computationally complex functions. Non-limiting examples of ZNA generation and ZNA-based genomic differentiation are discussed later in the disclosure.

Link Module

In embodiments, a link module 430 defines a set of CG-processes and related computational methods that allow two VDAXs (e.g., a first VDAX and a second VDAX) to securely exchange information that is necessary to enable di-symmetric engagement. In some embodiments, link exchange exhibits the same level of entropy as the di-symmetric engagement. In some embodiments, a link module 430 instance may be configured to confirm engagement eligibility and link-exchange correlation with another VDAX. In embodiments, engagement eligibility and link-exchange correlation allow a pair of VDAXs to successfully exchange links (e.g., spawn links, and host links). In embodiments, a link module 430 may be configured to confirm engagement eligibility with another VDAX based on its genomic engagement object (e.g., CNA or PNA). For example, a link module 430 may confirm engagement-correlation using its corresponding CNA object and/or eligibly-synchronization using its corresponding PNA object. In embodiments, a link module of a VDAX (e.g., a first VDAX) may be configured to confirm link-exchange-correlation with another VDAX based on a genomic correlation object of the first VDAX. In some embodiments, a link module 430 instance spawns a link for another VDAX (e.g., a second VDAX) based on a genomic correlation object (e.g., LNA object) of the first VDAX and information for the other VDAX to engage with the VDAX. In embodiments, a link module 430 instance of a VDAX (e.g., a first VDAX) may host a link by, in part, decoding information to engage with another VDAX from a link provided by or on behalf of the other VDAX using the genomic correlation object of the first VDAX. It is noted that different configurations of link modules 430 may utilize various CG genomic processes and related computational methods to execute secure link exchange across a wide range of interoperable digital communication media, digital networks, and/or digital devices. It is noted that link exchange between VDAXs may be executed asynchronously, in that the order of exchange does not affect the security of the protocol. Furthermore, in embodiments, link exchange may include one VDAX providing a link to another VDAX (e.g., symmetric) or both VDAXs providing links to the other respective VDAX (e.g., di-symmetric). In embodiments, a link module 430 may define CG-processes that prosecute genomic-based exchange of information, which may be computed in accordance with a wide range of computationally complex functions. In embodiments, the computationally functions may be cypher-based, cipherless, or hybrid functions.

As mentioned, a link may contain information that enables di-symmetric engagement. In embodiments, the information contained in a link may include genomic regulation instructions (GRI). In some embodiments, GRI may define instructions and/or data that are used to modify a genomic differentiation object (e.g., XNA or ZNA) in a deterministic manner, such that when a first VDAX provides a link to a second VDAX and the second VDAX successfully decodes the GRI contained in the link, both the first VDAX and the second VDAX are able to modify their respective genomic differentiation object using the GRI, which results in highly correlated copies of a modified genomic differentiation object (e.g., modified XNA or modified ZNA). As used herein, "highly correlated" when used in connection to genomic objects may refer to identical and/or otherwise sufficiently correlated genomic objects, whereby two genomic objects are said to be "sufficiently correlated" if the degree of correlation between two or more genomic objects enables an intended CG-operation or process to be performed successfully. In embodiments, GRI may include additional information such as instructions and/or data that are used by a VDAX during sequence mapping. As will be discussed in greater detail, such deterministic modification allows the two cohorts to differentiate themselves from all other cohorts to effectuate generation of secure VBLS. In embodiments, a link module 430 may generate GRI for a respective link, such that unique GRI are generated for any respective engagement. In some embodiments, a link module 430 may encode the GRI using a link-specific engagement factor to obtain encoded GRI. The link module 430 may generate genomic engagement cargo (GEC) that includes the encoded GRI and additional information that is used by the link hosting VDAX to decode the GRI from the GEC based on the information and the link hosting VDAX's genomic data. In embodiments, a link module 430 is further configured to decode a link (which is a part of "link hosting"), whereby a link module 430 obtains a transformation value based on the information contained in the GEC and its genomic data set and decodes the encoded GRI using the transformation value to obtain the GRI. The decoded GRI may then be used by the link hosting VDAX when generating VBLS for the link spawning VDAX that provided the link.

In embodiments, a link module 430 may be further configured to update links. Link updating may refer to a process by which the genomic regulation instructions (GRI) that were provided by a first VDAX to a second VDAX for a specific engagement between the pair of VDAXs are modified. A link may be updated for any number of reasons, including concerns that a link has been compromised and/or in accordance with routine security protocols (e.g., links are updated daily, weekly, or monthly, or in response to a cohort request to update a link). In some embodiments, a link module 430 may update a link by generating link update information, whereby the link update information is provided from the VDAX that spawned the link to a VDAX that is hosting the link. In embodiments, link update information may include new GRI that replace the current GRI. In other embodiments, link update information may include data that is used to modify the current GRI. For example, the link update information may be a value that is used to transform the GRI, such that the hosting VDAX applies the value to the current GRI using one or more computationally complex functions (e.g., cypher-based, cipherless, or hybrid functions) to obtain the updated GRI. In some embodiments, link updating differs from link exchange in that link update information can be encoded in VBLS, as opposed to link exchange which may include more computationally expensive operations. Thus, link exchange may be performed as a one-time process, and link updating may be performed any number of times and/or for any suitable reason.

In embodiments, links may be static links or dynamic links. In embodiments, dynamic links may refer to links that contain additional information that further differentiates a pair of cohorts. In some embodiments, dynamic links may contain executable code (or references to executable code) that is used to alter one or more of the functions performed by the pair of VDAXs, but only with respect to their engagement. For example, a dynamic link may include executable code that alters an XNA/ZNA modification function, sequence mapping function and/or a binary transformation function for a respective engagement. In this way, when a pair of VDAXs exchange a dynamic link, the pair of cohorts may execute the executable code in lieu of or in addition to the default code when performing a particular function (e.g., XNA/ZNA differentiation, sequence mapping, and/or binary transformation). In embodiments, static links may refer to links that are used in engagements where the configuration of a CG-ESP is unaltered for a particular engagement.

In embodiments, a static link modules 432 define CG processes that enable two VDAX (e.g., a first VDAX and a second VDAX) to securely exchange (e.g., spawn link and host link) information necessary to enable unique di-symmetric engagement, which exchange exhibits the same level of entropy. In embodiments, the rules and processes governing static links are prescribed by the highest class VDAX in the ecosystem (e.g., an ecosystem VDAX), whereby the rules may apply to all linking VDAXs in the ecosystem. In embodiments, static link module 432 instances may execute CG-processes related to CNA that are used for eligibility-correlation and/or PNA that are used for eligibility-synchronization. In some embodiments, static link module 432 instances execute CG-processes related to LNA that are used for link-exchange-correlation. In embodiments, a CG platform instance may be configured to execute processes to facilitate secure link exchange across a wide range of interoperable digital communications media, digital networks, and/or digital devices. In embodiments, VDAXs may perform link exchange asynchronously, in that the order of the exchange does not affect the security of the protocol. Furthermore, in embodiments, link exchange may include one VDAX providing a link to another VDAX (e.g., symmetric) or both VDAXs providing links to the other respective VDAX (e.g., di-symmetric). In some embodiments, static link modules 432 instances prosecute genomic-based engagement differentiation, which may be computed in accordance with a wide range of computationally complex functions, which may be cypher-based, cipherless, or hybrid computationally complex functions.

In embodiments, a dynamic link modules 434 define CG-processes that enable two VDAXs (e.g., a first VDAX and a second VDAX) to securely exchange (e.g., spawn link and host link) information necessary to enable unique di-symmetric engagement, whereby exchange exhibits the same level of entropy. In embodiments, the rules and processes governing dynamics links are prescribed by the highest class VDAX in the ecosystem (e.g., an ecosystem VDAX), including the authority to establish additional genomically compatible link-exchange instructions and processes.

In embodiments, a dynamic link module 434 may generate dynamic links that include executable instruction sets (e.g., binary code, script, and a like) that modify various CG-processes as allowed by the highest level VDAX in the CG-enabled ecosystem. In these embodiments, an executable instruction set in a dynamic link may override the functions of certain modules (e.g., XNA module, sequence mapping module and/or binary transformation module) for a specific engagement. In this way, a pair of VDAXs that have exchanged a dynamic link can change their CG-processes that are performed with respect to that specific engagement, which may provide an additional layer of security. In some embodiments, a dynamic link module 434 may include an interpreter or just-in-time compiler that processes the instruction set included in a dynamic link, such that the processed instruction set is executed with respect to a specific engagement to override one or more CG-processes that are performed during said engagement. In some embodiments, a first dynamic link module 434 instance may spawn a dynamic link that includes the executable instruction set. In these embodiments, a second dynamic link module 434 instance of a second VDAX may decode the dynamic link, such that when the second VDAX is generating VBLS to the first VDAXs, the respective dynamic link modules 434 may both use the overriding CG-process(s) for that specific engagement. The second VDAX may use the overriding CG-process(s) to generate the VBLS, while the first VDAX may use the overriding CG-process(s) to decode the VBLS. It is appreciated that data exchange in the opposite direction using a second dynamic link from the second dynamic link module 434 instance to the first dynamic link module 434 instance may operate in the same manner, in that the first VDAX uses the overriding CG-process(s), as defined in the second dynamic link, to generate second VBLS, while the second VDAX uses the overriding CG-process(s) to decode the second VBLS.

In embodiments, a dynamic link module 434 instances may establish instructions and related CG-processes processes not shared by other VDAXs, which may be governed by a wide range of options, circumstances, conditions, and objectives. In embodiments, dynamic links provide additional levels of security, as the CG-processes themselves are modified in a unique manner for a unique pair of VDAXs.

In embodiments, a dynamic link module 434 may perform dynamic link exchange asynchronously, in that the order of the exchange does not affect the security of the protocol. Furthermore, in embodiments, link exchange performed by a dynamic link module 434 may include one VDAX providing a link to another VDAX (e.g., symmetric) or both VDAXs providing links to the other respective VDAX (e.g., di-symmetric). In embodiments, dynamic link module 434 instances prosecute genomic-based engagement differentiation, which may be computed in accordance with a wide range of computationally complex functions, which may be cypher-based, cipherless, or hybrid computationally complex functions.

Sequence Mapping Module

In embodiments, a sequence mapping module 440 may define a set of CG-processes and computational methods that perform sequence mapping. In some embodiments, sequence mapping may be an important computation for transforming unique non-recurring digital objects. In embodiments, sequence mapping module 440 instances may be configured to map public sequences (e.g., public protocol and/or format dependent metadata) and/or private sequences (e.g., private and proprietary protocols and/or format dependent metadata) into a (modified) genomic data object. Regardless if the sequences are public or private, the sequences may be broadly disparate (e.g., TCP, UDP, TLS, HTTP, H.265, or other public or private sequences) and may be mapped into modified genomic data to obtain results (e.g., genomic engagement factors) that exhibit specific levels of entropy. In embodiments, a sequence mapping module 440 may include a public sequence mapping module 442 and/or a private sequence mapping module 444.

In embodiments, a public sequence mapping module 442 may define CG-enabled processes and related methods that are configured to select specific sequences from public sources (e.g., specific protocol or format dependent metadata). In some embodiments, a public sequence mapping module 442 instance may process a given public sequence ("PBS") to derive a specific value (e.g., a sequence conversion vector or "SCV"). In some implementations, the public sequence mapping module 442 derives the SCV based on the GRI and/or one or more computationally complex functions. In embodiments, the SCV may be processed with a genomic data object (e.g., XNA, ZNA, or LNA) and the GRI to produce a unique vector exhibiting specific entropy (e.g., a genomic engagement factor or transformation value). In embodiments, a resultant vector may exhibit a level of entropy that vastly exceeds the size of the public sequence used to derive the vector. In embodiments, public sequence mapping modules 442 produce unique vectors capable of leveraging specific facilities present in unrelated protocols and formats. In embodiments, public sequence mapping modules 442 execute genomic processes computed in accordance with computationally complex functions to produce unique vectors based on public sequences and a genomic differentiation object (e.g., a modified XNA object). In embodiments, these functions may be cypher-based, cipherless, or hybrid computationally complex functions.

In embodiments, a private sequence mapping module 444 may define CG-enabled processes and related methods that are configured to select specific sequences from private sources (e.g., private and/or proprietary protocol or format dependent metadata) and to derive a unique vector that exhibits specific entropy. In some implementations, a private sequence mapping module 444 instance may process a given private sequence ("PVS1") to derive a specific value (e.g., a sequence conversion vector (SCV)) based on the GRI. In embodiments, the SCV may be processed with a genomic data object (e.g., XNA, ZNA, or LNA) and the GRI to produce a unique vector exhibiting specific entropy (e.g., a genomic engagement factor or transformation value). In embodiments, a resultant vector may exhibit a level of entropy that vastly exceeds the size of the public sequence used to derive the vector. In embodiments, private sequence mapping module 444 instances produce unique vectors capable of leveraging specific facilities present in unrelated private protocols and formats. In embodiments, private sequence mapping module 444 instances execute genomic processes computed in accordance with a set of computationally complex functions to produce unique vectors based on public sequences and a genomic differentiation object (e.g., a modified XNA object). In embodiments, these functions may be cypher-based, cipherless, or hybrid computationally complex functions.

Example configurations of a sequence mapping module 440 are provided in greater detail below.

Binary Transformation Module

In embodiments, a binary transformation module 450 may define a set of CG-processes and related computational methods that are configured to generate virtual binary (e.g., object-to-object) language script (VBLS). In embodiments, binary transformation module 450 instances transform digital objects (e.g., packets, sectors, sequences, and/or frames) having specific formats and protocols by various computational methods (e.g., disambiguation methods and/or encryption methods). In embodiments, binary transformation module 450 instances are configured to encode digital objects based on values (e.g., genomic engagement factors) determined by a corresponding sequence mapping module 440 to produce encoded digital objects that may be unique, non-recurring, and/or computationally quantum proof. In embodiments, binary transformation module 450 instances may be further configured to decode the encoded digital objects using values (e.g., genomic engagement factors) that are determined by a corresponding sequence mapping module 440. In embodiments, binary transformation modules 450 may include disambiguation modules 452 and/or encryption modules 454.

In embodiments, a disambiguation module 452 may define CG-processes and computational methods that perform binary transformation of digital objects in accordance with genomically derived genomic engagement factors produced by a corresponding sequence mapping module 440 instance, whereby the resultant encoded digital objects are only subject to brute-force attack. In embodiments, a disambiguation module 452 instance may transform a digital object based on a genomic engagement factor by performing an XOR operation on the genomic engagement factor and the digital object to obtain the encoded digital object. In embodiments, a disambiguation module 452 instance may be configured to receive a different genomic engagement factor for each digital object, as disambiguation techniques may be attackable with more efficient attacks if a same genomic engagement factor is used to encode two or more digital objects. In embodiments, a disambiguation module 452 instance may be configured to decode an encoded digital object using an inverse disambiguation function and a genomic engagement factor. Assuming the genomic engagement factor matches the genomic engagement factor that was used to encode the digital object, the inverse disambiguation function outputs the decoded digital object given the genomic engagement factor and the encoded digital object. In embodiments, a disambiguation module 452 instance executes genomic processes in accordance with computationally complex functions. In embodiments, these functions may be cypher-based, cipherless, or hybrid computationally complex functions.

In embodiments, an encryption module 454 may define CG-processes and computational methods that perform binary transformation of digital objects in accordance with genomically derived genomic engagement factors produced by a corresponding sequence mapping module 440 instance, whereby the resultant encoded digital objects are only subject to brute-force attack. In embodiments, an encryption module 454 instance may transform a digital object based on a genomic engagement factor using any suitable encryption function that receives the genomic engagement factor and the digital object as input and outputs the encoded digital object. In embodiments, the encryption function that is used must have a corresponding inverse encryption function (or decryption function) that may be used to decode an encoded digital object. In embodiments, an encryption module 454 instance may be configured to receive a different genomic engagement factor for each digital object or may use the same transformation for two or more different digital objects.

In embodiments, an encryption module 454 instance may be configured to decode an encoded digital object using an inverse encryption function and a genomic engagement factor. Assuming the genomic engagement factor matches the genomic engagement factor that was used to encrypt the digital object, the inverse encryption function outputs the decoded digital object given the genomic engagement factor and the encoded digital object. In embodiments, encryption module 454 instances execute genomic processes in accordance with computationally complex functions. In embodiments, these functions may be cypher-based, cipherless, or hybrid computationally complex functions.

Authentication Module

In embodiments, an authentication module 460 may define CG-processes and computational methods that are configured to authenticate VDAXs that have a common genomic construction. As discussed, digital ecosystems that are constructed by a highest level VDAX (e.g., ecosystem VDAX) have specific distributions of genomic data (e.g., CNA, PNA, LNA, XNA, and/or ZNA) also have specific genomic eligibility-correlation, eligibility-synchronization link exchange-correlation, and/or engagement-correlation attributes. In embodiments, authentication module 460 instances may be configured to enables a corresponding VDAX to confirm engagement correlation of any other VDAX having common construction (e.g., related genomic data), regardless of their primary genomic construction (e.g., members of a different enclave in a digital ecosystem). In embodiments, an authentication module 460 may include a cohort-to-cohort module 462 that defines CG-processes and related computational methods that enable a corresponding VDAX to confirm engagement correlation with another VDAX from the same CG-enabled digital ecosystem based on their common genomic construction, regardless of which enclave(s) the VDAXs belong to. In embodiments, authentication module 460 instances are configured to prosecute secure genomic-based engagement correlation of genomic data sets in accordance with computationally complex functions which may be cypher-based, cipherless, or hybrid computationally complex functions.

Master Integrity Controller

As discussed, conformance of root DNA constructions and supporting genomic processes (e.g., link generation, engagement correlation, VBLS generation, and the like) are directly managed and controlled by a specific configuration of CG-modules. In embodiments, respective CG-ESPs may include a master integrity controller 470 CG-processes and related computational methods that manage module conformance on behalf of the VDAX. In embodiments, master integrity controllers 470 may include CG-processes and related computational methods that ensure the veracity of the operational performance and configuration management for VDAXs across digital ecosystems. In embodiments, a master integrity controller 470 may include a genomic process controller 472, an authorization module 474, and an engagement instances module 476.

In embodiments, the engagement of VDAXs, their genomic modules, and other such functional modules, may be controlled by respective master integrity controller 470 instances of respective CG-ESP instances (e.g., which may be executed by a corresponding VDAX). In embodiments, a master integrity controller 470 instance leverages computationally complex functions to engage with specific modules (e.g., 1 to N). In some of these embodiments, the master integrity controller 470 instance will have a respective genomic data set (e.g., CNA, PNA, LNA, and/or XNA) as do the modules and may use the computationally complex functions to engage with and manage specific modules. In some embodiments, the genomic process controller 472 may validate an integrity of the modules and authenticate the modules using its genomic data and the computationally complex functions. In these embodiments, genomic process controller 472 instances are not configured to determine the processes nor functions carried out by a respective VDAX. In order to protect the computationally complex genomic processes carried out by the respective VDAX, the genomic process controller 472 may control operational processes and functions attendant to the correct application of module processes and functions and may also render certain operational processes and functions to the correct application of module processes and functions under control of the specific modules. Put another way, in embodiments, the genomic process controller 472 may confirm the source of a CG-ESP module instance and/or confirm or deny the integrity of the CG-ESP instance, as well as any processes and operations that are performed in support of the module instances (e.g., the processes that connects the modules for various CG-based functions).

In embodiments, VDAXs that utilize the same computationally complex genomic functions as do the modules and master integrity controller 470 are capable of confirming or disqualifying specific CG-ESP configurations. For example, in embodiments VDAXs (e.g., ecosystem VDAX, enclave VDAX, cohort VDAX, and/or dependent VDAX) utilizing the same computationally complex genomic functions as do the modules and the master integrity controller 470, are capable of confirming or disqualifying specific CG-ESP configurations. In embodiments, a VDAX utilizing the same computationally complex genomic functions as do the modules and master integrity controller 470, is capable of confirming, disqualifying or modifying specific CG-ESP configurations. In embodiments, a master integrity controller 470 may include a genomic process controller 472, an authorization module 474, and an engagement instances module 476. In embodiments, genomic processes controller modules 472 instances prosecute secure genomic based confirmation, disqualification, and modification of VDAX modules and specific VDAX configurations which may be computed in accordance with a wide range of computationally complex functions. In embodiments, these functions may be cypher-based, cipherless, or hybrid computationally complex functions.

In embodiments, VDAXs (e.g., ecosystem VDAX, enclave VDAX, cohort VDAX, and/or dependent VDAX) provide tremendous adoption, deployment, and operational flexibility in that configuration control can be affected horizontally and or hierarchically. In embodiments, this flexibility derives from the same inherent computationally complex genomic functions (e.g., correlation and differentiation) facilitated by CG-ESP modules. In embodiments, a VDAX (e.g., ecosystem VDAX, enclave VDAX, cohort VDAX, and/or dependent VDAX) may be uniquely configured and enabled, such that a single ecosystem or enclave VDAXs (e.g., a progenitor) can determine the operational configuration of other VDAXs (e.g., master integrity controller 470 inter-communication). In embodiments, a progenitor (e.g., an Ecosystem VDAX or Enclave VDAX) can directly confirm or disqualify the operational standing of other VDAXs based on their configurations. In embodiments, a progenitor (e.g., an Ecosystem VDAX or Enclave VDAX) may possess unique genomic properties configured and enabled, such that authorized module updates of VDAXs may be executed in conjunctions with the other authorized CG-ESP modules. In embodiments, master authorization module 474 instances prosecute secure genomic based confirmation, disqualification, and modification of VDAX modules and specific VDAX configurations which may be computed in accordance with a wide range of computationally complex functions, which may be cypher-based, cipherless, or hybrid computationally complex functions.

In embodiments, engagement between two or more VDAXs (e.g., ecosystem VDAX, enclave VDAX, cohort VDAX, and/or dependent VDAX) using EG-CSP enabled computationally complex genomic functions constitutes a single security-instance. In some embodiments, these security-instances may be aggregated as per the hierarchical genomic relationship exhibited by a particular digital ecosystem community. In embodiments, security-instances aggregated at lower levels may be passed to the next or any other higher point of aggregation (e.g., cohort VDAXs to enclave VDAXs), and so on (e.g., cohort VDAXs and enclave VDAXs to ecosystem VDAXs). In embodiments, the communication between VDAX modules (e.g., security-instance reporting) may be based on the same or different computationally complex genomic functions by which their primary security-instances are managed. In embodiments, master engagement instance module 476 instances enable VDAXs (e.g., ecosystem VDAX, enclave VDAX, cohort VDAX, and/or dependent VDAX) to track security-instances as per a set of engagement tracking policies. In some embodiments, these policies may stipulate how security-instances are defined. In embodiments, these definitions may bear specific computationally complex security functions. In embodiments, master engagement instance module 476 instances enable VDAXs (e.g., ecosystem VDAX, enclave VDAX, cohort VDAX, and/or dependent VDAX) to calculate the number of security-instances are created, as per an Engagement Accounting Policies. In embodiments, these policies stipulate how security-instances are accumulated. In embodiments, such accumulation may bear specific computationally complex security functions. In embodiments, master engagement instance module 476 instances enable VDAXs (e.g., ecosystem VDAX, enclave VDAX, cohort VDAX, and/or dependent VDAX) having common construction to be capable to report security-instances to other VDAXs (e.g., ecosystem VDAX, enclave VDAX, cohort VDAX, and/or dependent VDAX) as per a set of engagement reporting policies. In embodiments, these policies stipulate how security-instances are reported, how frequently, and to whom. In embodiments, such reporting bears specific computationally complex security functions. In some embodiments, VDAXs (e.g., ecosystem VDAX, enclave VDAX, cohort VDAX, and/or dependent VDAX) may be uniquely configured and enabled, such that a single VDAX (e.g., ecosystem VDAX) may define the digital ecosystem (e.g., community) engagement tracking policies, engagement accounting policies, and/or engagement reporting policies. In some embodiments, a single engagement instances module 476 instance may execute multiple tracking policies, accounting policies, and/or reporting policies using specific computationally complex genomic functions.

In embodiments, the master engagement instances module enable a VDAX (e.g., ecosystem VDAX, enclave VDAX, cohort VDAX, and/or dependent VDAX) having common construction (e.g., an ecosystem VDAX) to be capable to aggregate security-instances from other VDAX (e.g., ecosystem VDAX, enclave VDAX, cohort VDAX, and/or dependent VDAX) enabled by specific computationally complex genomic functions, as per the engagement reporting policies. In embodiments, master engagement instances module 474 instances prosecute secure genomic based tracking, accounting, reporting, and aggregation of VDAX genomic specific security-instances which may be computed in accordance with a wide range of cryptographic computationally complex functions, which may be cypher-based, cipherless, or hybrid functions.

Master Corroboration Module

In some embodiments of the present disclosure, a CG-ESP may include a master corroboration module (MCM). As will be discussed, a master corroboration module may be configured to facilitate ledger-based architectures. In embodiments, API or VDAX specified material-data may involve a wide range of data having specific applications. Such data may be managed as per specific formats; which data is herein referred to as a block. These MDBs (MDBs) bear computationally complex encoding in accordance with the genomic relationship of the engaging VDAX. In implementations, the VDAX resident MCM is capable of aggregating genomically encoded blocks into dedicated, distributed, or interactive chains reflecting multiple genomic communities (e.g. may include many VDAXs).

In embodiments, MDBs transformed in accordance with specific VDAX controlled LNA and DNA possess highly scalable correlational uniqueness. MDB Chains (MDC) may be aggregated so as to form a sequence of computationally related blocks (e.g. Intra-Ledger Blockchain (ILB) and Inter-Ledger Blockchain (XLB)). MDC are hugely more efficient and less complex to administer than Distributed Ledger-based blockchain technology, e.g. cohorts may be established deeply within the supply chain ("deep chain") with little to no material impact on complexity or efficiency.

In embodiments, MDCs do not require production nor use of any form of distributed ledger (DL). In some embodiments, MDCs do not require any form of asymmetric facilitated consensus. In embodiments, MDCs do not require any form of in-band or out-of-band trusted-third-party facilitation. In embodiments, MDBs may bear all known protocols and formats; they may also be protocol and format agnostic. In embodiments, MDBs may have the same or different genomic encoding, while preserving mutual identity of interest. In embodiments, master corroboration modules enable MDBs to be aggregated as a dedicated chain, which blocks shear mutual identity of interests and genomic correlation. In embodiments, master corroboration modules enable MDBs to form chains having mutual identity of interests, which are distributed (e.g. stored) across multiple VDAX yet retain genomic correlation. In embodiments, master corroboration modules enable MDBs to form direct or distributed chains which are interactive in that they evidence different genomic correlation but may retain functional mutual identity of interests. In embodiments, master corroboration modules prosecute genomic-based secure MDC generation which may be computed in accordance with a wide range of computationally complex functions, which may be cipher-based, cipherless, or hybrid functions.

In embodiments a CG-ESP may include an intra-ledger function (ILF). In some of these embodiments, master corroboration modules (MCM) support an intra-ledger block computation (MDB) and formation of MDB chains (MDC). In these embodiments, VDAXs may possess operational ILF capabilities. In some embodiments, ILF-enabled MDBs may be aggregated as a dedicated chain, which blocks shear mutual identity of interests and genomic correlation. In embodiments, ILF enabled MDBs may form chains having mutual identity of interests, which are distributed (e.g. stored) across multiple VDAXs yet retain genomic correlation.

In some embodiments, a CG-ESP may include an Inter-ledger Function (ILX). In these embodiments, master corroboration modules may support an Inter-ledger block computation (MDB) and formation of MDB chains (MDC). In these embodiments, VDAXs may possess operational ILX capabilities. In these embodiments, ILX enabled MDBs may be aggregated as a dedicated chain, which blocks shear mutual identity of interests and genomic correlation. In embodiments, ILX-enabled MDBs may form chains having mutual identity of interests, which are distributed (e.g. stored) across multiple VDAXs yet retain genomic correlation. In embodiments, ILX enable MDBs to form direct or distributed chains which are interactive in that they evidence different genomic correlation but may retain functional mutual identity of interests.

In embodiments, MDC may include a set of computational attributes. The rigor of both ILB and XLB rests upon specific computationally complex genomic functions. In some embodiments, MDC have no asymmetric computational based processes or related attributes. In some embodiments, MDC enabled chains may be non-repudiated within VDAX communities having common genomic correlation and differentiation, and dimensions VDAX(N) by VDAX (M). In embodiments, MDC computational basis exhibits long term protection against computationally advanced technologies, e.g. quantum computing, which protocol is wholly application agnostic. In embodiments, MDCs may be rendered computationally quantum proof for no additional bandwidth. In embodiments, ILX enabled MDBs may be aggregated as a dedicated chain, which blocks shear mutual identity of interests and genomic correlation. The master corroboration module, ledger-based architectures, and MDCs are discussed in greater detail below.

It is appreciated that FIG. 4 is provided for explanatory purposes. Additional or alternative modules may be used to configure a CG-ESP without departing from the scope of the disclosure. As discussed, different CG-ESPs may be configured to perform different CG-operations on different configurations of genomic data sets. Examples of genomic data sets and different CG-operations that are performed with respect to genomic data are discussed in greater detail below.

Genomic Data Objects

Figure 5:
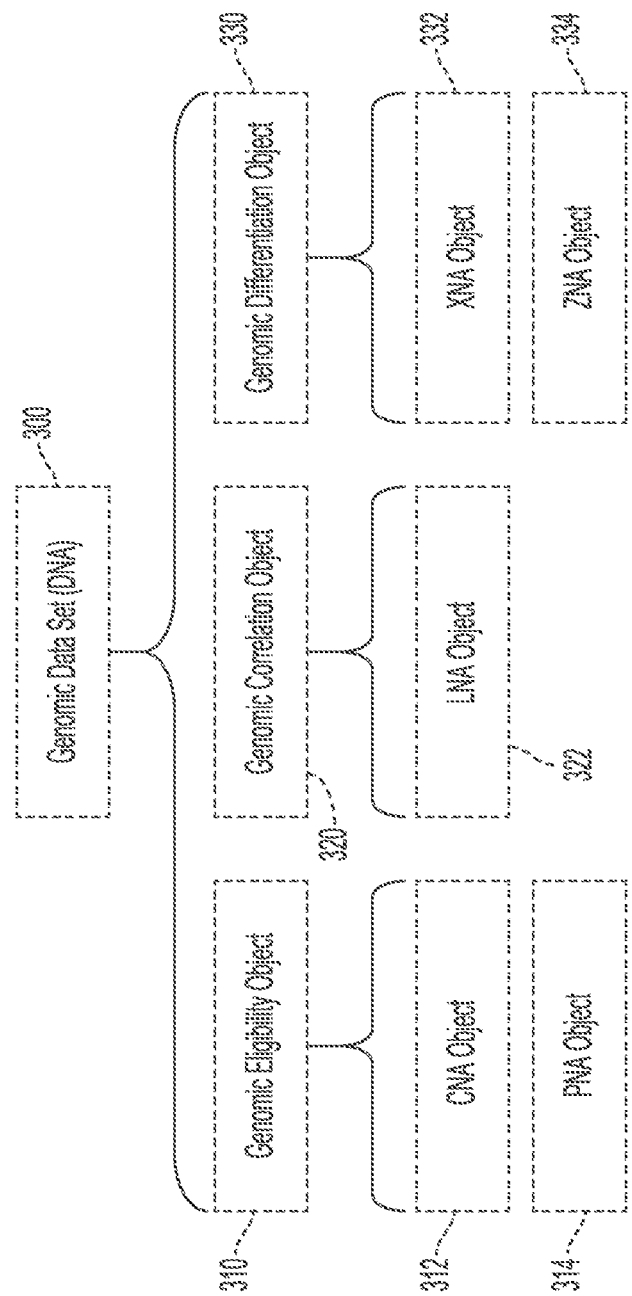
FIG. 5 illustrates example implementations of genomic data sets, in accordance with some embodiments of the present disclosure.

FIG. 5 illustrates example implementations of genomic data sets 300 (which are also referred to as a "digital DNA sets", "DNA sets" or "DNA"). As discussed, in embodiments a CG-ESP (e.g., CG-ESP 400) is configured with a set of CG-processes and related computational methods that operate on specific genomic data sets. FIG. 3 illustrates examples of different types of genomic data that may be implemented with respect to different CG-ESPs. It is appreciated that other types of genomic data may be later developed.

In embodiments, a DNA set 300 that is used in connection with a CG-ESP may include one or more different types of digitally generated mathematical objects that exhibit configurable entropy (instances of which may be generically referred to as "genomic data" or "DNA objects"). In some embodiments, the digitally generated mathematical objects of a DNA set may include any suitable combination of a genomic eligibility object 310, a genomic correlation object 320, and/or a genomic differentiation object 330. As will be discussed, different implementations of a respective CG-ESPs may utilize and support different combinations, types, and sizes of genomic data objects depending on the goals of respective community owners and/or the types of ecosystem that the respective platform instances support. Examples of different goals may include performance and efficiency goals, security goals, resource allocation goals (e.g., memory, storage, processing power, network bandwidth, etc.), economic goals, and the like. Furthermore, certain types of ecosystems have different constraints or advantages. For example, certain controlled ecosystems (e.g., some executable ecosystems) may only require certain cohorts (e.g., dependent cohorts such as applications, sensors, device drivers, processors, memory devices, or the like) to establish a very limited number of relationships (e.g., via links). In these scenarios, links for each respective relationship in the ecosystem may be generated at the time the ecosystem is created, such that each VDAX may have access to any and all links that will be needed. In such scenarios, a DNA set may not derive any additional benefit from having certain types of DNA objects, such that the DNA sets for such an ecosystem may be configured without a genomic eligibility object 310 or a genomic correlation object 320 but may include a genomic differentiation object 330. In another example scenario, the implementations two or more of engagement eligibility determination, link exchange, and/or differentiation/VBLS generation may be performed using a single DNA object (e.g., via a unique intersection of the respective DNA object of a respective pair of VDAXs that is used for engagement eligibility validation, link exchange, and VBLS determination). In this example, the community owner may wish to sacrifice additional security measures to reduce storage requirements associated with storing disparate types of genomic data objects. In other scenarios, a community owner can control the amount of entropy exhibited in each type of DNA object in a DNA set based on the type of data structure that is selected and/or the size of the data structure. For instance, genomic differentiation objects 330 that are implemented as 512×512-bit binary vectors or bit matrices may provide quantum proof levels of security.

In embodiments of the present disclosure, genomic eligibility objects 310 may refer to digitally generated mathematical objects that allow a pair of cohorts to confirm engagement eligibility, which may be performed in part of a "trustless" authentication process between two cohorts. In embodiments, a progenitor VDAX (e.g., an ecosystem VDAX or an enclave VDAX) may derive progeny genomic eligibility objects 310 for progeny VDAXs that are to join a respective digital ecosystem based on its genomic eligibility object (a "progenitor genomic eligibility object"). In these embodiments, each progeny VDAX may receive a unique but correlated derivation of the progenitor genomic eligibility object. Furthermore, in some implementations, all the genomic eligibility objects of an ecosystem may be derived from a progenitor genomic eligibility object, such that any member of an ecosystem can confirm some relationship to other ecosystem members based on their correlated genomic eligibility objects (e.g., intersecting or shared portions of the progenitor genomic eligibility object). Upon being assigned a genomic eligibility object 310 for a particular community, a progeny VDAX may receive its genomic eligibility object. In some embodiments, a progeny VDAX may receive its genomic eligibility object in its genomic data set via a one-time trusted event (e.g., upon admission to a particular enclave, when a device is manufactured, configured, or sold, or the like). After receiving their respective genomic eligibility objects 310, VDAXs can independently confirm engagement eligibility with one other VDAXs in their enclave and/or ecosystem using their respective genomic eligibility objects 310. In embodiments, the genomic eligibility objects 310 for a particular CG-enabled digital ecosystem may be selected from CNA objects 312, PNA objects 314, and/or other suitable mathematical constructions that allow two community members to confirm engagement eligibility and/or engagement integrity.

In embodiments, CNA may refer to genomic mathematical constructions that allow a VDAX to uniquely determine that another VDAX is part of the same ecosystem community. In embodiments, this ecosystem correlation may be rendered computationally quantum proof. In embodiments, VDAX-performed ecosystem correlation is based on common computationally complex genomic functions, which may be performed without any form of consultation with a central authority (e.g., trusted third-party). These correlation attributes enable two VDAXs in the same ecosystem activated years apart to confirm their ecosystem status without any prior knowledge of the other and without any consultation with a trusted third-party.

In embodiments, CNA objects 312 may be implemented as binary vectors, binary matrices, or the like. In embodiments, CNA objects 312 are configured to exhibit specific entropy. In some embodiments, the entropy of an ecosystem's CNA is controllable entropy, whereby the entropy may be configured by, for example, a community owner. In some implementations, a configurable level of entropy of a CNA object 312 may be a substantially quantum-proof level of entropy. For instance, substantially quantum-proof CNA objects may be configured to exhibit a level of entropy that is greater than or equal to 256-bit of entropy. For example, in some embodiments, such levels of entropy may be achieved by CNA objects implemented as 512×512-bit binary vector or binary matrix. It is appreciated that quantum-proof CNA objects 312 may exhibit less entropy in some example implementations. It is appreciated that CNA objects 312 exhibiting less entropy may be used, (e.g., determined by the community owner or any other party configurating a security platform). For example, a community owner may wish to comply with jurisdictional regulations and thusly may use CNA objects (or other genomic data sets) that exhibit lower levels of entropy, which comes at the cost of overall security but requiring less storage and processing demands. In embodiments, CNA 312 may be configured to establish specific relationships between individual ecosystem members and confirm eligibility for engagement using a set of genomic processes and related computational methods.

In embodiments, CNA generation for genomic eligibility-correlation applications results in large sets of random data which can be organized as specific binary vectors. In some embodiments, CNA generation for genomic eligibly-correlation applications may be enabled by high quality random processes, having controllable entropy. In embodiments, CNA generation for genomic eligibility-correlation applications may be enabled on a specific mathematical basis, having controllable entropy. In embodiments, CNA may be generated in accordance with a wide range of information theory-facilitated complex functions. In embodiments, these information theory-facilitated functions may be cypher-based, cipherless, or hybrid computationally complex functions. Example techniques for generating CNA objects and confirming eligibility for engagement are discussed in greater detail throughout the disclosure.

In embodiments, PNA may refer to a digital that allow a VDAX to uniquely determine that another VDAX is part of the same ecosystem community. In embodiments, this ecosystem correlation may be rendered computationally quantum proof. In embodiments, VDAX-performed ecosystem correlation is based on common computationally complex genomic functions, which may be performed without any form of consultation with a central authority (e.g., trusted third-party). These correlation attributes enable two VDAXs in the same ecosystem activated years apart to confirm their ecosystem status without any prior knowledge of the other and without any consultation with a trusted third-party.

In embodiments, PNA objects 314 may include a set of binary primitive polynomials, as well as other data used during eligibility synchronization. In embodiments, PNA objects 314 are configured to exhibit specific entropy. In some embodiments, the entropy of an ecosystem's PNA objects 314 is controllable entropy, whereby the entropy may be configured by, for example, a community owner. In some implementations, a configurable level of entropy of a PNA object 314 may be a substantially quantum-proof level of entropy. For instance, substantially quantum-proof PNA objects 314 may be configured to exhibit a level of entropy that is greater than or equal to 256 bits of entropy. For example, in some embodiments, such levels of entropy may be achieved by PNA objects implemented as two different sets (e.g., a first vector representing a 2048×2048 bit binary matrix and a second vector representing a set of $2^{16}$ randomly chosen binary primitive polynomials of degree 256). It is appreciated that quantum-proof PNA objects 314 may exhibit less entropy in some example implementations. It is appreciated that PNA objects 314 having less entropy may be used (e.g., as determined by the community owner or any other party configurating a security platform). For example, a community owner may wish to comply with jurisdictional regulations and thusly may use PNA objects (or other genomic data sets) that exhibit lower levels of entropy, which comes at the cost of overall security but requiring less storage and processing demands. In embodiments, PNA may be configured to establish specific relationships between individual ecosystem members and confirm eligibility for engagement using a set of genomic processes and related computational methods.

In embodiments, PNA generation for genomic eligibility-synchronization applications results in large sets of random data which can be organized as specific binary vectors. In some embodiments, PNA generation for genomic eligibly-correlation applications may be enabled by high quality random processes, having controllable entropy. In embodiments, PNA generation for genomic eligibility-eligibility-synchronization applications may be enabled on a specific mathematical basis, having controllable entropy. Example techniques for generating PNA objects and confirming eligibility for engagement are discussed in greater detail throughout the disclosure.

In embodiments, genomic correlation objects 320 may refer to digitally generated mathematical objects that enable VDAXs to establish correlation with one another. In embodiments, genomic correlation objects enable link exchange between VDAXs, whereby a first VDAX may spawn a link (also referred to as a "link") that is provided to and hosted by a second VDAX, whereby the link provides instructions that the second VDAX uses to generate VBLS that only the first cohort can decode (assuming that the link is safely held by the second VDAX). In embodiments, the genomic correlation objects 310 used in a CG-ESP to confirm link exchange correlation, which allows two ecosystem components (e.g., enclave VDAX, cohort VDAXs, and the like) to establish a specific relationship and engage one another.

In example implementations of a CG-ESP, the genomic correlation objects 320 of the community members of a digital ecosystem are implemented as LNA objects 322. In some embodiments, LNA is a core competence on which genomic correlation functions rely. In embodiments, LNA forms the basis by which VDAXs establish correlation with one another. The entropy that LNA objects 322 exhibits is critical in terms of the quality of correlation. The non-recurring correlation attributes that may be derived from specific computationally complex genomic functions. In some implementations of a CG-ESP, LNA may be generated (e.g., by an ecosystem VDAX) for genomic correlation applications in large sets of random data. In some embodiments, LNA objects 322 are implemented as binary vectors, bit matrices, or other suitable structures. In embodiments, LNA objects 322 are configured to exhibit configurable entropy, such that the level of entropy which an LNA object exhibits may be a factor in the overall degree of the correlation. In embodiments, LNA generation may be performed by high-quality random processes, having controllable entropy. In some embodiments, LNA generation for genomic correlation applications may be enabled on a specific mathematical basis, having controllable entropy. In embodiments, LNA may be generated in accordance with a wide range of information theory-facilitated complex functions. In embodiments, these information theory-facilitated functions may be cypher-based, cipherless, or hybrid computationally complex functions.

In embodiments, a pair of VDAXs can engage in di-symmetric link exchange and/or one-way link exchange based on their common LNA (e.g., both VDAXs were assigned their respective LNA from the same progenitor). In embodiments, a first VDAX may modify its LNA object and may encode genomic regulation instructions ("GRI") based on the modified LNA, such that the second cohort is the only other VDAX that able to decode the mapped GRI. In embodiments, GRI may include data (e.g., one or more values) and instructions indicating a manner by which the data is used to differentiate the pair of VDAXs for data exchange. In embodiments, the GRI may be used to modify a differentiation object, such that the data included in the GRI may include a differentiation value (e.g., embodied as a binary vector) that is used as an input parameter to an information theory-facilitated computationally complex function that modifies the genomic differentiation object based on the differentiation value. In some embodiments, the GRI may include a sequence modification value that is used during the sequence mapping process. In these embodiments, the sequence mapping process may be used as an input parameter to an information theory-facilitated computationally complex function that modifies a sequence into an intermediate value based on the differentiation value, such that the intermediate value and a modified differentiation object are used as input values into an information theory-facilitated computationally complex function that outputs a genomic engagement value corresponding to the original sequence.

It is appreciated that encoding the genomic regulation instructions based on the modified LNA may include intermediate operations. For example, in some implementations of CG-ESP, a VDAX may be configured to determine a mapping sequence, map the mapping sequence into the modified LNA using a computationally complex function, and encode the GRI based on the genomic engagement factor. In these example implementations, the VDAX may provide the link to the other VDAX, such that the other VDAX can successfully decode the encoded GRI if the other VDAX possesses highly correlated LNA. In some implementations of a CG-ESP, the LNA objects of the VDAXs may be highly correlated if they are identical or otherwise sufficiently correlated. In some embodiments, link exchange is a one-time process, such that link exchange is only performed once between a pair of cohorts, unless one of the cohorts explicitly updates its respective link to modify the GRI. Outside of such action, a pair of cohorts can continue to exchange data based on the respective links generated by each of the cohorts, even in some scenarios where the LNA objects of the respective VDAXs are mutated (e.g., persistently modified) by or at the instruction of, for example, a progenitor VDAX after successful link exchange. Examples of genomic operations involving LNA objects 322 are discussed in greater detail throughout the disclosure, including techniques for generating LNA objects 322, modifying LNA objects 322, and performing link exchange using LNA objects 322 are discussed in greater detail throughout the disclosure.

In embodiments of the present disclosure, genomic differentiation objects 330 may refer to digitally generated mathematical objects that allow a pair of community members (e.g., cohorts) to exchange and decode VBLS generated by the pair of community members, provided the pair of community members have successfully exchanged links and have sufficiently correlated genomic differentiation objects. In some embodiments, a first VDAX generates VBLS for a second VDAX in part by modifying its genomic differentiation object 330 in the manner defined in the genomic regulation instructions (GRI) provided to the first VDAX in a link from the second VDAX, and decodes VBLS from the second cohort in part by modifying its genomic differentiation object 330 in accordance with the GRI that were provided to the second cohort. In embodiments of the CG-ESP, the first VDAX may map a sequence (e.g., a private or public sequence) into the modified XNA object using a computationally complex function (e.g., cipher-based, cipherless, or hybrid computationally complex functions) to obtain a genomic engagement factor, which may then be used to encode a digital object. Examples of genomic differentiation objects 330 may include, but are not limited to, XNA 332 objects and ZNA 334 objects.

In example implementations, the genomic differentiation objects 330 of the community members of a digital ecosystem are XNA. In some embodiments, XNA is a core competence on which all genomic differences rely. In these embodiments, XNA forms the basis by which di-symmetric languages (e.g., VBLS) that VDAXs employ to control unique non-recurring engagement. In some embodiments, the unique non-recurring engagements may be quantum-proof. In embodiments, the entropy that XNA exhibits may be critical in terms of the security of VBLS, where higher entropy provides greater levels of security. In embodiments, the recurring difference attributes are derived from specific computationally complex genomic functions. In embodiments, XNA generation for genomic differentiation applications result in large sets of random data which can be organized as specific binary vectors. In embodiments, XNA generation for genomic differentiation applications may be performed by high-quality random processes, having controllable entropy. In some embodiments, XNA generation for genomic differentiation applications may be enabled on a specific mathematical basis, having controllable entropy. In embodiments, XNA may be generated in accordance with a wide range of information theory-facilitated complex functions. In embodiments, these information theory-facilitated functions may be cypher-based, cipherless, or hybrid computationally complex functions.

In some embodiments, an XNA object 332 may be implemented as a binary vector, matrix, or the like that exhibits configurable entropy. In some embodiments, the entropy which an XNA object 332 exhibits determines the security of the VBLS that is generated by a community member. In embodiments, the XNA that is assigned to respective community members (e.g., enclave members) from a progenitor VDAX is either identical and/or otherwise sufficiently correlated. In some embodiments, a first VDAX generating VBLS for a second VDAX modifies its XNA object 332 in accordance with the GRI provided by the second VDAX in a link. The first VDAX may then map a sequence (e.g., a public or private sequence) that is determinable by the second VDAX into the modified XNA object 332 to obtain a genomic engagement factor. A digital object (e.g., a processor instruction, a packet payload, a disk sector, or the like) may then be encoded using a cipher-based encryption or disambiguation and the genomic engagement factor to obtain the encoded digital object that is included in a VBLS object. In embodiments, the VBLS object may further include metadata, such as a sequence that was used to generate the genomic engagement factor. The VBLS resultant encoded digital object may then be provided to the second cohort. In these example implementations, the second cohort receives a VBLS object and modifies its XNA 332 in accordance with the GRI contained in the link that was provided by (or on behalf of) the second VDAX to the first VDAX and then maps the sequence into the modified XNA to recreate the genomic engagement factor. The genomic engagement factor may then be used to decode the encoded digital object to obtain a decoded digital object using the cipher-based decryption or disambiguation that was used to encode the digital object. In these example implementations, the ability for the VDAXs to both modify their respective XNA objects 332 using the same GRI and determine the genomic engagement factor in a deterministic manner allows the first cohort to securely provide the data object to the second VDAX and to potentially vary the genomic engagement factor for each instance of data exchange (e.g., every packet, every sector, every shard, every frame, or the like). In this way, VBLS may provide quantum proof levels of security. It is noted that the foregoing discussion is an example of how XNA or other genomic differentiation objects may be leveraged in a secure data exchange process.

In some embodiments, revocation of a community member (e.g., a cohort) from a community (e.g., an enclave) may be achieved by selectively mutating the XNA objects of some of the community members in the community by a progenitor VDAX. It is noted that "mutating" an XNA object may refer to providing instructions to a progeny VDAX to persistently modify its XNA object or providing a new XNA object to the progeny VDAX. In this way, the mutated XNA is used for subsequent VBLS coding and encoding with respect to the particular community. For example, in some example implementations, an ecosystem VDAX may mutate the XNA of only the cohorts that are to remain in an enclave. In this way, cohorts that have been revoked from the enclave can still attempt to engage with cohorts but will be unable to generate VBLS for or decode VBLS from cohorts that have a mutated XNA object. Should the community owner (e.g., a network administrator associated with the ecosystem and/or an enclave of the ecosystem) opt to reinstate the cohort, the enclave VDAX may mutate the XNA of the cohort to have sufficiently correlated XNA with the other community members whose XNA was previously mutated, such that the cohort can then commence exchanging data with other cohorts in the enclave using their previously established links and/or links established in the future.

In example implementations, the genomic differentiation objects 330 of the community members of a digital ecosystem are ZNA. In some embodiments, ZNA is a core competence on which all executable isolation components genomic differences rely. In these embodiments, ZNA forms the basis by which unique, non-recurring (potentially quantum proof) executable binaries are controlled. EIC recurring transformations may be derived from specific computationally complex genomic functions. In embodiments, ZNA generation for genomic differentiation applications result in large sets of random data which can be organized as specific binary vectors. In embodiments, ZNA generation for genomic differentiation applications may be performed by high-quality random processes, having controllable entropy. In some embodiments, ZNA generation for genomic differentiation applications may be enabled on a specific mathematical basis, having controllable entropy. In embodiments, ZNA may be generated in accordance with a wide range of information theory-facilitated complex functions.

In embodiments, these information theory-facilitated functions may be cypher-based, cipherless, or hybrid computationally complex functions.

In some embodiments, a ZNA object 334 may be implemented as a binary vector, matrix, or the like, whereby ZNA objects 334 exhibit configurable entropy. In some embodiments, ZNA may be structurally similar to XNA but is used in executable ecosystems. In embodiments, ZNA may be used to generate VBLS that is exchanged between components of an executable ecosystem. In some embodiments, the entropy which an ZNA object 334 exhibits determines the security of the VBLS that is generated by a community member. In embodiments, the ZNA that is assigned to respective community members (e.g., device components) from a progenitor VDAX is either identical and/or otherwise sufficiently correlated. In some embodiments, a first VDAX (e.g., a first EIC) generating VBLS for a second VDAX (e.g., a second EIC) modifies its ZNA object 334 in accordance with the GRI provided by the second VDAX in a link. The first VDAX may then map a sequence (e.g., a public or private sequence) that is determinable by the second VDAX into the modified ZNA object 334 to obtain a genomic engagement factor. A digital object (e.g., a processor instruction, a disk sector, or the like) may then be encoded using a complex function and the genomic engagement factor to obtain the encoded digital object that is included in a VBLS object. In embodiments, a VBLS object may further include metadata, such as a sequence that was used to generate the genomic engagement factor. The VBLS resultant encoded digital object may then be provided to the second VDAX. In these example implementations, the second VDAX receives a VBLS object and modifies its ZNA object 334 in accordance with the GRI contained in the link that was provided on behalf of the second VDAX to the first VDAX and maps the sequence into the modified ZNA object 334 to recreate the genomic engagement factor. The genomic engagement factor may then be used to decode the encoded digital object to obtain a decoded digital object using the inverse of the two-way function that was used to encode the digital object. In these example implementations, the ability for the VDAXs to both modify their respective ZNA objects 334 using the same GRI and determine the genomic engagement factor in a deterministic manner allows the first cohort to securely provide the data object to the second VDAX and to potentially vary the genomic engagement factor for each instance of data exchange (e.g., every packet, every sector, every shard, every frame, or the like). In this way, VBLS may provide quantum proof levels of security. It is noted that the foregoing discussion is an example of how ZNA or other genomic differentiation objects may be leveraged in a secure data exchange process.

As can be appreciated from the disclosure, the core genomic competences (e.g., differentiation and correlation that support CG-ESP processes) rely upon generation (e.g., DNA generation that may include LNA generation, XNA generation, ZNA generation, CNA generation, and/or PNA generation), modification (e.g., DNA modification that may include LNA modification, XNA modification, ZNA modification, CNA modification, and/or PNA modification), and allocation (e.g., DNA allocation that may include LNA allocation, XNA allocation, ZNA allocation, CNA allocation, and/or PNA allocation) of specific genomic (e.g., digital DNA that may include some combination of LNA, XNA, ZNA, CNA, and/or PNA). In embodiments, these application specific DNA constructions (e.g., some combination of LNA, XNA, CNA, PNA, and/or ZNA) have specific transformations and are critical to the controllable virtualization of differentiation.

In embodiments, an ecosystem progenitor (e.g., ecosystem VDAX) may mutate (e.g., persistently modify) the genomic data 300 of some or all of the ecosystem members. In embodiments, mutation of genomic data 300 may refer to persistent modification or updating of a genomic data object. For example, in embodiments, an ecosystem may mutate the LNA objects 322, XNA objects 332, CNA objects 312, and/or PNA objects 314 of some or all of the ecosystem members, such that VDAXs will use the mutated genomic data in place of the previous genomic data. It is noted that the term "mutation" may be used to refer to modifications to DNA objects 300 that are persistent, as opposed to modification during link exchange or VBLS generation, which may be transient modification. It is noted, however, that modification and mutation may have similar effects to a DNA construction, and that the term "modification" may be used in connection with persistent modifications when context so suggests.

In embodiments, the LNA objects of community members may be modified (e.g., for link exchange) and mutated (e.g., persistently modified/updated). As discussed, non-recurring correlation objects (e.g., LNA) may be derived from specific computationally complex genomic functions, which correlation may involve digital ecosystems having dimension N×M, comprised of VDAXs having various enclave relationships N×Ma. Such digital ecosystem relationships may require modification of their correlation attributes, to prevent establishment of future or additional ecosystem relationships. Mutation of LNA enables specific (broad and narrow) redetermination of correlation attributes. In embodiments, LNA genomic constructions may be tailored to specific digital ecosystem organizations, which constructions are modifiable. In some embodiments, LNA random vectors can be uniformly or discreetly (broadly and narrowly) modified on the basis of specific instructions. LNA modifications preserve the genomic integrity of the LNA construction, and its correlation attributes. In embodiments, VDAXs in possession of modified LNA are unable to affect future correlation with VDAXs in possession of non-modified LNA. In embodiments, LNA may be genomically modified in accordance with a wide range of Information theory-facilitated cryptographic computationally complex functions. In embodiments, these information theory-facilitated functions may be cypher-based, cipherless, or hybrid computationally complex functions.

In embodiments, the XNA of community members may be mutated (e.g., persistently modified/updated). As discussed, non-recurring differentiation objects (e.g., XNA) may be derived from specific computationally complex genomic functions, which differentiation may involve digital ecosystems having dimension N×M, comprised of VDAXs having various enclave relationships N×Ma. Such digital ecosystem relationships may require modification of their differentiation attributes, one of the most challenging problems in security management (e.g., relationship revocation). Mutation of XNA enables specific (broad and narrow) redetermination of differentiation attributes, efficiently resolving the relationship revocation challenge. In embodiments, XNA genomic constructions may be tailored to specific digital ecosystem organizations, which constructions are modifiable. In some embodiments, XNA random vectors can be uniformly or discreetly (broadly and narrowly) modified on the basis of specific instructions. XNA modifications preserve the genomic integrity of the XNA construction, and its correlation attributes. In embodiments, VDAXs in possession of mutated XNA are unable to affect future differentiation with VDAX in possession of non-mutated XNA. In embodiments, XNA may be genomically mutated in accordance with a wide range of Information theory-facilitated cryptographic computationally complex functions. In embodiments, these information theory-facilitated functions may be cypher-based, cipherless, or hybrid computationally complex functions.

In embodiments, the CNA objects 312 of community members may be mutated (e.g., persistently modified/updated). As discussed, non-recurring eligibility objects (e.g., CNA or PNA) may be derived from specific computationally complex genomic functions, which modification may involve digital ecosystems having dimension N×M, comprised of VDAXs having various enclave relationships N×Ma. Such digital ecosystem relationships may require modification of their differentiation attributes, one of the most challenging problems in security management (e.g., relationship revocation). Modification of VDAX ecosystem eligibility objects preserves common computationally complex genomic functions. Such digital ecosystem relationships may require modification of their eligibility objects, preventing VDAXs from establishing future or additional ecosystem relationships. Mutation of CNA or PNA enables specific (broad and narrow) redetermination of eligibility objects.

In embodiments, CNA genomic constructions may be tailored to specific digital ecosystem organizations, which constructions are modifiable. In some embodiments, CNA random vectors can be uniformly or discreetly (broadly and narrowly) modified on the basis of specific instructions. CNA modifications preserve the genomic integrity of the CNA construction, and its eligibility-correlation attributes. In embodiments, VDAXs in possession of mutated CNA are unable to establish future eligibility-correlation with VDAXs in non-mutated CNA. In embodiments, CNA may be genomically mutated in accordance with a wide range of information theory-facilitated computationally complex functions. In embodiments, these information theory-facilitated functions may be cypher-based, cipherless, or hybrid computationally complex functions.

In embodiments, PNA genomic constructions may be tailored to specific digital ecosystem organizations, which constructions are modifiable. In some embodiments, PNA random primitive polynomials can be uniformly or discreetly (broadly and narrowly) modified on the basis of specific instructions. PNA modifications preserve the genomic integrity of the PNA construction, and its eligibility-synchronization attributes. In embodiments, VDAXs in possession of mutated PNA are unable to establish future eligibility-synchronization with VDAXs in non-mutated PNA. In embodiments, PNA may be genomically mutated in accordance with a wide range of information theory-facilitated computationally complex functions.

In embodiments, an ecosystem progenitor (e.g., an ecosystem VDAX) may allocate DNA to community members (e.g., enclaves, cohorts, and the like). In embodiments, each of the specific DNA constructions has unique genomic relationships. LNA provides for correlation, XNA for differentiation, CNA for engagement-integrity, and PNA for engagement-eligibility. The overall capabilities facilitated by these constructions derive substantially from the relationship of their genomic mathematical constructions, and finally their specific VDAX allocation. These VDAX relationships may be modified in accordance with the specific modification of the DNA (e.g., LNA, XNA, CNA, and PNA).

In embodiments, an ecosystem progenitor (or a suitable progenitor VDAX) may allocate LNA to community members. In embodiments, LNA correlation capabilities are germane to all digital ecosystems having dimension N×M, comprised of VDAXs, which may also have various enclave and cohort relationships N×Ma. In embodiments, LNA genomic based constructions are allocated to specific digital ecosystem VDAXs (e.g., ecosystem VDAX, enclave VDAX, cohort VDAX, and/or dependent VDAX), and determine their related correlation capabilities. In embodiments, LNA allocation preserves the genomic integrity of the LNA construction, and its correlation attributes. In embodiments, VDAXs (e.g., ecosystem VDAX, enclave VDAX, cohort VDAX, and the like) whose initial LNA allocation is modified are no longer able to affect correlation with VDAXs in possession of non-modified LNA may now be able to affect future correlation with other VDAXs having the same modified LNA allocation. In embodiments, LNA may be genomically allocated in accordance with a wide range of Information theory-facilitated computationally complex functions. In embodiments, these information theory-facilitated functions may be cypher-based, cipherless, or hybrid computationally complex functions.

In embodiments, an ecosystem progenitor (or a suitable progenitor VDAX) may allocate XNA to community members. In embodiments, XNA differentiation capabilities are germane to all digital ecosystems having dimension N×M, comprised of VDAXs (e.g., ecosystem VDAX, enclave VDAX, cohort VDAX, and/or dependent VDAX), which may also have various enclave and cohort relationships N×Ma. In embodiments, XNA genomic based constructions are allocated to specific digital ecosystem VDAXs (e.g., ecosystem VDAX, enclave VDAX, cohort VDAX, and/or dependent VDAX), and determine their related differentiation capabilities. In embodiments, XNA allocation preserves the genomic integrity of the XNA construction, and its differentiation attributes. In some embodiments, VDAX (e.g., ecosystem VDAX, enclave VDAX, cohort VDAX, and the like) whose initial XNA allocation is modified are no longer able to affect differentiation with VDAXs in possession of non-modified XNA may now be able to affect differentiation with other VDAX having the same modified XNA allocation. In embodiments, XNA may be genomically allocated in accordance with a wide range of Information theory-facilitated computationally complex functions. In embodiments, these information theory-facilitated functions may be cypher-based, cipherless, or hybrid computationally complex functions.

In embodiments, an ecosystem progenitor (or a suitable progenitor VDAX) may allocate CNA to community members. In embodiments, CNA engagement-integrity capabilities are germane to all digital ecosystems having dimension N×M, comprised of VDAXs (e.g., ecosystem VDAX, enclave VDAX, cohort VDAX, and/or dependent VDAX), which may also have various enclave and cohort relationships N×Ma. In embodiments, CNA genomic based constructions are allocated to specific digital ecosystem VDAXs (e.g., ecosystem VDAX, enclave VDAX, cohort VDAX, and/or dependent VDAX). In embodiments, these CNA genomic-based constructions determine their related engagement-integrity capabilities within an ecosystem. In some embodiments, CNA genomic based constructions allocated to specific digital ecosystem VDAXs may also be unique.

In embodiments, CNA allocation preserves the genomic integrity of the CNA construction, and its engagement-integrity attributes. In some embodiments, VDAXs (e.g., ecosystem VDAX, enclave VDAX, cohort VDAX, and the like) whose initial CNA allocation is modified are no longer able to affect engagement-integrity with VDAXs in possession of non-modified CNA and may now be able to affect engagement-integrity with other VDAX having the same modified CNA allocation. In embodiments, CNA may be genomically allocated in accordance with a wide range of Information theory-facilitated computationally complex functions. In embodiments, these information theory-facilitated functions may be cypher-based, cipherless, or hybrid computationally complex functions.

In embodiments, an ecosystem progenitor (or a suitable progenitor VDAX) may allocate PNA to community members. In embodiments, PNA engagement-eligibility capabilities are germane to all digital ecosystems having dimension N×M, comprised of VDAXs (e.g., ecosystem VDAX, enclave VDAX, cohort VDAX, and/or dependent VDAX), which may also have various enclave and cohort relationships N×Ma. In embodiments, PNA genomic based constructions are allocated to specific digital ecosystem VDAX (e.g., ecosystem VDAX, enclave VDAX, cohort VDAX, and/or dependent VDAX), and determine their related engagement-eligibility capabilities. In embodiments, PNA genomic based constructions allocated to specific digital ecosystem VDAXs may also be unique.

In embodiments, PNA allocation preserves the genomic integrity of the PNA construction, and its engagement-eligibility attributes. VDAX (e.g., ecosystem VDAX, enclave VDAX, cohort VDAX, and the like) whose initial PNA allocation is modified are no longer able to affect engagement-eligibility with VDAX in possession of non-modified PNA and may now be able to affect engagement-eligibility with other VDAX having the same modified PNA allocation. In embodiments, PNA may be genomically allocated to VDAXs in accordance with a wide range of Information theory-facilitated computationally complex functions. In embodiments, these information theory-facilitated functions may be cypher-based, cipherless, or hybrid computationally complex functions.

Link Exchange

As discussed, a pair of sufficiently correlated VDAXs may engage using links. In embodiments, a main purpose of links is to enable exchange of information necessary for a pair of VDAXs to perform higher level computationally complex genomic functions. In embodiments, the information exchanged in a link is referred to as genomic-engagement-cargo (GEC). In embodiments, link processes may include link spawning, link hosting, and link updating. Link spawning may refer to the generation and transport of a link by a spawning VDAX. Link hosting may refer to the acquisition and integration of the information contained in a link by a recipient VDAX. Link updating may refer to a CG-process where a VDAX may modify the genomic basis used to engage with another VDAX. The process of link updating may also be referred to as "link modification". In embodiments, the link processes (spawning, hosting, updating) rely upon specific information theory constructions. For example, in embodiments, LNA may be used as a basis for genomic correlation, CNA may be used as a basis for genomic engagement-integrity, and PNA may be used as a basis for genomic engagement-eligibility). These DNA constructions (e.g., LNA, CNA, and PNA) are application specific genomic constructions, which enable specific genomic transformation functions that facilitate the link processes. In embodiments, the link processes may be defined in a link module 430 of a CG-ESP, whereby some or all of the CG-ESP instances may be configured with link module 430 instances that perform these functions. For example, any VDAX whose role requires to spawn, host, and/or update links may be configured with such link modules 430 instances, which may define processes for static links and/or dynamic links.

In embodiments, a pair of VDAXs (e.g., a first VDAX and a second VDAX) that belong to the same CG-enabled digital ecosystem may spawn and host links without any prior arrangement. In these embodiments, a VDAX (e.g., a first VDAX) intending to spawn a genomic link for reception and use of genomic engagement cargo (GEC) by another VDAX (e.g., second VDAX) utilizes its CNA to establish engagement-integrity with the other VDAX (e.g., second VDAX) for which the link was generated. In some embodiments, a VDAX (e.g., first VDAX) spawns a genomic link for reception and use of the contained GEC by another VDAX (e.g., second VDAX), whereby the pair of VDAXs (e.g., the first and second VDAXs) may have multiple genomic links that utilize the same CNA to establish engagement-integrity.

In embodiments, the VDAX (e.g., first VDAX) intending to spawn a genomic link for reception and use of GEC by another VDAX (e.g., second VDAX) may utilize its PNA to establish engagement-eligibility with the other VDAX for which the link was generated. In some embodiments, a VDAX (e.g., first VDAX) spawns a genomic link for reception and use of the contained GEC by another VDAX (e.g., second VDAX), whereby the pair of VDAXs (e.g., the first and second VDAXs) may have multiple genomic links that utilize the same PNA to establish engagement-eligibility. It is noted that in some embodiments, the GEC contained in a link may include additional link activation requirements.

In some embodiments, a spawning VDAX that is spawning a link for transmission and use (e.g., "link hosting") by another VDAX (e.g., second VDAX) may utilize its LNA to establish genomic correlation with the other VDAX for which the link was generated. As discussed, LNA-based genomic processes may enable an entire digital ecosystem (community) to achieve VDAX to VDAX correlation based on a single genomic construction (e.g., LNA). In embodiments, LNA-based genomic processes enable a VDAX to modify its respective LNA construction by using specific computationally complex functions, whereby these LNA-based genomic processes exploit sub-constructions of genomic information (e.g., LNA-based genomic sub-constructions). In embodiments, LNA-based genomic sub-constructions may be utilized to compute unique transformation information by the link spawning VDAX that may be only reproduced by the link hosting VDAX, at the same level of entropy as underlying computationally complex genomic functions. In embodiments, the unique genomic engagement factor is utilized to prepare GEC for digital transport from the spawning VDAX to the hosting VDAX. In some of these embodiments, the link hosting VDAX may use the unique genomic engagement factor to decode encoded GRI contained in the GEC. In some embodiments, the unique genomic engagement factor may be rendered as multiple sub-constructions for application in multiple digital transport channels.

In some scenarios, ecosystem correlation is not available. In some embodiments, VDAX authentication may be necessary for link spawning and hosting when ecosystem correlation is not available. In these embodiments, VDAX authentication may be accomplished by use of alternate genomic sub-constructions to facilitate free-form-correlation (FFC). For example, a scenario may arise where a pair of VDAXs are in unique genomic digital ecosystems (which may be referred to as "republics"). In some embodiments, these unrelated VDAXs may form a unique genomic digital ecosystem (which may be referred to as a "federation") for specific operations and uses. In these embodiments, the VDAXs may spawn links as members of the federation as well as within their respective republics.

In embodiments, link spawning genomic processes may be carried out in accordance with a wide range of computationally complex functions which facilitate execution of genomic functions and processes. In embodiments, these functions may be cypher-based, cipherless, or hybrid computationally complex functions.

As mentioned, genomic link hosting (or "link hosting") may include acquisition and integration of link information by a VDAX (e.g., a second VDAX), such that a link contains specific genomic-engagement-cargo (GEC) from another VDAX (e.g., a first VDAX). In embodiments, link hosting may be performed in accordance with specific computationally complex genomic functions. In embodiments, a hosting VDAX (e.g., second VDAX) receives the unique transformation information sub-constructions via one or multiple digital transport channels. In embodiments, a hosting VDAX (e.g., a second VDAX) intending to use (host) genomic-engagement-cargo (GEC) transported by a link spawned by a spawning VDAX (e.g., first VDAX) may utilize its CNA to establish engagement-integrity with the spawning VDAX. In embodiments, a hosting VDAX (e.g., a second VDAX) intending to use (host) genomic-engagement-cargo (GEC) transported by a link spawned by a spawning VDAX (e.g., first VDAX) may utilize its PNA to establish engagement-eligibility with the spawning VDAX.

In embodiments, a hosting VDAX may leverage its digital ecosystem correlation-enabling LNA by modifying its LNA using specific computationally complex functions which exploit unique transformation information sub-constructions. In embodiments, LNA based genomic sub-constructions are utilized to compute unique genomic engagement factor by the link hosting VDAX, at the same level of entropy as underlying computationally complex genomic functions. In embodiments, the hosting VDAX (e.g., second VDAX) utilizes the unique genomic engagement factor to extract the GEC from a link provided by the spawning VDAX (e.g., first VDAX). In embodiments, the hosting VDAX (e.g., second VDAX) may be required to complete additional link activation requirements that are imposed by the spawning VDAX, whereby the additional link activation requirements are provided in the GEC.

As discussed, a scenario may arise where a pair of VDAXs are in unique genomic digital ecosystems (which may be referred to as "republics"). In some embodiments, these unrelated VDAXs may form a unique genomic digital ecosystem (which may be referred to as a "federation") for specific operations and may use, as discussed above.

In embodiments, link hosting genomic processes may be carried out in accordance with a wide range of computationally complex functions. In embodiments, these functions may be cypher-based, cipherless, or hybrid computationally complex functions. In embodiments, these functions may be necessary to perform the genomic operations.

In embodiments, VDAXs may update links hosted by other VDAXs. For example, to increase security levels, a VDAX may update a link hosted by another VDAX to decrease the possibility that a malicious party may determine or otherwise obtain the link information (e.g., GRI). In these embodiments, a pair of VDAXs (e.g., a first VDAX and a second VDAX) having previously completed "link spawning" and "link hosting" protocols, may update one or both links. In this way, a VDAX (e.g., the first VDAX) may modify the genomic basis used to engage with another VDAX (e.g., the second VDAX), and/or vice-versa. In some embodiments, a new genomic link spawned by a VDAX (e.g., first VDAX) and transmitted for hosting to another VDAX (e.g., second VDAX) may be used to replace one or more existing hosted links by the other VDAX with the newly spawned link, thereby updating the link. In embodiments, a genomic link spawned link by a VDAX and transmitted for hosting to another VDAX may be used to modify portions or all of the GRI data of an existing hosted link.

As discussed above, a scenario may arise where a pair of VDAXs are in unique genomic digital ecosystems (which may be referred to as "republics"). In some embodiments, these unrelated VDAXs may form a unique genomic digital ecosystem (or "federation") for specific operations and uses. In some of these embodiments, the federation of VDAXs may also update their links for the specific operations and uses.

In embodiments, link updating genomic processes may be carried out in accordance with a wide range of computationally complex functions. In embodiments, these functions may be cypher-based, cipherless, or hybrid computationally complex functions, necessary to execute genomic functions and processes.

Sequence Mapping and Binary Transformation

As discussed throughout the disclosure, sequence mapping and binary transformation are CG operations that may be performed to form VBLS. In embodiments, sequence mapping may be performed with public sequences and/or private sequences. In embodiments, a sequence may refer to a sequence of data (e.g., a sequence of bits). In embodiments, public sequences may refer to public protocol and format dependent information (e.g., TCP, UDP, TLS, HTTP, H.265, and the like), while private sequences may refer to private and/or proprietary protocol and format dependent information. In embodiments, sequences (e.g., public or private sequences) are computationally transformed into non-recurring values. While sequences may be broadly disparate (e.g., protocol independent and having preexisting entropy), sequences are processed in such a manner that results in values having specific levels of entropy. In embodiments, this process is compatible with a broad range of protocols and formats and may be initiated with different sequences exhibiting respective preexisting entropies. In embodiments, this process may be performed using complex genomic processes and functions that result in genomic engagement factor exhibiting specific levels of entropy.

In embodiments, CG-based security management systems and architectures may require the use of genomic engagement factors in conjunction with genomic data constructions. In embodiments, these genomic engagement factors may be derived in part by the use of recurring data (e.g., sequences). Prior to the use of sequences in conjunction with genomic data constructions, sequences are processed so the entropy of the resulting genomic engagement factors is consistent with that of the genomic construction (e.g., XNA). This process may be referred to as "sequence mapping" and its products are called genomic engagement factor. No matter that sequences may be broadly disparate, resultant genomic engagement factors exhibit a specific level of entropy. In embodiments, a genomic engagement factor may be produced from the integration of XNA Vectors. In some embodiments, multiple genomic engagement factors may be produced from a set of XNA vectors. In some embodiments, this process may be critical to the open architecture application which rely upon specific digital objects transformation, which objects potentially involve disparate protocols and formats (e.g., TCP, UDP, TLS, HTTP, H.265).

In some embodiments, broadly disparate external format and protocol resident data, without modification, is used to construct sequences. In some embodiments, broadly disparate external format and protocol resident data, with modification, is used to construct sequences. In some embodiments, sequences are used in conjunction with specific genomic based data constructions to determine unique vectors exhibiting specific entropy. In some embodiments, sequences are mapped in accordance with computationally complex genomic processes and functions in conjunction with specific genomic data constructions to derive a specific genomic engagement factor. In embodiments, sequence mapping results in a genomic engagement factors that exhibit entropy consistent with that of the genomic data construction, regardless of the inherent entropy of the sequence. In some embodiments, genomic engagement factors may be produced from sequence mapping that leverages internal CG-ESP formats and protocols in conjunction with these external formats and protocols. It is noted that genomic engagement factors should be determined in a manner that cannot be exploited to reveal format and protocol resident data and the genomic based construction (e.g., using computationally complex functions).

In embodiments, sequence mapping carries out the genomic engagement factor-generation genomic processes computed in accordance with computationally complex functions. In embodiments, these functions may be cypher-based, cipherless, or hybrid computationally complex functions, by which a sequence (public or private) and XNA produce a unique genomic engagement factor. Sequence mapping examples are discussed in greater detail below.

Hyper-Scalability

In some embodiments, a CG-ESP may implement genomic processes to facilitate hyper-scalable correlation. In embodiments, virtual authentication (e.g., unique correlation) of ecosystem, enclave, and cohort engagement relationships may be achieved with hyper-scalable correlation. As discussed, hyper-scalability technologies can be used to powerfully enhance ecosystem, enclave, and cohort engagements that depend on precise and unique correlation. As discussed, organic ecosystems (e.g., biological ecosystems) evidence powerful, although bounded, correlation across species, progeny, and siblings, which is derived from complex bio-chemical processes. The principles governing these bio-chemical processes may be reflected by specific digital genomic constructions facilitated by information theory, which exhibit unique correlation across ecosystems, enclaves, and cohorts. In embodiments, digital genomic correlation is practically unbounded and exhibits specific and user controllable entropy. In embodiments, genomic eligibility objects (e.g., CNA and/or PNA) and genomic correlation objects (e.g., LNA) may be used for digital genomic correlation.

In embodiments, ecosystem VDAXs may leverage computationally complex genomic processes to achieve virtual affiliation with enclaves and cohorts. Similarly, enclave VDAXs may use these computationally complex genomic processes to achieve hyper-scalable correlation with cohorts and cohort VDAXs may use the computationally complex genomic processes to achieve hyper-scalable correlation with other cohorts. In embodiments, unique hyper-scalable correlation between ecosystems, enclaves, and cohorts may be modified by computationally complex genomic processes. For example, an ecosystem VDAX may modify the LNA for a given enclave, so as to prevent future link exchange in that particular enclave for one or more of the enclave members. In some embodiments, enclave VDAXs and cohort VDAXs that are constituents of a given ecosystem may employ computationally complex genomic processes to correlate engagement with enclave VDAXs and cohort VDAXs that are constituents of other ecosystems. For example, in some embodiments, two ecosystem VDAXs may form a derived genomic data set from their respective genomic data sets, whereby members of the ecosystem may use the derived genomic data (or derivations thereof) to engage across ecosystems. In this way, enclave VDAXs and cohort VDAXs are capable of achieving unique hyper-scalable correlation across multiple ecosystems based on computationally complex genomic processes and their respective genomic data sets. In embodiments, hyper-scalable correlation carries out the genomic processes computed in accordance with a wide range of computationally complex functions, by which PNA, CNA, and LNA produce unique genomic engagement factors. These functions may be cipher-based, cipherless, or hybrid computationally complex functions.

In some embodiments, a CG-ESP may implement computationally complex processes to facilitate hyper-scalable differentiation. In some examples, hyper-scalable differentiation may be needed or may be required to provide unique affiliation between ecosystems, enclaves, and cohorts based on digital network-facilitated relationships. In embodiments, hyper-scalability technology can be used to powerfully enhance affiliation of ecosystems, enclaves, and cohorts that depends on precise and unique differentiation. Some example organic ecosystems may show evidence of powerful, although bounded, differentiation across species, progeny, and siblings that may be derived from complex bio-chemical processes. The principles governing these example bio-chemical processes may be reflected by specific digital genomic constructions governed by information theory, which may exhibit unique differentiation across ecosystems, enclaves, and cohorts. In some examples, this digital genomic differentiation may be practically unbounded and may exhibit specific and user controllable entropy.

There may be various example implementations for applying hyper-scalable differentiation in ecosystems, enclaves, and/or cohorts. For example, members of CG-enabled ecosystems may leverage computationally complex genomic processes to achieve hyper-scalable differentiation that facilitates unique non-recurring virtual affiliation between ecosystems, enclaves, and cohorts. In some examples, CG-enabled enclaves leverage computationally complex genomic processes to achieve hyper-scalable differentiation to facilitate unique non-recurring virtual affiliation between enclaves and cohorts. In some examples, cohorts may use computationally complex genomic processes to achieve hyper-scalable differentiation that facilitate unique non-recurring virtual affiliation between cohorts. In embodiments, unique hyper-scalable differentiation between ecosystems, enclaves, and cohorts may be modified by computationally complex genomic processes. In some embodiments, the enclaves and cohorts that are members of a given ecosystem may employ computationally complex genomic processes to affiliate with enclaves and cohorts that are members of other ecosystems. In this way, enclaves and cohorts may be capable of achieving unique virtual affiliation across multiple ecosystems based on computationally complex genomic processes, according to some embodiments of the present disclosure. In some examples, hyper-scalable differentiation may carry out genomic processes computed in accordance with a wide range of cypher-based, cipherless, or hybrid (e.g., cypher-based and/or cipherless) computationally complex functions, by which sequences and XNA may produce unique genomic engagement factors that may be used to generate VBLS.

In some embodiments, a CG-ESP may implement genomic processes to facilitate virtual agility. In some examples, virtual agility may provide unique engagement between ecosystems, enclaves, and cohorts that may require the abilities to execute hyper-scalable differentiation and hyper-scalable correlation at a network (e.g., open systems interconnection (OSI)), at software stack levels, and/or in hardware components. Both network and software engagement traditionally require creation, negotiation, and maintenance of session-based protocols. In some examples, these protocols may be computationally expensive and may limit network and software stack adoption options. Virtual agility may enhance engagement of ecosystems, enclaves, and cohorts by powerfully eliminating at least some of the requirements for session-based protocols. Virtual agility may reflect specific digital genomic constructions that may be generated by computationally complex processes, and which may be practically unbounded and exhibit specific and user-controllable entropy.

There may be various example implementations for applying virtual agility in ecosystems, enclaves, and/or cohorts. For example, virtual agility may be adoptable at a network stack level, software stack level, and/or hardware level, thereby supporting a large number of ecosystems, enclaves, and/or cohorts. In embodiments, virtual agility may eliminate a requirement to create, negotiate, and maintain session-based protocols for network communication engagement, for software application engagement, and/or for hardware component engagement.

Virtual Binary Language Script (VBLs)

In some embodiments, a CG-ESP may implement computationally complex processes to generate and/or decode VBLS. As discussed, a CG-ESP may be configured to perform link exchange (e.g., link spawning and/or link hosting) and sequence mapping that may allow for digital objects bearing specific formats and protocols (e.g., packets, sectors, sequences, and frames) to be computationally transformed into VBLS objects. In embodiments, the VBLS objects produced by this process may be unique, non-recurring, and/or computationally quantum proof. In some embodiments, VBLS may be a consummation of genomic information theory-controlled and facilitated link, sequence, correlation, differentiation, and agility functions and processes. Computationally quantum proof VBLS may form the foundation by which specific network, software, and hardware architectures may be constructed, whether in current or newly developed deployments.

There may be various example implementations for applying virtual binary language script (VBLS) in ecosystems, enclaves, and/or cohorts. For example, VBLS may allow for control of wide range and highly flexible complements of relationships of an ecosystem, an enclave, and/or a cohort. In embodiments, VBLS may facilitate consummation and control of dynamic genomic-based architectures. In some examples, VBLS rendered digital objects may be unique, non-recurring, and computationally quantum proof, while eliminating the need for secret key generation, exchange, and retention. VBLS rendered objects may require de minimis overhead and bandwidth for engagement of VDAX(s). In some examples, VBLS rendered objects may exhibit ecosystem, enclave, and/or cohort-directed genomic modifications. In embodiments, VBLS applications may be protocol-agnostic (e.g., interoperable with network, software, and/or hardware solutions). In examples, VBLS may facilitate unique, non-recurring, and computationally quantum proof engagements between community members (e.g., ecosystem-to-ecosystem, ecosystem-to-enclave, ecosystem-to-cohort, enclave-to-cohort, and/or cohort-to-cohort engagements) based on their unique computationally complex genomic constructions and processes. In some example embodiments, any VBLS-enabled VDAX may participate in multiple VBLS relationships with other VDAX(s). In these embodiments, a VDAX may form a unique relationship with each VDAX. In some embodiments, genomic engagement factors used to be generated may be used simultaneously for primary and secondary applications that also require unique non-recurring values at a specific entropy.

In embodiments, VDAXs may be configured to engage in symmetric and/or di-symmetric VBLS-based engagements. For example, in some embodiments, VBLS-enabled VDAX(s) may engage on the bases of link exchange (e.g., spawned and hosted) which may use genomic link instructions and genomic constructions that may be the same, resulting in symmetric-based engagement. In embodiments, VBLS-enabled VDAXs may engage in di-symmetric engagement based on highly correlated genomic constructions (e.g., identical or otherwise sufficiently correlated XNA). In these embodiments, the VBLS-enabled VDAXs exchange links containing unique genomic regulation instructions (GRI). In some scenarios, however, VBLS-enabled VDAXs may engage in symmetric engagements when link exchange involves identical GRI. For example, a CG-ESP may be configured to perform one-way link exchange, whereby one VDAX may provide GRI that is used by both VDAXs in a VBLS-generation process. In this way, VBLS-enabled VDAXs may engage with other VDAXs based on symmetric and/or di-symmetric binary languages without recurring coordination between VDAXs. In some of these embodiments, VBLS-enabled VDAX engagement may proceed without negotiation of a formal session, as their symmetric or di-symmetric binary languages simultaneously encapsulate authentication, integrity, and privacy.

Virtual Trusted Execution Domains

The rapid expansion of remote network centric highly distributed solutions and services (e.g., remote-cloud and edge-cloud) has created a situation where sensitive binaries are possibly executed in open or semi-open environments leaving them exposed to untrusted third parties (e.g., adversary). Homomorphic cryptography (cogent processing of data in encrypted state), functional obfuscation (cogent processing of data and application code in encrypted state), and various trusted execution environments (e.g., physical and software isolation of executable code) are current approaches to resolving such critical exposure. While these methods may improve markedly, none of these solutions addresses the critical scalability required for broad commercial application, as each imposes critical performance impact.

According to some embodiments of the present disclosure, CG-ESP technology enables computationally quantum proof, highly efficient, and hyper-scalable virtual trusted executable domains for processing of data and application code, which may be organized as genomic ecosystems. In some of these embodiments, virtual trusted execution domain allow unique transformation of component resident executable binaries and data, such as Applications (e.g., API, Libraries, and Threads), Operating System (e.g., Kernel, Services, Drivers, and Libraries), and System on a Chip (e.g., Processing Units, e.g., Core). In embodiments, CG-ESP Executable Isolation Components (EIC) facilitate component-binary-isolation (CBI) necessary for required transformations. In some embodiments, isolation is enabled by 1) unique genomic correlation between distributed components belonging to the same ecosystem, and 2) unique genomic differentiation with other executable ecosystem components. This correlation and differentiation process forms the basis by which virtual trusted execution domain (VTED) enable highly flexible and scalable component-binary-isolation (CBI).

In embodiments, hyper-scalable differentiation enables highly flexible component binary isolation (CBI) of ecosystems, enclaves, and cohorts. In some of these embodiments, virtual trusted execution domain (VTED) isolation may be achieved through the sharing of genomic components within a VTED and CBI with their VTED ecosystem VDAX, thereby establishing a hierarchical link between these members. In embodiments, a VTED provides functional replacement of homomorphic cryptography where CBIs are held at rest and runtime operations are undertaken on the encoded binaries and associated data.

In embodiments, VTED virtual-agility enables highly flexible component-binary-isolation (CBI) and control of dynamic genomic based architectures. In further embodiments, genomic correlation and differentiation enable the dynamic genomic based systems to configure dynamic genomic network topologies without the requirement to modify physical operating environments.

In embodiments, VTED-transformed executable binaries are unique, non-recurring, and computationally quantum proof. In embodiments, this transformation eliminates the requirement for secret key generation, exchange, and retention often required by trusted execution environment (TEE) technologies. In embodiments, VTED executable binaries are transformed through the application of genomic constructions (for example LNA or ZNA) to build transformed executable binaries.

In embodiments, VTED hyper-scalable-correlation, hyper-scalable-differentiation, and hyper-scalable-agility uniquely enable CBI to operate at de minimis overhead and bandwidth. In further embodiments, large numbers of genomic constructions are applied to vast numbers of CBI providing for hyper scalability of the VTED ecosystem.

In embodiments, VTED-enabled CBI for ecosystems, enclaves and cohorts may be directly genomically modified without compromise of the binary executable relationships. In embodiments, VTED enabled CBI modify binary information while the VTED maintains the ability to execute the CBI within its ecosystem.

In embodiments, VTED-enabled CBI may be compatible with known cipher-based and cipherless computational methods. In further embodiments, the compatibility of the VTED and CBI with cipher-based and cipherless computational methods is maintained by transparent genomic construction-based transformations.

In embodiments, a VTED may enable CBI executables that are unique, non-recurring, and computationally quantum proof between specific ecosystems based on their unique computationally complex genomic constructions and processes. In further embodiments, the CBI construction process applies genomic constructions that do not rely on traditional computationally expensive operations.

In embodiments, a VTED may enable CBI executables to have a number of characteristics including, unique, non-recurring, and computationally quantum proof engagements between specific ecosystems and enclaves. In embodiments, CBI executables exhibit these characteristics based on their unique computationally complex genomic constructions and processes. In further embodiments, the VTED applies genomic constructions to deploy CBI executables that enable quantum proof operations between CBI executables and genomic VTED.

In embodiments, a VTED may enable CBI executables based on their unique computationally complex genomic constructions and processes. In further embodiments, in scenarios where a VTED includes multiple cohorts across multiple enclaves, the VTED may apply genomic components to enable CBI executables that may have certain desirable characteristics such as being unique, non-recurring and quantum proof between entities. In further embodiments, an ecosystem VDAX can provide for genomic construction-based CBI licensing models where individual cohorts can have specific features or CBIs enabled for operation within their ecosystem, enclave, or cohort.

Cyphergenics-Enabled Digital Ecosystems and Architectures

Figure 6:
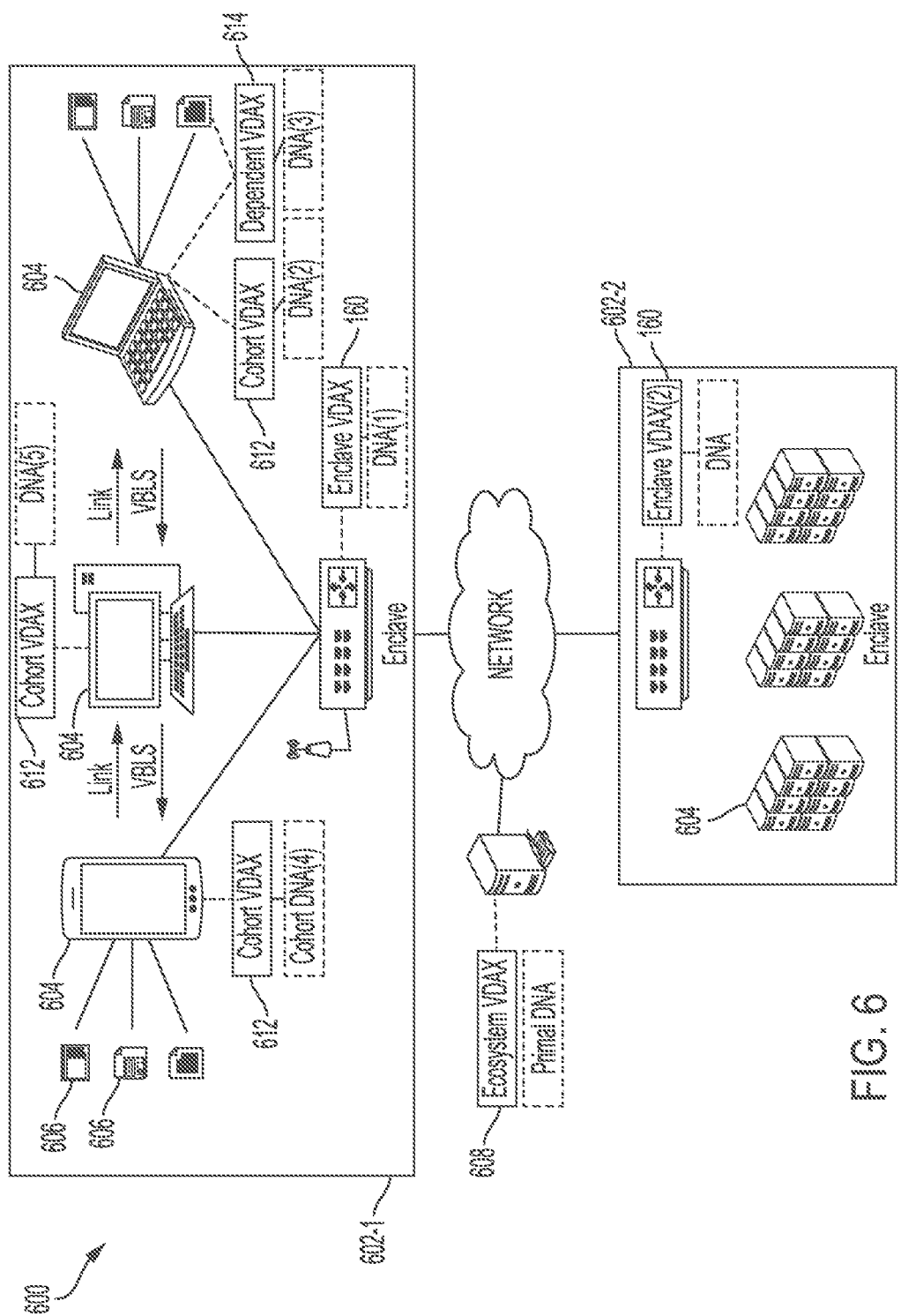
FIG. 6 illustrates an example Cyphergenics-enabled digital ecosystem that is managed by a set of CG-enabled VDAXs, in accordance with some embodiments of the present disclosure.

Referring now to FIG. 6, an example CG-enabled digital ecosystem 600 is depicted according to some example embodiments of the present disclosure. It is noted that the example configuration of the CG-enabled digital ecosystem 600 depicted in FIG. 6, including the topography and architecture of the depicted security platform depicted in the figure, are provided as a non-limiting example and are not intended to limit the scope of the disclosure. As is discussed throughout the disclosure, a configuration of CG-ESP may be defined by the community owner of a digital ecosystem. When referencing a "community owner", the term may refer to the entity that administers, maintains, or owns the community, representatives thereof (e.g., network administrator, CIO, IT administrator, homeowner, consultant, security expert, artificial intelligence software acting on behalf of the community owner, or any other suitable representative), and/or any other suitable party that may define the configuration of a CG-ESP that is used in connection with the CG-enabled ecosystem 600.

In embodiments, a set of VDAXs (e.g., VDAXs 608, 610, 612, 614) perform a set of genomic security functions on behalf of the digital ecosystem 600. It is noted that VDAXs may also be referred to as "CG-security controllers" or "security controllers". In embodiments, the CG-enabled digital ecosystem 600 includes a set of enclaves 602, and, for each enclave, a respective set of cohorts. It is noted that general references to a CG-ESP may be a reference to the configurations of the VDAXs (e.g., ecosystem VDAXs 608, enclave VDAXs 610, cohort VDAXs 612, and/or dependent VDAXs 614) that participate in the digital ecosystem. In embodiments, the set of cohorts can include independent cohorts 604. As discussed, independent cohorts 604 may include a collection of one or more devices that operate as an independent entity. Examples of independent cohorts 604 include, but are not limited to, grids, networks, cloud services, systems, computers, appliances, devices, IoT devices, and the like. In some embodiments, the set of cohorts may further include dependent cohorts 606. A dependent cohort 606 may refer to an individual digital entity which is enabled by a digital container-based VDAX or for which an independent cohort acts as a surrogate. Examples of dependent cohorts include, but are not limited to, sensors, applications, data, files, databases, media contents, cryptocurrency, smart contracts, and the like. An enclave 604 may be a collection of two or more cohorts (e.g., independent cohorts 604 and/or dependent cohorts 606) having a mutual identity of interest. As discussed, mutual identity of interest may be any logical commonality between the cohorts within an enclave. For example, a mutual identity of interest may be a set of devices, servers, documents, applications, and the like that are used by a business unit within an enterprise organization. In another example, a mutual identity of interest may be the devices, documents, applications, and the like belonging to a single family or user. In another example, a mutual identity of interest may be a set of autonomous vehicles driving on a particular grid. In embodiments, the topography of a digital community (and the architecture of the corresponding CG-ESP) may be defined by the community owner with consideration of these mutual identities of interest. In embodiments, eligibility for membership into an ecosystem 600 and/or one or more enclaves 602 thereof may be defined by a community owner and membership and revocation thereto may be administered by the community owner and/or in accordance with a set of one or more rules. It is noted that in some embodiments, certain CG-enabled digital ecosystems and the respective architectures of the corresponding CG-ESP may be defined in accordance with a default configuration, such that the community owner purchases or otherwise obtains the digital ecosystem pre-configured with the default configuration.

In some embodiments, an ecosystem progenitor (e.g., ecosystem VDAX 608) is configured to construct one or more enclaves 602 and may add a respective set of cohorts to each enclave 602 in accordance with an architecture and configurations defined by the community owner. In some embodiments, the architecture and configurations relating to a CG-enabled digital ecosystem 600 may be defined by a CG-ESP (e.g., as discussed in FIG. 4). In these embodiments, the VDAXs that participate in the digital ecosystem 100 may each execute a respective instance of the CG-ESP, such that each VDAX executes a CG-ESP instance such that the CG-ESP instance enables a respective VDAX to perform a respective role with respect to the ecosystem 600 and to form relationships with intended ecosystem members. For example, the set of VDAXs may include any suitable combination of an ecosystem VDAX 608 that serves an ecosystem-level role, one or more enclave VDAXs 610 that serve enclave level roles, one or more cohort VDAXs 612 that serve cohort-level roles, and/or one or more dependent VDAXs 614 that serve dependent cohort roles. For example, in some example implementations, an ecosystem VDAX 608 may be configured (e.g., via a CG-ESP instance) to generate, allocate, and persistently modify the genomic data of other ecosystem members, confirm engagement eligibility, exchange links, and generate VBLS; while a cohort VDAX 612 (e.g., via a cohort CG-ESP instance) may not have the capability to create or allocate genomic data with respect to the ecosystem to other cohorts, but is configured to confirm engagement eligibility, exchange links, and generate VBLS.

In embodiments, a VDAX may be implemented as any combination of software, hardware, firmware, and/or middleware that performs a specific set of genomic functions with respect to an ecosystem. It is noted that the existence of a dependent cohort 606 depends on at least one independent cohort (e.g., a file depends on the device on which it is stored or an application instance depends on the device on which the application is executed). Thus, in some embodiments, a dependent VDAX 614 of a dependent cohort 606 (e.g., a file, a media content, an application, or the like) may be executed by an independent cohort 604

(e.g., user device, smart device, gaming device, personal computing device, server, cloud system, or the like) on which the dependent cohort 606 depends.

In embodiments, an ecosystem VDAX 608 performs security related functions for a digital ecosystem and may be considered the "progenitor" of the ecosystem, as an ecosystem VDAX 608 does not require any subsequent interaction with an enclaves or the cohorts of the enclave after the ecosystem VDAX initializes assigns an enclave its genomic data set. It is noted that in embodiments, an ecosystem may be configured to enable independent sub-ecosystems and may include multiple lower level VDAXs which have functional ecosystem-level VDAX capabilities but are derived from the primary ecosystem VDAX 608.

In embodiments, an ecosystem VDAX 608 digitally generates respective genomic data sets for one-time distribution to ecosystem enclaves 602 and/or the cohorts 604, 606 within respective enclaves 602. While the genomic data objects in a genomic data set may have similar or identical constructions, mathematical competences, and/or entropy levels, each serves a different purpose. In embodiments, genomic eligibility objects (e.g., CNA or PNA objects) provide the core genomic competence by which community members (e.g., enclaves or cohorts) computationally correlate their individual ecosystem identities. In embodiments, genomic correlation objects (e.g., LNA objects) provide the competence for member-to-member link exchange (e.g., ecosystem-to-enclave, enclave-to-enclave, enclave-to-cohort, cohort-to-cohort, and/or the like), which controls a member's ability to establish engagement with another member. In embodiments, genomic differentiation objects (e.g., XNA or ZNA objects) provide the competency for VBLS based member-to-member di-symmetric communications. In embodiments, the digital-genomic constructions of CNA, PNA, LNA, and XNA are complex and unique. In embodiments, CNA, LNA, XNA, and PNA may be derived using complex mathematical functions.

According to some embodiments of the present disclosure, an ecosystem VDAX 608 may generate a genomic data set that it assigns to itself. The genomic data set may include one or more different types of genomic data objects. For example, in some embodiments the ecosystem VDAX may generate a genomic eligibility object (e.g., a CNA object and/or a PNA object), a genomic correlation object (e.g., an LNA object), and a genomic differentiation object (e.g., an XNA object or a ZNA object) in accordance with the platform instance requirements (e.g., types of genomic object, levels of entropy of each genomic object, and specific algorithms that are used to generate such genomic data objects). In embodiments, the genomic data set that is initially generated by the ecosystem VDAX 608 and assigned to the entire ecosystem 600 may be the genomic data set from which all the progeny genomic data sets of the digital ecosystem 600 are derived. For purposes of explanation, the genomic data set of the ecosystem progenitor may be referred to as a "progenitor genomic data set" (or a "progenitor DNA set"). In some embodiments, the ecosystem VDAX 608 may initially generate the progenitor genomic data sets. For instance, the ecosystem VDAX 608 may, for each progenitor genomic data object, generate a respective binary vector having specific dimensionality.

In some embodiments, the ecosystem VDAX 608 may generate a respective progeny genomic data set for each enclave from the progenitor genomic data set. In some embodiments, the ecosystem VDAX 608 may modify the progenitor genomic data set using a set of predefined genomic operations to obtain a progeny genomic data set (or "enclave data set") that is then propagated to a respective enclave. For example, the ecosystem VDAX 608 may modify a progenitor genomic eligibility object of the progenitor genomic data set using computationally complex functions to obtain a different enclave genomic eligibility object for each respective enclave in the ecosystem; modify a progenitor correlation object of the progenitor genomic data set using computationally complex functions to obtain a different enclave correlation object for each respective enclave in the ecosystem; and modify a progenitor differentiation object of the progenitor genomic data set using computationally complex functions to obtain a different enclave differentiation object for each respective enclave in the ecosystem. In embodiments, the techniques by which different types of genomic objects are modified may differ as the different genomic objects may be implemented in different types of data structures and/or may be required to exhibit different properties. Different modification techniques are described throughout the disclosure. It is noted that in some implementations of a security platform, there may be only a single enclave. Depending on the various techniques implemented in a specific CG-ESP, certain types of genomic objects (e.g., LNA and XNA) may be highly correlated (e.g., identical or otherwise sufficiently correlated) some or all enclaves, while other types of genomic objects (e.g., CNA or PNA) are unique to each respective community members but still sufficiently correlated. It is noted that even if some types of genomic objects in a progeny genomic data set are not modified from the corresponding genomic objects of a progenitor genomic data set, the modification of one or more other portions of the genomic data set and subsequent assignment of the progeny genomic data set to a progeny community member (e.g., enclave or cohort) may also be referred to as a "derivation", such that the progeny genomic data set (e.g., enclave genomic data set or cohort genomic data set) may be said to be derived from the progenitor genomic data set (e.g., the progenitor genomic data set or an enclave genomic data set) even if one or more genomic objects of the progeny genomic data set were unmodified from the progenitor genomic data set.

In embodiments, an enclave VDAX 610 may be configured to add cohorts to a corresponding enclave by modifying the enclave genomic data set of the corresponding enclave and assigning the resultant progeny genomic data sets to respective cohorts in the enclave. In some embodiments, an enclave VDAX 610 may generate a cohort genomic data set for each new independent cohort 604 that is being added to an enclave 602. In some embodiments, CG-ESP may be configured so that an enclave VDAX 610 generates a unique, but highly correlated, genomic eligibility object (e.g., CNA) for each independent cohort 604 that is added or to be added to the corresponding enclave 602. In some of these embodiments, the ecosystem VDAX 608 or an enclave VDAX 610 may generate the genomic eligibility object such that any pair of cohorts in the enclave have a unique correlation of genomic eligibility objects. For example, in some embodiments, each cohort in an enclave 602 is assigned a genomic eligibility object that is generated based on a genomic eligibility of object of a progenitor (e.g., ecosystem or enclave), such that the cohorts are unique while maintaining a high level of correlation. In this way, any pair of cohorts may confirm eligibility to engage with one another based on the correlation of their respective genomic eligibility objects. In some embodiments, members of an enclave (e.g., cohort VDAXs) are assigned highly correlated (e.g., identical or otherwise sufficiently correlated) genomic correlation objects and genomic differentiation objects. In some embodiments, a pair of cohorts may authenticate one another based on each cohort's respective genomic correlation object and may differentiate themselves from the other cohorts based on each cohort's respective genomic differentiation object. In embodiments, the genomic correlation object and the genomic differentiation object of a cohort may be separate objects (though they may be similar or identical in structure). Alternatively, in some embodiments, the genomic correlation object and the genomic differentiation object of a cohort may be the same object.

While in some embodiments a cohort genomic data set is assigned to only one entity (e.g., device, document, sensor, or the like), it is noted that in other embodiments a community owner may allow a cohort's genomic data set to be cloned to one or more additional community members. For example, a user may have two devices that they use in connection with their employment (e.g., a desktop and a laptop computer). The community owner may opt to have devices in this scenario be assigned identical copies of a genomic data set. In this way, each device associated with a user may be granted the same access rights with respect to a respective enclave 602. It is noted that in some of these embodiments, each respective device with a cloned genomic data set would still be required to independently confirm eligibility, authenticate, and/or exchange links with other cohorts in the enclave 602.

It is noted that in some embodiments, when a VDAX is assigned a genomic data set and added to the digital ecosystem 600, the VDAX may also receive configuration data (e.g., as defined in a CG-ESP instance) as well as other suitable data that may be required to participate in the ecosystem. Such configuration data may allow the VDAX to use the correct genomic functions when performing genomic operations such as eligibility correlation, link spawning, link hosting, sequence mapping, LNA modification, XNA modification, binary object transformation, and the like. In these embodiments, such configuration data allows community members to successfully engage and exchange data with other community members. In some embodiments, a VDAX may also receive genomic community progeny (GCP) data that uniquely identifies a community member. In these embodiments, the GCP may be used in confirming engagement eligibility of cohorts.

In some embodiments, a cohort VDAX 612 may be configured to perform genomic security operations and processes on behalf of an independent cohort 604. In some embodiments, a cohort VDAX 612 facilitates data exchange with sufficiently correlated community members (e.g., other cohorts in an enclave 602). In some of these embodiments, the facilitation of data exchange with another community members may include confirming engagement eligibility (e.g., engagement integrity and engagement synchronization) and exchanging links with the other respective community member (e.g., with another independent cohort 604). In some embodiments, confirming engagement eligibility and link exchange is a one-time process, such that once a pair of cohorts have successfully completed this "handshake", the pair of VDAXs can exchange data securely for as long as they continue to share highly correlated (e.g., identical or otherwise sufficiently correlated) differentiation objects. For example, a pair of VDAXs may initially confirm engagement eligibility and exchange links and, unless they no longer share the common differentiation object, the VDAXs can continue to communicate securely for days, weeks, months, or years. Once the cohorts no longer share common differentiation objects, they can attempt to exchange data, but will be no longer able to decode any encoded digital objects provided by the other respective cohort.

In embodiments, a pair of VDAXs engage with one another via virtual binary language script (VBLS) that is generated and decoded by the respective VDAXs. As discussed, VBLS may refer to unique, non-recurring (or recurring with infinitesimal probabilities) binary languages. In embodiments, individual instances of VBLS may be referred to VBLS objects. In embodiments, a first VDAX (e.g., cohort VDAX 612 or an enclave VDAX 610) may generate VBLS objects for a second VDAX (e.g., cohort VDAX 612 or an enclave VDAX 610) based on genomic regulation instructions (GRI) encoded in a link provided to the first VDAX by the second VDAX and the genomic data (e.g., XNA) of the first VDAX. In these embodiments, the second VDAX may receive VBLS objects from the first VDAX and may decode the VBLS based on the GRI provided in the link to the first VDAX and the genomic data set of the VDAX. In some embodiments, a VBLS object includes metadata that the second VDAX processes to decode an encoded digital object that is included in the VBLS object. For example, in some embodiments, a VBLS object is a data packet that includes packet header and an encoded digital object (e.g., a payload). In some of these embodiments, the metadata that is used to decode the encoded digital object includes a public sequence or private sequence that appears in one or more protocol layers of the digital object (e.g., TCP, UDP, TLS, HTTP, H.256, or any other suitable protocol layer types).

In embodiments, the first VDAX may generate a VBLS object corresponding to a digital object that is to be provided to the second digital object by determining a genomic engagement factor based on a sequence (e.g., public or private sequence) and the genomic differentiation object of the first VDAX. In embodiments, the first VDAX modifies its genomic differentiation object according to the GRI provided by the second VDAX in the link provided by the second VDAX and maps a sequence (or a value derived therefrom) contained in the digital object (e.g., protocol or format data in the digital object) into the modified genomic differentiation object to obtain the genomic engagement factor. In embodiments, the first VDAX may use a computationally complex function (e.g., cipher-based function, non-cipher-based function, or hybrid function) to map the sequence into the modified genomic differentiation object. The first VDAX may then encode a digital object (e.g., a packet payload, a shard of a file, a video or audio frame, or any other suitable type of digital object) using the genomic engagement factor to obtain the encoded digital object. In embodiments, the first VDAX leverages a computationally complex function (e.g., encryption function or a disambiguation/XOR function) to encode the digital object based on the genomic engagement factor. The first VDAX may then provide a VBLS object that includes the metadata (e.g., the sequence) and the encoded digital object to the second VDAX (e.g., via a network and/or a data bus).

In embodiments, the second VDAX receives the VBLS object and may decode the encoded digital object in the VBLS object based on the metadata included in the VBLS object and the genomic differentiation object of the second VDAX. In embodiments, the second VDAX is configured to extract a sequence from the VBLS object (e.g., a public or private sequence unencrypted portion of a data packet or data frame). The second VDAX may also modify its genomic differentiation object using the GRI contained in the link that was provided to the first VDAX (e.g., during a link exchange process), such that the second VDAX maps the sequence (or a value derived therefrom) into the modified genomic differentiation object using the same computationally complex function to obtain a genomic engagement factor. Assuming that the first VDAX and the second VDAX have matching (or sufficiently correlated in some embodiments) genomic differentiation objects and both use the same instructions to modify the respective genomic differentiation objects, then the same genomic engagement factor will be produced given the same sequence and the modified genomic differentiation object. In embodiments, the second VDAX leverages a function (e.g., decryption function or a disambiguation/XOR function) to decode the digital object based on the same genomic engagement factor. In this way, the first VDAX and the second VDAX are able to differentiate themselves in a unique manner from other community members that share the same genomic differentiation object, as the other community members not in possession of the link provided by the second VDAX to the first VDAX cannot modify their genomic differentiation object in the same manner. Thus, the other community members will be unable to generate the genomic engagement factor even if those community members are configured to execute the same computationally complex mapping function and are able to determine the public sequence. Interloping or otherwise malicious devices that do not have access to the genomic data would be further limited, as such interlopers may be unknowing of one or more of: the computationally complex functions used to generate the genomic engagement factor, how to extract the sequences, or the common genomic differentiation object. As such, they would be unable to determine the genomic engagement factor without brute-force methods. Furthermore, as a CG-ESP may be configured such that a first VDAX calculates a new genomic engagement factor for every digital object (e.g., every data packet, shard of a file, video frame, audio frame, or the like), each encoded VBLS object would require a separate brute force determination of the digital object, making the VBLS generated by the first VDAX for a second VDAX quantum-proof.

In some embodiments, the metadata in a VBLS object may further include data integrity information. For example, the data integrity information may be a value that is calculated by the first VDAX over the plain data and then used as sequence. In this way, the second VDAX may verify, that the VBLS object was not tampered with.

In embodiments, digital objects may refer to OSI components (e.g., level 2-7 components) and/or computer-executable code/instructions. Examples of digital objects include packets, sectors, frames, and sequences. VBLS may refer to languages spoken by an enclave or a cohort to another enclave or cohort that is uniquely understood by the recipient enclave or cohort—that is, languages that are only understandable by the recipient enclave or cohort. In this way, interlopers aiming to include unauthorized cohorts, viruses, and/or malware, cannot generate or decipher VBLS between authorized cohorts.

It is appreciated that the foregoing discussion is provided for as an example of a CG-enabled digital ecosystem 600. It is appreciated that different configurations of a CG-ESP may perform different functions and operations and may have different CG-ESP modules. For example, different configurations of CG-ESP may use different encryption functions, different hash functions, different sequence mapping functions, different types of genomic constructions, or the like.

It is further noted that CG-ESPs may be configured for different ecosystems which may enable different architectures.

FIGS. 7-12 illustrate different types of digital ecosystems and corresponding architectures. Contemporary network capabilities substantially reflect their underlying deployment architecture. In embodiments, CG-enabled architectures that enable VBLS using genomic constructions may operate at the bit level and, therefore, may remain interoperable with the underlying deployment architecture. VBLS provides unprecedented facility and flexibility to uniquely tailor applications for network, software, and/or hardware-centric architectures. Examples of CG-ESP ecosystem architectures may include, but are not limited to: directed architectures that support static ecosystems, free-form architectures that are configured for transient ecosystems, spontaneous architectures that support dynamic ecosystems, ephemeral architectures that support executable ecosystems, and Interledger architectures that support affirmation ecosystems. In embodiments, these architectures, which may overlay existing physical network topologies, evidence genomic constructed topologies. In some embodiments, multiple genomic constructed topologies may exist simultaneously and interoperably. For example, a computing device may be an executable ecosystem, such that internal components of the computing device exchange VBLS; at the same time, the computing device may be a member of a static ecosystem, such that the computing device may engage with other devices in the static ecosystem using a different set of genomic data.

Figure 7:
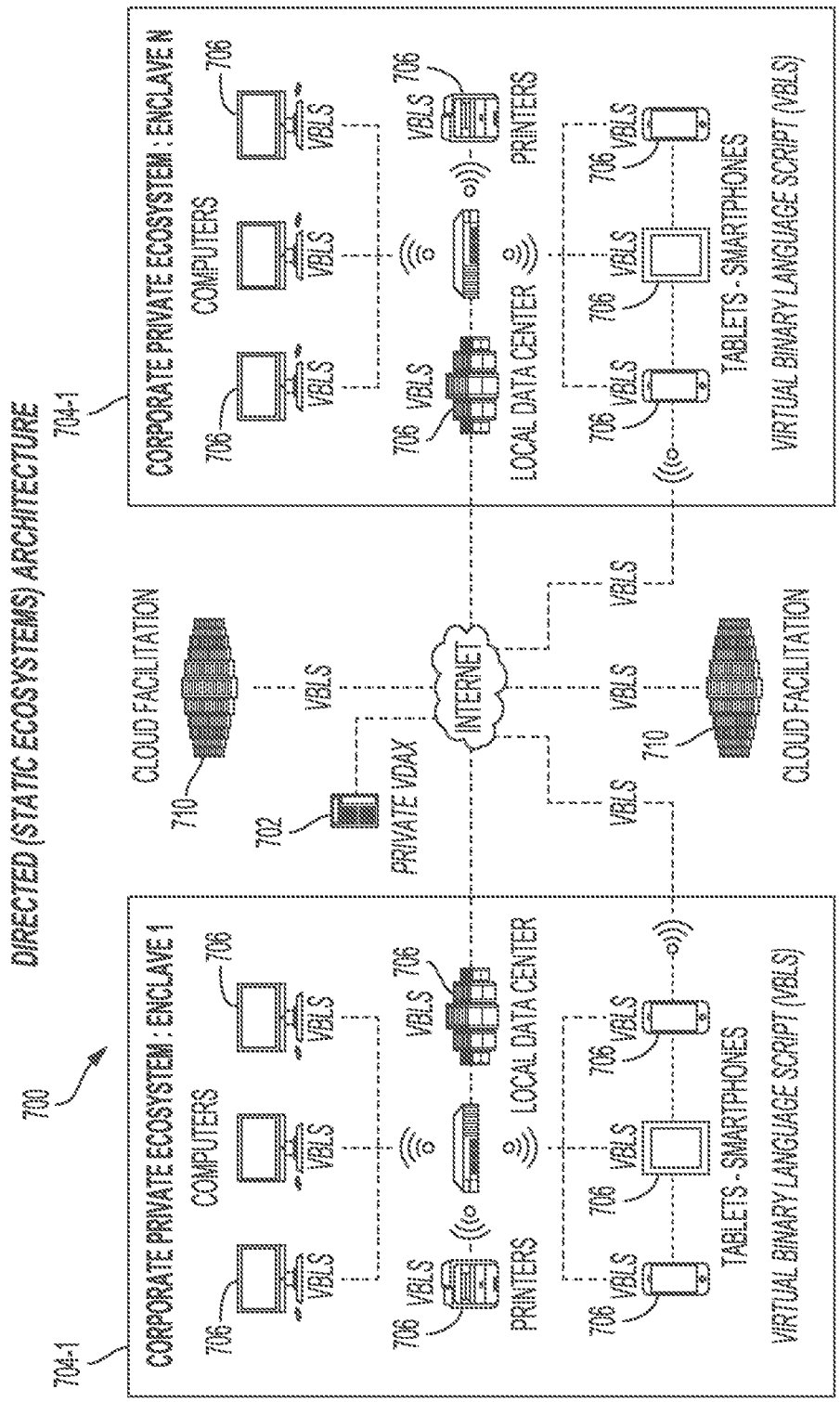
FIG. 7 illustrates example implementations of security platform instances that are configured in accordance with directed architectures in support of static ecosystems, in accordance with some embodiments of the present disclosure.

Referring to FIG. 7, a directed architecture may be implemented in a static ecosystem, as the features of such ecosystems and the enclaves and cohorts that participate in these ecosystems exhibit a fairly stable configuration. For example, in an enterprise deployment, the majority of users will use similar devices (e.g., desktops, laptops and mobile devices), email clients, software solutions (both cloud-based and locally executed), devices (e.g., printers, IoT devices) and the like, all of which are unlikely to change much over time. These ecosystems provide relationship stability without loss or stifling of flexibility. These architectures' attributes are uniquely extended and enhanced—such that they may be capable of standing alone. In some example embodiments, a provision that may be enabled by static architectures, as opposed to free-form architectures, may be the manner by which correlation is executed and managed. In the case of static architectures, correlation is accomplished on the basis of common genomic constructions, which is provisioned by a single ecosystem VDAX.

In embodiments, directed architectures reflect configurations where an ecosystem VDAX establishes one or more enclaves that exhibit specific genomic correlation and differentiation. In some of these embodiments, each enclave VDAX may correspondingly establish one or more cohorts, which also exhibit specific genomic correlation and differentiation. In embodiments, such ecosystem, enclave, and cohort configuration may be exhibit hierarchical genomic correlation and differentiation, which may be beneficial in directed architectures. In embodiments, directed architectures, ecosystem, enclave, and cohort VDAXs may have multiple genomic correlations and differentiation attributes. For example, enclaves in directed architectures may propagate both subordinate enclaves and cohorts. In embodiments, different architectures may be configured to exhibit different correlation properties. For example, directed architectures may exhibit inherently common correlation, while free-form architectures may exhibit arranged common correlation.

In embodiments, genomic correlation and differentiation enable directed architectures to configure genomic network topologies without the requirement to modify physical topology. For example, in these embodiments, a community owner may be able to control engagement of cohorts in different enclaves using different LNA and XNA, such that engagement (e.g., via link exchange) between cohorts in different enclaves may be prevented by a community by controlling the LNA and/or XNA that is provided to different enclave members. Similarly, in these examples, the community owner can create new enclaves also by controlling the LNA and XNA that are provided to different cohorts.

In embodiments, the genomic topologies enabled by directed architectures may be incrementally genomically modified. In some of these embodiments, a community owner may periodically modify certain genomic constructions (e.g., XNA and/or LNA) of some or all ecosystem and/or enclave members for any number of considerations (e.g., security, removing cohorts that are no longer, dissolving an enclave, and the like).

FIG. 7 illustrates an example of a CG-enabled ecosystem 700 having a directed architecture, whereby the ecosystem 700 is a static ecosystem. In embodiments, static ecosystems include enclaves and the cohorts that support more traditional deployments to include local, internally managed but distributed, and remote on-demand IT resources and capabilities. Static ecosystems require seamless performance and security. These deployments are often found in enterprise class organizations and institutions, but owing to their complexity, security has been a challenge for small and medium size businesses (SMB). These implementations tend to be relatively static and centrally managed. For example, in a static ecosystem a business unit may include a number of employees that are allowed to access (e.g., read, write, and/or edit) a common set of files. Furthermore, employees may work on special projects (e.g., a product release), and those employees typically are allowed to access another common set of files. In some scenarios, a community owner (e.g., represented by an IT administrator or any other party affiliated with an enterprise) may define a set of policies that define the type of access individual cohorts may be granted with respect to certain files or folders, one or more enclaves that each cohort belongs to, the cohorts and/or enclaves that each cohort may digitally engage with (e.g., printers, local file servers, and the like), and/or other suitable policies. As discussed, such policies may be enforced using genomic constructions, such as XNA, CNA, PNA, and LNA, which can be used to define permissible relationships and genomic topologies across the ecosystem.

In embodiments, a security platform may be implemented as a directed architecture when the digital ecosystem is a static ecosystem 700. Using a directed architecture, an ecosystem VDAX (e.g., private VDAX 702) defines one or more enclaves 704 corresponding to the static ecosystem. In the example of FIG. 7, the ecosystem VDAX has defined N enclaves 704, including a first enclave 704-1 and an Nth enclave 704-N, in a hierarchical manner (e.g., a directed architecture). For each enclave 704-1 . . . 704-N, the ecosystem VDAX 702 can create an enclave VDAX (which executes an enclave VDAX) for the enclave 704-1 and can assign one or more cohorts 706 to the enclave 704-1. In this example, the cohorts 706 of the first enclave 704-1 and the Nth enclave 704-N include workstations, tablets, local data centers, printers, IoT devices, mobile devices, and the like.

It is noted that in this example, the router in each enclave is not considered a cohort and does not communicate using VBLS. Rather, each router is a pass-through device that routes data packets containing VBLS to cohorts 706 within the enclave 704, within the ecosystem 700, and/or to any broader network (e.g., the Internet). In embodiments where the routers are cohorts, each router may have its own genomic data set (XNA, LNA, and CNA), and other cohorts 706 within the enclave 704 would communicate with the router using VBLS that only the router could understand. It is appreciated that such decisions are design choices that can be made by the community owner or a provider of the CG-ESP. It is further noted that the cloud facilities 710 in this example are not enclaves of the ecosystem 700. In this example, the cloud facilities 710 host third party applications and/or data. In some example embodiments, the ecosystem VDAX 702 of the ecosystem 700 may be configured to negotiate an arrangement with a VDAX (not shown) of the third party application system and/or the cloud facility to obtain genomic materials that correlate to the cohorts of the directed ecosystem, thereby enabling authentication, linking, and engagement between the ecosystem and the third party application system/cloud facility. Additionally or alternatively, the community owner may decide that certain third party service providers (e.g., cloud services) may be added to the ecosystem as cohorts, such that the community owner may restrict the third party service provider's access to the ecosystem to specific uses via LNA and XNA construction. In this way, the third party service would only be able to exchange links with other cohorts that have similar LNA (e.g., intended users of the third party service). Similarly, when the relationship ends with the third party service provider, the community owner may revoke the third party service provider via XNA modification.

In some embodiments, an enclave VDAX of an enclave 704 (or the ecosystem VDAX), can generate and allocate genomic materials to the VDAXs of each cohort 706 in an enclave 704. In embodiments, the ecosystem VDAX 702 creates genomic information (e.g., XNA, LNA, and CNA) for each respective enclave. In response to receiving its genomic information, an enclave VDAX may generate respective genomic information for each cohort 706 included in the enclave 704. For example, the enclave VDAX (or the ecosystem VDAX) may generate CNA that is allocated to new cohorts and/or may provide its LNA and/or XNA to the members of the enclave 704. Depending on the configuration of a CG-ESP and the genomic constructions thereof, two cohort VDAXs that have been admitted to an enclave, may be required to participate in link exchange. Once two cohort VDAXs have participated in link exchange, they may begin to exchange VBLS based on the hosted link(s).

In a directed architecture, the ecosystem owner (e.g., via an ecosystem VDAX 702) can manage the security features of enclaves 704 and/or cohorts 706 within the enclaves 704 by initiating modification of the XNA and/or LNA of a cohort 706 and/or enclave 704. For example, if a certain employee is no longer part of a business unit, the employee's access to certain resources (e.g., documents, printers, file systems, or the like) may be revoked. In embodiments, a VDAX can "revoke" access to the cohorts (e.g., workstation, mobile device, or the like) of the employee by initiating a modification of the XNA (and in some scenarios LNA) of the cohorts 706 that will remain in the enclave 704 and/or ecosystem 700 without initiating the same XNA modification to the cohorts 706 corresponding to the removed employee. In another example, if the employee had access to a first folder of documents and a second folder of documents, and the employee's access to the first folder is being revoked but not his or her access to the second folder, the VDAX can initiate the modification of the XNA of the second folder and the DNA and LNA of the other cohorts of the enclave without providing the modification to the cohort(s) of the employee whose access to the second folder has been revoked. In these provided examples, a community owner is able to control engagement of cohorts in different enclaves using genomic constructions (e.g., LNA and/or XNA).

It is appreciated that the foregoing discussion provides some example implementations of directed architectures. It is appreciated that CG-ESPs can be configured in accordance with directed architectures in other suitable ecosystems without departing from the scope of the disclosure.

Figure 8:
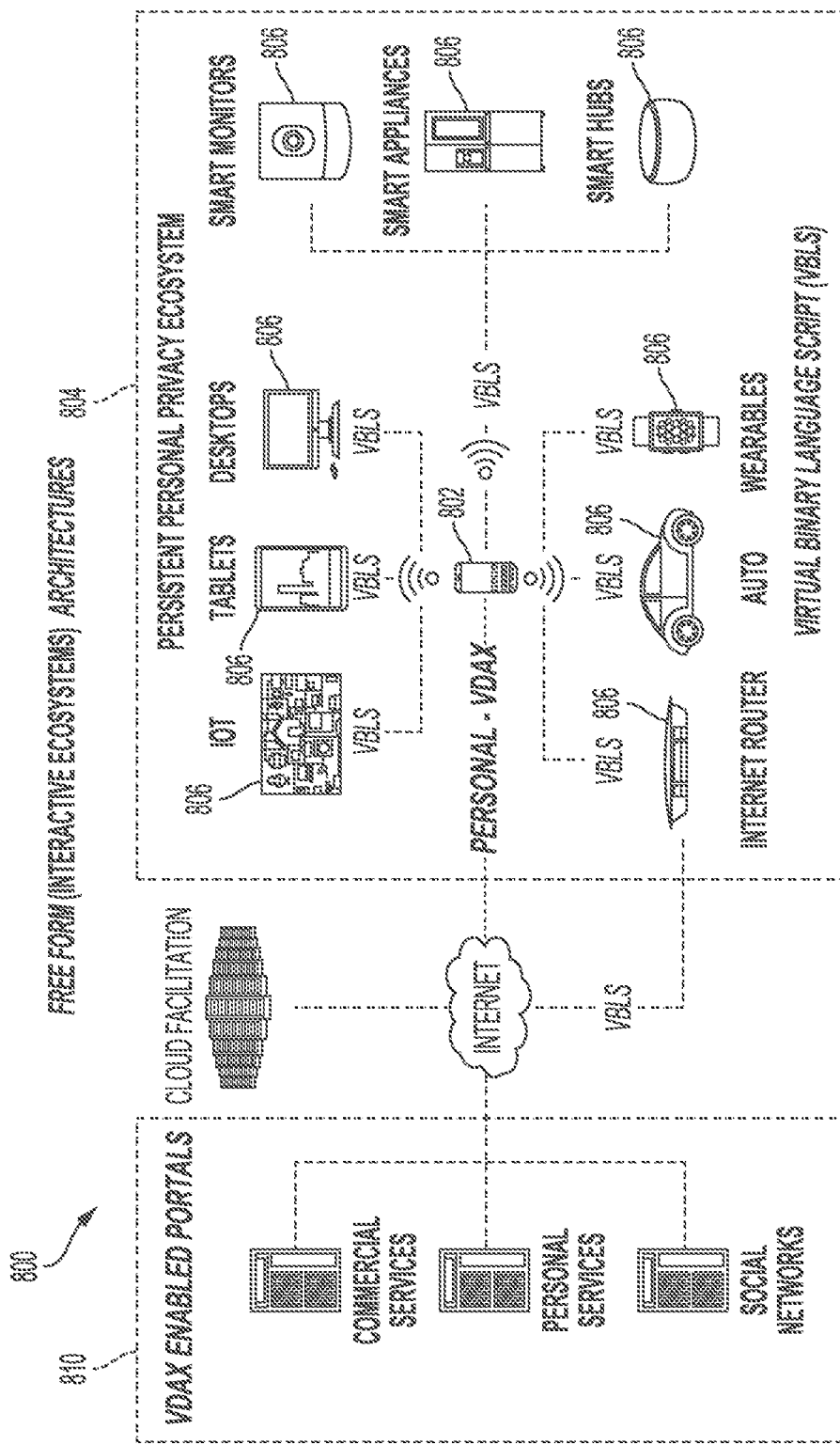
FIG. 8 illustrates an example implementation of a security platform instance that is configured in accordance with a free-form architecture in support of a transient ecosystem, in accordance with some embodiments of the present disclosure.

Referring now to FIG. 8, free-form architectures feature ecosystems, enclaves, and cohorts which are potentially unrelated. In such ecosystems, the configurations of the enclaves (e.g., a limited number of users, devices, and the like) are fairly stable, but may change in accordance as per their mutual identity of interest (e.g., changes to the ecosystem are less predictable than in static ecosystems). Thus, free-form architectures may provide relationship stability without loss or stifling of flexibility. In some embodiments, these architectures' attributes may be uniquely extended and enhanced—such they are capable of standing alone. In embodiments, a provision that may be enabled by free-form architectures, as opposed to Static Architectures, is the manner by which correlation is executed and managed. In the case of free-form architectures, common genomic correlation cannot be accomplished on the same basis as in the case of static architectures, such is accomplished by use of alternate genomic sub-constructions in order to facilitate common genomic correlation, e.g., free-form.

In embodiments, free-form architectures may facilitate genomic construction of application-specific network topologies. For example, in some embodiments, ecosystem VDAXs independently initiate unique genomic correlation and/or differentiation constructions (e.g., LNA and/or XNA). In some embodiments, enclave VDAXs and/or cohort VDAXs in a directed architecture may acquire their unique genomic correlation constructions directly (e.g., LNA). For example, the ecosystem VDAX may control which cohorts should belong to which enclaves via genomic construction generation and modification.

In embodiments, ecosystem VDAXs in free-form architectures may acquire their unique genomic correlation constructions via alternate genomic sub-constructions. In some of these embodiments, each ecosystem VDAX may have a unique genomic construction by which correlation and differentiation attributes are derived. In some of these embodiments, these derived attributes control the genomic topology of an ecosystem's enclaves. In some of these embodiments, each enclave (e.g., via its enclave VDAX) may have a unique genomic construction by which correlation and differentiation attributes are derived, these attributes control the genomic topology of the enclave's cohorts (e.g., cohort VDAXs). In embodiments, multiple genomic constructed topologies, which overlay physical network topologies, may exist simultaneously and in an interoperable manner. In some embodiments, genomic-based digital network topologies are independent from underlying technologies used to enable physical or logical digital networks. In these embodiments, genomic-based digital networks render their topologies, which in some scenarios, may be solely dependent upon genomic construction-facilitated VBLS.

FIG. 8 illustrates an example of a security platform having a free-form architecture that serves an interactive ecosystem 800. In embodiments, an interactive ecosystem 800 may include one or more enclaves 804 (e.g., personal residence, home office, small business, or the like) and each enclave may include one or more cohorts 806 (e.g., computers, appliances, hubs, media devices, IoT devices, wearable devices, smart speakers, and the like) that share mutual identity of interests, and are capable of interacting with a wide range of network enabled web portals (e.g., Facebook, Amazon, banking servers, healthcare servers, and the like) which services and applications are interactive but require user-controlled security. An example of an interactive ecosystem 800 may be a home network, a small office network, or the like.

In a free-form architecture, a cohort 806 within the ecosystem 800 may be designated as the VDAX 802 of the ecosystem 800. For example, a user may designate a mobile device, a desktop, or a router to act as the VDAX 802 of the ecosystem 800. Furthermore, via the VDAX 802, a user may define one or more enclaves (e.g., via a user interface). For example, in some situations a user may define a single enclave 804 (e.g., all devices associated with the user). In another example, a user may define different enclaves 804 for different family members, different device classes, and/or other logical commonalities (e.g., an enclave for the devices used by the parents, an enclave for devices used by the minors, and an enclave for smart devices, such as thermostats, appliances, televisions, speakers, and the like). In embodiments, the user may define, via the VDAX 802, one or more settings (e.g., rules, policies, blacklists, whitelists, and the like) for enclaves 804 and/or individual devices. These parameters may be used when generating the genomic data (e.g., XNA, LNA, CNA and/or PNA) of an enclave 804 or cohort 806. The VDAX 802 may generate the genomic data for each enclave 804. In some embodiments, the VDAX 802 may also generate the genomic data for each cohort (independent and dependent). In other embodiments, another device may host an enclave VDAX, whereby the enclave VDAX generates the XNA, LNA, PNA and/or CNA of the cohorts 806 in the enclave 804.

In an interactive ecosystem 800, the external systems that a cohort 806 may access are wide ranging. For example, a user may use their workstation or mobile device to access web portals to stream videos, access social media platforms, visit websites, read emails and messages, open attachments, and the like. Similarly, the user may have devices in their home that can detect motion, record audio, capture video, or record sensor measurements or other data relating to the user or his or her home or office. These devices also access web portals to report data or to leverage a service of the web portal (e.g., ordering goods, adjusting thermostat, or the like). In the former example, the user may be concerned with privacy and/or malicious software (e.g., viruses or malware) being installed on their devices. In the latter example, users may be concerned with privacy (e.g., who has access to the data captured by their smart devices or unknown surveillance). In an interactive ecosystem 800, a security platform implemented as a free-form architecture mitigates these concerns. In some embodiments, the VDAX 802 of the ecosystem 800 may negotiate a secure relationship with a VDAX (not shown) of a portal 810. In some of these embodiments, the VDAXs of the user and the web portal generate correlated genomic data. In these embodiments, the VDAX 802 of the interactive ecosystem may then generate genomic data for a cohort (e.g., by way of the cohort's VDAX) that attempts to access the web portal 810. When the cohort 806 attempts to access the web portal, the cohort 806 and the web portal 810 generate and exchange engagement information that allows the pair of corresponding VDAXs to confirm eligibility-integrity and/or synchronization and ultimately exchange links. Once the web portal 810 and the cohort 806 have spawned and exchanged links, the cohort 806 and the web portal 810 may respectively host the other party's link. The cohort 806 may use the link spawned and hosted by the web portal 810 to generate VBLS that is sent to the web portal 810, and the web portal 810 may use the link spawned by the cohort 806 to generate VBLS that is sent to the cohort 806. The foregoing example is but a single example of a free-form architecture, and other implementations are within the scope of the disclosure.

Figure 9:
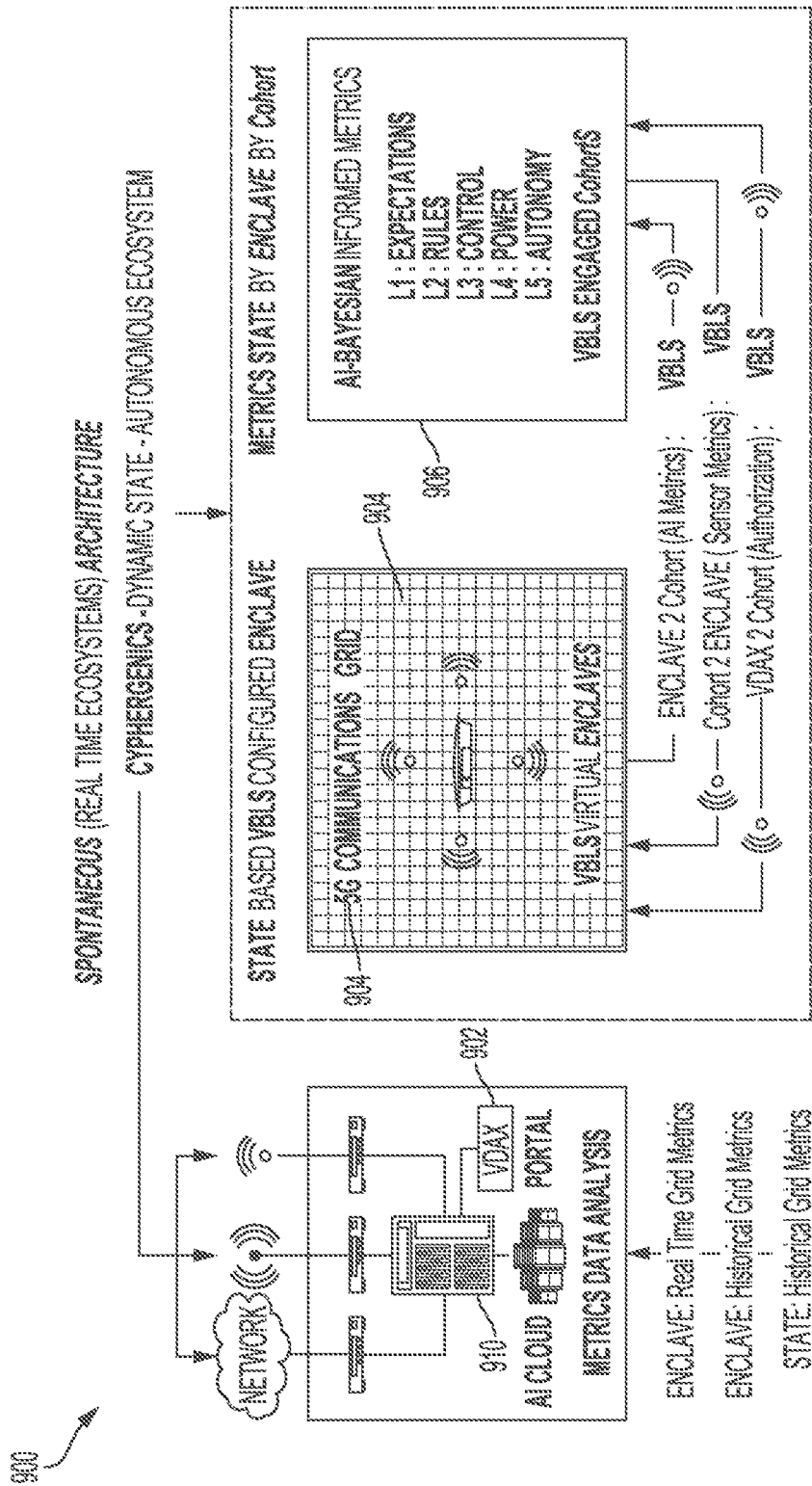
FIG. 9 illustrates an example implementation of a security platform instance that is configured in accordance with a spontaneous architecture in support of a real-time/dynamic ecosystem, in accordance with some embodiments of the present disclosure.

Referring now to FIG. 9, a spontaneous architecture may be implemented to support applications and services subject to highly dynamic changes in metric (e.g., time, data, condition, demand, coordinate, action, relative position, and event) states. For example, an autonomous car management system may manage an ecosystem of autonomous vehicles moving throughout a grid of control where the grid of control is dynamically controlled based on the traffic situation on the road. In embodiments, this grid topology may be dynamically reconfigured to enable the support of highly dynamic changes in environment and state. In a further example, the spontaneous architecture may provide for an air traffic control system or a military theater or swarm of drones where the cohorts are constantly changing and may have highly dynamic security responses to the environment. In embodiments, the spontaneous topology can change by altering the DNA in response to situational events. To respond to these situational events modified DNA may be dynamically distributed to different cohorts or groups.

In embodiments, such architectures—spontaneous architectures—may benefit from complete and/or real time reconstruction of their network topologies to address specific control parameter such as metric states or operator preference(s). In certain situations, network architectures are required to address an additional challenge in that they are incapable of supporting highly dynamic changes in metrics and the variety of their possible state. In embodiments, a spontaneous architecture addresses these highly dynamic changes in metrics allowing for support of emerging ultra-bandwidth applications or artificial intelligence portals. Further examples of applications of spontaneous architectures may include military theaters, management of electrical power grids or highly distributed financial trading systems.

In embodiments, ecosystem VDAXs may construct and control genomic network topologies that support applications requiring dynamic state attributes. In embodiments, an ecosystem VDAX may be able to control engagement of cohorts in an ecosystem using different genomic constructions (for example, LNA and XNA), such that engagement (e.g., via link exchange) between cohorts in the ecosystem may be enabled, prevented, and/or revoked by a community owner by controlling the LNA and/or XNA that is provided to different members. Similarly, in these examples, the ecosystem VDAX can alter the dynamic network topology of the ecosystem by controlling the LNA and XNA that are provided to different cohorts.

In embodiments, enclave VDAXs can be configured to control respective portions of an ecosystem's genomic network topology, whereby an enclave VDAX is responsible for specific VDAX-designated functions and processes with respect to the enclave VDAX's portion of the genomic network topology. In further embodiments, genomic correlation and differentiation enable the enclave VDAXs to configure dynamic genomic network topologies without the requirement to modify physical topology. For example, in these embodiments, the Enclave VDAXs may be able to control engagement of cohorts in different enclaves using different genomic constructions (for example, LNA and XNA), such that engagement (e.g., via link exchange) between cohorts in different enclaves may be dynamically enabled or prevented or revoted by an enclave VDAX by controlling the LNA and/or XNA that is provided to different enclave members. Similarly, in these examples, the enclave VDAXs can create new dynamic spontaneous enclaves also by controlling the genomic constructions (e.g., LNA and XNA) that are provided to different cohorts. In some embodiments, cohort VDAXs may control respective portions of the ecosystem genomic network topology. In these embodiments, a cohort VDAX may be responsible for performing specific functions for a respective portion of the genomic network topology as designated by an Ecosystem VDAX and/or enclave VDAX. In further embodiments, cohort VDAXs performing such functions may enable spontaneous architectures by configuring dynamic genomic network topologies without the requirement to modify a physical network topology. For example, in these embodiments, a cohort VDAX may be able to control engagement of VDAXs for a designated portion of a genomic network topology using different genomic constructions (for example, LNA and XNA), such that engagement (e.g., via link exchange) between VDAXs in the designated portion may be dynamically enabled, prevented, and/or revoked by a designated cohort VDAX by selectively modifying the LNA and/or XNA of those VDAXs.

In embodiments, various types of interactions (e.g., ecosystem VDAX-to-enclave VDAX, enclave VDAX-to-cohort VDAX, ecosystem VDAX-to-cohort VDAX, and/or cohort VDAX-to-cohort VDAX interactions) may be controlled by specific genomic constructions (e.g., CNA, PNA, LNA and XNA) determined by the ecosystem VDAX. For example, in these embodiments, an ecosystem VDAX may control engagement between VDAXs corresponding to respective portions of a genomic network topology by dynamically modifying portions of some or all of the genomic constructions (e.g., LNA or XNA) of ecosystem, enclaves, and/or cohort VDAXs in the respective portion of the genomic network topology. In this way, VDAXs can be added, prevented, and/or revoked from different portions of the genomic network topology via their respective genomic constructions. For example, in some embodiments, an enclave VDAX that is designated with controlling a respective portion of a genomic network topology can alter that portion of the genomic network topology by selectively modifying the genomic constructions of VDAXs that are to be added and/or revoked from the respective portion of the genomic network topology. In embodiments, the genomic constructions (e.g., CNA, PNA, LNA and/or XNA) responsible for ecosystem, enclave, and cohort engagements may be modified to change the basis of differentiation and/or correlation, which in turn modifies the genomic network topology. In some embodiments, such modifications may be effected as part of updating the genomic network topology (e.g., cohort revocation). In embodiments, these genomic constructions may be modified to enable control the engagement of cohorts in the ecosystem using different genomic constructions (for example, LNA and XNA), such that engagement (e.g., via link exchange) between members in the ecosystem may be enabled or prevented or revoked by controlling the genomic constructions. Similarly, in these examples, the ecosystem CNA, PNA, LNA and/or XNA can alter the dynamic network topology of the ecosystem by controlling the genomic constructions that are provided to different cohorts.

In embodiments, spontaneous architectures retain their operational integrity irrespective of the dynamic frequency of the metric states they support (for example, time, data, condition, demand, coordinate, action, or event). For example, in some embodiments, cohorts may operate in an environment where the reporting frequency of the metrics can be variable. In these embodiments, the spontaneous architecture handles these variations in the overall metric data while maintaining the overall integrity of the ecosystem.

FIG. 9 illustrates an example of a security platform having a spontaneous architecture that serves a dynamic ecosystem 900. In embodiments, dynamic ecosystems 900 include enclaves and their cohorts that support applications and services that are subject to highly dynamic changes in state (time, data, conditions, demand, coordinates, actions, et al). Examples of dynamic ecosystems 900 include artificial intelligence applications, autonomous vehicle systems, and real-time supply chain systems. Spontaneous ecosystems 900 often require complete reconstruction in real time in response to specific states and or operator preference(s). The security requirements of these ecosystems are such that traditional cryptographic protocols are both incapable of supporting the dynamic frequency and incompatible with variety of states possibly attended to. In embodiments, a security platform is implemented as a spontaneous architecture to serve a spontaneous ecosystem 900. These architectures hold great promise for the emerging integration of ultra-bandwidth and artificial intelligence (AI) portals.

In a spontaneous architecture, an ecosystem VDAX 902 may be configured to dynamically define enclaves 904 and/or to assign cohorts 906 to one or more enclaves 904 in real time. In some of these embodiments, an AI portal may be leveraged by the VDAX 902 to define the enclaves 904 and to assign cohorts 906 thereto. For each cohort 906, the VDAX 902 may initially generate and provide genomic information for the cohort 906. This genomic information may be generated and provided each day, each time the cohort 906 is powered on, or at other suitable intervals. The genomic information may be correlated with all the other cohorts 906 in the ecosystem 900, but without being assigned to a particular enclave 904. As the cohort 906 participates in the ecosystem 900, the VDAX 902 and the AI portal 910 may determine which enclaves 904 that the cohort 906 belongs to and which enclaves 904 the cohort 906 should be revoked from. For each enclave 904 that the cohort 906 belongs to, the VDAX 902 may communicate modifications to the cohort's XNA and LNA, such that the AI portal 910 may be able to decipher VBLS generated by cohorts 906 within those enclaves 904. Similarly, for each enclave 904 that a cohort 906 has been revoked from, the VDAX may communicate modifications to the cohort's XNA and LNA, such that the cohort 906 may be no longer able to decipher VBLS generated for remaining cohorts 906 within those enclaves 904. In spontaneous ecosystems, the VDAX (or multiple VDAXs) may manage membership for the enclaves 904 within the ecosystem 900 in this manner, such that cohorts 906 within a grid 912 maintain a high level of correlation with other cohorts 906 within the enclave 904, cohorts 906 that are no longer within the grid 912 no longer maintain a high level of correlation.

In the illustrated example, the spontaneous ecosystem 900 is an autonomous vehicle environment. In such an environment, vehicles may traverse the roadways of an area (e.g., an entire city, state, or the like). At times, there may be hundreds of thousands of cars traversing the roadways and at other times there may be less vehicles. Each vehicle may be configured to report its sensor data (e.g., LIDAR, radar, video, moisture, etc.) to a cloud-based system, such that the cloud based system may maintain state data relating to the roadways (e.g., where there are vehicles, obstacles, traffic, or the like). The cloud-based system may be configured to report relevant state data to each vehicle, so as to inform the vehicle of conditions along a route of the vehicle (or other suitable data, such as instructions to particular vehicles). Because each vehicle is traveling along its own route and the amount of data collected every second from the collection of vehicles may be vast. In the illustrated example, the VDAX 902 and the AI portal facilitate the reporting of relevant state data to vehicles along the grid using VBLS. In this example, the VDAX 902 may generate a grid corresponding to an area (e.g., a city, a county a state, or the like), where the grid 912 has cells. The cells may be fixed in size or may be dynamically sized depending on the amount of traffic on the roadways. Similarly, the cells may be fixed in number or may be dynamically allocated depending on the amount of traffic on the roadways. In some embodiments, the AI portal determines the number of cells and/or the sizes of the cells in response to the conditions of the roadways (e.g., how many vehicles are on the roadways, how many vehicles are traditionally on the roadways at this time, etc.). In embodiments, each cell is considered an enclave 904 and the cloud-based system may report relevant state data to those vehicles within an enclave 904. In some embodiments, communication towers (e.g., 5G towers) may host the enclave VDAXs that communicate with cohorts 906 within an enclave 904. As a vehicle traverses the roadways, the vehicle may exit one cell and enter another. Furthermore, as a vehicle is likely to go straight, right, or left, the VDAX 902 may assign the vehicle to multiple cells (i.e., enclaves), such that a vehicle may receive relevant state data of one or more cells directly ahead of the vehicle, one or more cells to the right of the vehicle, and one or more cells to the left of the vehicle. The VDAX 902 may provide a vehicle with genomic information for each of these enclaves (e.g., one or more cells to the right, left, and ahead of the vehicle). For each cell/enclave, the vehicle (e.g., a cohort VDAX executing thereon) may generate a GEC and exchange GEC with the cloud-based system to authenticate itself for the particular cell. Once authenticated, the vehicle and the cloud-based system may exchange links to engage with respect to each cell. As the vehicle collects sensor data, the vehicle may generate VBLS based on the collected sensor data, its XNA, and the information contained in the link received from the cloud-based system. Similarly, the cloud-based system may, for each cell, broadcast VBLS that is generated in a VBLS that is specific to the cell (e.g., understood by any cohort that is assigned to the enclave). As a vehicle exits a cell, the VDAX may modify the genetic information of the vehicle for that cell, so that the vehicle will no longer be able to understand VBLS that corresponds to that cell or to generate VBLS that corresponds to that cell.

Application Ecosystems continue to evolve featuring complex services and processes which require richer resource availability and low latency networks. This is evidenced in part by the redistribution of processes and reallocation of infrastructure. Applications generally require sophisticated OS. OS services are increasingly bifurcated, where those having lesser complexity and resource requirements are locally hosted (e.g., Client OS) and those having greater complexity and resource requirements are remotely hosted (e.g., Cloud OS). This efficient OS bifurcation has other profound advantages: proliferation of very low-cost client devices that retain access to powerful non-resident capabilities, exceedingly lower cost bandwidth budgets, and free form distribution and development of powerful new applications. These decidedly new and beneficial applications, like their predecessors, will impose significantly more complex challenges to access and propriety control.

Figure 10:
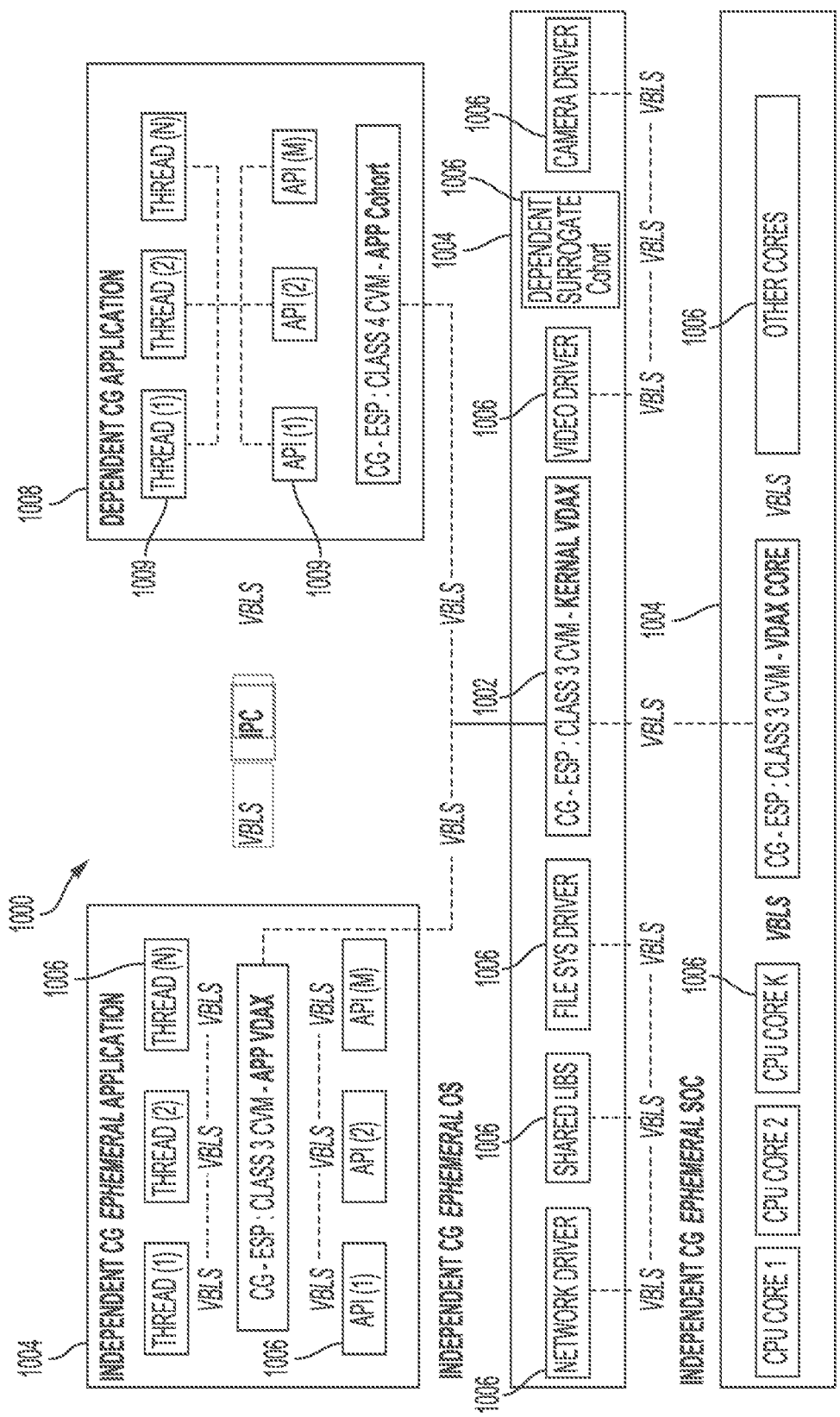
FIG. 10 illustrates an example implementation of a security platform instance that is configured in accordance with an ephemeral architecture in support of a virtual trusted execution domain, in accordance with some embodiments of the present disclosure.

Referring now to FIG. 10, by implementing computationally complex genomic constructions, CG-ESPs enable methods for uniquely transforming engagement between different software and hardware components, "Executable Ecosystems", e.g.: applications (API, libraries, and threads), operating system (kernel, services, drivers, and libraries), and System on a Chip (processing units, e.g., core). These Ecosystem components may prosecute Executable Binaries collaboratively or independently. In embodiments, the methods may enable specific designation and organization of such ecosystems and enclaves, and cohorts (independent cohorts and dependent cohorts)—which best attend their capabilities, limitations, and performance efficiencies—to form a gnomically constructed ephemeral architectures. In embodiments, ephemeral architectures are capable of transforming executable binaries to VBLS digital objects and resultant VBLS streams, which exhibit unique genomic differentiation and correlation. In some of these embodiments, CG-ESPs in ephemeral architectures are capable of computationally complex genomic construction facilitated engagement with other CG-enabled architectures, such as directed (static ecosystems and free-form ecosystems) and spontaneous (dynamic state).

In embodiments, ephemeral architectures may provide many benefits, in that many of their attributes exhibit direct correlation with other architectures (e.g., Directed, and Spontaneous). Ephemeral architectures, however, constitute a very different attack surface in that their components are generally closely coupled and the processes are highly observable and modifiable prior-to and in-process. Thus virtual variety of such conditions may benefit from VBLS facilitated dynamic virtual trusted execution domains.

In embodiments, genomic correlation and differentiation enable ephemeral architectures, which may be genomically configured by VDAX to enable Executable Ecosystems (e.g., ecosystem VDAX, enclave VDAXs, cohort VDAXs, and dependent VDAXs). In further embodiments, and ephemeral architecture based provides for an executable ecosystem where a VDAX of different hierarchical levels provides deep knowledge of source allowing for establishment of trusted components. In a further embodiment, a complex ecosystem such as an autonomous vehicle, or spaceship or mobile phone, or webs services architecture, consisting of a vast array of components that are each made of further subcomponents, in this example each layer of ecosystem allows for their respective VDAX and genomic constructions to build a system of knowledge of source of components. In further embodiments, each component can execute operations to validate the source and veracity of operation of the sub-components. In this example, the veracity of operation may be undertaken by genomic construction enabled exchanges with trusted provisioning sources.

In embodiments, genomically constructed application-specific executable ecosystems do not require modification of their underlying architectural embodiments. In further embodiments, the underlying architecture remains unaltered and executable ecosystems exist as an information overlay that can provide knowledge of source. In further embodiments, the knowledge of the source of the components of the ephemeral architecture may be applied to verify the operational parameters of the executable ecosystem.

In embodiments, an executable ecosystem VDAX may independently initiate unique genomic correlation constructions. In further embodiments, the correlation constructions may provide for verification of attribution of subcomponents within the Enclave VDAX. In some embodiments, the correlation constructions may include—LNA (genomic correlation), CNA (genomic engagement-integrity), and/or PNA (genomic engagement-eligibility. In this example, these constructions may enable virtual authentication.

In embodiments, an executable ecosystem VDAX may independently initiate unique genomic differentiation constructions (e.g., ZNA). In some of these embodiments, the executable ecosystem-initiated differentiation constructions may be applied to determine what components are responsible for specific operations within the ecosystem and/or the determination that the component is isolated. In some embodiments, the differentiation constructions may include ZNA (genomic code-isolation). In this example, these differentiations may enable virtual affiliation.

In embodiments, executable ecosystem VDAXs may acquire their unique genomic correlation constructions directly. In further embodiments, the correlation constructions may provide for verification of attribution of subcomponents within genomic descendent VDAX such as an enclave VDAX or a cohort VDAX. In some embodiments, the correlation constructions may include LNA (genomic correlation), CNA (genomic engagement-integrity), and/or PNA (genomic engagement-eligibility. In this example, these constructions may enable virtual authentication.

In embodiments, executable enclave VDAXs may acquire their unique genomic differentiation constructions directly. In further embodiments, the executable enclave-initiated differentiation constructions may be applied to determine what components are responsible for specific operational or the determination that the component is alone. In some embodiments, the differentiation constructions may include ZNA (genomic code-isolation). In this example, these differentiations may enable virtual affiliation.

In embodiments, executable enclave VDAXs may acquire their unique genomic correlation constructions directly. In further embodiments, the correlation constructions may provide for verification of attribution of subcomponents within genomic decedent VDAX such as a dependent VDAX or a cohort VDAX. In some embodiments, the correlation constructions may include LNA (genomic correlation), CNA (genomic engagement-integrity), and/or PNA (genomic engagement-eligibility. In this example, these constructions may enable virtual authentication.

In embodiments, executable cohort VDAXs may acquire their unique genomic correlation constructions directly. In further embodiments, the correlation constructions may provide for verification of attribution of subcomponents within genomic decedent VDAX such as a dependent VDAX. In some embodiments, the correlation constructions may include LNA (genomic correlation), CNA (genomic engagement-integrity), and/or PNA (genomic engagement-eligibility. In this example, these constructions may enable virtual authentication.

In embodiments, executable cohort VDAX may acquire their unique genomic differentiation constructions directly. In further embodiments, the Executable Enclave initiated differentiation constructions may be applied to determine what components are responsible for specific operational or the determination that the component is isolated. In some of these embodiments, the executable ecosystem initiated differentiation constructions may be applied to determine what components are responsible for specific operations within the ecosystem and/or the determination that the component is isolated. In some embodiments, the differentiation constructions may include ZNA (genomic code-isolation). In this example, these differentiations may enable virtual affiliation.

In embodiments, an executable VDAX (where unrelated VDAX engage) may acquire their unique genomic correlation constructions via alternate genomic sub-constructions. In further embodiments, the correlation constructions may provide for verification of attribution of unrelated components. In some embodiments, the correlation constructions may include—LNA (genomic correlation), CNA (genomic engagement-integrity), and/or PNA (genomic engagement-eligibility. In this example, these constructions may enable virtual authentication.

In embodiments, executable VDAX (where unrelated VDAXs engage) may acquire their unique genomic differentiation constructions via alternate genomic sub-constructions. In further embodiments, the Executable Enclave initiated differentiation constructions may be applied to determine what components are responsible for specific operational or the determination that the component is isolated. In some of these embodiments, the executable ecosystem-initiated differentiation constructions may be applied to determine what components are responsible for specific operations within the ecosystem and/or the determination that the component is isolated. In some embodiments, the differentiation constructions may include ZNA (genomic code-isolation). In this example, these differentiations may enable virtual affiliation.

In embodiments, multiple constructed executable genomic topologies may exist simultaneously. In some embodiments, these multiple genomic topologies may provide genomically enabled operations for different architectural functions. In these example embodiments, the different architectural functions may include, verification of source, validation of operation or validation of payment of license fees.

In embodiments, each executable ecosystem has a unique genomic construction by which correlation and differentiation attributes are derived, these attributes control the genomic topology of its enclaves. In some embodiments, each executable enclave may have a unique genomic construction by which correlation and differentiation attributes are derived, whereby these genomic attributes control the genomic topology of its cohorts. In further embodiments, these unique constructions provide for differentiation across species, progeny, and siblings.

In embodiments, ephemeral architectures, having various genomically constructed configurations are capable of transforming binary data into as VBLS based digital objects and or streams. In embodiments, the ephemeral architecture security platform provides virtual agility. In embodiments, VBLS may refer to languages spoken by an enclave or a cohort to another enclave or cohort that may be uniquely understood by the recipient enclave or cohort—that is, languages that are only understandable by the recipient enclave or cohort. In this example, interlopers aiming to include unauthorized cohorts, viruses, and/or malware, cannot produce or decipher VBLS between authorized cohorts.

In embodiments, VBLS transformed binary data may be exchanged and prosecuted by components from two or more different configurations having common genomic correlation and differentiation. In embodiments, the different configurations provide for state information for Executable Ecosystem operational parameters. In further embodiments, these different configurations are each able to operate subject to their state and functional components with knowledge of associated configuration.

In embodiments, ephemeral architectures may have a plurality of genomically constructed configurations, where certain components maybe capable of transforming executable binaries into Virtual Binary Language Script (VBLS) based digital objects and or streams. In further embodiments, executable binaries may be transformed into VBLS digital objects or VBLS streams, this transformation is accomplished by the application of genomically constructed configuration components. In further embodiments, transformation is accomplished by applying genomic sequence mapping and transformations. In embodiments, the sequences, are central to the computational transformation of digital objects into unique non-recurring genomic engagement factors. In examples, sequences may be broadly disparate, sequences may require processing resulting in specific levels of entropy. In embodiments, the sequence mapping may be compatible with a broad range of protocols and formats or may be initiated with objects exhibiting preexisting entropy, where these objects may be transformed by computationally complex genomic processes and functions into objects exhibiting specific levels of entropy.

In embodiments, VBLS transformed executable binaries may be exchanged and prosecuted by components from two or more different configurations having common genomic correlation and differentiation.

In embodiments, within a specific ephemeral architecture, components may transform VBLS executable binaries (e.g., proprietary computer application) such that the transformed executable binary may only be correctly processed by a specific hardware component (e.g., SoC Core), which components share common genomic correlation and differentiation. In further embodiments, the specific hardware is part of a genomic ecosystem and is able to apply genomic correlation processes to enable processing of the VBLS executable binaries.

In embodiments, an ephemeral architecture VDAX resident component may transform (VBLS) executable binaries (e.g., proprietary computer application) such that the transformed executable binary may only be correctly processed by another Ephemeral Architecture VDAX specific hardware component (e.g., SoC Core), which components share common genomic correlation and differentiation. In further embodiments, another Ephemeral Architecture VDAX may be part of the genomic ecosystem.

In embodiments, within a specific ephemeral architecture, two or more components may transform executable binaries (e.g., proprietary computer application) based on unique genomic constructions, which constructions are known to another component. These transformed binaries may only be reformed as executable binaries by one of these components and no others. The reformation and prosecution of the executable binaries occur in-place. In embodiments, the components are part of the same genomic ecosystem or genomic enclave.

In embodiments, within a specific ephemeral architecture, specific components may transform executable binaries (e.g., proprietary computer application) based on unique genomic constructions, which constructions are known to specific components of another ephemeral architecture. Transformed binaries originating in one architecture may only be reformed as executable binaries by specific components of the other architecture. The reformation and prosecution of the executable binaries occur in-place. In further embodiments, the ephemeral architectures sharing components are part of the same genomic ecosystem or genomic enclave. In further embodiments, the components that are sharing transformed executable binaries conduct a genomic link exchange to provide for knowledge of the source of components. In further embodiments, the knowledge of source of components is used with further genomic constructions to establish a trust relationship between components.

In embodiments, within a specific ephemeral architecture, a component VDAX may transform executable binaries (e.g., proprietary computer application) based on specific unique genomic constructions, which constructions are known only to that component. Such transformed binaries may only be reformed as executable binaries by this specific component and no other. The reformation and prosecution of the executable binaries by this specific component occurs in-place. In embodiments, these component specific transformations apply genomic constructions based on genomic data known only the component VDAX associated. In further embodiments, the transformed components can operate in a secure way where non component applied alterations to the transformed binaries will render the transformed executable binaries inoperable.

FIG. 10 illustrates an example of a security platform having an ephemeral architecture that serves an executable ecosystem 1000. As discussed, an executable ecosystem 100 may be any ecosystem that is self-contained, such as a computing device (e.g., a server, a mobile device, a personal computer, a laptop computer, or the like). In embodiments, an ephemeral architecture provides a framework for cohorts 1006 to create and decipher VBLS based isolations of executable code instances, thereby providing a real-time virtual trusted executing domain that is not subject to intelligent external observation. For example, in a computing device, enclaves 1004 may include the system-on-chip (SoC) of the computing device, the operating system of the device, and applications. In this example, ecosystem, the independent cohorts 1006 of the system-on-chip enclave may include processor cores, memory devices (e.g., RAM, ROM), and the like. The independent cohorts 1006 of the operating system enclave may include a kernel of the operating system, various drivers (network drivers, file system driver, print driver, video driver, camera driver, dependent "surrogate" cohort, and the like), shared libraries, and the like. In the example, the dependent cohorts 1008 of an application may include threads, APIs, files, and the like. In some embodiments, each enclave (SoC, operating system, application) may be assigned a genomic data set (e.g., ZNA, LNA, CNA, and/or PNA), which is inherited by the cohorts of each respective enclave. In embodiments, an ecosystem VDAX may create an ephemeral enclave when an application is accessed, whereby the ephemeral enclave is created for the cohorts of the application, the cohorts of the operating system that are implicated by the application, and the cohorts of the SoC that are called by the operating system in executing the application. In this example, the cohorts within the ephemeral enclave can authenticate one another, exchange links, and generate VBLS. At execution time, certain threads of an application may request resources from the kernel of the operating system. When a certain thread is executed, an independent cohort VDAX representing the application thread generates VBLS based on the executable code of the certain thread that requests the resource of the kernel. In this scenario, the application thread may be authenticated by an independent cohort VDAX representing the kernel (e.g., a kernel VDAX) using an ecosystem genomic progeny data that was generated using the ecosystem CNA assigned to the thread application (and vice-versa). In response, the kernel VDAX and a thread VDAX representing the thread exchange links that were generated using the respective LNA of the kernel and the application thread. The thread VDAX may then generate VBLS based on the executable code instance(s) requesting the resource, the ZNA assigned to the application thread, and the link provided by the kernel VDAX. The thread VDAX provides the VBLS to the kernel VDAX, which in turn deciphers the VBLS. The kernel VDAX may then interface with a VDAX corresponding to the requested resource (e.g., a camera driver to access a camera of the computing device, dependent "surrogate" cohort) using VBLS that is only decipherable by the kernel or the requested resource.

In some embodiments, dependent applications (as opposed to independent applications) are not capable of secure VBLS isolation of their internal API and thread components. However, both independent and dependent applications are capable of secure VBLS inter-process communication with each other and with authenticated external resources (e.g., operating system, systems on chip). In these embodiments, ephemeral enclaves enable secure VBLS isolation of the kernel and processing cores, ensuring all digital objects on the system bus may only engage with specific application, operating system, and/or SoC cohorts.

Figure 11:
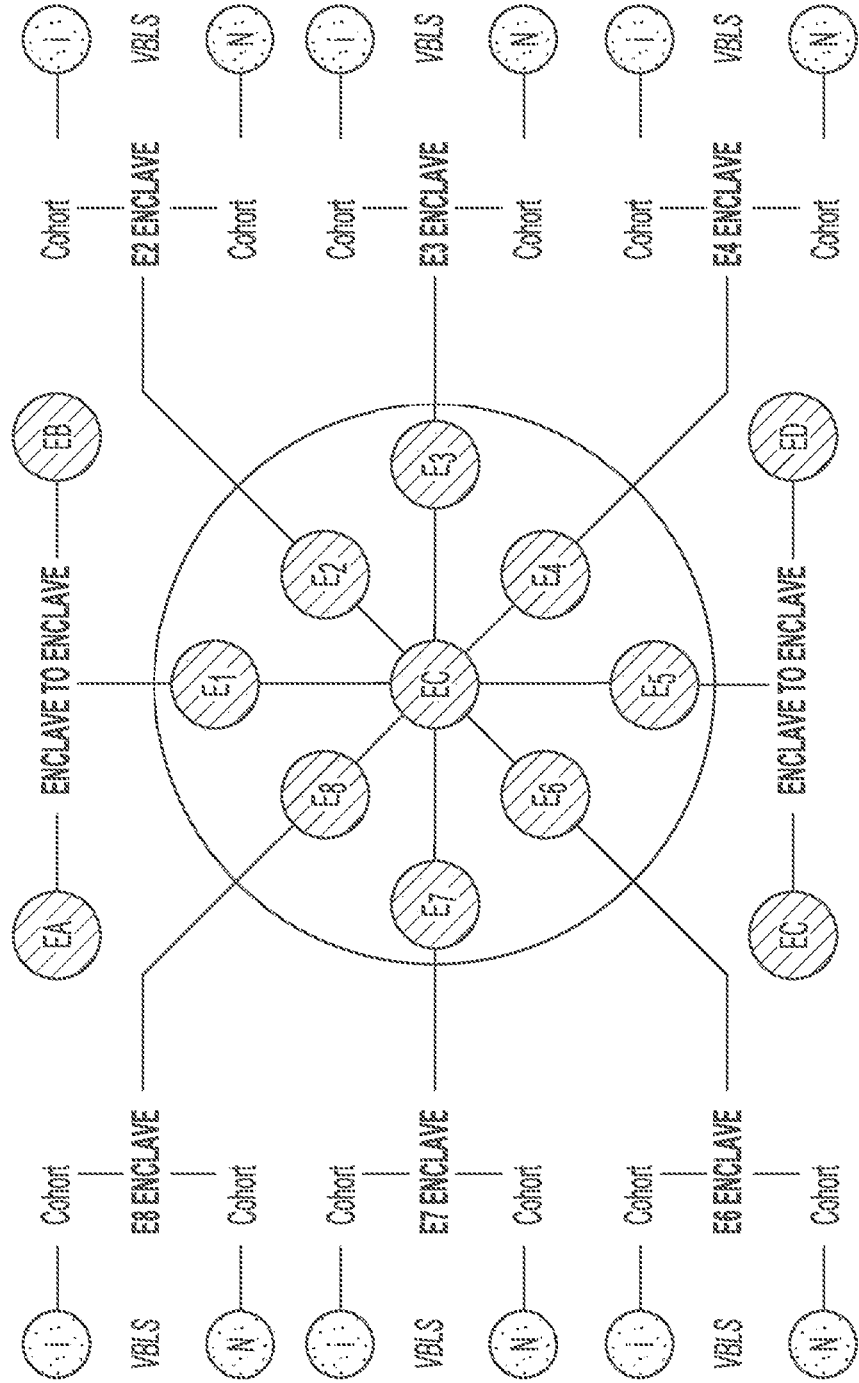
FIGS. 11 and 12 illustrate examples of different CG-enabled digital ecosystems that may be formed in accordance with some embodiments of the present disclosure.
Figure 12:
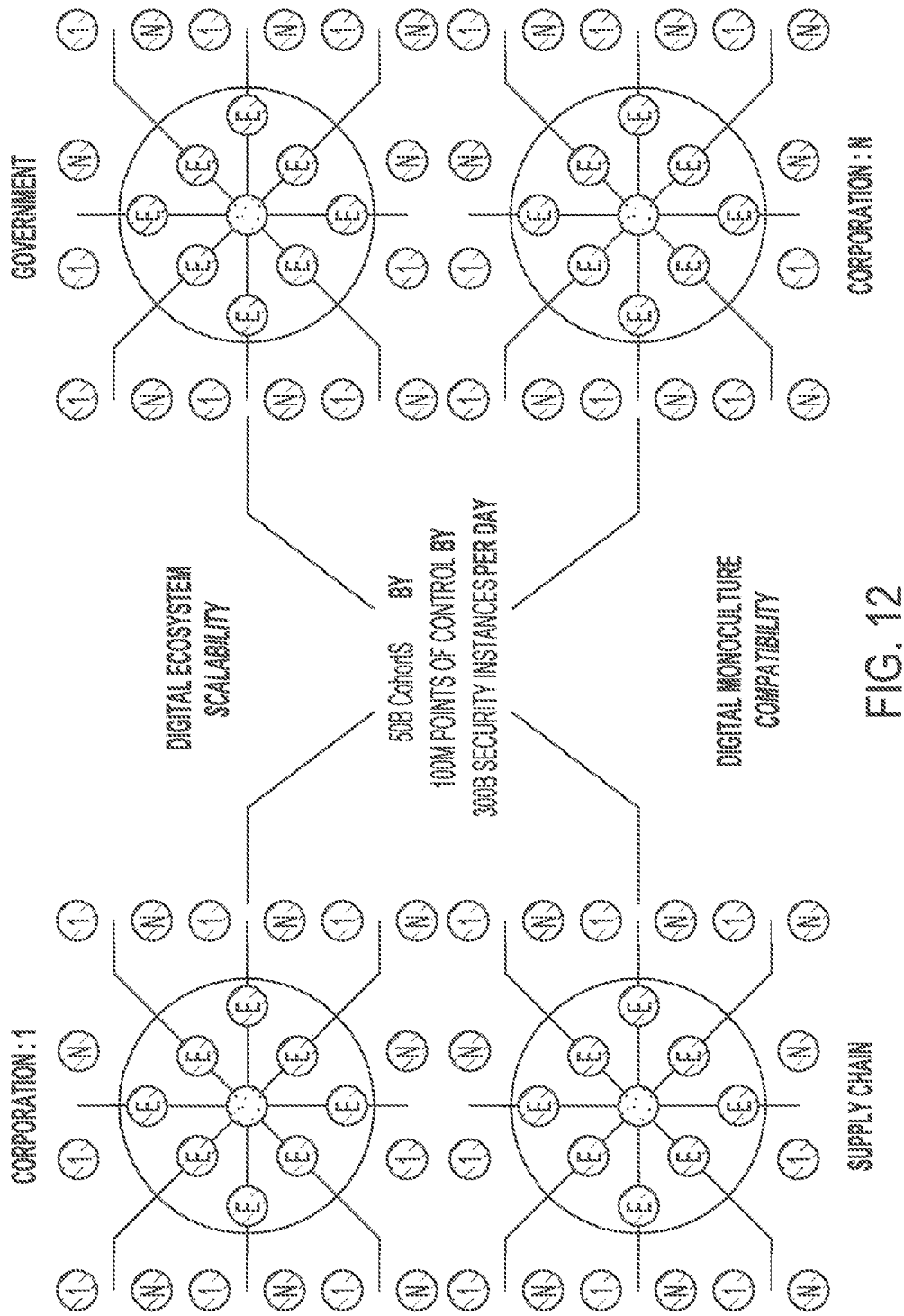

FIGS. 11 and 12 illustrate additional non-limiting examples of CG-enabled digital ecosystems that may be implemented using the teachings of the disclosure. As can be appreciated multiple genomic network topologies may be implemented at various levels of these digital ecosystems.

Cyphergenics Processes

Referring back to FIG. 4, a CG-ESP 400 can be configured with a set of modules that enable an ecosystem member to participate in a digital ecosystem. As discussed, the module configurations of a particular CG-ESP and the genomic constructions that are used in connection with the particular CG-ESP may vary depending on the type of ecosystem, the purpose of the ecosystem, the security requirements of the ecosystem, the decisions of the community owner, and/or the like. FIGS. 13-24 illustrate example methods that may be implemented by various modules of a CG-ESP to perform certain Cyphergenics-based processes. As discussed, in some implementations of the present disclosure, the modules of the CG-ESP may be arranged in a VDAX that may be integrated in a processing device (e.g., as a special-purpose processor/chipset or a dedicated core of the processing device). Additionally or alternatively, the modules of the CG-ESP may be embodied as executable instructions that are executed by one or more processing devices. The following example configurations are provided for example only and are not intended to limit the scope of the disclosure. It is appreciated that additional module configurations may be later developed and implemented in a CG-ESP without departing from the scope of the disclosure.

Genomic Data Generation and Allocation

In some implementations of a CG-ESP, a root DNA module 410 of a progenitor VDAX (e.g., ecosystem VDAX) generates and updates genomic data sets that are assigned to progeny VDAXs of digital ecosystem members (e.g., enclave VDAXs and/or cohort VDAXs). As discussed, the genomic data sets may include genomic eligibility objects, genomic correlation objects, and genomic differentiation objects. In some implementations, the root DNA module 410 of a progenitor VDAX generates a primal genomic data set (also referred to as a "primal DNA set", "master DNA set", or "master genomic data set"). In some of these implementations, the master DNA set is used by the progenitor VDAX to generate genomic data sets (also referred to as "DNA sets" or simply "DNA") for respective members of the digital ecosystem (e.g., enclave VDAXs and/or cohort VDAXs), whereby the generated genomic data sets are assigned to respective members of the digital community. In some implementations, the master DNA set may be assigned to the progenitor VDAX (e.g., ecosystem VDAX), such that the progenitor VDAX uses the master DNA set to engage with the various community members of the digital ecosystem. In other implementations, the progenitor VDAX may generate its genomic data set from the master genomic data set, such that the genomic data set of the progenitor VDAX is generated in the same manner as the genomic data sets of the other community members of the digital ecosystem.

In some implementations of a CG-ESP 400, the root DNA module 410 of a progenitor VDAX is configured to generate one or more master eligibility objects (e.g., a master CNA object and/or a master PNA object), a master correlation object (e.g., a master LNA object), and a master differentiation object (e.g., a master XNA object). It is noted that in some implementations, an EIC module 420 may include a root DNA module 410 that generates genomic data sets that are used in connection with ephemeral architectures. In these implementations, genomic data sets may include differentiation objects (e.g., ZNA objects) as well as any other suitable genomic constructions (e.g., CNA, PNA, and/or LNA objects).

In some example implementations, the root DNA module 410 (e.g., the PNA module 414 and/or the CNA module 412) may derive one or more unique eligibility objects (e.g., PNA objects and/or CNA objects) for each ecosystem member (enclave and/or cohort) of the digital ecosystem based on one or more master genomic eligibility objects (e.g., master PNA object and/or master CNA object). In some of these implementations, each ecosystem member is assigned one or more unique genomic eligibility objects (e.g., a unique PNA object and/or a unique CNA object) that is/are correlated to the respective genomic eligibility objects of each other respective members of the digital ecosystem. As discussed throughout the disclosure, ecosystem members may use their respective genomic eligibility objects to confirm engagement eligibility and engagement integrity with one another during the link exchange process.

In some implementations, the root DNA module 410 (e.g., the LNA module 416) is configured to generate unique genomic correlation objects (e.g., LNA objects) that are assigned to each respective enclave (e.g., which may be assigned to one or more enclave VDAXs that represent the enclave). As discussed, the genomic correlation objects enable informed genomic correlation amongst community members. In some implementations, the root DNA module 410 generates a master genomic correlation object (e.g., a master LNA object) from which the root DNA module 410 generates one or more genomic correlation objects (e.g., enclave-specific LNA objects). In some of these implementations, each enclave is assigned a respective enclave-specific genomic correlation object, whereby the cohorts of a respective enclave are each assigned and use the enclave-specific correlation object (or an otherwise sufficiently correlated derivation of the enclave-specific correlation object) to exchange links with other members (other cohort VDAXs and/or the enclave VDAX) of the enclave. Additionally or alternatively, an ecosystem-level genomic correlation object may be assigned to an ecosystem VDAX, such that any members of the digital ecosystem may be assigned the ecosystem-level genomic correlation object. In these implementations, the genomic correlation object may be the master genomic correlation object or may be a genomic correlation object derived from the master genomic correlation object (e.g., as discussed below).

Similarly, the root DNA module 410 (e.g., the XNA module or EIC module) of a progenitor VDAX generates unique differentiation objects (e.g., XNA objects or ZNA objects) that are assigned to each respective enclave (e.g., which may be assigned to one or more enclave VDAXs that represent the enclave), whereby the cohorts of each enclave are respectively assigned and use the enclave-specific differentiation object (or an otherwise sufficiently correlated derivation of the enclave-specific correlation object) to exchange for unique relationships with other members (other cohort VDAXs and/or the enclave VDAX) of the enclave. In implementations, the root DNA module 410 of a progenitor VDAX may be configured to generate genomic differentiation objects for the ecosystem in the same or similar manner as genomic correlation objects.

Figure 13:
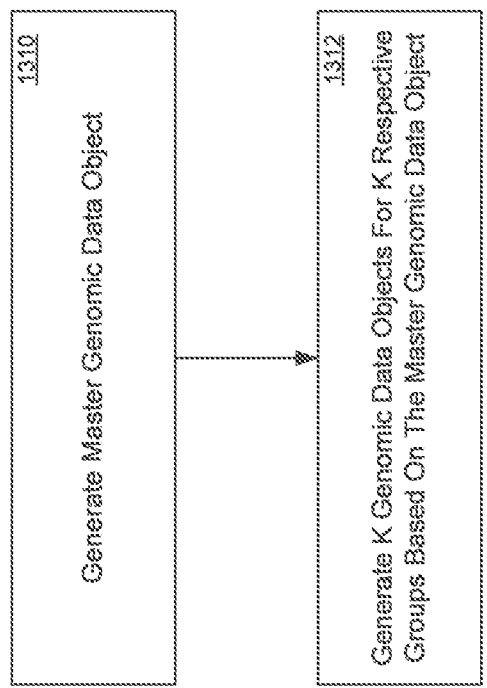
FIG. 13 illustrates an example process for generating genomic data objects in accordance with some embodiments of the present disclosure.

It should be appreciated from this disclosure that the root DNA module 410 may be configured with different algorithms to generate correlation objects and/or differentiation objects for a digital ecosystem without departing from the scope of the disclosure. FIG. 13 illustrates a process that may be executed by a progenitor VDAX (e.g., root DNA module 410) to generate genomic correlation objects and/or genomic differentiation objects according to some implementations of the present disclosure. For purposes of explanation, the term genomic data object may include genomic correlation objects and/or genomic differentiation objects. In the example of FIG. 13, the data structure (e.g., binary matrix, vector, and/or the like) that embodies the master genomic data object may be referred to as "GDX", while the derived genomic data objects (e.g., enclave-level genomic correlation objects and/or enclave-level genomic differentiation objects) may be referred to as $GDX_Y$, where $GDX_Y$ is the genomic data object assigned to the $Y^{th}$ group (e.g., enclave) of K groups in the digital ecosystem.

At 1310, the root DNA module 410 generates the master genomic data object. As discussed, the master genomic data object may refer to a master genomic correlation object or a master genomic differentiation object. In implementations, the root DNA module 410 generates a random binary information data set, GDX (e.g., master correlation object and/or master differentiation object), having dimension N. The random binary information data set, GDX, may have any suitable structure. In some implementations, the root DNA object is a binary matrix.

At 1312, the root DNA module 410 generates genomic data objects (e.g., genomic correlation objects and/or genomic differentiation objects) for K groups (e.g., enclaves) of the digital ecosystem. In some implementations, the root DNA module 410 derives k additional binary information data sets, $GDX_{1 \ldots k}$, representing unique genomic ecosystems or enclaves, where each of $GDX_{1 \ldots K}$ has dimension N and exhibits the same level of entropy as GDX. Table-1 illustrates an example process for deriving the K additional binary information data sets, $GDX_{1 \ldots k}$.

TABLE 1

| Number | Operation |
|--------|-----------|
| 1. | Select T primitive binary polynomials of degree P; |
| 2. | Modify GDX by using T primitive binary polynomials to derive $GDX_T$; |

TABLE 1-continued

| Number | Operation |
| --- | --- |
| 3. | Generate k genomic data objects for K respective ecosystem groups; |

In the example of Table 1, the root DNA module 410 may select the T primitive binary polynomials of degree P, such as T=N/X. The root DNA module 410 may then modify the master genomic data object, GDX, using the T primitive binary polynomials. For example, the root DNA module 410 may apply the following to modify GDX into $GDX_T$: $g(x)=1+a_1*x+ \ldots +a_{P-1}*x^{P-1}+x^P$. It is appreciated that the root DNA module 410 may use other suitable techniques to modify GDX into $GDX_T$. The root DNA module 410 may use the transformed master genomic data object, $GDX_T$, to generate k genomic data objects for K groups.

In some implementations, the root DNA module 410 may generate a genomic data object ($GDX_y$) for the $y^{th}$ group of the k groups according to the example process depicted in Table 2 below. It is noted that the example of Table 2 is shown as being performed as part of the generation of a genomic data object. Additionally, in some implementations of the present disclosure, the example process of Table 2 or variations thereof may be used by the root DNA module 410 to modify genomic data objects (e.g., when updating the genomic data objects of an enclave and/or ecosystem).

TABLE 2

| Number | Operation |
| --- | --- |
| 1. | Select an L-bit sequence, $S_y$; |
| 2. | Map $S_y$ into $GDX_T$ to obtain a transformation value, $TV_y$; |
| 3. | Modify GDX using $TV_Y$ to obtain $GDX_y$. |

In the example of Table 2, the L-bit binary sequence, $S_y$, is a value between 0 and ($2^L$-1). In some implementations, the number of unique ecosystems and/or enclaves, k, is bounded by L. The sequence, $S_y$ may be a private sequence, a public sequence, or a randomly generated sequence. In some implementations a new sequence, $S_y$, may be randomly generated for each group. In this way, each genomic data object, $GDX_y$, is generated using a different sequence. Alternatively, the root DNA module 410 may be configured to select a public or private sequence from any suitable data source. In these implementations, each genomic data object, $GDX_y$, is still generated using a different sequence, thereby ensuring that each group (e.g., enclave) has a different genomic data object assigned thereto.

In some implementations, the mapping step of the example provided in Table 2 may be performed by the sequence mapping module 440, whereby the root DNA module 410 provides the sequence and $GDX_T$ as input to the sequence mapping module 440 and the sequence mapping module 440 maps the sequence into $GDX_T$ to obtain the transformation value, $TV_Y$. In some implementations, the root DNA module 410 may be configured to map the sequence into the $GDX_T$.

In some implementations, the root DNA module 410 may use a computational function (e.g., a cipher, cipherless, or hybrid function) to modify GDX. In some of these implementations, the computational function receives the master genomic data object, GDX, and the transformation value, $TV_y$, and outputs the genomic data object, $GDX_y$, that is assigned to the $y^{th}$ group of the digital ecosystem. In some implementations, the modification of GDX is performed by the binary transformation module 450, whereby the root DNA module 410 invokes the binary transformation module 450 when generating a genomic data object.

In the examples of Tables 1 and 2, the root DNA module may use a wide range of different configurations (e.g., executable computational methods) to modify GDX using the primitive polynomials, determine $TV_K$, select S, map $S_K$ into $R_T$, and/or transform $GDX_T$. Furthermore, the examples of Tables 1 and 2 depict a process for generating a genomic data objects that are assigned to respective groups of an ecosystem. As discussed, an ecosystem VDAX and/or an enclave VDAX may be configured to modify the master genomic data object and/or one or more genomic data objects of one or more groups. For example, an ecosystem VDAX may modify a genomic data object of an enclave so as to alter the genomic topology of the enclave (e.g., to remove one or more cohorts from the enclave). In some implementations, an ecosystem VDAX or an enclave VDAX may modify the genomic data objects using the processes presented in Tables 1 and 2. For example, in modifying a current genomic data object of a particular enclave, an ecosystem VDAX or the enclave VDAX representing the enclave may select T binary polynomials of degree P, transform the current genomic data object using the T polynomials, select an L-bit sequence, map the sequence into the transformed genomic data object to obtain a transformation value, and modify the current genomic data object using the transformation value to obtain a new genomic data object for the particular enclave. This new genomic data object may then be provided to the cohorts of the enclave that are to remain in the enclave. In this way, any cohorts in the enclave that were not provided the new genomic data object will no longer be able to engage with the remaining cohorts of the enclave. Similarly, if an unauthorized VDAX were able to obtain a genomic data object (e.g., genomic correlation object or genomic differentiation object) for the ecosystem or an enclave thereof, the ecosystem VDAX or the enclave VDAX may generate an updated genomic data object and distribute the updated genomic data to the authorized VDAXs of the ecosystem or enclave. It is appreciated that the modification of genomic data objects may be performed using later developed processes as well without departing from the scope of the disclosure.

In certain scenarios, the genomic data objects (e.g., master genomic data objects and/or allocated or unallocated genomic data objects) of a digital ecosystem may require special protection due to the sensitivity of this data. In some implementations, a CG-ESP 400 (e.g., the root DNA module 410) is configured to securely retain genomic data objects (e.g., master genomic data objects and/or allocated or unallocated genomic data objects of ecosystem members) and/or data used to generate the genomic data objects. In some of these implementations, the CG-ESP 400 may be configured to store genomic data objects and/or data used to generate the genomic data objects using a Shamir threshold scheme (also referred to as "Shamir's Secret Sharing"). In implementations, the Shamir threshold scheme may be adapted to store any type of genomic data object (e.g., an LNA object, a CNA object, a PNA object, a XNA object, a ZNA object, or the like). For example, in the case of a master genomic data object, GDX, that is of dimension 4096×4096, GDX may be segmented into $2^{14}$ 1024-bit sections. For example, the GDX matrix may be segmented by generating two sections for each $2^{12}$ rows of GDX. In this example, each of the respective 1024-bit sections is represented as a 1024-bit polynomial. A Shamir (5,3) threshold scheme may then be applied to each of the respective 1024-bit polynomials (which respectively represent the segments). In some implementations, the Shamir (5,3) threshold scheme may be further applied to store the data used to generate the k genomic data objects that were derived from GDX. For example, the Shamir (5,3) threshold scheme may be applied to each of the primitive binary polynomials (e.g., sixteen 256-bit primitive binary polynomials) that were used to modify GDX into $GDX_T$. Additionally or alternatively, the Shamir (5,3) threshold scheme may be applied to each of the Sequences, $S_y$, that were used to generate the group-specific genomic data objects, $GDX_y$. For example, if each sequence, $S_y$, is a 256-bit value, then each 256-bit value may be represented as a binary polynomial and Shamir (5,3) threshold scheme may be applied to each of the binary polynomials. It is appreciated that the foregoing are examples of how Shamir Secret Sharing may be applied to store genomic data objects and related data and that the values provided are for example only. Furthermore, additional or alternative techniques may be developed for securely storing the genomic data objects.

Figures 14, 15:
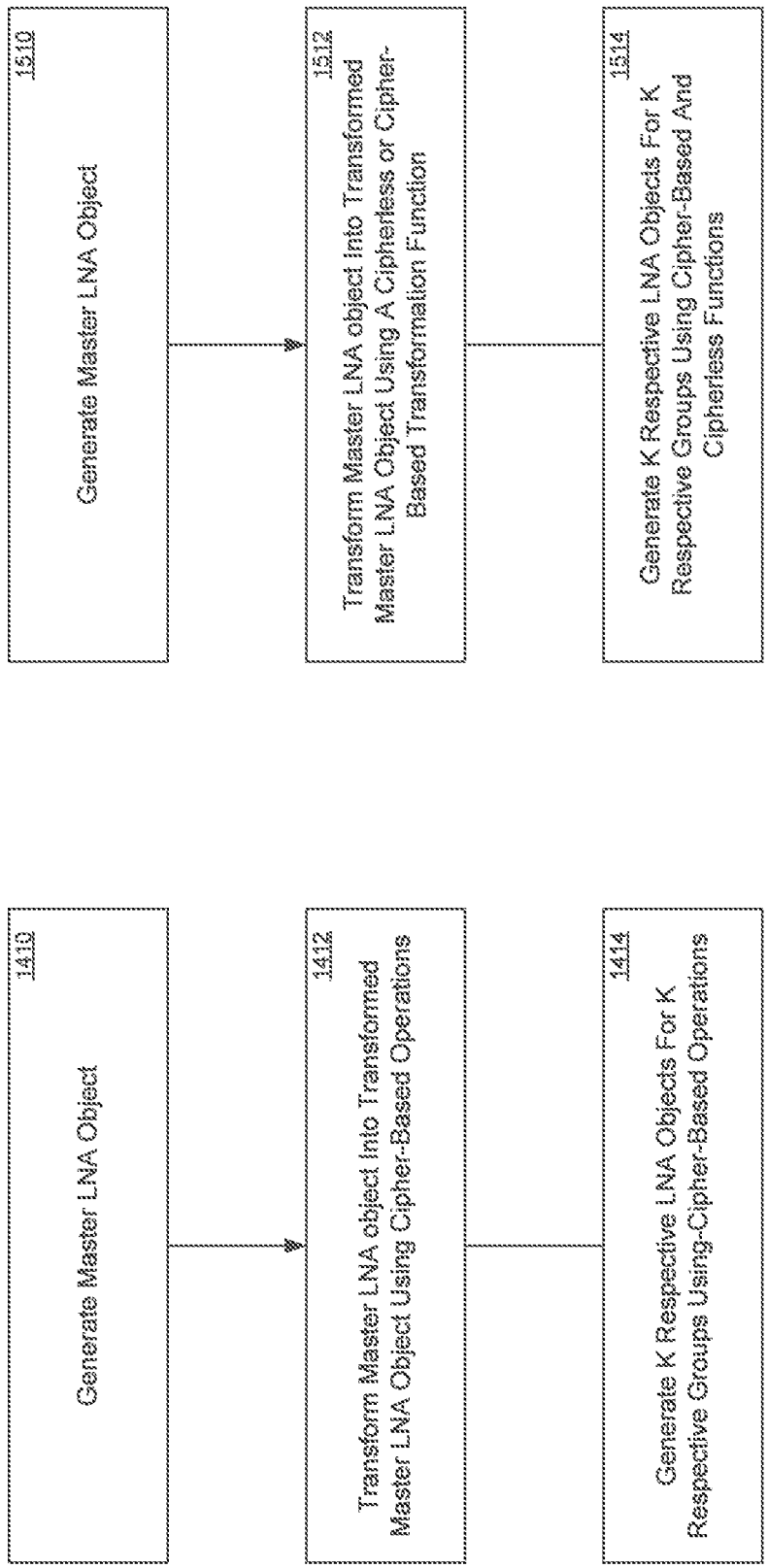
FIGS. 14 and 15 illustrates example processes for generating LNA objects in accordance with some embodiments of the present disclosure.

As mentioned, the example process may be implemented in a root DNA module 410 to generate genomic correlation objects (e.g., LNA objects) and/or genomic differentiation objects (e.g., XNA or ZNA objects). The example processes may be cipher-based, cipherless, or hybrid. FIGS. 14 and 15 provide examples of cipher-based and hybrid generation of LNA objects. In these examples, certain values (e.g., dimensions of genomic data objects and other data structures, sizes of sequences, the numbers of groups, etc.) are defined for purposes of explanation. The values are provided for example only and may be adjusted to achieve different optimizations and/or effects.

LNA Generation

In some implementations of the present disclosure, a root DNA module 410 may include an LNA module 416 that is configured to generate LNA objects that are assigned to members of a digital ecosystem. As discussed, the configuration of the LNA module 416 may be cipher-based, cipherless, or hybrid. In some implementations, the process of FIG. 13 may be implemented in an LNA module 416 to generate genomic correlation objects (e.g., LNA objects). For example, FIGS. 14 and 15 provide example methods for generation genomic correlation objects according to some implementations of the present disclosure. In these examples, the LNA module 416 is configured to generate a master LNA object and to derive a set of k LNA objects. In some implementations, the members (e.g., cohorts) in a respective group have a mutual identity of interest. In implementations, a respective LNA object may be assigned to a respective group (e.g., enclave or the entire ecosystem) in a digital ecosystem, such that the community members (e.g., cohort VDAXs) in the respective enclave may use the respective LNA object to exchange links. In these example configurations, the LNA module 416 is configured to generate LNA objects that are structured in fixed-size binary matrices (e.g., n×m matrices). It is appreciated that the binary matrices may be represented as binary vectors.

As can be appreciated from the disclosure, the configurable properties of a CG-ESP allow a community owner (e.g., the entity defining the size, structure, security levels, intended use, and/or membership requirements) to parameterize the LNA module 416 with a maximum number of groups (K), the dimensions of the LNA object (e.g., n×m), the size of LNA object zones, and/or other suitable parameters. Furthermore, as is discussed throughout the present disclosure, the community owner may define the types and ordering of computational operations that are used in the LNA object generation process. For example, the community owner may configure an LNA module 416 with specific cipher-based functions (e.g., different encryption functions, disambiguation functions, and/or the like) and/or cipherless functions (e.g., hash functions, parameterized cyclic bit-shift operations, and/or the like) that are used to, for example, generate a master genomic correlation object and/or modify a genomic correlation object.

In discussing the examples of FIGS. 14 and 15, the example LNA objects are described as 4096 bit×4096 bit matrices. It is appreciated that the LNA objects may be larger or smaller depending on the type of the digital community, the security requirements of the digital community, the intended size of the digital community, the purpose of the digital community, and/or other suitable configurations. For example, the size of the LNA objects may be 9182 bits×9182 bits, 1024 bits×1024 bits, 512 bits×512 bits, 1024 bits×256 bits, or any other suitable value. Furthermore, in this example the maximum number of enclaves, k, for which LNA objects are generated is 4096 groups (enclaves or ecosystems). It is appreciated that the value k may be adjusted in accordance with the needs of the digital community and the community owner. For example, larger and/or more complex ecosystems may have hundreds or thousands of enclaves, while smaller and/or less complex ecosystems may have as little as ten, five, two, or one enclave. In some example implementations, the LNA module 416 may use computationally complex mathematical structures, such as binary primitive polynomials (e.g., of degree 256), to generate the k (e.g., k=4096) unique LNA objects of size n×m (e.g., 4096 bits×4096 bits). While in the provided examples n is equal to m (e.g., n=4096 and m=4096), it is not required that n equal m. In implementations, the LNA module 416 may randomly generate a master LNA object (which may be referred to as "LNA" in the examples below), and may generate k different LNA objects from the master LNA object (where the $y^{th}$ LNA object generated from LNA is referred to as "$LNA_y$") for k respective groups of the digital ecosystem.

FIG. 14 below provides an example cipher-based method for generating LNA objects for a digital ecosystem according to some example implementations of the present disclosure. It is appreciated that the LNA module 416 may be configured to generate LNA objects in other suitable cipher-based manners without departing from the scope of the disclosure.

At 1412, the LNA module 416 generates a master LNA object. In example implementations, the LNA module 416 generates a random binary information data set structured in a 4096-bit×4096-bit matrix. In some of these implementations, the random binary information data set is the master LNA object, where each row of the master LNA object is organized in a set of j fixed-length zones (e.g., 16 256-bit zones), such that the $i^{th}$ row of LNA may be defined as: $(t_{i,1}, \ldots, t_{i,j})$. For example, the master LNA object may be defined for i=1 . . . 4096 and for j=16. In this example, the master LNA object may comprise 4096 rows, where each row includes 16 zones that are each 256 bits long. It is appreciated that the foregoing values are provided for example only.

At 1414, the LNA module 416 transforms the master LNA object, LNA, into a transformed LNA object, $LNA_T$. In implementations, the LNA module 416 transforms LNA into $LNA_T$ using j (e.g., j=16) randomly selected binary primitive polynomials, $g_h(x)$ for h=1 j. In some of these implementations, the binary primitive polynomials are each of a specified degree (e.g., 256-degree binary primitive polynomials). In these implementations, each respective value represented by each respective row $t_i$ of is transformed to a respective modified value, $t_i(m)$. In some of these implementations, each row of LNA may be transformed according to:

$$t_i(m)=(x^{t_{i,1}} \bmod g_1(x) \| x^{t_{i,2}} \bmod g_2(x) \| \ldots \| x^{t_{i,j}} \bmod g_j(x)).$$

In this example, the foregoing transformation function is cipher-based, as the function is reversable by solving a discrete logarithm problem. It is appreciated that the master LNA object may be transformed in other suitable manners without departing from the scope of the disclosure.

At 1416, the LNA module 416 generates k LNA objects for k respective groups of a digital ecosystem. In some implementations, the LNA module 416 generates a respective LNA object for each respective group in a digital community. In some of these implementations, the LNA module 416 derives the LNA object based on the master LNA object and the transformed LNA object, $LNA_T$. Table 3 defines an example process for generating an LNA object based on a master LNA object (denoted as LNA) and a transformed master LNA object (denoted as $LNA_T$). In this example, the LNA module 416 may generate a $y^{th}$ LNA object for a $y^{th}$ group (e.g., Group)), of the digital ecosystem as follows:

TABLE 3

| Number | Operation |
|---|---|
| 1. | Select an L-bit sequence, $S_y$; |
| 2. | Map $S_y$ into $LNA_T$ to obtain a transformation value, $TV_y$; |
| 3. | Modify LNA using $TV_Y$ to obtain $LNA_y$. |

In an example implementation, the LNA module 416 may select a 256-bit sequence, $S_y$. In the example configuration, the value of L is 256, such that the value of $S_y$ is between 0 and ($2^{256}$−1). Depending on the configuration of the LNA module 416, the $S_y$ may be a private sequence, a public sequence, or a randomly generated sequence. As discussed, a new sequence, $S_y$, may be randomly generated for each group. In this way, each LNA object, $LNA_y$, is generated using a different sequence. Alternatively, the LNA module 416 may be configured to select a public or private sequence from any suitable data source. In these implementations, LNA object, $LNA_y$, is still generated using a different sequence, thereby ensuring that each group (e.g., enclave) has a different genomic data object assigned thereto.

In some implementations, the mapping step of the example provided in Table 3 may be performed by the sequence mapping module 440, whereby the LNA module 416 provides $S_y$ and $LNA_T$ as input to the sequence mapping module 440 and the sequence mapping module 440 outputs a transformation value, $TV_y$, that is determined by mapping the sequence into $LNA_T$. In some implementations, the LNA module 416 may be configured to determine the transformation value by mapping the sequence into the $LNA_T$.

In the example of Table 3, the LNA module 416 executes a cipher-based function to modify the master LNA object, LNA, using the transformation value, $TV_y$, to obtain an LNA object, $LNA_y$, for a respective group of the digital ecosystem. In example implementations, the cipher-based function may be an encryption function or a disambiguation function. In some of these implementations, the LNA module 416 is configured to determine the LNA object by providing the transformation value and the master LNA object as input to the binary transformation module 450 when generating a respective LNA object. Alternatively, the LNA module 416 may be configured to determine the LNA object, $LNA_y$, by executing a cipher-based transformation function. Once generated, the progenitor VDAX may assign the LNA object, LNAy, to the $y^{th}$ group (e.g., enclave or ecosystem), whereby the LNA object may be provided to the members of the group (e.g., cohorts within the enclave or ecosystem).

The example of FIG. 14 is provided for example only. It is appreciated that a wide range of different configurations (e.g., executable computational methods) may be developed to, for example, modify the master LNA object in a cipher-based manner, determine a transformation value $TV_K$, select a sequence, map the sequence into the transformed master LNA object, and/or transform the master LNA object to an LNA object.

FIG. 15 below provides an example hybrid method (e.g., at least one cipher-based operation and at least one cipherless operations) for generating LNA objects for a digital ecosystem according to some example implementations of the present disclosure. In some example implementations, the techniques of FIG. 15 may be implemented in the LNA module 416 to generate LNA objects for a digital ecosystem using a combination of cipher-based and cipherless functions. In discussing the example implementations of FIG. 15, the LNA module 416 is described as generating LNA objects of size 4096 bits×4096 bits. In these example configurations, the LNA module 416 derives up to k LNA objects (e.g., k=4096) for k different groups from a master LNA object (e.g., "GDX" in Table 2 above). In example implementations, the cipherless functions may include parameterizable cipherless operations that are parameterizable using one or more secure modification parameters. In example implementations, the cipherless operations may be a combination of XOR and cyclic-shift operations, where the LNA module 416 randomly generates the secure modification parameters to parameterize the combination of XOR and cyclic-shift operations, example implementations of which are described below.

At 1512, the LNA module 416 generates a master LNA object. In example implementations, the LNA module 416 generates a random binary information data set structured in a n×m matrix (e.g., 4096-bit×4096-bit matrix). In some of these implementations, the random binary information data set is the master LNA object, where each row of the master LNA object is organized in a set of n rows $[R_1, R_2, \ldots R_n]$. In this example, $R_i$ may be the $i^{th}$ row of the randomly generated master LNA object and may be defined as $[R_{i,1}, R_{i,2}, \ldots R_{i,m}]$, where $R_{i,j}$ is an individual bit value of the $j^{th}$ column of the $i^{th}$ row. In this example, the master LNA object may comprise 4096 rows, where each row includes 16 zones that are each 256 bits long. It is appreciated that the foregoing values are provided for example only and that the LNA module 416 may be configured to generate the master LNA object in other suitable manners.

At 1514, the LNA module 416 transforms the master LNA object, LNA, into a transformed LNA object, $LNA_T$, using a cipherless transformation function. In implementations, the LNA module 416 transforms LNA into $LNA_T$ using a set of secure modification parameters (SMP). In some implementations, the SMP may define a set of parameters that are used to parameterize a set of parameterizable operations that are applied to a master LNA object. Examples of parameterizable operations may include cyclic bit shifting operations, XOR operations, and/or the like. In these examples, the SMP may define, for each row of the master LNA object, a respective number of bit positions to shift the row in a defined direction and/or a value to XOR the row (e.g., after shifting, before shifting, or in lieu of shifting). For example, the $SMP_i$ may define the secure modification parameters for the $i^{th}$ row and may include a first parameter that indicates a number of bit locations to cyclically shift the $i^{th}$ row (e.g., n bits to the right) and a second parameter that defines a random value that is XOR'd with the $i^{th}$ row. It is appreciated that the second parameter may be a value between 0 and $(2^m-1)$, where m is the number of bits in a row of an LNA object. In these implementations, the LNA module 416 may transform each row of the LNA object using a set of parameterizable operations that are parameterized with the respective SMPs corresponding to the row to obtain the transformed master LNA object, $LNA_T$. In these example implementations, the LNA module 416 may determine the SMPs in any suitable manner, including randomly generating the set of SMPs (e.g., SMP) for each transforming each respective row of the master LNA object. It is appreciated that the LNA module 416 may be configured to transform the master LNA object in other cipherless manners or in cipher-based manners (e.g., step 1414 of FIG. 14) without departing from the scope of the disclosure.

At 1516, the LNA module 416 generates k LNA objects for k respective groups of a digital ecosystem. In some implementations, the LNA module 416 generates a respective LNA object for each respective group (e.g., enclave) in a digital community. In some of these implementations, the LNA module 416 derives the LNA object based on the master LNA object and the transformed LNA object, $LNA_T$. Table 4 defines an example process for generating an LNA object based on a master LNA object (denoted as LNA) and a transformed master LNA object (denoted as $LNA_T$). In this example, the LNA module 416 may generate a $y^{th}$ LNA object for a $y^{th}$ group (e.g., $Group_y$), of the digital ecosystem as follows:

TABLE 4

| Number | Operation |
|---|---|
| 1. | Select an L-bit sequence, $S_y$; |
| 2. | Map $S_y$ into $LNA_T$ to obtain a transformation value, $TV_y$, using a cipher-based mapping function |
| 3. | Modify LNA using $TV_y$ to obtain $LNA_y$. |

In an example implementation, the LNA module 416 may select a 256-bit sequence, $S_y$. In the example configuration, the value of L is 256, such that the value of $S_y$ is between 0 and $(2^{256}-1)$. Depending on the configuration of the LNA module 416, the $S_y$ may be a private sequence, a public sequence, or a randomly generated sequence. As discussed, a new sequence, $S_y$, may be randomly generated for each group. In this way, each LNA object, $LNA_y$, is generated using a different sequence. Alternatively, the LNA module 416 may be configured to select a public or private sequence from any suitable data source. In these implementations, LNA object, $LNA_y$, is still generated using a different sequence, thereby ensuring that each group (e.g., enclave) has a different genomic data object assigned thereto.

In some implementations, the mapping step of the example provided in Table 4 may be a cipher-based sequence mapping function. In some of these implementations, the cipher-based sequence mapping function may be performed by the sequence mapping module 440. In these example implementations, the LNA module 416 determines the transformation value by providing $S_y$ and $LNA_T$ as input to the sequence mapping module 440 and the sequence mapping module 440 maps the sequence into $LNA_T$ to obtain the transformation value, $TV_y$. In some implementations, the LNA module 416 may be configured to perform the sequence mapping function to determine the transformation value.

In some implementations, the LNA module 416 may use a cipherless transformation function to modify the master LNA object, LNA, using the transformation value $TV_y$, to obtain the LNA object, $LNA_y$, for a respective group ($Group_y$) of the digital ecosystem. In example implementations, the cipherless function may include a pre-image resistant hash function, a set of parameterizable operations that are parameterized using the transformation value, or the like.

The example of FIG. 15 is provided for example only. It is appreciated that a wide range of different configurations (e.g., executable computational methods) may be developed to, for example, modify the master LNA object to obtain a transformed master LNA object, select a sequence, determine a transformation value, $TV_k$, and/or transform the master LNA object to an LNA object. Furthermore, in some implementations the cipher-based operations of the example process of FIG. 15 may be replaced with cipherless operations, such that the LNA module 416 may be configured in a cipherless manner.

In the examples of FIGS. 14 and 15, the LNA module 416 may assign a resulting LNA object, $LNA_y$, to a respective enclave of a digital community. In some of these example implementations, an enclave VDAX representing the respective enclave may then assign its LNA object, $LNA_y$, to members (e.g., cohort VDAXs of cohorts) of the enclave. In implementations, the link module 430 of a respective cohort VDAX may modify its assigned LNA object each time the respective cohort VDAX spawns a link for or decodes a link from another cohort VDAX of a cohort in the corresponding enclave. In this way, an LNA object provides a mechanism for facilitating hyper-scalable correlation between members of a corresponding enclave and/or ecosystem. It is appreciated that the examples provided in FIGS. 14 and 15 are example configurations of an LNA module 416 and additional and alternative means for generating LNA objects for community members may be later developed.

Furthermore, the examples of FIGS. 14 and 15 depict processes for generating LNA objects that are assigned to respective groups of an ecosystem. As discussed, an ecosystem VDAX and/or an enclave VDAX may be configured to modify the master LNA object and/or one or more LNA objects of one or more enclaves. For example, an ecosystem VDAX may modify an LNA object of an enclave so as to alter the genomic topology of the enclave (e.g., to remove one or more cohorts from the enclave, to periodically change the LNA object for security reasons, or the like). In this scenario, modification of an LNA object of an enclave would prevent a cohort from exchanging links with other cohorts in the enclave in the future. Absent a modification to the genomic differentiation object (e.g., XNA object), the cohort would still be able to exchange VBLS with cohorts with which links were successfully exchanged. In some implementations, an ecosystem VDAX or an enclave VDAX may modify an LNA object for such purposes using the example process presented in Table 3 or Table 4. For example, in modifying a current LNA object of a particular enclave, an ecosystem VDAX or the enclave VDAX representing the enclave may transform the current LNA object to obtain a transformed LNA object, select an L-bit sequence, map the sequence into the transformed LNA object to obtain a transformation value, and modify the current LNA object using the transformation value to obtain a new LNA object for the particular enclave. This new LNA object may then be provided to the cohorts that are to remain in the enclave. In this way, any cohorts in the enclave that were not provided the new LNA object will no longer be able to exchange links with the cohorts remaining in the enclave. It is appreciated that the modification of genomic data objects may be performed using later developed processes as well without departing from the scope of the disclosure.

XNA Generation

Figure 17:
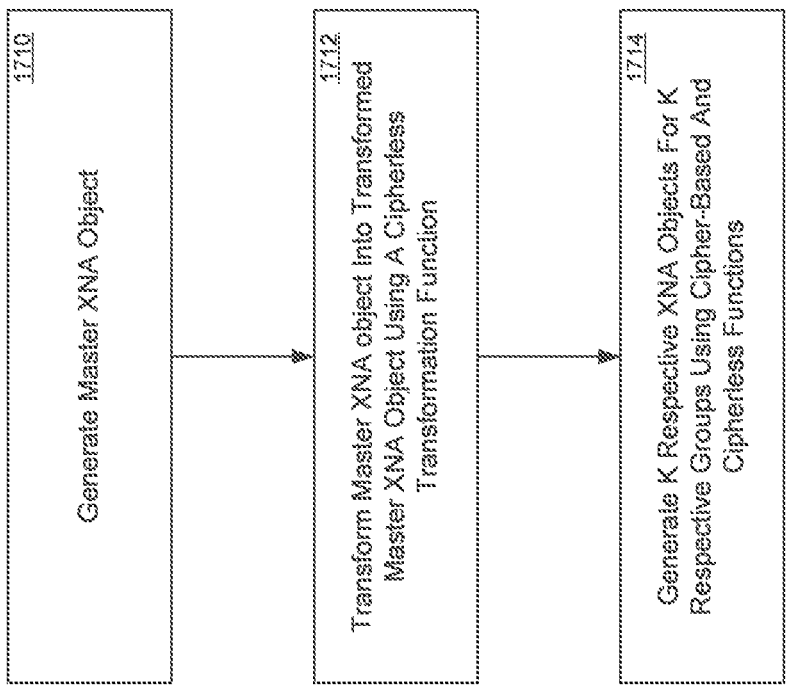
FIGS. 16 and 17 illustrates example processes for generating XNA objects in accordance with some embodiments of the present disclosure.
Figure 16:
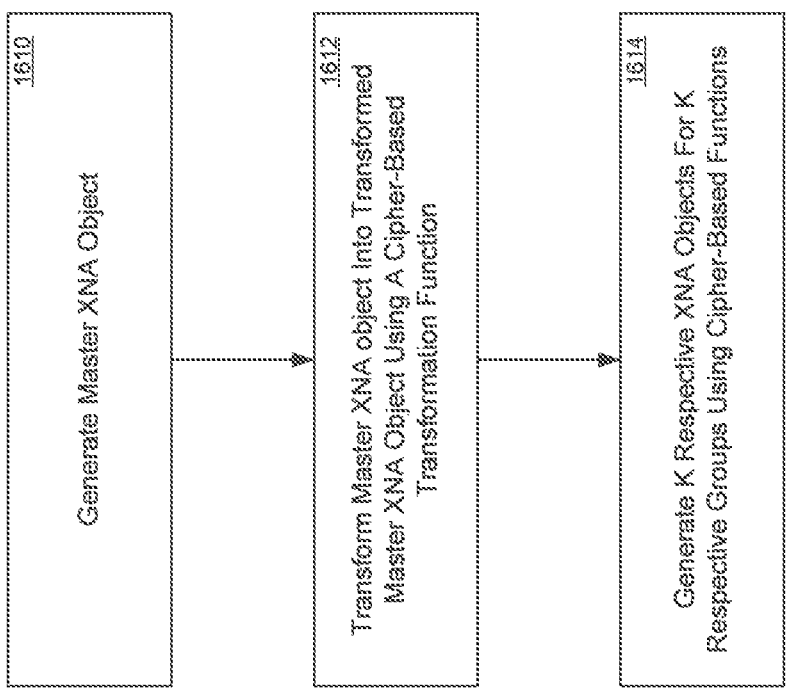

In some implementations of the present disclosure, a root DNA module 410 may include an XNA module 418 that is configured to generate XNA objects that are assigned to members of a digital ecosystem. As discussed, the configuration of the XNA module 418 may be cipher-based, cipherless, or hybrid. In some implementations, the process of FIG. 13 may be implemented in an XNA module 418 to generate genomic differentiation objects (e.g., XNA objects). The examples of FIGS. 16 and 17 provide example methods for generating genomic differentiation objects according to some implementations of the present disclosure. In these examples, the XNA module 418 is configured to generate a master XNA object and to derive a set of k XNA objects for k groups of a digital ecosystem. In these implementations, a respective XNA object may be assigned to a respective group in a digital ecosystem (e.g., an enclave of the digital ecosystem or digital ecosystem in its entirety), such that the respective XNA object is provided to the group members (e.g., cohort VDAXs, enclave VDAXs, and/or the like) thereby allowing the group members to securely exchange VBLS using the respective XNA object (assuming those group members have exchanged links).

As can be appreciated from the disclosure, the configurable properties of a CG-ESP allow a community owner (e.g., the entity defining the size, structure, security levels, intended use, and/or membership requirements) to parameterize the XNA module 418 with a maximum number of groups (k), the dimensions of the XNA object (e.g., n×m), the size of XNA object zones, and/or other suitable parameters. Furthermore, as is discussed throughout the present disclosure, the community owner may define the types of computational functions that are used in the XNA object generation process. For example, the community owner may use specific cipher-based functions (e.g., different encryption functions, disambiguation functions, and/or the like) and/or cipherless functions (e.g., hash functions, parameterized cyclic bit-shift operations, and/or the like) to configure the XNA module 418.

In some example implementations, the XNA module 418 is configured to generate XNA objects that are structured in fixed-size binary matrices (e.g., n×m matrices). It is appreciated that the binary matrices may be represented as binary vectors. In the examples of FIGS. 16 and 17, the example XNA objects are 4096 bit×4096 bit matrices. It is appreciated that the XNA objects may be larger or smaller depending on the type of the digital community, the security requirements of the digital community, the intended size of the digital community, the purpose of the digital community, and/or other suitable configurations. For example, the size of the XNA objects may be 9182 bits×9182 bits, 1024 bits×1024 bits, 512 bits×512 bits, 1024 bits×256 bits, or any other suitable value. Furthermore, in this example the maximum number of enclaves, k, for which XNA objects are generated is 4096 groups (enclaves or ecosystems). It is appreciated that the value k may be adjusted in accordance with the needs of the digital community and the community owner.

For example, larger and/or more complex ecosystems may have hundreds or thousands of enclaves, while smaller and/or less complex ecosystems may have as little as ten, five, two, or one enclave. As will be discussed with respect to the example implementations of FIGS. 16 and 17, the XNA module 418 may use computationally complex mathematical structures, such as binary primitive polynomials (e.g., of degree 256), to generate the k (e.g., k=4096) unique XNA objects of size n×m (e.g., 4096 bits×4096 bits). While in the provided examples n is equal to m (e.g., n=4096 and m=4096), it is not required that n equal m. In implementations, the XNA module 418 may randomly generate a master XNA object (which may be referred to as XNA in the examples below), and may generate k different XNA objects (where a $y^{th}$ XNA object may be referred to as $XNA_y$) from the master XNA object fork respective groups of the digital ecosystem, wherein each group has mutual identity of interest.

FIG. 16 below provides an example cipher-based method for generating XNA objects for a digital ecosystem according to some example implementations of the present disclosure. It is appreciated that the XNA module 418 may be configured to generate XNA objects in other suitable cipher-based manners without departing from the scope of the disclosure.

At 1612, the XNA module 418 generates a master XNA object. In example implementations, the XNA module 418 generates a random binary information data set structured in a 4096-bit×4096-bit matrix. In some of these implementations, the random binary information data set is the master XNA object, where each row of the master XNA object is organized in a set of j fixed-length zones (e.g., 16 256-bit zones), such that the $i^{th}$ row of XNA may be defined as: $(t_{i,1}, t_{i,j})$. For example, the master XNA object may be defined for i=1 . . . 4096 and for j=16. In this example, the master XNA object may comprise 4096 rows, where each row includes 16 zones that are each 256 bits long. It is appreciated that the foregoing values are provided for example only and the master XNA object may have other suitable dimensions as defined by the community owner.

At 1614, the XNA module 418 transforms the master XNA object, XNA, into a transformed XNA object, $XNA_T$. In implementations, the XNA module 418 transforms XNA into $XNA_T$ using j (e.g., j=16) randomly selected binary primitive polynomials, $g_h(x)$ for h=1 . . . j. In some of these implementations, the binary primitive polynomials are each of a specified degree (e.g., 256-degree binary primitive polynomials). In these implementations, each respective value represented by each respective row $t_i$ of is transformed to a respective modified value, $t_i(m)$. In some of these implementations, each row of XNA may be transformed according to:

$$t_i(m) = (x^{r_{i,1}} \mod g_1(x) \| x^{r_{i,2}} \mod g_2(x) \| \ldots \| x^{r_{i,j}} \mod g_j(x)).$$

In this example, the foregoing transformation function is cipher-based, as the function is reversible by solving a discrete logarithm problem. It is appreciated that the master XNA object may be transformed in other suitable manners without departing from the scope of the disclosure.

At 1616, the XNA module 418 generates k XNA objects for k respective groups of a digital ecosystem. In some implementations, the XNA module 418 generates a respective XNA object for each respective group in a digital community. In some of these implementations, the XNA module 418 derives the XNA object based on the master XNA object and the transformed XNA object, $XNA_T$. Table 5 defines an example process for generating an XNA object based on a master XNA object (denoted as XNA) and a transformed master XNA object (denoted as $XNA_T$). In this example, the XNA module 418 may generate a $y^{th}$ XNA object for a $y^{th}$ group (e.g., $Group_y$), of the digital ecosystem as follows:

TABLE 5

| Number | Operation |
|---|---|
| 1. | Select an L-bit sequence. $S_y$; |
| 2. | Map $S_y$ into $XNA_T$ to obtain a transformation value, $TV_y$; |
| 3. | Modify XNA using $TV_Y$ to obtain $XNA_y$. |

In an example implementation, the XNA module 418 may select a 256-bit sequence, $S_y$.

In the example configuration, the value of L is 256, such that the value of $S_y$ is between 0 and ($2^{256}-1$). Depending on the configuration of the XNA module 418, the $S_y$ may be a private sequence, a public sequence, or a randomly generated sequence. As discussed, a new sequence, $S_y$, may be randomly generated for each group. In this way, each XNA object, $XNA_y$, is generated using a different sequence. Alternatively, the XNA module 418 may be configured to select a public or private sequence from any suitable data source. In these implementations, XNA object, $XNA_y$, is still generated using a different sequence, thereby ensuring that each group (e.g., enclave) has a different genomic data object assigned thereto.

In some implementations, the mapping step of the example provided in Table 5 may be performed by the sequence mapping module 440, whereby the XNA module 418 provides $S_y$ and $XNA_T$ as input to the sequence mapping module 440 and the sequence mapping module 440 outputs a transformation value, $TV_y$, that is determined by mapping the sequence into $XNA_T$. In some implementations, the XNA module 418 may be configured to determine the transformation value by mapping the sequence into the $XNA_T$.

In the example of Table 5, the XNA module 418 executes a cipher-based function to modify the master XNA object, XNA, using the transformation value, $TV_y$, to obtain an XNA object, $XNA_y$, for a respective group of the digital ecosystem. In example implementations, the cipher-based function may be an encryption function or a disambiguation function. In some of these implementations, the XNA module 418 is configured to determine the XNA object by providing the transformation value and the master XNA object as input to the binary transformation module 450 when generating a respective XNA object. Alternatively, the XNA module 418 may be configured to determine the XNA object, $XNA_y$, by executing a cipher-based transformation function. Once generated, the progenitor VDAX may assign the XNA object, XNAy, to the $y^{th}$ group (e.g., enclave or ecosystem), whereby the XNA object may be provided to the members of the group (e.g., cohorts within the enclave or ecosystem).

The example of FIG. 16 is provided for example only. It is appreciated that a wide range of different configurations (e.g., executable computational methods) may be developed to, for example, modify the master XNA object in a cipher-based manner, determine a transformation value $TV_K$, select a sequence, map the sequence into the transformed master XNA object, and/or transform the master XNA object to an XNA object.

In implementations, the XNA module 418 may be configured with a hybrid configuration. In these implementations, the XNA module 418 with a combination of cipher-based and cipherless functions that, when executed, generate XNA objects. In example implementations, the XNA module 418 is configured to generate XNA objects of size 4096 bits×4096 bits. In the example configuration, the XNA module 418 generates XNA objects for up to k (e.g., k=4096) different groups, each group having a mutual identity of interest from a master XNA object (GDX in Table 2) using a combination of cipher-based and cipherless functions. In some example implementations, the cipherless function(s) may include a set of parameterizable cipherless operations that are parameterizable using one or more secure modification parameters (SMP). In example implementations, the cipherless operations may be a combination of XOR and cyclic-shift operations, where the XNA module 418 randomly generates the secure modification parameters to parameterize the combination of XOR and cyclic-shift operations, examples of which are described below.

FIG. 17 below provides an example hybrid process (e.g., at least one cipher-based operation and at least one cipherless operations) for generating objects for a digital ecosystem according to some example implementations of the present disclosure. It is appreciated that the XNA module 418 may be configured to generate XNA objects in other suitable hybrid manners without departing from the scope of the disclosure.

At 1712, the XNA module 418 generates a master XNA object. In example implementations, the XNA module 418 generates a random binary information data set structured in a n×m matrix (e.g., 4096-bit×4096-bit matrix). In some of these implementations, the random binary information data set is the master XNA object, where each row of the master XNA object is organized in a set of n rows $[R_1, R_2, \ldots R_n]$. In this example, $R_i$ may be the $i^{th}$ row of the randomly generated master XNA object and may be defined as $[R_{i,1}, R_{i,2}, \ldots R_{i,m}]$, where $R_{i,j}$ is an individual bit value of the $i^{th}$ column of the $i^{th}$ row. In this example, the master XNA object may comprise 4096 rows, where each row includes 16 zones that are each 256 bits long. It is noted that the foregoing values are provided for example only and other suitable values may be used to configure the XNA module 418.

At 1714, the XNA module 418 transforms the master XNA object, XNA, into a transformed XNA object, $XNA_T$ using a transformation function (e.g., a cipherless or cipher-based transformation function). In some implementations, the XNA module 418 transforms XNA into $XNA_T$ using a cipherless function that receives a set of secure modification parameters (SMP). In some implementations, the SMP may define a set of parameters that are used to parameterize a set of parameterizable operations that are applied to a master XNA object. Examples of parameterizable operations may include cyclic bit shifting operations, XOR operations, and the like. In these examples, the SMP may define, for each row of the master XNA object, a respective number of bits to cyclically shift. Additionally or alternatively, the SMP may define a value that is used to XOR a specific row. For example, the $SMP_i$ may define the secure modification parameters for the $i^{th}$ row and may include a first parameter that indicates a number of bit locations to cyclically shift the $i^{th}$ row (e.g., to the right) and a second parameter that defines a random value that is XOR'd with the $i^{th}$ row. It is appreciated that the second parameter may be a value between 0 and ($2^m-1$), where m is the number of columns in the XNA object. In these implementations, the XNA module 418 may transform each row of the XNA object using a set of parameterizable operations that are parameterized with the respective SMPs corresponding to the row to obtain the transformed master XNA object, $XNA_T$. It is appreciated that the master XNA object may be transformed in other cipherless manners or in cipher-based manners (e.g., step 1614 of FIG. 16) without departing from the scope of the disclosure.

At 1716, the XNA module 418 generates k XNA objects for k respective groups of a digital ecosystem. In some implementations, the XNA module 418 generates a respective XNA object for each respective group in a digital community. In some of these implementations, the XNA module 418 derives the XNA object based on the master XNA object and the transformed XNA object, $XNA_T$. Table 6 defines an example process for generating an XNA object based on a master XNA object (denoted as XNA) and a transformed master XNA object (denoted as $XNA_T$). In this example, the XNA module 418 may generate a $y^{th}$ XNA object for a $y^{th}$ group (e.g., $Group_y$), of the digital ecosystem as follows:

TABLE 6

| Number | Operation |
| --- | --- |
| 1. | Select an L-bit sequence, $S_y$; |
| 2. | Map $S_y$ into $XNA_T$ to obtain a transformation value, $TV_y$, using a cipher-based mapping function |
| 3. | Modify XNA using $TV_Y$ to obtain $XNA_y$. |

In an example implementation, the XNA module 418 may select a 256-bit sequence, $S_y$. In the example configuration, the value of L is 256, such that the value of $S_y$ is between 0 and ($2^{256}-1$). Depending on the configuration of the XNA module 418, the $S_y$ may be a private sequence, a public sequence, or a randomly generated sequence. As discussed, a new sequence, $S_y$, may be randomly generated for each group. In this way, each XNA object, $XNA_y$, is generated using a different sequence. Alternatively, the XNA module 418 may be configured to select a public or private sequence from any suitable data source. In these implementations, XNA object, $XNA_y$, is still generated using a different sequence, thereby ensuring that each group (e.g., enclave) has a different genomic data object assigned thereto.

In some implementations, the mapping step of the example provided in Table 6 may be a cipher-based, cipherless, or hybrid sequence mapping function (examples of which are described in further detail below). In some of these implementations, the cipher-based sequence mapping function may be performed by the sequence mapping module 440. In these example implementations, the XNA module 418 determines the transformation value by providing $S_y$ and $XNA_T$ as input to the sequence mapping module 440 and the sequence mapping module 440 maps the sequence into $XNA_T$ to obtain the transformation value, $TV_y$. In some implementations, the XNA module 418 may be configured to perform the sequence mapping function to determine the transformation value.

In some implementations, the XNA module 418 may use a cipherless transformation function to modify the master XNA object, XNA, using the transformation value $TV_y$ to obtain the XNA object, $XNA_y$, for a respective group ($Group_y$) of the digital ecosystem. In example implementations, the cipherless function may include a hash function (e.g., a pre-image resistant hash function or any other suitable hash function) that is keyed with the transformation value, a set of parameterizable operations that are parameterized using the transformation value, or the like.

The example of FIG. 17 is provided for example only. It is appreciated that a wide range of different configurations (e.g., executable computational methods) may be developed to, for example, modify the master XNA object to obtain a transformed master XNA object, select a sequence, determine a transformation value, $TV_k$, and/or transform the master XNA object to an XNA object. Furthermore, in some implementations the cipher-based operations of the example process of FIG. 17 may be replaced with cipherless operations, such that the XNA module 418 may be configured in a cipherless manner.

In the examples of FIGS. 16 and 17, the XNA module 418 may assign a resulting XNA object, XNA, to a respective enclave VDAX of a digital community. The enclave VDAX may then assign its XNA object, $XNA_y$, to members (e.g., cohort VDAXs of cohorts) of the enclave. In implementations, the link module 430 of a respective cohort VDAX may modify its assigned XNA object each time the respective cohort VDAX spawns a link for or decodes a link from another cohort VDAX of a cohort in the corresponding enclave. In this way, an XNA object provides a mechanism for facilitating hyper-scalable correlation between members of a corresponding enclave and/or ecosystem. It is appreciated that the examples provided in FIGS. 16 and 17 are example configurations of an XNA module 418 and other means for generating XNA objects for community members may be later developed.

Furthermore, the examples of FIGS. 16 and 17 depict processes for generating XNA objects that are assigned to respective groups of an ecosystem. As discussed, an ecosystem VDAX and/or an enclave VDAX may be configured to modify the master XNA object and/or one or more XNA objects of one or more enclaves. For example, an ecosystem VDAX may modify an XNA object of an enclave so as to alter the genomic topology of the enclave (e.g., to remove one or more cohorts from the enclave, to periodically change the XNA object for security reasons, or the like). In some implementations, an ecosystem VDAX or an enclave VDAX may modify an XNA object for such purposes using the example process presented in Table 5 or Table 6. For example, in modifying a current XNA object of a particular enclave, an ecosystem VDAX or the enclave VDAX representing the enclave may transform the current XNA object to obtain a transformed XNA object, select an L-bit sequence, map the sequence into the transformed XNA object to obtain a transformation value, and modify the current XNA object using the transformation value to obtain a new XNA object for the particular enclave. This new XNA object may then be provided to the cohorts that are to remain in the enclave. In this way, any cohorts in the enclave that were not provided the new XNA object will no longer be able to generate VBLS for or decipher VBLS from the cohorts remaining in the enclave. It is appreciated that the modification of genomic differentiation objects may be performed using later developed processes as well without departing from the scope of the disclosure.

ZNA Generation

In some implementations of the present disclosure, a CG-ESP may include an EIC module 420 that is configured to generate ZNA objects that are assigned to members of a digital ecosystem. In these implementations, the digital ecosystem may be a virtual trusted execution environment (VTEE), where a respective ZNA object may be assigned to a respective computer program (e.g., operating system, a software application, a firmware application, a middleware application, or the like) or to a group of computer programs (e.g., a software suite). Alternatively, the EIC module 420 may be configured to generate a single ZNA object (e.g., the master ZNA object), whereby each respective computer program has corresponding GRI associated therewith that the EIC module 420 uses when facilitating component binary isolation. As discussed, the configuration of the EIC module 420 may be configured in a cipher-based, cipherless, or hybrid manner.

Figure 18:
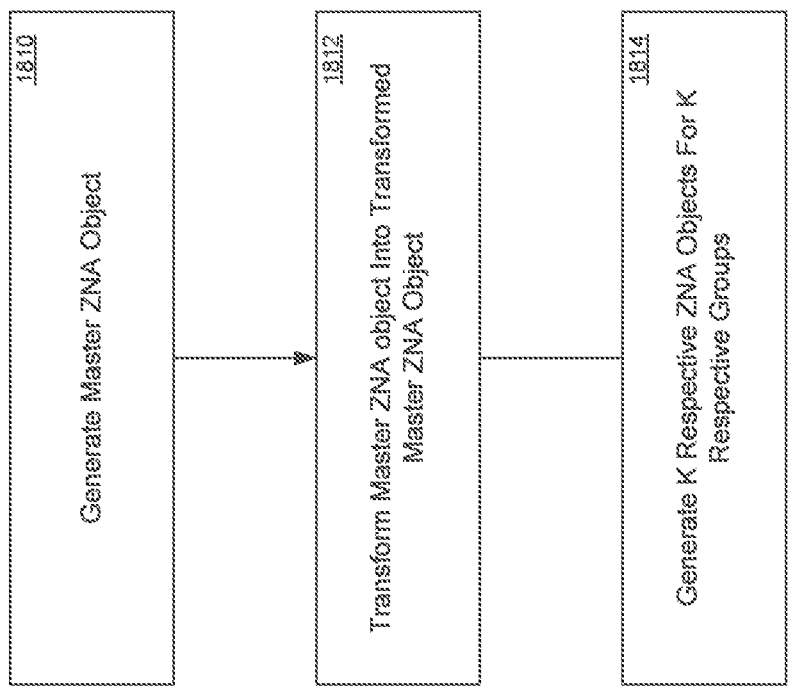
FIG. 18 illustrates an example process for generating ZNA objects in accordance with some embodiments of the present disclosure.

In some implementations, the process of FIG. 13 may be implemented in an EIC module 420 to generate ZNA objects for members of the VTEE. FIG. 18 provides example implementations of a process for generating ZNA objects. In these example implementations, the EIC module 420 is configured to generate a master ZNA object. In some of these implementations, the EIC module 420 assigns the master ZNA object to each member of the VTEE. In other implementations, the EIC module 420 is further configured to derive a set of k ZNA objects, wherein the EIC modules 420 may assign each respective ZNA objects to a respective community member or a respective group of community members. As will be discussed in greater detail below, ZNA may be used when encoding and decoding executable instructions of a computer program and/or data input to and/or output by the computer program. As such, the VBLS-encoded instructions may be stored in memory and decoded at run-time, thereby greatly reducing the risk of malicious code or other similar exploits. As can be appreciated, such ecosystems differ from other ecosystems, as there is less likelihood that the instructions and/or program data will be intercepted by a malicious party In some example configurations, the EIC module 420 is configured to generate ZNA objects that are structured in fixed-size binary matrices (e.g., n×m matrices). It is appreciated that the binary matrices may be represented as binary vectors. As can be appreciated from the disclosure, the configurable properties of a CG-ESP allow a community owner (e.g., the entity defining the size, structure, security levels, intended use, and/or membership requirements) to parameterize the EIC module 420 with a maximum number of ZNA objects (K), the dimensions of the ZNA object (e.g., n×m), the size of ZNA object zones, and/or other suitable parameters. Furthermore, as is discussed throughout the present disclosure, the community owner may define the types of computational functions that are used in the ZNA object generation process. For example, the community owner may use specific cipher-based functions (e.g., different encryption functions, disambiguation functions, and/or the like) and/or cipherless functions.

FIG. 18 below provides an example cipher-based method for generating ZNA objects for a digital ecosystem according to some example implementations of the present disclosure. It is appreciated that the EIC module 420 may be configured to generate ZNA objects in other suitable cipher-based manners without departing from the scope of the disclosure. In the example implementations of FIG. 18, the example ZNA object are 1024 bit×1024 bit matrices. It is appreciated that the ZNA objects may be larger or smaller depending on the purpose of the VTEE, the security requirements of the VTEE, the intended size of the digital community, and/or other suitable configurations.

At 1810, the EIC module 420 generates a master ZNA object. In example implementations, the EIC module 420 generates a random binary information data set structured in a 1024-bit×1024-bit matrix. In some of these implementations, the random binary information data set is the master ZNA object, where each row of the master ZNA object is organized in a set of j fixed-length zones (e.g., 4 256-bit zones), such that the $i^{th}$ row of ZNA may be defined as: $(t_{i,1} \ldots, t_{i,j})$. For example, the master ZNA object may be defined for i=1 ... 1024 and for j=14. In this example, the master ZNA object may comprise 1024 rows, where each row includes 4 zones that are each 256 bits long. It is appreciated that the foregoing values are provided for example only and the master ZNA object may have other suitable dimensions as defined by the community owner. In some implementations, the EIC module 420 may use the master ZNA object for each community member (e.g., computer program) in a VTEE and may assign unique GRI to each community member. In other implementations, however, the EIC module 420 may transform the master ZNA object and may assign.

At 1814, the EIC module 420 transforms the master ZNA object, ZNA, into a transformed ZNA object, $ZNA_T$. In implementations, the EIC module 420 transforms ZNA into $ZNA_T$ using j (e.g., j=4) randomly selected binary primitive polynomials, $g_h(x)$ for h=1 ... j. In some of these implementations, the binary primitive polynomials are each of a specified degree (e.g., 256-degree binary primitive polynomials). In these implementations, each respective value represented by each respective row $t_i$ of is transformed to a respective modified value, $t_i(m)$. In some of these implementations, each row of ZNA may be transformed according to:

$$t_i(m) = (x^{t_{i,1}} \mod g_1(x) \| x^{t_{i,2}} \mod g_2(x) \| \ldots \| x^{t_{i,j}} \mod g_j(x)).$$

In this example, the foregoing transformation function is cipher-based, as the function is reversable by solving a discrete logarithm problem. It is appreciated that the master ZNA object may be transformed in other suitable manners without departing from the scope of the disclosure.

At 1816, the EIC module 420 generates k ZNA objects for k respective community members (e.g., computer programs) of a VTEE. In some implementations, the EIC module 420 generates a respective ZNA object for each respective member in a digital community. In some of these implementations, the EIC module 420 derives the ZNA object based on the master ZNA object and the transformed ZNA object, $ZNA_T$. Table 7 defines an example process for generating an ZNA object based on a master ZNA object (denoted as ZNA) and a transformed master ZNA object (denoted as $ZNA_T$). In this example, the EIC module 420 may generate a $y^{th}$ ZNA object for a $y^{th}$ community member, of the digital ecosystem as follows:

TABLE 7

| Number | Operation |
|---|---|
| 1. | Select an L-bit sequence, $S_y$; |
| 2. | Map $S_y$ into $ZNA_T$ to obtain a transformation value, $TV_y$; |
| 3. | Modify ZNA using $TV_Y$ to obtain $ZNA_y$. |

In an example implementation, the EIC module 420 may select a 256-bit sequence, $S_y$. In the example configuration, the value of L is 256, such that the value of $S_y$ is between 0 and $(2^{256}-1)$. Depending on the configuration of the EIC module 420, the $S_y$ may be a private sequence, a public sequence, or a randomly generated sequence. As discussed, a new sequence, $S_y$, may be selected or randomly generated for each community member. In this way, each ZNA object, $ZNA_y$, is generated using a different sequence.

In some implementations, the mapping step of the example provided in Table 5 may be performed by the sequence mapping module 440, whereby the EIC module 420 provides $S_y$ and $ZNA_T$ as input to the sequence mapping module 440 and the sequence mapping module 440 outputs a transformation value, $TV_y$, that is determined by mapping the sequence into $ZNA_T$. In some implementations, the EIC module 420 may be configured to determine the transformation value by mapping the sequence into the $ZNA_T$.

In the example of Table 7, the EIC module 420 may execute a transformation function that modifies the master ZNA object, ZNA, using the transformation value, $TV_y$, to obtain an ZNA object, $ZNA_y$. The transformation function may be cipher-based, cipherless, or hybrid. Examples of cipher-based, cipherless, and hybrid transformation functions are discussed throughout the disclosure. Once generated, the EIC module 420 may assign the ZNA object, ZNAy, to the $y^{th}$ community member (e.g., computer program), whereby the ZNA object may be stored in memory and retrieved by the EIC module 420 when the computer program is being executed.

The example of FIG. 18 is provided for example only. It is appreciated that a wide range of different configurations (e.g., executable computational methods) may be developed to, for example, modify the master ZNA object, determine a transformation value $TV_K$, select a sequence, map the sequence into the transformed master ZNA object, and/or transform the master ZNA object to an ZNA object.

In some implementations, an EIC module 420 may modify a ZNA object from time to time (e.g., to maintain security, to remedy a security breach, or the like). In such scenarios, the EIC module 420 may apply the example process depicted in Table 7 to modify the ZNA object. For example, in modifying a current ZNA object, the EIC module 420 may transform the current ZNA object to obtain a transformed ZNA object, select an L-bit sequence, map the sequence into the transformed ZNA object to obtain a transformation value, and modify the current ZNA object using the transformation value to obtain a new ZNA object. It is appreciated that the modification of genomic differentiation objects may be performed using later developed processes as well without departing from the scope of the disclosure.

Genomic Eligibility Object Generation and Allocation

In implementations, the root DNA module 410 is configured to generate genomic eligibility objects. As discussed, genomic eligibly objects include CNA objects and/or PNA objects. In some implementations, CNA objects may be used by ecosystem members to confirm engagement-integrity during link exchange. In some implementations, PNA objects may be used by ecosystem members to confirm engagement synchronization during link exchange.

CNA Generation and Allocation

In some implementations of a CG-ESP, the root DNA module 410 of a progenitor VDAX includes a CNA module 412 that generates CNA objects. In some of these implementations, the CNA module 412 of a progenitor VDAX (e.g., an ecosystem VDAX) generates a master CNA object and allocates a respective unique subset of the master CNA object to each respective member of a digital community (e.g., enclaves, cohorts, and the like). In this way, each respective pair of ecosystem members may form a unique relationship based on their shared portions of the master CNA object. In some implementations, this unique correlation may be used to confirm engagement integrity with one another during the link exchange.

FIG. 19 illustrates an example configuration of a CNA module 412 for generating a master CNA object and allocating CNA objects to ecosystem community members. It is noted that the example process of FIG. 19 is provided as an example process for generating a master CNA object. Additional CNA generation and allocation processes may be later developed and may be used to generate CNA for an ecosystem.

At 1910, the CNA module 412 randomly generates a master CNA object. In some of these implementations, the CNA module 412 generates a random binary information data set, CNAR, having a specific size, U. The size of U may be selected based on a number of factors, such as the expected size of a digital community, the architecture of the system, the types of users expected (e.g., family members, employees, general public, etc.), and/or any other factors. For example, U may be $2^{24}$ bits (~2 MB), $2^{23}$ (~1 MB), $2^{22}$ (~500 kB), or any other suitable size. The CNA module 412 structures the random binary information data set, CNAR, into a master CNA object. In some of these implementations, the CNA module 412 may reorganize CNAR by selecting and enumerating unique binary vector segments, $S_j$, of size V from the CNAR object to obtain the master CNA object. For example, in implementations, the CNA module 412 may partition CNAR into a set of non-overlapping binary vector segments, $S_j$, each of size V (e.g., V=8 bits, 16 bits, 1028 bits, 4096 bits or the like), for $$0 < j < \frac{U}{V},$$

such that each respective segment, $S_j$, defines a respective $j^{th}$ portion of the master CNA object, and where U/V is an integer. In these implementations, each respective portion of the CNA may be indexed with a corresponding value from 0 to $$\left(\left(\frac{U}{V}\right)-1\right),$$

such that the value "0" references the first portion of the master CNA object, the value "1" references the second portion of the master CNA object, . . . , and the value of $$\left(\left(\frac{U}{V}\right)-1\right)$$

references the (U/V)$^{th}$ portion of the master CNA object. As will be discussed below, in implementations, the CNA objects of respective community members may be derived from the master CNA object, in part, by determining and assigning a unique codeword vector (also referred to as a "codeword") of length U/V, such that the bit locations of the 1 s in the codeword vector correspond to the respective portions of the master CNA object that are inherited by the respective community member. For example, if a community members codeword vector is [1001 . . . 01], the CNA object of the community member includes the first portion, the fourth portion, . . . , and the (U/V)$^{th}$ portion of the master CNA object.

At 1912, the CNA module 412 allocates CNA objects to one or more digital community members based on the master CNA object. In some implementations, the CNA module 412 is configured to allocate a unique subset of portions of the master CNA object to each respective digital community member, such that the CNA objects of no two digital community members have the identical subset of master CNA object portions allocated thereto.

In implementations, the CNA module 412 may execute a code mapping function that applies a code mapping to generate unique codeword vectors for respective community members (e.g., enclaves, cohorts, and the like). In implementations, a code mapping includes a basic binary bit vector index that respectively associates Z values to a set of Z basic binary vectors (e.g., the Z basic binary vectors are enumerated from 0 to Z−1 (e.g., $C_i$, $0 \leq i \leq Z-1$)). In some implementations, the value of Z may be selected such that the number of portions of the master CNA object (i.e., U/V) is a multiple of Z $$\left(\text{i.e., } \frac{U}{V} \mod Z = 0\right).$$

In some or these implementations, the basic binary vectors may be selected such that any pair of the basic binary vectors (e.g., $C_i$ and q, for $0 \leq i, j < Z$) from the set of basic binary vectors possess unique addressable correlation. Unique addressable correlation may refer to a property of a set of binary vectors when the intersection of any pair of vectors (i.e., ($C_i$ AND $C_j$)) is a unique vector. In implementations, the basic binary bit vector index associates each respective basic binary vector, $C_i$, with a corresponding value between 0 and Z−1. For example, when Z=4, the basic binary vector index consists of ([00], [01], [10], and [11]) and an example code mapping may be defined as {[00]→$C_0$, [01]→$C_1$, [10]→$C_2$, and [11]→$C_3$}, such that the code mapping maps any given two-bit value to a corresponding basic binary vector of the four basic binary vectors. As will be discussed with respect to CNA allocation processes, the coding function may be used to generate unique codewords corresponding to respective members of a digital community, whereby a respective codeword corresponding to a digital community member provides an index to the portions of the master CNA object that are allocated to the CNA object of the digital community member.

FIG. 20 illustrates an example process for allocating a CNA object for a community member according to some implementations of the present disclosure. The process of FIG. 20 is described as being performed by a CNA module 412 of a progenitor VDAX. It is appreciated that a CNA module 412 may be configured to execute alternative CNA generation processes without departing from the scope of the disclosure. Furthermore, the process of FIG. 20 is described with respect to a single community member. It is appreciated that the CNA module 412 may be configured to generate CNA objects for a virtually unbounded number of community members.

At 2010, the CNA module 412 determines a unique codeword for the ecosystem community member. As mentioned above, the codeword of the ecosystem community member may be used as an index to the portions of the master CNA object that are allocated to the CNA object of the digital community member. In some implementations, a codeword may be structured as a binary vector of size U/V (i.e., the number of V-sized portions of the master CNA object). In some of these implementations, each respective bit of a codeword indicates whether a corresponding portion of the master CNA object is allocated to the community member corresponding to the codeword (e.g., with "1" indicating a particular portion is allocated to the community member).

In implementations, the CNA module 412 determines the codeword, CW, of the specific ecosystem member using one or more collision resistant processes (e.g., collision resistant hash function). In some of these implementations, the CNA module 412 receives and/or assigns a unique obtainable data set to the specific ecosystem member (e.g., credentials of the ecosystem member), which may or may not be human readable. An obtainable data set may refer to any digital information that other ecosystem member VDAXs (e.g., cohort VDAXs, enclave VDAXs, ecosystem VDAX) in the ecosystem have access to, or may otherwise obtain during the link exchange process. For example, a unique obtainable data set corresponding to a cohort VDAX of a device associated with a human user (e.g., personal computing device, mobile device, wearable device, and/or the like) may be information that is unique to the human user (e.g., a combination of a name, email address, and/or phone number of the human user), where the information contained in the data set is structured according to a defined format. In another example, an obtainable data set corresponding to a cohort VDAX of a device (e.g., server, printer, IoT sensor, smart appliance, and/or the like) or system of devices (e.g., cloud computing system) that may or may not be associated with a single user may include information that is unique to the device or system of devices (e.g., a combination of a MAC address of the devices or one or more of the devices in a set of devices, a device name of the device or one or more of the devices in a set of devices, and/or the like). It is noted that in implementations, the unique information that is obtainable may be publicly available to any device, regardless of its affiliation with the digital ecosystem, or may be obtainable by a limited number of entities (e.g., only by members of the digital ecosystem). In some implementations, the obtainable data sets of ecosystem members are organized in "credentials" that are indexed in a data structure (e.g., an association table, a database, an index, or the like), such that credentials containing the unique information of any ecosystem member may be obtained by a VDAX in the ecosystem by querying the device or system that stores the data structure. It is appreciated that the unique obtainable data set of an ecosystem member may be determined in any other suitable manner.

In implementations, the CNA module 412 inputs the credentials of the ecosystem member into an encoding function that receives the credentials and outputs an unmapped codeword, $CW_A$ corresponding thereto. In these example implementations, the unmapped codeword is a binary vector, $CW_A$, of fixed size, P, where:

$$P = \frac{\frac{U}{V}}{\log_2 Z}$$

For example, if U/V=4096 and Z=4, then the encoding function is configured to output unmapped codewords that are 2048 bits long; whereas if U/V=4096 and Z=16, then the encoding function outputs unmapped codewords that are 1024 bits long. In some implementations, the encoding function may receive the credentials of a community member and apply a hash function (e.g., a collision resistant function, a pre-image resistant function, a second preimage resistance function, or the like) to the credentials to obtain a P-bit vector, which may be referred to as an "unmapped codeword".

In implementations, the CNA module 412 inputs the unmapped codeword, $CW_A$, into the code mapping function (e.g., the example code mapping function provided in the description of FIG. 19), which outputs a codeword corresponding to the digital community member. In some implementations, the code mapping function initializes a binary vector, $CWS_A$. In these implementations, the code mapping function uses the unmapped codeword, $CW_A$, as a sequence of indices to the basic binary vectors, $C_i$, to construct the codeword by concatenating the specific basic binary vectors indicated by the unmapped codeword, $CW_A$, to the binary vector $CWS_A$. In some of example implementations, the code mapping function processes subsegments of the unmapped codeword starting from the least significant bit, where each subsegment of the unmapped codeword is $\log_2 Z$ bits, which is the length of each entry in the basic binary vector index. In some of these implementations, the code mapping function may identify, for each successive subsegment of the unmapped codeword (e.g., each two bits of $CW_A$), a basic binary vector corresponding to the subsegment based on the value of the subsegment and the code mappings defined in the code mapping function. In some of these implementations, the code mapping function successively concatenates each identified basic binary vector to the binary vector $CWS_A$. For example, if the code mappings of the code mapping function consist of: $\{[00] \rightarrow C_0, [01] \rightarrow C_1, [10] \rightarrow C_2, \text{ and } [11] \rightarrow C_3\}$ and first four bits of the unmapped codeword are [1101 . . . ], the code mapping function may first identify a first basic binary vector $C_3$ based on the first subsegment [11] of the unmapped codeword and may concatenate $C_3$ to $CWS_A$ (which is initially null and contains no bits). The code mapping function may then identify a second basic binary vector $C_1$ based on the second subsegment [01] of the unmapped codeword and may concatenate the second basic binary vector, $C_1$, to $CWS_A$. The code mapping function may continue in this manner until $CW_A$ is processed in its entirety. It is appreciated that the CNA module 412 may be configured to determine a codeword in other suitable manners and/or using different code mapping functions without departing from the scope of the disclosure.

At 2012, the CNA module 412 of the progenitor VDAX generates a CNA object for the digital community member based on the codeword and the master CNA object. In some implementations, the CNA module 412 allocates a unique subset of the master CNA object to the digital community member based on the codeword of the community member. In implementations, the CNA module 412 may initially initialize a CNA object, $CNA_A$, that is to be assigned to the community member. In some of these implementations, the CNA object, $CNA_A$, has the same structure as the master CNA object (e.g., a U×V matrix) and is initially populated with zeros.

In some of these implementations, the CNA module 412 may use the codeword vector of the community member, $CW_A$, as a sequence of indices to the respective portions of the master CNA object. In these implementations, each bit location of the codeword references a respective segment of the master CNA object, such that CNA module 412 may treat each bit location as a flag indicating whether a corresponding portion of the master CNA object is allocated to the CNA object of the community member. In implementations, the CNA module 412 may, for each bit in the codeword vector, determine whether to allocate the corresponding portion of the master CNA object to the based on the value of the bit. For example, if the value of bit, is "1", then the CNA module 412 allocates the $(i-1)^{th}$ portion of the master CNA object, $S_{(i-1)}$, to $(i-1)^{th}$ portion of the CNA object of the community member. In this example, if the value of bit, is "0", then the CNA module 412 does not allocate the $(i-1)^{th}$ portion of the master CNA object to the CNA object of the community member. In this scenario, the CNA module 412 may fill an unallocated portion of the community member CNA object with a random value. For example, the CNA module 412 may generate a random value and then perform one or more computational operations on the random value to obtain a V-bit value, whereby the CNA module 412 adds V-bit value to the $(i-1)^{th}$ portion of the CNA object. For purposes of explanation, the foregoing may be referred to as adding "noise" to the CNA object. In a specific example, the master CNA object may be $[S_0, S_1, S_2, \ldots, S_{(U-2)}, S_{(U-1)}]$. In this example, if the codeword of the community member, $CWS_A$, is [011 . . . 01], then the CNA module 412 generates the following CNA object, $CNA_A$: $[Noise_0, S_1, S_2, \ldots, NOISE_{(U-2)}, S_{(U-1)}]$, where $S_1$, $S_2$, and $S_{(U-1)}$ are allocated to $CNA_A$ and $NOISE_0$ and $NOISE_{(U-2)}$ are randomly generated bit strings of length V that are allocated to the $0^{th}$ and $(U-2)^{th}$ portions of the CNA object respectively. The CNA module 412 may be configured to add allocated portions of the master CNA object and/or noise to the CNA object in any suitable manner. For example, the CNA module 412 may use concatenation operations and/or combinations of bit shifting and OR operations) to add allocated portions of the master CNA object and/or noise to the CNA object. The CNA module 412 may then assign the generated CNA object, $CNA_A$, to the respective digital community member.

It is appreciated that the foregoing description provides example implementations of CNA generation and allocation. The techniques provided are provided for example only and new manners for generating and allocation CNA may be later developed and implemented in a CNA module 412.

PNA Generation and Allocation

In some implementations of a CG-ESP, the root DNA module 410 of a progenitor VDAX of a digital ecosystem includes a PNA module 414 that is configured to generate PNA objects for members of the digital ecosystem (e.g., cohort VDAXs, enclave VDAXs, and/or the ecosystem VDAX). In these implementations, PNA objects enable ecosystem members to confirm engagement-eligibility during link exchange by way of an eligibility synchronization process. In some implementations, the PNA module 414 of the progenitor VDAX initially generates a master PNA object corresponding to the digital ecosystem and derives a unique PNA object for each respective ecosystem member from the master PNA object based on the credentials corresponding to the ecosystem member (discussed in greater detail below). Once a PNA object is generated, the PNA object may be provided to the digital community member via one or more digital mediums.

Figure 21:
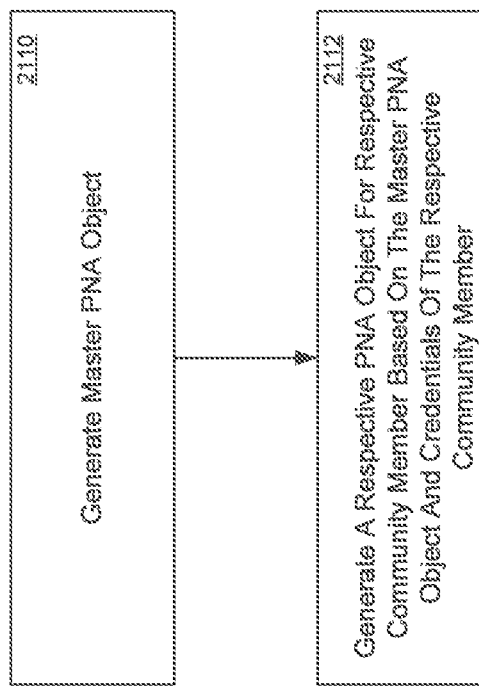
FIG. 21 illustrates an example process for generating and allocating PNA objects for ecosystem members of a digital ecosystem in accordance with some embodiments of the present disclosure.

FIG. 21 illustrates example implementations for allocating PNA objects to members of a digital ecosystem. In these implementations, the PNA module 414 generates a master PNA object and then derives and allocated PNA objects for respective members of the digital cohort. For purposes of explanation, the method is explained with respect to generating a PNA object for a cohort of a digital ecosystem. The method of FIG. 21, however, may be executed to generate PNA objects for other types of community members as well (e.g., enclaves, ecosystem, or the like). The method of FIG. 21 is described with respect to a PNA module 414. It is appreciated that the method may be executed by other suitable computing resources without departing from the scope of the disclosure. Furthermore, the techniques described in FIG. 21 are provided as example means of generating PNA objects and that later techniques may be further developed.

At 2110, the PNA module 414 of the progenitor VDAX generates a master PNA object. In some implementations, the master PNA object includes a secret component (denoted as $PNA^S$) and a public component, (denoted as $PNA^P$). In implementations, the secret component, $PNA^S$, of the master PNA object is private and stored securely, such that only the progenitor VDAX has access to $PNA^S$. In implementations, $PNA^S$ includes a secret binary primitive polynomial of degree M (denoted as $g_C^S(x)$), a secret M-bit value (referred to as a "secret value" and denoted as d), and a secret object comprising N pairs of M-bit random numbers. In some implementations, the PNA module 414 may generate or otherwise determine the secret primitive polynomial, $g_C^S(x)$. It is noted that references the polynomials and primitive polynomials refer to binary polynomials and binary primitive polynomials respectively, unless otherwise stated. In some implementations, the PNA module 414 may randomly generate an M-degree binary primitive polynomial, which may be used as the secret binary primitive polynomial, $g_C^S(x)$. In implementations, the PNA module 414 may randomly generate, or otherwise determine, the secret number d, such that d is represented in a M-bit vector. In some implementations, the PNA module may randomly generate the secret number, d, such that d is defined in an M-bit vector. As noted, $g_C^S(x)$ is a binary primitive polynomial of degree M and d is a M-bit number (e.g., M=256).

In implementations, the secret object of the secret component, $PNA^S$, includes N pairs of M-bit values, which may be denoted as $(t_{i,0}^s, t_{i,1}^s)$ for i=1 ... N. In this example, $t_{i,0}^s$ may be the first M-bit value of the $i^{th}$ pair and $t_{i,1}^s$ may be the second M-bit value of the $i^{th}$ pair. It is noted that the number of pairs, N, of M-bit numbers may be equal to the number of bits used to represent the respective credentials of the respective members of the digital ecosystem. For example, if the credentials of cohorts (e.g., once in a structured format, such as a fixed length vector or the like) are represented in 256-bit vectors then N=256. In some implementations, the PNA module 414 may randomly generate each pair of M-bit values. In some of these implementations, the PNA module 414 may generate each of the M-bit values with the condition that each of the M-bit values is relatively prime to a specific value. For example, in some implementations, each of $(t_{i,0}^s t_{i,1}^s)$ for i=1 ... N are relatively prime to $(2^M-1)$.

In implementations, the public component, $PNA^P$, of the master PNA object is public within the digital ecosystem, such that $PNA^P$ may be shared with any member (e.g., cohort, enclave, or the like) that is admitted to the digital ecosystem. In some of these implementations, $PNA^P$ is the same size as $PNA^S$ (e.g., 16 KB, 8 KB, 32 KB, or the like). In implementations, the public component, $PNA^P$, of the master PNA object includes two initial M-degree binary primitive polynomials, $g_{C0}^P(x)$ and $g_{C1}^P(x)$, and a public object. In some of these implementations, the PNA module 414 may generate, or otherwise determine, any two initial M-degree binary primitive polynomials of degree M. In implementations, the public object of $PNA^P$ may include N-1 pairs of M-bit values, which may be denoted as $(t_{i,0}^P t_{i,1}^P)$ for i=2 ... N. In this example, $t_{i,0}^P$ may be the first M-bit value of the $i^{th}$ pair and $t_{i,1}^P$ may be the second M-bit value of the $i^{th}$ pair. In some implementations, the PNA module 414 may randomly generate each pair of M-bit values. In some of these implementations, the PNA module 414 may randomly generate each of the M-bit values with the condition that that each of the M-bit values is relatively prime to a specific value (e.g., each of $(t_{i,0}^P, t_{i,1}^P)$ for i=2 ... N are relatively prime to $(2^M-1)$).

At 2112, the CG-ESP allocates and distributes a PNA object for each respective member of the digital ecosystem based on the master PNA object and unique credentials of the ecosystem member. For purposes of explanation, this step is described for a single cohort while noting that the techniques disclosed may be repeated for any number of ecosystem members (e.g., other cohorts, enclaves, or the ecosystem at large).

In implementations, the PNA module 414 generates a unique PNA object (denoted as $PNA_i$) for a respective cohort (e.g., an $i^{th}$ cohort) of a digital ecosystem based on the master PNA object and credentials of the cohort.

In some implementations, the credentials of the cohort may refer to a data structure containing data that is indicative of the cohort, where the credentials may or may not be human-understandable. In some implementations, the credentials may be structured in a fixed-size bit vector (e.g., an N-bit vector) that is unique to the cohort. Additionally or alternatively, the credentials of the cohort may be transformed from a variable length vector into an N-bit vector (e.g., using a transformation function) that is unique to the cohort. In implementations, the PNA module 414 may determine the credentials based on data received from a data source of many potential types of data sources (e.g., as discussed with respect to the CNA module 412 above).

In some implementations, the unique PNA object, $PNA_i$, of a cohort (e.g., an $i^{th}$ cohort) includes a secret ratio, $t_i^S/t_i^P$, a public binary primitive polynomial, $g_{t_i^s \cdot d}(x)$, and the public component, $PNA^P$, of the master PNA object. In these implementations, the PNA module 414 may determine the secret value and public polynomial specifically for the cohort based on the credentials thereof. In embodiments, the PNA module 414 generates the public primitive polynomial, $g_{t_i^s \cdot d}(x)$, based on the secret primitive polynomial, $g_C^S$, a secret value, $t_i^S$, obtained from the secret object, and the secret value d. In some of these implementations, the PNA module 414 may determine secret value, $t_i^S$, by applying a first mapping function to the secret component, $PNA^s$, of the master PNA component given the credentials of the cohort as input. In these implementations, the first mapping function outputs the secret ratio, $t_i^S/t_i^P$, as an M-bit value. In some implementations the secrete ratio $t_i^S/t_i^P$ can be derived from $PNA^S$, $PNA^P$, and the credentials of the $i^{th}$ cohort. For example, in some implementations, the PNA module 414 may obtain the credentials of the cohort in a fixed length vector (e.g., $IC_A=(b_1^A, \ldots, b_{256}^A)$ when the credentials of the cohort is 256 bits long). The PNA module 414 may then select and combine corresponding elements from the secrete object $(t_{i,0}^s t_{i,1}^s)$ of the secret component, $PNA^S$, based on the values of the individual bits, $b_i^A$, of the credentials to obtain a first value, $t_i^S$ of the $i^{th}$ cohort. Similarly, the PNA module 414 may select and combine elements from the public object $(t_{i,0}^P t_{i,1}^P)$ of the public component, $PNA^P$, according to the values of the individual bits, $b_i^A$, of the credentials of the cohort to obtain a second value, $t_i^P$, of the cohort. The PNA module 414 may then determine the secret ratio, $t_i^S/t_i^P$, of the $i^{th}$ cohort given the first value, $t_i^S$, and the second value, $t_i^P$ of the cohort. It is noted that in some implementations, the first and second values, $t_i^S$ and $t_i^P$ are not shared with the cohort; rather, only the secret ratio $t_i^S/t_i^P$ is shared with the cohort.

In example implementations, the PNA module 414 may determine the public binary primitive polynomial, $g_{t_i^S \cdot d}(x)$, by applying a second mapping function to the secret component, $PNA^S$, and the public component, $PNA^P$, of the master PNA object given the credentials of the cohort as input. In these implementations, the PNA module 414 may determine the public primitive polynomial, $g_{t_i^S \cdot d}(x)$, based on the output of the second mapping function, the first value, $t_i^S$, the secret value, d, of the secret component, $PNA^S$, of the master PNA object, and the secret binary primitive polynomial, $g_C^S(x)$, of the secret component, $PNA^S$.

In implementations, the PNA module 414 may allocate the resultant PNA object, $PNA_i$, to the cohort, such that the cohort receives the public component, $PNA^P$, of the master PNA object, the secret ratio, $t_i^S/t_i^P$, and the public binary primitive polynomial, $g_{t_i^S \cdot d}(x)$ (e.g., $PNA_i = [PNA^P, t_i^S/t_i^P, g_{t_i^S \cdot d}(x)]$). It is noted that any two cohorts i and j will be able to calculate a public ratio $t_i^P/t_j^P$ based on the public object and the pair of public primitive polynomials, $g_{C0}^P(x)$ and $g_{C1}^P(x)$, of the public component $PNA^P$, of the master PNA object, and the credentials of the cohorts i and j.

As will be discussed, the PNA object may be used by a VDAX of the cohort during link exchange to confirm engagement eligibility by performing eligibility synchronization vis-à-vis another cohort of the community. For example, in some implementations the cohort VDAX of a first cohort (e.g., "Cohort A") may generate a correlation vector, $C_{PNA}(A, B)$ when spawning a link for and/or decoding a link from a second cohort (e.g., "Cohort B") based on the PNA object of the first cohort and the credentials of the first and second cohorts (e.g., as described in greater detail below).

The implementations of FIG. 21 are provided as example techniques for generating PNA objects for the members of an ecosystem. It is appreciated that a progenitor VDAX may be configured to generate a master PNA object and PNA objects for ecosystem members in other suitable manners without departing from the scope of the disclosure. It is further appreciated that additional techniques for generating components of the master PNA objects and/or PNA objects for ecosystem members may be later developed.

Sequence Mapping

As discussed, sequence mapping may refer to a set of operations that include "mapping a sequence" into a genomic data object (e.g., an LNA object, an XNA object, or a ZNA object) to obtain a transformation value (TV) or a genomic engagement factor (GEF). Generally, sequence mapping is a computational process that receives a sequence, a genomic data object, and a set of instructions (e.g., GRI, instructions indicated by a window vector, or the like) and outputs a fixed length vector (e.g., a GEF or a TV) based thereon. For example, a sequence mapping module 440 may receive a sequence (PSS) (e.g., a public or private symmetric sequence taken from metadata that is obtainable to ecosystem member and ecosystem member B (e.g., Cohort A and Cohort B)) and may determine the vector based on the sequence, a genomic data object that is assigned to both A and B (e.g., XNA, LNA, or ZNA), and sequence mapping instructions that are shared between A and B (denoted as D(A, B)). As will be discussed, the sequence mapping instructions, D(A, B) may vary depending on the process that invokes the sequence mapping (e.g., link spawning/hosting v. VBLS encoding/decoding) and the configuration of the CG-ESP of the ecosystem. In example implementations, D(A,B) may be GRI provided by A to B (e.g., during link exchange or subsequent link updating), or instructions indicated by a "window" generated by A when spawning a link for B, or other suitable data structures used by the sequence mapping module 440 when performing a sequence mapping operation. As described elsewhere, sequence mapping instructions, such as GRI or instructions indicated by a "window", may be embodied in binary vectors and/or may embodied in parameterized instruction sets, such as a script or executable code. In the later implementations, the instructions may be parameterized with values (e.g., randomly generated values to parameterized GRI or a randomly selected window to parameterize instructions used in link exchange-based sequence mapping), such that the sequence mapping instructions are varied for different relationships. In implementations, a sequence mapping function receives a genomic data object as input (e.g., LNA, XNA, and ZNA), where the type of genomic data object depends on the process that invokes the sequence mapping process.

In some scenarios, the sequence mapping module 440 is invoked to generate a genomic engagement factor (GEF) (e.g., for VBLS generation). As discussed, a GEF may refer to a value that is used to transform a digital object into a VBLS object. In implementations, the sequence mapping module 440 may generate a GEF by "mapping" a sequence (e.g., a public sequence or a private sequence) into a modified or unmodified genomic differentiation object (e.g., a modified or unmodified XNA object or a modified or unmodified ZNA object) given specific genomic regulation instructions (GRI). It is appreciated that "mapping a sequence into" a modified or unmodified genomic data object may refer to a series of specified operations that are performed on the sequence, GRI, and genomic data object to obtain a resultant value (e.g., GEF or TV).

In implementations, the sequence mapping module 440 may receive the GRI and a genomic differentiation object as input (which may be a modified or an unmodified genomic differentiation object). In some implementations, the sequence mapping module 440 may further receive the sequence that is to be mapped (which may be a private sequence or a public sequence) as input. Alternatively, the sequence mapping module 440 may receive a digital object (or VBLS object) and may be configured to extract the sequence to be mapped from the digital object (or VBLS object).

It is noted that in some implementations, sequence mapping instructions (e.g., GRI or the like) may be generated by an ecosystem member and not shared with any other ecosystem members. For example, where the sequence mapping is being performed within a trusted execution environment (e.g., a processor is encoding and decoding instructions of a computer program and/or related data used or output by the program at run-time), the GRI used to perform sequence mapping within the trusted execution environment may be GRI that is not shared with any other ecosystem members, but rather that is only known to the VDAX (e.g., an EIC VDAX, discussed below) that generated the GRI. In some of these implementations, an EIC VDAX may generate the GRI, which the EIC VDAX uses to generate GEFs that are used by the EIC VDAX to encode and decode the instructions and/or related data. As such, in some implementations the GRI are not shared with any other VDAXs but are still used in the sequence mapping process to generate GEFs. Thus, while the example implementations of sequence mapping discussed below discuss GRI exchanged between VDAXs, the techniques discussed may be applied to the scenario where a VDAX is performing the sequence mapping using GRI (or other suitable sequence mapping instructions) that are only known to the VDAX. In such scenarios, descriptions of techniques performed using GRI (or other suitable sequence mapping instructions) exchanged between community members may be applied to handle these scenarios when configuring a sequence mapping module/CG-ESP that generates GEFs and/or transformation values using GRI (or other suitable sequence mapping instructions) that were generated and secretly stored by a single community member (e.g., EIC VDAX). There are other scenarios where certain GRI is not exchanged with any other ecosystem members, such as when notarizing a material data block (MDB), as discussed below. For purposes of explanation, the term "secret GRI" or "secret instructions" may refer to instructions that are not shared with any other ecosystem members.

Analogous to a GEF, a transformation value (TV) may refer to a value that is used to transform genomic engagement cargo (GEC) during link spawning, which facilitates the secure link exchange process. In some implementations, the sequence mapping module 440 may generate a transformation value by "mapping" a sequence (e.g., a public sequence or a private sequence) into a modified genomic correlation object (e.g., a modified LNA object) given a "window" extracted from the genomic correlation object (as discussed with respect to link exchange processes). In implementations, the sequence mapping module 440 may receive the window and a genomic correlation object (e.g., LNA object) as input (which may be a modified or an unmodified genomic differentiation object). In some implementations, the sequence mapping module 440 may further receive the sequence that is to be mapped as input. For example, in some implementations the sequence mapping module may receive a mapping sequence that is generated by the link module 430 (e.g., a value derived from the window and GRI generated during the link spawning processes). Alternatively, the sequence mapping module 440 may be configured to receive input values (e.g., a window and GRI) and may be configured to generate the mapping sequence from the input values using a set of computational functions. It is noted that the term "transformation value" may be used with respect to other types of operations, such as when generated to modify a genomic differentiation object or a genomic correlation object.

In some implementations, the sequence mapping module 440 generates GEFs and TVs using the same sequence mapping process. In these implementations, the sequence mapping module 440 may receive a sequence (e.g., a private sequence or a public sequence) and a genomic data object (e.g., an LNA object, an XNA object, or a ZNA object) and may output a transformation value (e.g., in the case that an LNA object is received) or a GEF (e.g., in the case that an XNA or ZNA object is received) using the same series of computational functions. Alternatively, the sequence mapping process used to generate transformation values and the sequence mapping process used to generate GEFs may be different processes. The examples of FIGS. 22 and 23 depict different variations of sequence mapping processes that may be used to generate transformation values and/or GEFs. As can be appreciated, the sequence mapping processes may be cipher-based, cipherless, or hybrid. It is appreciated that additional or alternative sequence mapping processes may be implemented in a CG-ESP without departing from the scope of the disclosure.

Sequence Mapping into Unmodified Genomic Data Object

FIG. 22 illustrates an example method for generating a sequence. In these example implementations, the sequence mapping module 440 receives an unmodified genomic differentiation object and maps the sequence into the genomic differentiation object using a series of computational functions. For purposes of explanation, the process is described as generating a GEF based on a sequence, an unmodified genomic differentiation object (e.g., XNA or ZNA) and GRI. The process may be adapted for generating TVs by substituting windows for GRI and an unmodified correlation object (e.g., LNA object) for an unmodified genomic differentiation object. The sequence mapping process of FIG. 22 may be performed in a cipher-based manner, a cipherless manner, or a hybrid manner.

At 2210, the sequence mapping module 440 obtains sequence mapping data, including a genomic differentiation object, GRI, and a sequence. In implementations, the input to the sequence mapping module 440 may include a genomic differentiation object (e.g., XNA or ZNA) and GRI. In the example of FIG. 22, the genomic differentiation object has not been modified and is undifferentiated from the enclave-specific or ecosystem-specific genomic differentiation object. In some implementations, the GRI correspond to a specific relationship that the host VDAX has formed with another sufficiently correlated digital ecosystem member. Alternatively, in some implementations, the GRI is secret GRI that has not been exchanged with another ecosystem member.

In some implementations, the sequence may be a symmetric sequence, such that the sequence is obtainable by both VDAXs. In implementations, the sequence may be a public sequence or a private sequence. In some examples provided below, "PSS" may refer to any type of sequence. As noted, a sequence may be a public sequence or a private sequence, where "PBS" may refer to a public sequence and "PVS" may refer to a private sequence. In implementations, the sequence, PSS, is provided to the sequence mapping module 440 as input. Alternatively, in some implementations the sequence is extracted by the sequence mapping module 440. In these implementations, the sequence mapping module 440 is configured to extract a specified set of bits (e.g., as defined in the configuration of the sequence mapping module 440 and/or as defined in the GRI). For example, in the case of a digital object (or a corresponding VBLS object), such as a data packet (or a corresponding VBLS-encoded data packet), a set of bits may be extracted from a defined set of bit locations of one or more packet headers. In these implementations, the sequence may be selected from the unencoded portion of the digital object. In this way, the symmetry of the sequence may be maintained through the encoding and decoding process.

At 2212, the sequence mapping module 440 transforms the sequence, PSS, into a sequence conversion vector (SCV) based on the GRI. In some implementations, PSS may be transformed into the SCV using a transformation function that includes a set of one or more computational functions. In implementations, SCV may be determined according to:

$$SCV_{GRI}=F1_{GRI}(PSS)$$

where F1 is a transformation function (which may be referred to as a "sequence transformation function") that receives the sequence, PSS, as input and transforms PSS using the one or more computational functions to obtain SCV. In embodiments, the sequence transformation function may be cipher-based (e.g., keyed-disambiguation, encryption, and/or other keyed-reversable computational functions), cipherless (e.g., hash functions, a series of parameterized combination of cyclic shift and/or XOR functions, one-way non-reversable functions, and/or the like), or hybrid functions (some combination of cipher-based and cipherless functions). In some implementations, the sequence transformation function receives the PSS and the GRI and executes one or more computational functions (e.g., cipher-based function(s) and/or cipherless function(s)), resulting in the SCV. It is noted that the size of SCV may be defined by as part of the CG-ESP's default configuration and/or in GRI, whereby larger SCVs may be used to enhance the overall security of the CG-ESP. For purposes of explanation and example, SCV is described as a 256-bit vector.

In some implementations, the sequence transformation function, F1, may be included in a standard configuration of the sequence mapping module 440. Alternatively, the GRI may indicate a particular configuration that is to be used to transform the PSS into the SCV. For example, a set of n bits in the GRI may indicate a specific transformation technique (e.g., which computational functions) to use to convert PSS. Additionally or alternatively, the GRI may include specific instructions that, when executed, transform the sequence into the SCV. In some implementations, the GRI may indicate parameters that are used to convert PSS. For example, the GRI may indicate a key to use when performing a cipher-based transformation of PSS, secure modification parameters (SMP) that are used to parameterize cipherless operations (e.g., a combination of cyclic shift and XOR functions), an input to a hash function, and/or the like. Additionally or alternatively, the transformation function may be configured to combine the sequence and the GRI (e.g., (PSS GRI)) and to transform the combined sequence and GRI using the set of one or more computational functions to obtain SCV. It is appreciated that additional or alternative techniques may be applied by the sequence mapping module to determine the SCV given an input sequence.

At 2214, the sequence mapping module 440 maps the unmodified genomic differentiation object based on the SCV to obtain a mapped differentiation object. In some implementations, the sequence mapping module 440 maps the genomic differentiation object (e.g., XNA or ZNA) into N binary vectors based on the SCV to obtain a mapped genomic differentiation object (denoted as $[S_{1,XNA}, S_{2,XNA} \ldots S_{N,XNA}]$). In some implementations, the sequence mapping module 440 executes a mapping function, F2, as shown below:

$$[S_{1,XNA}, S_{2,XNA} \ldots S_{N,XNA}] = F2_{GRI}(XNA)SCV)$$

It is appreciated that the mapping function (denoted as F2 above) may be configured in different manners. In some implementations, the manner by which the mapping function, F2, is configured is at least partially defined in the GRI. In these implementations, the manner by which the mapping function maps the unmodified genomic differentiation object may be designated and/or parameterized by the GRI. In some embodiments, the mapping function, F2, may be provided as a default configuration.

In some implementations, the mapping function, F2, may select a set of N vectors from the genomic differentiation object based on the SCV to obtain a set of N vectors (denoted as $[A_0, A_1, \ldots, A_{N-1}]$ or ($A_{S_{i-1}}$ for i=1 ... N). For example, in some implementations, the mapping function, F2, may select N vectors $[A_0, A_1, \ldots, A_{N-1}]$ from the genomic differentiation object based on N values indicated by the SCV. For instance, in some implementations, the mapping function may separate SCV into N sections (e.g., $[s_1 s_2 \ldots s_N]$, where the value represented by the $i^{th}$ section, $s_i$ of the SCV indicates a starting location in the genomic differentiation object from which the $i^{th}$ vector is extracted. In these example implementations, the mapping function may extract a predefined number of bits starting from the $s_i^{th}$ bit of the genomic differentiation object to obtain a respective vector, $A_{S_i}$. In some of these example implementations, the mapping function, F2, may output $[A_0, A_1, \ldots, A_{N-1}]$ as:

$$[S_{1,XNA}, S_{2,XNA} \ldots S_{N,XNA}].$$

In some implementations, the mapping function may be configured to additionally modify each of the N vectors ($A_{S_{i-1}}$ for i=1 ... N) according to a configuration of the sequence mapping module 440 and/or based on the SCV and/or GRI to obtain the set of mapped binary vectors (e.g., $L_{S_{i-1}}$ for i=1 ... N). In these example implementations, the mapping function, F2, may output $[L_0, L_1, \ldots, L_{N-1}]$ as $[S_{1,XNA}, S_{2,XNA} \ldots S_{N,XNA}]$. In this way, the mapped genomic differentiation object (e.g., $[S_{1,XNA}, S_{2,XNA} \ldots S_{N,XNA}]$), object may be further obfuscated to increase the level of security of the CG-ESP. In these example implementations, the mapping function may perform one or more computational functions on each of the N vectors ($A_{S_{i-1}}$ for i=1 ... N) to obtain the set of N mapped vectors ($L_{S_{i-1}}$ for i=1 ... N). For example, in some example implementations, the mapping function may execute a respective cyclic shift operation on each of the N vectors, $[A_0, A_1, \ldots A_{N-1}]$, to obtain the N mapped vectors $[L_0, L_1, \ldots L_{N-1}]$). In some of these implementations, each respective cyclic shift operation that is applied to a respective vector may be parameterized based on a value indicated by a respective segment of the SCV or the GRI. In these example implementations, each vector $A_{S_{i-1}}$ may be shifted by a value equal to $M_i$, where M is a value represented by the $i^{th}$ section of the SCV or the GRI. For example, in some implementations the mapping function may cyclically bit shift each respective vector, A, by $M_i$ bits to the right. The value of $M_i$ may be derived from SCV or GRI in any other suitable manner.

It is noted that the foregoing are examples implementations of a mapping function for mapping a genomic differentiation object based on an SCV and that alternative mapping functions may be developed and implemented in a sequence mapping module 440. Furthermore, as the example mapping functions implementations are described with respect to XNA objects, the descriptions above may be applied to map ZNA objects and/or LNA objects without departing from the scope of the disclosure.

At 2216, the sequence mapping module 440 modifies the mapped differentiation object using a set of computational functions to obtain a modified mapped genomic differentiation object (also referred to as a "modified genomic differentiation object). For instance, in some implementations, the sequence mapping module 440 may include a modification function, F3, that modifies the mapped genomic differentiation object according to:

$$[S_{1,XNA}^M, S_{2,XNA}^M \ldots S_{N,XNA}^M] = F3_{GRI}([S_{1,XNA}, S_{2,XNA} \ldots S_{N,XNA}])$$

where $[S_{1,XNA}^M, S_{2,XNA}^M \ldots S_{N,XNA}^M]$ denotes a modified genomic differentiation object having M rows. In some implementations, the modification function, F3, modifies the mapped genomic differentiation object based on the GRI. In some of these implementations, the modification function, F3, modifies the mapped genomic differentiation object based on one or more modification parameters (MP) that correspond to the GRI using a set of computational functions. In some implementations, the modification parameters may be defined in the GRI or may otherwise be indicated by the GRI. Additionally or alternatively, the one or more modification parameters may include the SCV that was determined based in part on the GRI (e.g., at 2122). Additionally or alternatively, a modification parameter may be otherwise determined based on the GRI. In embodiments, the modification function, F3, may be configured in a cipher-based, cipherless, or hybrid manner. In implementations, the modification function can output a set of N modified vectors, $[S_{1,XNA}^M, S_{2,XNA}^M \ldots S_{N,XNA}^M]$.

In some implementations, the modification function, F3, may be a cipher-based modification function. In these implementations, the modification function may include a disambiguation function and/or an encryption function that transforms the mapped genomic differentiation object using the modification value. In some of these implementations, the modification function F3 may use the modification value as a key for disambiguation or encryption. In these implementations, the modification function may apply the disambiguation and/or encryption functions to each vector of the N mapped vectors (e.g., Encrypt($[S_{1,XNA}, S_{2,XNA} \ldots S_{N,XNA}]$, MP) or XOR ($[S_{1,XNA}, S_{2,XNA} \ldots S_{N,XNA}]$, MP)) to obtain the N modified vectors, $[S_{1,XNA}^M, S_{2,XNA}^M \ldots S_{N,XNA}^M]$. As previously discussed, any number of different encryption algorithms may be applied to the N mapped vectors to obtain the set of N modified vectors. It is appreciated that the modification of the modified genomic data object may be performed on each of the N mapped vectors or to specified segments of the mapped differentiation object.

In some implementations, the modification function, F3, may be a cipherless modification function that perform one or more cipherless computational functions on the set of N mapped vectors information using a modification value. In some of these implementations, the modification function may include a hash function that is keyed by a modification parameter. In these implementations, the hash function may be any suitable hash function that may be keyed with a value. The hash function may be applied to the individual vectors of the N mapped vectors (e.g., $\text{Hash}_{GRI}(S_{i,XNA}, S_{i+1,XNA})$, for i=1 . . . N, where $S_{N+1}$=1) to obtain the N modified vectors, $[S_{1,XNA}^M, S_{2,XNA}^M \ldots S_{N,XNA}^M]$).

In some implementations, a cipherless modification function, F3, may execute a combination of parameterized XOR and cyclic shift operations to the mapped genomic differentiation object to obtain the modified genomic differentiation object. In some of these implementations, the XOR and cyclic shift operations are parameterized using a set of secure modification parameters (SMP) that define the manner by which bits are shifted and/or XOR'd. In implementations, the SMP may be defined by the one or more modification parameters. In some of these implementations, the modification function may apply the parameterized cipherless operations to mapped differentiation object (e.g., Cipherless_Modify($[S_{1,XNA}, S_{2,XNA} \ldots S_{N,XNA}]$, SMP)) to obtain the set of N modified vectors, $[S_{1,XNA}^M, S_{2,XNA}^M \ldots S_{N,XNA}^M]$. It is appreciated that the modification may be performed on each of the N mapped vectors or to specified segments of the mapped differentiation object.

In some implementations, the modification function, F3, may be a hybrid modification function. In these implementations, the modification function may apply these functions to each vector of the N mapped vectors (e.g., Hybrid_Modify$_{GRI}([S_{1,XNA}, S_{2,XNA} \ldots S_{N,XNA}])$ to obtain the N modified vectors, $[S_{1,XNA}^M, S_{2,XNA}^M \ldots S_{N,XNA}^M]$. In these implementations, a hybrid modification function may include at least one cipher-based operation and at least one cipherless modification function. In some of these implementations, the hybrid modification function may use a modification parameter as input parameters to the cipherless and/or cipher-based functions.

It is noted that the foregoing are examples implementations of a modification function for modifying a genomic differentiation object and that alternative mapping functions may be developed and implemented in a sequence mapping module 440. Furthermore, as the example modification functions implementations are described with respect to mapped XNA objects, the descriptions above may be applied to modify mapped ZNA objects and/or mapped LNA objects without departing from the scope of the disclosure.

At 2218, the sequence mapping module 440 converts the modified genomic differentiation object into a GEF. In implementations, the sequence mapping module 440 applies a conversion function, F4, that receives the modified differentiation object and converts the modified differentiation object into a GEF using a set of computational operations. In these implementations, a GEF may be determined according to:

$$GEF = F4([S_{1,XNA}^M, S_{2,XNA}^M \ldots S_{N,XNA}^M]).$$

Depending on the configuration of the sequence mapping module 440, the conversion function, F4, may be cipher-based, cipherless, or hybrid. The conversion function may be configured to output a vector of fixed size. For example, in some example implementations, the conversion function may be configured to output a GEF of fixed length (e.g., 128 bits, 256 bits, 512 bits, or the like). It is appreciated that the size of GEF may be a standard size defined in the CG-ESP or may be indicated by the GRI (e.g., a predetermined subset of bits of the GRI). As discussed, the larger the GEF the greater levels of security. In some implementations, the conversion function, F4, is a cipher-based function. For example, in some implementations GEF may be determined according to:

$$GEF = \text{CMAC}_{GRI}(S_{1,XNA}^M \| S_{2,XNA}^M \| \ldots \| S_{N,XNA}^M)$$

In this example, the conversion function, F4, includes a block cipher-based message authentication code (CMAC) function that receives the GRI and the modified mapped differentiation object (e.g., concatenated vectors) and outputs the GEF based thereon, such that GEF is of fixed length (e.g., 256 bits). It is appreciated that additional or alternative cipher-based operations may be applied to the modified vectors to obtain the GEF without departing from the scope of the disclosure.

In some implementations, the conversion function is a cipherless function. For example, in some implementations GEF may be determined according to:

$$GEF = \text{hash}_{256}(S_{1,XNA}^M \| S_{2,XNA}^M \| \ldots \| S_{N,XNA}^M)$$

In these example implementations, the conversion function may concatenate the vectors in the set of modified vectors ($[S_{1,XNA}^M, S_{2,XNA}^M \ldots S_{N,XNA}^M]$) and then may apply a hash function (e.g., an image-resistant function) to the result of the concatenation operations to output a fixed length vector, GEF. In the provided example, the hash function outputs 256-bit vectors. It is appreciated that the conversion function may be configured to output vectors of different lengths (e.g., a 128-bit hash value, a 512-bit hash value, or the like), however, without departing from the scope of the disclosure. It is appreciated that the length of the GEF may be varied in this example and could be equal to, less than, or greater than the length of the vectors in $[S_{1,XNA}^M, S_{2,XNA}^M \ldots S_{N,XNA}^M]$. It is appreciated that the conversion function may apply additional or alternative cipherless functions to the modified vectors to obtain the GEF without departing from the scope of the disclosure.

In some implementations, the conversion function, F4, is a hybrid function. For example, in some implementations GEF may be determined according to:

$$GEF = Hash_{256}(Encrypt_{GRI}(S_{1\_XNA}{}^{M} \| S_{2\_XNA}{}^{M} \| \ldots \| S_{N\_XNA}{}^{M}))$$

In this example implementation, the conversion function, F4, may concatenate each of the modified vectors into a single vector and may encrypt the resultant vector to obtain an encrypted vector. In the example implementation, the conversion function, F4, may then hash the encrypted vector to obtain the GEF (e.g., a 256 bit GEF). In the provided example, the hash function outputs 256-bit vectors. It is appreciated that the conversion function may be configured to output vectors of different lengths (e.g., a 128-bit hash value, a 512-bit hash value, or the like), however, without departing from the scope of the disclosure. It is appreciated that additional or alternative cipher-based and/or cipherless operations may be applied to the modified vectors to obtain the GEF without departing from the scope of the disclosure.

Figures 22, 23:
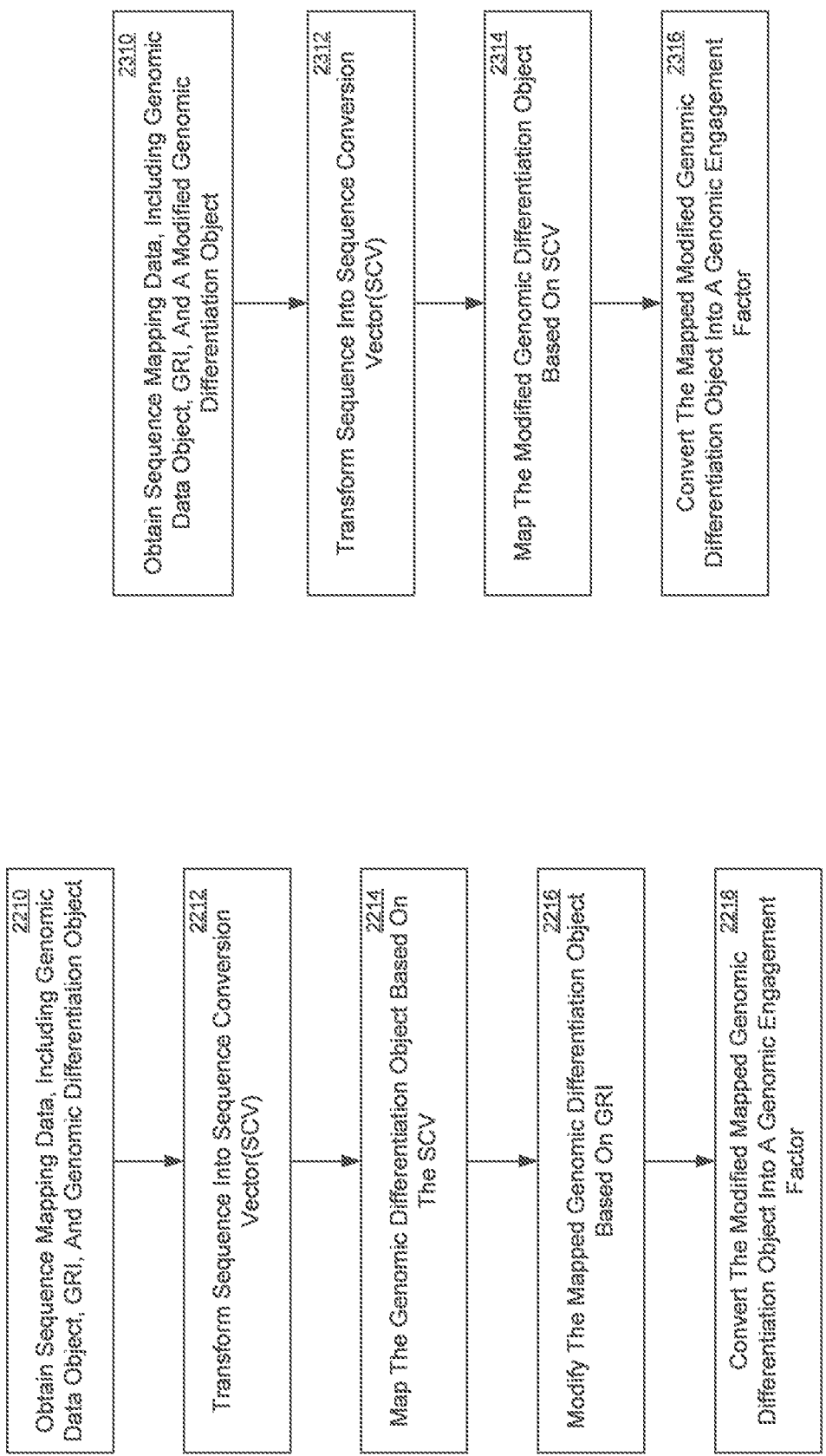
FIG. 22 illustrates an example process for performing sequence mapping on an unmodified genomic data object in accordance with some embodiments of the present disclosure.
FIG. 23 illustrates an example process for performing sequence mapping on a modified genomic data object in accordance with some embodiments of the present disclosure.

The foregoing method of FIG. 22 provides example implementations of a sequence mapping module 440. The techniques provided above are used to illustrate example configurations of a sequence mapping modules 440, including example configurations of functions (e.g., F1, F2, F3, and F4) that may be used in a sequence mapping module 440. It should be appreciated from the disclosure that additional or alternative techniques may be implemented and applied in a sequence mapping module 440 without departing from the scope of the disclosure. Furthermore, the techniques described above may be applied to either XNA or ZNA to generate a GEF. Furthermore, as mentioned above, the sequence mapping module 440 may be configured in accordance with the techniques described above or with other suitable sequence mapping operations to determine transformation values that are used during the link exchange process. In some of these implementations, the techniques discussed above may be applied to generate transformation values as well. In these implementations, the sequence mapping may obtain a genomic correlation object (e.g., an LNA object), a sequence, and a window. In these implementations, the window may be structured in the same manner as the GRI, such that the window is indicative of the information used to perform the sequence mapping operations. In some of these implementations, the sequence that is obtained during link exchange may be a value that is generated by the link spawning VDAX and encrypted using the common genomic eligibility information shared by the link spawning VDAX and the link hosting VDAX.

Sequence Mapping with Modified DNA

FIG. 23 illustrates an example process for performing sequence mapping according to some implementations of the present disclosure. In the example of FIG. 23, the sequence mapping module 440 obtains a modified genomic differentiation object (e.g., modified XNA or modified ZNA) or a modified genomic correlation object (e.g., modified LNA) and determines a GEF or a transformation value based thereon. For purposes of explanation, the example process is described with respect to a genomic differentiation object and the sequence mapping module 440 is producing a GEF.

At 2310, the sequence mapping module 440 obtains sequence mapping data, including a modified genomic differentiation object, GRI, and a sequence. In some implementations, the input to the sequence mapping module 440 may include a modified genomic differentiation object (e.g., a modified XNA object or a modified ZNA object) and GRI. For example, in some implementations a VDAX may store the modified genomic differentiation object in memory, whereby the modified genomic differentiation object was modified to generate or decode VBLS with respect to a specific cohort or enclave of the digital community.

As discussed with respect to FIG. 22, the GRI correspond to a specific relationship that the host VDAX has formed with another sufficiently correlated digital community member and the sequence is a symmetric sequence that may be a public sequence or a private sequence. In some implementations, the sequence is provided to the sequence mapping module 440 as input. Alternatively, in some implementations the sequence is extracted by the sequence mapping module 440. In these implementations, the sequence mapping module 440 is configured to extract a specified set of bits (e.g., as defined in the configuration of the sequence mapping module 440 and/or as defined in the GRI). For example, in the case of a digital object, such as a data packet, a defined set of bit values may be extracted from one or more packet headers, such that the sequences. In some implementations, the sequence may be selected from the unencoded portion of the digital object. In this way, the symmetry of the sequence may be maintained through the encoding and decoding process by the respective VDAXs.

At 2312 the sequence mapping module 440 transforms the sequence, PSS, into a sequence conversion vector (SCV) based on the GRI. As discussed with respect to FIG. 22, PSS may be transformed into the SCV using a transformation function that includes a set of one or more computational functions. In some implementations, the sequence mapping module 440 may transform PSS into the SCV using a transformation function that includes a set of one or more computational functions. In implementations, SCV may be determined according to:

$$SCV_{GRI} = F1_{GRI}(PSS)$$

where F1 is a transformation function (referred to as a "sequence transformation function") that receives the sequence, PSS, as input and transforms PSS using the one or more computational functions. As discussed with respect to FIG. 22, the computational functions of the transformation function, F1, may be cipher-based functions (e.g., disambiguation, encryption, and/or other reversable computational functions), cipherless functions (e.g., keyed-hash functions, executing a series of parameterized combination of cyclic shift and/or XOR functions, and/or other suitable one-way computational functions), or hybrid functions (some combination of cipher-based and cipherless functions). In some implementations, the sequence transformation function receives the PSS and the GRI and executes the computational functions, resulting in the SCV. It is noted that the size of SCV may be defined by as part of the CG-ESP's default configuration and/or in GRI, whereby larger SCVs may be used to enhance the overall security of the CG-ESP. For purposes of explanation and example, however, SCV is described as a 256-bit vector.

In some implementations, the sequence transformation function, F1, may be included in a standard configuration of the sequence mapping module 440. Alternatively, the GRI may indicate a particular configuration that is to be used to transform the PSS into the SCV (e.g., the first n bits of the GRI may indicate a specific transformation technique (e.g., one or more particular cipher-based functions and/or cipherless functions) to use to convert PSS. In some implementations, the GRI may indicate parameters that are used to convert PSS. For example, the GRI may indicate a key to use when performing a cipher-based transformation of PSS, secure modification parameters (SMP) that are used to parameterize cipherless operations (e.g., a combination of cyclic shift and XOR functions), an input to a hash function, and/or the like. Additionally or alternatively, the sequence transformation function may be configured to combine the sequence and the GRI (e.g., (PSS GRI)) and to transform the combined sequence and GRI using the set of computational functions to obtain SCV. It is appreciated that additional or alternative techniques may be applied by the sequence mapping module to determine the SCV given an input sequence.

At 2314 the sequence mapping module 440 maps the modified genomic differentiation object using the SCV to obtain a mapped differentiation object. In some of these implementations, the sequence mapping module 440 includes a mapping function that maps a modified genomic differentiation object based on the SCV to obtain a mapped modified genomic differentiation object (or simply a mapped genomic differentiation object). In implementations, the sequence mapping module 440 may execute the mapping function, F2, where the mapping function receives the modified genomic differentiation object and SCV as input. In some of these implementations, the sequence mapping module 440 may execute:

$$[S_{1,XNA}^M, S_{2,XNA}^M \ldots S_{N,XNA}^M] = F2_{GRI}(XNA^m, SCV)$$

where $XNA^m$ is the modified XNA object that was provided as input to the sequence mapping module 440 and $[S_{1,XNA}^M, S_{2,XNA}^M \ldots S_{N,XNA}^M]$ is the resultant mapped XNA object produced by the mapping function, F2, given the modified XNA object and the SCV. In some implementation, the mapping function, F2, may be configured in the same manner as was discussed with respect to FIG. 22. It is appreciated that the mapping function, F2, may be configured in alternative manners as well without departing from the scope of the disclosure.

As was discussed with respect to FIG. 22, in some implementations the mapping function, F2, may select a set of N vectors from the modified genomic differentiation object based on the SCV to obtain a set of N vectors (denoted as $[A_0, A_1, \ldots, A_{N-1}]$ or $(A_{S_{i-1}}$ for i=1 ... N).). For example, in some implementations, the mapping function may select N vectors $[A_0, A_1, \ldots, A_{N-1}]$ from the modified genomic differentiation object based on N values indicated by the SCV, as was described with respect to FIG. 22. In some of these example implementations, the mapping function, F2, may output $[A_0, A_1, \ldots A_{N-1}]$ as $[S_{1,XNA}^M, S_{2,XNA}^M \ldots S_{N,XNA}^M]$.

In some implementations, the mapping function may be configured to additionally modify each of the N vectors $(A_{S_{i-1}}$ for i=1 ... N) according to a configuration of the sequence mapping module 440 and/or based on the SCV and/or GRI to obtain the set of mapped vectors (e.g., $L_{S_{i-1}}$ for i=1 ... N). In these example implementations, the mapping function, F2, may output $[L_0, L_1, \ldots, L_{N-1}]$ as $[S_{1,XNA}^M, S_{2,XNA}^M \ldots S_{N,XNA}^M]$. In this way, the mapped genomic differentiation object, $[S_{1,XNA}^M, S_{2,XNA}^M \ldots S_{N,XNA}^M]$, object may be further obfuscated to increase the security of the CG-ESP. In these example implementations, the mapping function may perform one or more computational functions on each of the N vectors $(A_{S_{i-1}}$ for i=1 ... N) to obtain the set of N mapped vectors $(L_{S_{i-1}}$ for i=1 ... N) (e.g., as was described with respect to FIG. 22).

It is appreciated that the foregoing provides example implementations of a mapping function, F2, for mapping a modified genomic differentiation object using an SCV, and alternative mapping functions may be developed and implemented in a sequence mapping module 440.

At 2316, the sequence mapping module 440 converts the mapped genomic differentiation object into a GEF. In implementations, the sequence mapping module 440 applies a conversion function that receives the mapped differentiation object and converts the mapped genomic differentiation object into a GEF. In some implementations, the sequence mapping module 440 may execute the conversion function, F4, as was described with respect to FIG. 22. In these implementations, the sequence mapping module 440 may determine the GEF according to:

$$GEF = F4([S_{1,XNA}^M, S_{2,XNA}^M \ldots S_{N,XNA}^M]).$$

Depending on the configuration of the sequence mapping module 440, the conversion function, F4, may be cipher-based, cipherless, or hybrid. The conversion function may be configured to output a vector of fixed size. For example, in some example implementations, the conversion function may be configured to output a GEF of fixed length (e.g., 128 bits, 256 bits, 512 bits, or the like). It is appreciated that the size of GEF may be a standard size defined in the CG-ESP or may be defined by the GRI. As discussed, the larger the GEF the greater levels of security.

In some implementations, the conversion function, F4, is a cipher-based function. For example, in some implementations GEF may be determined according to:

$$GEF = CMAC_{GRI}(S_{1,XNA}^M \| S_{2,XNA}^M \| \ldots \| S_{N,XNA}^M)$$

In this example, the conversion function, F4, includes a block cipher-based message authentication code (CMAC) function that receives the GRI and the modified mapped differentiation object (e.g., concatenated vectors) and outputs the GEF based thereon, such that GEF is of fixed length (e.g., 256 bits). It is appreciated that additional or alternative cipher-based operations may be applied to the modified vectors to obtain the GEF without departing from the scope of the disclosure. It is appreciated that additional or alternative cipher-based operations may be applied to the modified vectors to obtain the GEF without departing from the scope of the disclosure.

In some implementations, the conversion function is a cipherless function. For example, in some implementations GEF may be determined according to:

$$GEF = hash_{256}(S_{1,XNA}^M \| S_{2,XNA}^M \| \ldots \| S_{N,XNA}^M)$$

In these example implementations, the conversion function may concatenate the vectors in the set of modified vectors $([S_{1,XNA}^M, S_{2,XNA}^M \ldots S_{N,XNA}^M])$ and then may apply a hash function (e.g., an image-resistant function) to the result of the concatenation operations to output a fixed length vector, GEF. In the provided example, the hash function outputs 256-bit vectors. It is appreciated that the conversion function may be configured to output vectors of different lengths (e.g., a 128-bit hash value, a 512-bit hash value, or the like), however, without departing from the scope of the disclosure. It is appreciated that the length of the GEF may be varied in this example and could be equal to, less than, or greater than the length of the vectors in $[S_{1,XNA}^M, S_{2,XNA}^M \ldots S_{N,XNA}^M]$. It is appreciated that the conversion function may apply additional or alternative cipherless functions to the modified vectors to obtain the GEF without departing from the scope of the disclosure.

In some implementations, the conversion function, F4, is a hybrid function. For example, in some implementations GEF may be determined according to:

$$GEF = Hash_{256}(Encrypt_{GRI}(S_{1,XNA}^M \| S_{2,XNA}^M \| \ldots \| S_{N,XNA}^M))$$

In this example implementation, the conversion function, F4, may concatenate each of the modified vectors into a single vector and may encrypt the resultant vector to obtain an encrypted vector. In the example implementation, the conversion function, F4, may then hash the encrypted vector to obtain the GEF (e.g., a 256-bit GEF). In the provided example, the hash function outputs 256-bit vectors. It is appreciated that the conversion function may be configured to output vectors of different lengths (e.g., a 128-bit hash value, a 512-bit hash value, or the like), however, without departing from the scope of the disclosure. It is appreciated that additional or alternative cipher-based and/or cipherless operations may be applied to the modified vectors to obtain the GEF without departing from the scope of the disclosure.

The foregoing method of FIG. 23 provides example implementations of a sequence mapping module 440. The techniques provided above are used to illustrate example configurations of a sequence mapping modules 440, including example configurations of functions (e.g., F1, F2, F3, and F4) that may be used in a sequence mapping module 440. It should be appreciated from the disclosure that additional or alternative techniques may be implemented and applied in a sequence mapping module 440 without departing from the scope of the disclosure. Furthermore, the techniques described above may be applied to either modified XNA or modified ZNA objects to generate a GEF. Furthermore, as mentioned above, the sequence mapping module 440 may be configured in accordance with the techniques described above or with other suitable sequence mapping operations to determine transformation values (TVs) that are used during the link exchange process. In some of these implementations, the techniques discussed above may be applied to generate transformation values as well. In these implementations, the sequence mapping may obtain a modified genomic correlation object (e.g., a modified LNA object), a sequence, and a window. In these implementations, the window may be structured in the same manner as the GRI, such that the window is indicative of the information used to perform the sequence mapping operations. In some of these implementations, the sequence that is obtained during link exchange may be a value that is generated by the link spawning VDAX and encrypted using the common genomic eligibility information shared by the link spawning VDAX and the link hosting VDAX.

Link Exchange Examples

As discussed, the link module 430 may be configured to spawn and decode links in accordance with some implementations of the present disclosure. In implementations, the link module 430 of a VDAX may leverage the genomic eligibility object (e.g., a CNA object and/or a PNA object) assigned to the VDAX to verify engagement eligibility with another VDAX during the link exchange process. As can be appreciated from the present disclosure, the link exchange process enables virtually unbounded hyper-scalable correlation—that is, the ability for two sufficiently affiliated ecosystem cohorts to authenticate one another without a trusted third party to participate in the authentication. In some implementations, hyper-scalable correlation may be achieved using genomic correlation objects (e.g., LNA objects) during the link exchange process, whereby information used to spawn and host a link may be encrypted or otherwise transformed using a correlation vector (e.g., $C_{CNA}$(A,B) or $C_{PNA}$(A,B)) that is indicative of the unique correlation between the ecosystem cohorts exchanging a link.

In some implementations, the link module 430 confirms engagement eligibility using CNA objects, a process which may be referred to as engagement correlation. As discussed, in some implementations a CNA object of the VDAX may be derived from a master CNA object, which may be a randomly generated matrix. In these implementations, the master CNA object may be private and inaccessible by any VDAX outside the progenitor VDAX. In some implementations, the progenitor VDAX determines a codeword vector corresponding to a unique obtainable data set corresponding to a respective community member. In these implementations, the progenitor VDAX may use the unique codeword vector of the respective community member to determine a unique subset of the master CNA object to allocate to the respective community member and may generate a CNA object based on the allocated subset of the CNA object, as described above. In some implementations, the unique obtainable data set may be used by a community member as credentials of the community member, such that the credentials may be used by other community members to determine the codeword vector of the ecosystem member. In this way, any two community members (e.g., Cohort A and Cohort B) of the same ecosystem can both determine their own codeword vector and the codeword vector of the other community member based on the respective credentials of each community member. In these implementations, each of the community members may then generate a common correlation vector based on an intersection of the codeword vectors of the two community members, whereby the common correlation vector may be used to secure the link exchange process. For purposes of explanation, $C_c$ (A, B) may refer to a correlation vector that can be generated by a first community member (e.g., Cohort A) and a second community member (e.g., Cohort B) based on the first credentials of the first, second credentials of the second community members, and the CNA object of the first community member or the CNA object of the second community member. It is noted that both the first community member and the second community member is able to generate the same correlation vector, $C_c$(A, B), using only their respective CNA object and the first and second credentials.

In some implementations, the link module 430 confirms engagement eligibility using PNA objects, a process which may be referred to as eligibility synchronization. In these implementations, the link module 430 of a VDAX may be configured to obtain a common correlation vector $C_{PNA}$(A, B) using PNA, as described in further detail below.

Figure 24:
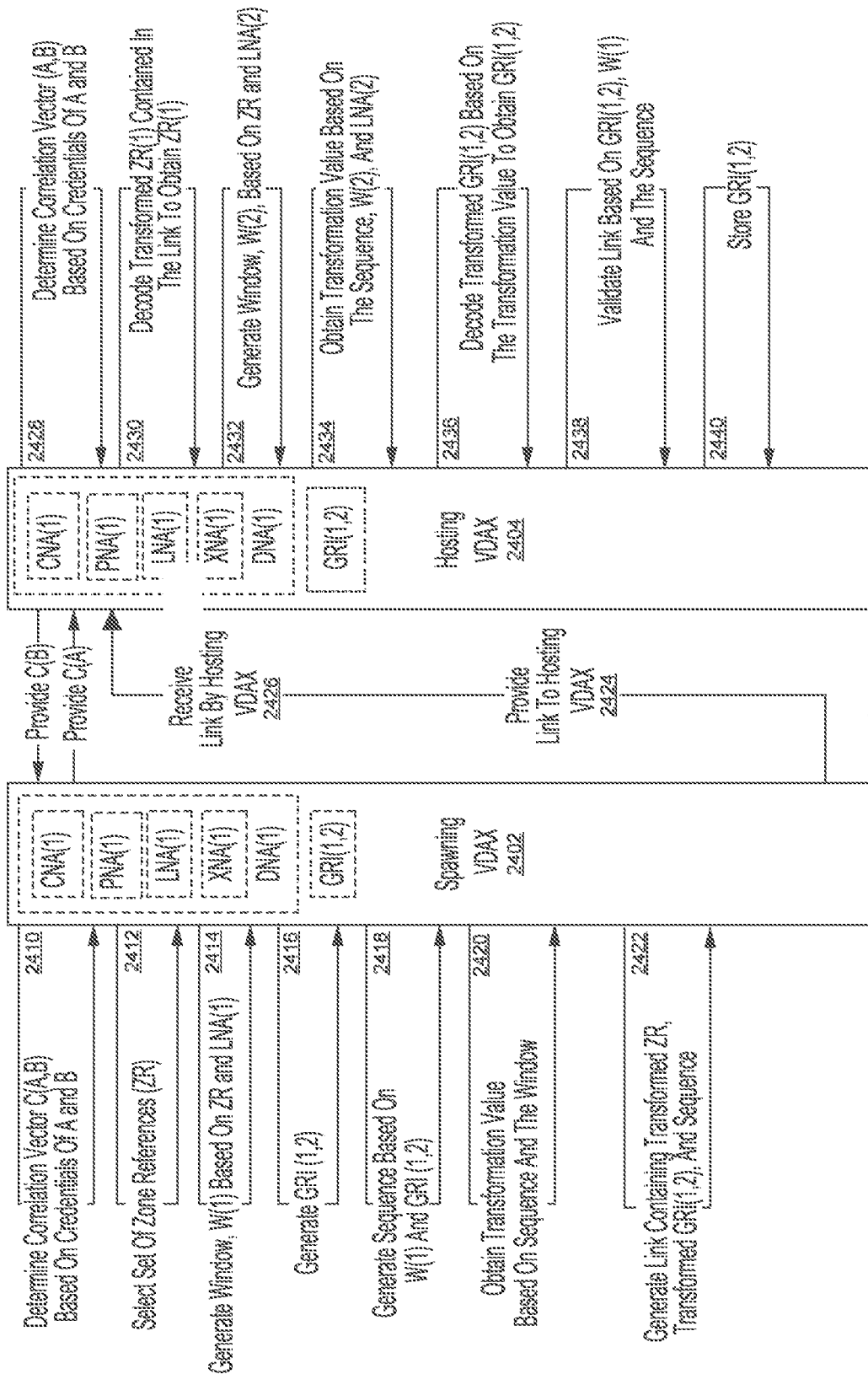
FIG. 24 illustrates an example process for performing link exchange in accordance with some embodiments of the present disclosure.

FIG. 24 illustrates an example link exchange process according to some implementations of the present disclosure. The link exchange process may include link spawning and link hosting. For purposes of explanation, an example link spawning process is described as being performed by a link module 430 of a link spawning VDAX 2402 and is depicted on the right side of FIG. 24. Similarly, an example link hosting process is described as being performed by a link module 430 of a link hosting VDAX 2404 and is depicted on the left side of FIG. 24. It is appreciated that in some implementations, some or all of the steps may be executed by other suitable modules of a respective VDAX.

In the example of FIG. 24, a link spawning VDAX 2402 generates a link containing genomic regulation instructions (GRI) that is provided to a link hosting VDAX 2404, which the link hosting VDAX 2404 decodes to obtain the GRI that are used to generate VBLS that is decoded by the link spawning VDAX 2402. In the illustrated example, the link spawning VDAX 2402 and the link hosting VDAX 2404 are configured with the same CG-ESP configuration. The link spawning VDAX 2402 is assigned a first genomic data set (e.g., a first CNA object and/or a first PNA object, a first LNA object, and a first XNA object) and the link hosting VDAX 2404 is assigned a second genomic data set (e.g., a second CNA object and/or a second PNA object, a second LNA object, and a second XNA object). Assuming the link hosting VDAX 2404 and the link spawning VDAX 2402 are members of the same digital ecosystem, a progenitor VDAX of the digital ecosystem may generate and assign the first genomic data set to the link spawning VDAX 2402 and the second genomic data set to the link hosting VDAX 2404. In these implementations, the CNA objects and/or PNA objects of the link spawning VDAX 2402 and link hosting VDAX 2404 are unique but correlated. In these implementations, the LNA objects of the link spawning VDAX 2402 and the link hosting VDAX 2404 may be the same LNA object when the two community members have a mutual identity of interest (e.g., as designated by a community owner and enforced by the ecosystem VDAX).

At 2410, the link module 430 of the link spawning VDAX 2402 determines a correlation vector, C(A,B), indicating a unique correlation between the link spawning VDAX 2402 and a link hosting VDAX 2404. In some implementations, the link module 430 of the link spawning VDAX 2402 determines the correlation vector $C_{CNA}(A,B)$, based on first credentials corresponding to the link spawning VDAX 2402, second credentials corresponding to the link hosting VDAX 2404, and a first CNA object assigned to the link spawning VDAX 2402. In some implementations, the link spawning VDAX 2402 and the link hosting VDAX 2404 exchange credentials that are unique to the respective community members represented by the link spawning VDAX 2402 and the link hosting VDAX 2404. For example, first credentials of the link spawning VDAX 2402 may include information relating to the community member (e.g., a first cohort) represented by the link spawning VDAX 2402 and second credentials of the link hosting VDAX 2404 may include information relating to a second community member (e.g., a second cohort) represented by the link hosting VDAX 2404. In some implementations, the link spawning VDAX 2402 may provide the first credentials to the link hosting VDAX 2404 and the link hosting VDAX 2404 may provide the second credentials to link spawning VDAX 2402. Alternatively, the VDAXs may obtain the credentials of the other community from a data source that maintains the obtainable information of the respective community members.

In some implementations, the link module 430 of the link spawning VDAX 2402 determines a first codeword vector corresponding to the link spawning VDAX 2402 based on the first credentials by applying the code mapping function to the first credentials. In these implementations, the code mapping function receives the first credentials and outputs the unique codeword vector corresponding to the first community member represented by the link spawning VDAX 2402 (e.g., as described elsewhere in the disclosure). Similarly, the link module 430 determines a second codeword vector corresponding to the link hosting VDAX 2404 based on the second credentials of the community member represented by the link hosting VDAX 2404. In some of these implementations, the link module 430 may apply the same code mapping function to the first credentials and the second credentials. The link module 430 may then determine an intersection vector based on the first codeword vector and the second codeword. For example, the link module 430 may determine an intersection of the first codeword vector and the second codeword vector (e.g., Codeword(A) AND Codeword(B)) to obtain the intersection vector.

In some implementations, the intersection vector is a sequence of indices to the respective portions of the master CNA object of the digital ecosystem that are commonly shared by the respective CNA objects assigned to the respective digital ecosystem members represented by the link spawning VDAX 2402 and the link hosting VDAX 2404. As will be discussed below, the link hosting VDAX 2404 is also configured to calculate the same intersection value based on the first credentials and the second credentials. In this way, both the link hosting VDAX 2404 and the link spawning VDAX 2402 can calculate the same intersection vector; and because the intersection vector indexes respective portions of the master CNA object that are allocated to both the CNA objects of the link spawning VDAX 2402 and the link hosting VDAX 2404, both the link hosting VDAX 2404 and the link spawning VDAX 2402 can extract the common portions of the CNA object from their respective CNA objects.

In implementations, the link module 430 of the link spawning VDAX 2402 extracts the portions of the CNA object indicated by the intersection vector and concatenates those portions to obtain a binary vector. In some implementations, this resultant vector may be used as the correlation vector, $C_{CNA}(A,B)$. In other implementations, the resultant vector may be modified using one or more computational functions to obtain the correlation vector, $C_{CNA}(A,B)$.

It is appreciated that the link module 430 of the link spawning VDAX 2402 may generate the correlation vector C(A, B) in other suitable manners without departing from the scope of the disclosure. In some implementations, the link module 430 of the link spawning VDAX may determine a PNA-based correlation vector, $C_{PNA}(A, B)$ based on a PNA object assigned to the link spawning VDAX 2402 and engagement information corresponding to the community member for which the link is being spawned (e.g., the credentials and a public primitive polynomial of the link hosting VDAX). Examples of PNA-based generation of correlation vectors are discussed in greater detail below.

At 2412, the link module 430 generates a set of zone references. In some implementations, a zone reference may refer to a value that indicates a portion of an LNA object. For example, a zone reference may be a value that indicates a starting bit location of a portion of the LNA object, where the portion has a specified bit size. In these example implementations, the link module 430 may randomly generate M zone references, where each zone reference is a value that is less than the number of zones in the LNA object and greater than or equal to zero.

At 2414, the link module 430 generates a window based on the genomic correlation object and the zone references. In some implementations, the link module 430 of the link spawning VDAX 2402 may extract M zones from the LNA object indicated by the M zone references to obtain a set of M vectors (e.g., $[L_1 \ldots L_M]$). In some implementations, the window is structured as a binary vector of fixed length. In some of these implementations, the link module 430 may concatenate the M vectors to obtain the window. In some implementations, the link module 430 may concatenate the M vectors and then may apply a transformation function to the concatenated vectors to obtain the window. For example, in some of these implementations the link module 430 may apply a pre-image resistant transformation function to the concatenated vectors to obtain the window. In some of these implementations, the link module 430 may include information that is unique to the link spawning VDAX and the link hosting VDAX 2404 as input to the pre-image resistant transformation function. For example, the link module 430 may include the respective credentials of the link spawning VDAX 2402 and the link hosting VDAX 2404 (or values derived therefrom) as input to the pre-image resistant transformation function to obtain the window. It is appreciated that the window may be determined in other suitable manners.

At 2416, the link module 430 generates genomic regulation instructions (GRI) to be sent to the link hosting VDAX 2404. In implementations, the link module 430 generates genomic regulation instructions that are generated for specifically for the link hosting VDAX 2404, such that the link hosting VDAX 2404 uses the GRI when generating VBLS that is decipherable by the link spawning VDAX 2402. In some implementations, the GRI may be represented as a binary vector of fixed length, L, (e.g., 256 bits, 512 bits, or the like). In some implementations, the link module 430 may generate the GRI by randomly generating a binary vector of length L. In these implementations, the link module 430 may generate a random value greater than or equal to 0 and less than $2^L$, where L is the length of the randomly generated binary vector.

In some implementations, various portions of the binary vector containing the GRI may be mapped to instructions that are used by the link hosting VDAX 2404 when generating VBLS for the link spawning VDAX 2402 and by the link spawning VDAX when deciphering VBLS from the link hosting VDAX 2404 LS02. Non-limiting examples of instructions that may be indicated by the GRI may include sequence selection parameters that indicate how to extract a public or private sequence for sequence extraction (e.g., which bits of a digital object, how many bits to extract, and/or the like), configuration parameters that indicate which computational functions to use when performing various tasks (e.g., which functions to use when generating a GEF or transformation value, which functions to use when transforming a digital object, which functions to use when transforming a genomic data object, and/or the like), and/or input parameters (e.g., a value used to modify a genomic data object when performing sequence mapping, secure modification parameters (SMP), and/or the like. In some implementations, the link module 430 of either VDAX may be configured to extract specific portions of the GRI binary vector and, for each extracted portion, determine an instruction associated with the value defined in the extracted portion (e.g., using an association table, index, or the like).

At 2418, the link module 430 generates a sequence based on the window and the GRI. In some implementations, the link module 430 generates the sequence by combining the window and the GRI. For example, the link module 430 may concatenate a window vector to a GRI vector or vice-versa to obtain the sequence. Alternatively, the link module 430 may apply a pre-image resistant function (or any other suitable computational one-way function) to a combination of the GRI and the window to obtain the sequence. The link module 430 may determine a sequence based on the window and the GRI in other suitable manners as well. In some implementations, a sequence generated using the window and the GRI may be used by the link hosting VDAX 2404 430 to validate the integrity of the link (as discussed further below).

At 2420, the link module 430 obtains a transformation value based on the sequence and the window. In implementations, the link module 430 provides the window, the sequence, and the LNA object to the sequence mapping module 440. The sequence mapping module 440 may determine the transformation value based on the window, the sequence, and the LNA object (e.g., as described above). In some of these implementations, the sequence mapping module 440 may be configured process the window to extract specific portions of the window and, for each extracted portion of the window, determine an associated instruction that is used for generating the transformation value given the sequence and the LNA object. It is noted that the sequence mapping examples described above where described with respect to the generation of a GEF given GRI, a sequence, and a genomic differentiation object. As was discussed, those various implementations are adapted to generate transformation values given a window, a sequence, and an LNA object.

At 2422, the link module 430 generates a link based on the sequence, GRI, the transformation value, the zone references, and the correlation vector. In these implementations, the link module 430 may transform the GRI using the transformation value to obtain transformed GRI. The link module 430 may further transform the zone references using the correlation vector to obtain transformed zone references. In these implementations, the link includes the sequence (unencoded), the transformed zone references, and the transformed GRI.

In implementations, the link module 430 transforms the GRI using the transformation value. In some implementations, the link module 430 may transform the GRI using an encryption function, whereby the GRI may be encrypted using the transformation value as a key. In some implementations, the link module 430 transforms the GRI using a disambiguation function, whereby the GRI may be XORed with the transformation value. In some of these implementations, the link module 430 may provide the GRI and the transformation value to the transformation module 450, which executes the transformation function on the GRI given the transformation value.

In implementations, the link module 430 transforms the zone references using the correlation vector. In some implementations, the link module 430 may transform the zone references using an encryption function, whereby the zone references may be encrypted using the transformation value as a key. In some implementations, the link module 430 transforms the zone references using a disambiguation function, whereby the zone references may be XORed with the transformation value. In some of these implementations, the link module 430 may provide a zone reference vector indicating the set of zone references and the correlation vector to the transformation module 450, which executes the transformation function on the zone reference vector given the correlation vector.

At 2424, the link spawning VDAX 2402 provides the transformed zone references, the transformed link, and the sequence to the link hosting VDAX 2404. In some implementations, the link spawning VDAX 2402 may use separate channels (e.g., networks, communication mediums, and/or the like) to provide the transformed zone references, the transformed link, and the sequence to the link hosting VDAX 2404. For example, in some implementations the link spawning VDAX 2402 may provide the transformed zone references via a first channel (e.g., via a LAN) and may provide the sequence and the transformed GRI using a second channel (e.g., via a cellular network). In other implementations, the link spawning VDAX 2402 provides the transformed zone references, the transformed link, and the sequence to the link hosting VDAX 2404 using the same channel. As discussed, the forgoing data may be collectively referred to as "genomic engagement cargo".

The link hosting VDAX 2404 may receive the genomic engagement cargo provided by the link spawning VDAX 2402 and may execute a link hosting process based on the received genomic engagement cargo. Example implementations of link hosting processes are described further below.

As 2426, the link hosting VDAX 2404 receives the genomic engagement cargo (e.g., transformed zone references, the transformed link, and the sequence) from the link spawning VDAX 2402. As discussed above, the transformed zone references, the transformed link, and the sequence may be received via one or more channels.

At 2428, the link module 430 of the link hosting VDAX 2404 determines a correlation vector indicating a unique correlation between the link hosting VDAX 2404 and the link spawning VDAX 2402. In implementations, the link module 430 may generate the correlation vector in the same manner that was used by the link spawning VDAX 2402 to generate the correlation vector. For example, in some implementations the link module 430 may obtain the first credentials of the link spawning VDAX 2402 and the second credentials of the link hosting VDAX 2404 and may determine the correlation vector based on the first credentials, the second credentials, and a second CNA object of the link hosting VDAX 2404. In these implementations, the correlation vector references portions of the master CNA object that are common to both the link spawning VDAX 2402 and the link hosting VDAX 2404. As such, the link modules 440 of both the link spawning VDAX 2402 and the link hosting VDAX 2404 will generate identical correlation vectors, provided they are eligible to engage (e.g., are from the same digital ecosystem).

As was discussed with respect to the link spawning VDAX 2402, the link module 430 of the link hosting VDAX 2404 may generate the correlation vector in other suitable manners. For example, in some implementations the link module 430 of the link hosting VDAX 2404 may determine a correlation vector, $C_{PNA}(B,A)$ based on a PNA object assigned to the link hosting VDAX 2404, credentials corresponding to the community member represented by the link hosting VDAX 2404, and engagement information corresponding to the community member represented by the link spawning VDAX 2402. In these implementations, the correlation vector, $C_{PNA}(B,A)$, generated by the link hosting VDAX 2404 will match the correlation vector, $C_{PNA}(A,B)$ generated by the link spawning VDAX 2402 only if the respective VDAXs have access to the secret components of their respective PNA objects. Put another way, malicious entities attempting to use the public engagement information of a valid community member will be unable to recreate the correlation vectors without having access to the secret components of the community member's PNA object. Examples of PNA-based generation of correlation vectors are discussed in greater detail below.

At 2430, the link module 430 of the link hosting VDAX 2404 decodes the transformed zone references using the correlation vector to obtain the set of zone references. As discussed, the link module 430 of the link spawning VDAX 2402 may transform the set of zone references using a transformation function (e.g., an encryption function or a disambiguation function (XOR)) using the correlation vector as the transformation value. As such, the link module 430 of the link hosting VDAX 2404 may decode the transformed zone references using the correlation vector as the transformation value. For instance, in implementations where the transformed zone references were encrypted by the link spawning VDAX 2402 using the correlation vector, the link module 430 of the link hosting VDAX 2404 may decrypt the transformed zone references using the correlation vector to obtain the set of zone references. In implementations where the transformed zone references were transformed by the link spawning VDAX 2402 using a disambiguation function, the link module 430 of the link hosting VDAX 2404 may disambiguate the transformed zone references using the correlation vector (e.g., XOR of the transformed zone references and the correlation vector) to obtain the set of zone references.

At 2432, the link module 430 of the link hosting VDAX 2404 generates a window based on the genomic correlation object and the set of zone references. In some implementations, the link module 430 of the link hosting VDAX 2404 uses the same techniques employed by the link spawning VDAX 2402 to generate the window. For example, in some implementations, the link module 430 of the link hosting VDAX 2404 may extract M zones from the link hosting VDAX 2404's LNA object indicated by the M zone references to obtain a set of M vectors (e.g., $[L_1 \ldots L_M]$). In some of these implementations, the link module 430 may concatenate the M vectors to obtain the window. In some implementations, the link module 430 may concatenate the M vectors and then may apply a transformation function to the concatenated vectors to obtain the window. For example, in some of these implementations the link module 430 may apply a pre-image resistant transformation function to the concatenated vectors to obtain the window. In some of these implementations, the link module 430 may include information that is unique to the link spawning cohort and the link hosting cohort as input to the pre-image resistant transformation function, such as the respective credentials of the link spawning VDAX 2402 and the link hosting VDAX 2404 (or values derived therefrom). It is appreciated that the window may be determined in other suitable manners, so long as the link spawning VDAX 2402 and the link hosting VDAX 2404 are able to generate the same window when having identical or otherwise sufficiently correlated LNA objects.

At 2434, the link module 430 of the link hosting VDAX 2404 obtains a transformation value based on the sequence and the window. In implementations, the link module 430 of the link hosting VDAX 2404 obtains the transformation value by the same operations performed by the link module of the link spawning VDAX 2402. For example, in some implementations the link module 430 provides the window, the sequence, and the LNA object to the sequence mapping module 440, which determines the transformation value based on the window, the sequence, and the LNA object (e.g., as described above).

At 2436, the link module 430 decodes the transformed GRI using the transformation value to obtain the GRI. In implementations, the link module 430 of the link hosting VDAX 2404 decodes the transformation value using the inverse operations performed by the link module 430 of the link spawning VDAX 2402. As discussed, the link module 430 of the link spawning VDAX 2402 may transform the GRI using a transformation function (e.g., a decryption function or a disambiguation function (XOR)) based on the transformation value. As such, the link module 430 of the link hosting VDAX 2404 may decode the transformed GRI using the transformation value determined at 2436. For instance, in implementations where the transformed GRI were encrypted by the link spawning VDAX 2402 using the transformation value as the encryption key, the link module 430 of the link hosting VDAX 2404 may decrypt the transformed GRI using the transformation value to obtain the decoded GRI. In implementations where the transformed GRI were transformed by the link spawning VDAX 2402 using a disambiguation function, the link module 430 of the link hosting VDAX 2404 may disambiguate the transformed GRI using the transformation value (e.g., XOR of the transformed GRI and the transformation) to obtain the decoded GRI.

At 2438, the link module 430 of the link hosting VDAX 2404 validates the integrity of the link based on the decoded GRI, the window generated by the link hosting VDAX 2404, and the sequence received from the link spawning VDAX 2402. In some implementations, the link module 430 of the link hosting VDAX generates a validation sequence based on the decoded GRI and the window generated at 2438. If the validation sequence matches the sequence provided by the link spawning VDAX 2402, the link module 430 validates the integrity of the link. The link module 430 of the link hosting VDAX 2404 may execute the same process to generate the validation sequence as the link spawning VDAX 2402 executed when generating the provided sequence. In some example implementations, the link module 430 of the link hosting VDAX 2404 may combine (e.g., concatenate) the decoded GRI and the window to obtain the validation sequence. Alternatively, the link module 430 may apply a pre-image resistant function (or any other suitable computational one-way function) to the combination of the decoded GRI and the window to obtain the validation sequence. The link module 430 may determine a validation sequence based on the window and the decoded GRI in other suitable manners as well, assuming that the link spawning VDAX 2402 and the link hosting VDAX 2404 are configured with functionally congruent link modules 430.

In some implementations, the link module 430 of the link hosting VDAX 2404 may then compare the validation sequence to the sequence provided by the link spawning VDAX 2402 to validate the integrity of the link. If the validation sequence and the received sequence match, then the link module 430 of the link hosting VDAX 2404 may validate the link and may store the decoded GRI (and any other suitable link information), as shown at 2440. Once a link has been stored and hosted, the link hosting VDAX 2404 uses the decoded GRI when generating VBLS intended for the link spawning VDAX 2402.

It is noted that the example of FIG. 24 illustrates a one-way link exchange (i.e., from the link spawning VDAX 2402 to the link hosting VDAX 2404). It is appreciated that the foregoing may be performed in a dissymmetric manner as well, whereby each of the VDAXs spawns a respective link for the other VDAX and decodes another link from the other VDAX. In these implementations, the exchanged links will be different, as the VDAXs independently generate zone references and GRIs. Furthermore, the example implementations provided in FIG. 24 are provided for illustrative purposes and other techniques for performing link exchange may be later developed without departing from the scope of the disclosure.

PNA-Based Correlation Vectors and Eligibility Synchronization

As discussed, in some implementations of a CG-ESP, a link module 430 may be configured to generate correlation vectors based on PNA objects. In some implementations of a CG-ESP, link modules 430 of ecosystem member VDAXs (e.g., cohort VDAXs, enclave VDAXs, ecosystem VDAXs, or the like) are configured to generate PNA-based correlation vector using PNA and public engagement information of counterpart ecosystem members. As discussed with respect to FIG. 21, a PNA object of a respective community member, $PNA_i$, may include the public component, $PNA^P$, of the master PNA object, the secret ratio, $t_i^S/t_i^P$, of the ecosystem member, and the public binary primitive polynomial, $g_{t_i}s._d(x)$, of the ecosystem member (e.g. $PNA_i$=[$PNA^P$, $t_i^S/t_i^P$, $g_{t_i}s._d(x)$]). In implementations, the engagement information of an ecosystem member may include the credentials and public binary primitive polynomial, $g_{t_i}s._d(x)$, of the ecosystem member. Upon a VDAX of an ecosystem member receiving the engagement information of a counterpart ecosystem member, the VDAX is able to generate a correlation vector based on the credentials and PNA object of the ecosystem member and the engagement information of the counterpart ecosystem member.

Example implementations of PNA-based generation of correlation vectors is provided below. For purposes of explanation, the provided example describes link exchange between a first cohort VDAX (referred to as "Cohort A") and a second cohort VDAX (referred to as "Cohort B"). In this example, the PNA object of Cohort A is designated as $PNA_A$=[$PNA^P$, $t_A^S/t_A^P$, $g_{t_A}s._d(x)$]). Similarly, the PNA object of Cohort B is designated as $PNA_B$=[$PNA^P$, $t_B^S/t_B^P$, $g_{t_B}s._d(x)$]). Tables 8 and 9 illustrate example processes that are executed respectively by the first cohort VDAX (e.g., Cohort A) and the second cohort (e.g., Cohort B) when performing PNA-based eligibility synchronization.

TABLE 8

Cohort A Eligibility Synchronization Process

| | |
|---|---|
| 1. | Receive Credentials and public primitive polynomial, $g_{t_B}s._d(x)$, of Cohort B |
| 2. | Determine a public ratio of Cohort A to Cohort B, $t_A^P/t_B^P$, based on Credentials of Cohort A, Credentials of Cohort B, and $PNA^P$ |
| 3. | Generate first M-degree primitive polynomial, $P1_{PNA}(A, B)$, based on Cohort B's public primitive polynomial, $g_{t_B}s._d(x)$, and the secret ratio, $t_A^S/t_A^P$, of Cohort A |
| 4 | Generate second M-degree primitive polynomial, $P2_{PNA}(A, B)$, based on $P1_{PNA}(A, B)$ and the public ratio, $t_A^P/t_B^P$ |
| 5 | Output Correlation Vector $C_{PNA}(A, B)$ |

In the example of Table 8, Cohort A receives engagement information corresponding to Cohort B. As discussed, the engagement information of Cohort B may include the credentials and the public polynomial of Cohort B. For example, Cohort B may provide the credentials and its public primitive polynomial, $g_{t_B}s._d(x)$, when either Cohort A or B initiate the link exchange. Alternatively, the engagement information may be obtained from a public or semi-public data source that stores the credentials and public polynomials of ecosystem members.

Upon receiving the engagement information of Cohort B, Cohort A determines a public ratio of Cohort A to Cohort B, $t_A^P/t_B^P$, based on the credentials of Cohort A, the credentials of Cohort B, and the public component of the of the master PNA object, $PNA^P$. In some implementations, the public component, $PNA^P$ includes two public M-degree primitive polynomials, $g_{C0}^P(x)$ and $g_{C1}^P(x)$, and a public object that includes N−1 pairs of M-bit values (e.g., ($t_{i,0}^P$, $t_{i,1}^P$) for i=2 . . . N). As mentioned, a sufficiently configured VDAX in possession of the public component of the master PNA object, $PNA^P$, can determine the public ratio of two members of the digital ecosystem, given the credentials of the ecosystem members and the public component of the master PNA object, $PNA^P$. Thus, given the credentials of Cohort A and Cohort B, Cohort A determine the public ratio of Cohort A to Cohort B, $t_A^P/t_B^P$, based on the respective credentials of Cohort A and Cohort B and the public object of $PNA^P$. As mentioned, in some implementations the credentials of an ecosystem member may be defined in a fixed-length data structure, such as a N-length binary vector. For example, the credentials of Cohort A and Cohort B may be defined as $IC_A$=($b_1^A$, . . . , $b_{256}^A$) and $IC_B$=($b_1^B$, . . . , $b_{256}^B$) respectively when N=256. In implementations, Cohort A selects and combines elements from the public object, $(t_{i,0}^P, t_{i,1}^P)$ for i=2 . . . N, based on the pair of primitive polynomials, $g_{C0}^P(x)$ and $g_{C1}^P(x)$, and the respective values (1 or 0) at each individual bit locations of the respective credentials of Cohort A and Cohort B to obtain the public ratio, $t_A^P/t_B^P$.

In the example of Table 8, Cohort A determines a first binary-primitive polynomial, $P1_{PNA}(A, B)$, based on the public ratio of Cohort A to Cohort B, $t_A^P/t_B^P$, the public binary primitive polynomial of Cohort B, $g_{t_B}s_{\cdot d}(x)$, and the secret ratio, $t_A^s/t_A^P$, of Cohort A. As discussed with respect to FIG. 21, the secret ratio of Cohort A was determined by a progenitor VDAX (e.g., ecosystem VDAX) and included in the PNA object of Cohort A. The secret ratio, is stored by Cohort A and not shared with any other ecosystem members. In example implementations, Cohort A determines the first binary primitive polynomial $P1_{PNA}(A, B)$ by constructing a first system to linear equations and determining a first binary primitive polynomial given the secret ratio $t_A^s/t_A^P$, the public binary primitive polynomial of Cohort B, $g_{t_B}s_{\cdot d}(x)$, and the system of linear equations. In these example implementations, Cohort A solves the first system of equations to determine the first binary primitive polynomial, such that the first binary primitive polynomial is an M-degree polynomial and the distance between the first binary primitive polynomial and the public binary primitive polynomial of Cohort B, $g_{t_B}s_{\cdot d}(x)$, is equal to the secret ratio, $t_A^s/t_A^P$. In implementations, the first binary primitive polynomial, $P1_{PNA}(A, B)$, is represented in a binary vector.

Upon determining the first binary primitive polynomial, $P1_{PNA}(A, B)$, Cohort A determines a second binary primitive polynomial, $P2_{PNA}(A, B)$, based on first binary primitive polynomial, $P1_{PNA}(A, B)$, and the public ratio of Cohort A to Cohort B, $t_A^P/t_B^P$. In example implementations, Cohort A constructs a second system of liner equations and determines the second binary primitive polynomial given the public ratio, the first binary primitive polynomial, and the second system of linear equations. In these implementations, Cohort A solves the system of linear equations and determines the second binary primitive polynomial, such that second binary primitive polynomial is an M-degree polynomial and the distance between the second binary primitive polynomial and the first binary primitive polynomial is equal to the public ratio of Cohort A, $t_A^P/t_B^P$. In implementations, the second binary primitive polynomial, $P2_{PNA}(A, B)$, is represented in a binary vector.

In some implementations, Cohort A determines the correlation vector, $C_{PNA}(A, B)$ based on the first primitive polynomial, $P1_{PNA}(A, B)$, and the second primitive polynomial $P2_{PNA}(A, B)$. In some of these embodiments, Cohort A may append the binary representation of second polynomial, P2(A, B), to the binary representation of the first primitive polynomial, P1(A, B) (or vice-versa). It is appreciated that Cohort A may be configured to determine a correlation vector based on the first and second primitive-polynomials in other suitable manners as well. Furthermore, in some implementations, Cohort A may use the bit vector representation of the first binary primitive polynomial as a correlation vector when spawning a link and the bit vector representation of the second binary primitive polynomial as a correlation vector when hosting a link.

As discussed, Cohort B is also configured to generate a correlation vector during link exchange. Table 9 provides an example implementation of an eligibility synchronization process. In these example implementations, Cohort B generates a correlation vector, $C_{PNA}(B, A)$ based on the engagement information of Cohort A, the credentials of Cohort B, the PNA object of Cohort B, and the public component of the master PNA object, $PNA^P$, as is discussed in greater detail below.

TABLE 9

Cohort B Eligibility Synchronization Process

1. Receive Credentials and public primitive polynomial $g_{t_A}s_{\cdot d}(x)$ of Cohort A
2. Determine a public ratio of Cohort B to Cohort A, $t_B^P/t_A^P$ based on Credentials of Cohort B, Credentials of Cohort A, and $PNA^P$
3. Generate first M-bit vector, $P1_{PNA}(B, A)$ based on Cohort A's public primitive polynomial, $g_{t_A}s_{\cdot d}(x)$, and the secret ratio, $t_B^s/t_B^P$, of Cohort B
4. Generate second M-degree primitive polynomial, $P2_{PNA}(B, A)$, based on $P1_{PNA}(B, A)$ and the public ratio, $t_B^P/t_A^P$
5. Output correlation vector $C_{PNA}(B, A)$ In the example of Table 9, Cohort B receives engagement information corresponding to Cohort A. As discussed, the engagement information of Cohort A may include the credentials and the public polynomial of Cohort A. For example, Cohort A may provide the credentials and its public primitive polynomial, $g_{t_A}s_{\cdot d}(x)$, when either Cohort B or A initiate the link exchange. Alternatively, the engagement information may be obtained from a public or semi-public data source that stores the credentials and public polynomials of ecosystem members.

Upon receiving the engagement information of Cohort A, Cohort AB determines a public ratio of Cohort B to Cohort A, $t_B^P/t_A^P$, based on the credentials of Cohort B, the credentials of Cohort A, and the public component of the of the master PNA object, $PNA^P$. As discussed, the public component, $PNA^P$ includes two public M-degree primitive polynomials, $g_{C0}^P(x)$ and $g_{C1}^P(x)$, and a public object that includes N−1 pairs of M-bit values (e.g., $(t_{i,0}^P, t_{i,1}^P)$ for i=2 . . . N). As discussed with respect to Cohort A, a sufficiently configured VDAX in possession of the public component of the master PNA object, $PNA^P$, can determine the public ratio of two members of the digital ecosystem, given the credentials of the ecosystem members and the public component of the master PNA object, $PNA^P$. Thus, given the credentials of Cohort B and Cohort A, Cohort B determine the public ratio of Cohort B to Cohort A, $t_B^P/t_A^P$, based on the respective credentials of Cohort B and Cohort A and the public object of $PNA^P$. As mentioned, in some implementations the credentials of an ecosystem member may be defined in a fixed-length data structure, such as a N-length binary vector (e.g., $IC_A=(b_1^A, b_{256}^A)$ and $IC_B=(b_1^B, \ldots, b_{256}^B)$ respectively when N=256). In implementations, Cohort B selects and combines elements from the public object, $(t_{i,0}^P, t_{i,1}^P)$ for i=2 . . . N, based on the pair of primitive polynomials, $g_{C0}^P(x)$ and $g_{C1}^P(x)$, and the respective values (1 or 0) at each individual bit locations of the respective credentials of Cohort B and Cohort A to obtain the public ratio, $t_B^P/t_A^P$.

In the example of Table 9, Cohort B determines a first binary primitive polynomial, $P1_{PNA}(B, A)$, based on the public ratio of Cohort B to Cohort A, $t_B^P/t_A^P$, the public binary primitive polynomial of Cohort A, $g_{t_A}s_{\cdot d}(x)$, and the secret ratio of Cohort B, $t_B^s/t_B^P$). In example implementations, Cohort B determines the first primitive polynomial, $P1_{PNA}(B, A)$, by constructing a first system to linear equations and determining the first binary primitive polynomial given the secret ratio $t_B^s/t_B^P$), the public binary primitive polynomial of Cohort A, $g_{t_A}s_{\cdot d}(x)$, and the first system of linear equations. In these example implementations, Cohort B solves the first system of equations for the first binary primitive polynomial, such that first binary primitive polynomial is an M-degree polynomial and the distance between the first binary primitive polynomial and the public binary primitive polynomial of Cohort A, $g_{t_A^S t_A}(x)$ is equal to the secret ratio of Cohort B, $t_B^S/t_B^P$. In implementations, the first binary primitive polynomial, $P1_{PNA}(B, A)$, is represented in a binary vector.

Upon determining the first, binary primitive polynomial $P1_{PNA}(B, A)$, Cohort B determines a second binary primitive polynomial, $P2_{PNA}(B, A)$, based on the first binary primitive polynomial, $P1_{PNA}(B, A)$, and the public ratio of Cohort B to Cohort A, $t_B^P/t_A^P$. In example implementations, Cohort B constructs a second system of liner equations and determines the second binary primitive polynomial based on the public ratio, $t_B^P/t_A^P$, the first binary primitive polynomial, P2(B, A), and the second system of linear equations. In these implementations, Cohort B solves the system of linear equations to determine the second binary primitive polynomial, $P2_{PNA}$(B, A), such that second binary primitive polynomial is an M-degree polynomial and the distance between the second binary primitive polynomial, $P2_{PNA}(B, A)$, and the first binary primitive polynomial, $P1_{PNA}(B, A)$, is equal to the public ratio of Cohort B to Cohort A, $t_B^P/t_A^P$. In implementations, the second binary primitive polynomial, $P2_{PNA}(B, A)$, is represented in a binary vector.

In some implementations, Cohort B determines the correlation vector, $C_{PNA}(B, A)$ based on the binary representation of the first primitive polynomial, $P1_{PNA}(B, A)$, and the binary representation of the second primitive polynomial $P2_{PNA}(B, A)$. It is noted that in some implementations, when Cohort A and Cohort B have sufficiently correlated PNA objects, the first polynomial $P1_{PNA}(B, A)$, will equal the second polynomial, $P2_{PNA}(A, B)$ that was generated by Cohort A. Similarly, the second polynomial, $P2_{PNA}(B, A)$ that was generated by Cohort B will equal the first, polynomial $P1_{PNA}(A, B)$, that was generated by Cohort A. As such, in some implementations, Cohort B may append the binary representation of the first primitive polynomial, $P1_{PNA}(B, A)$, to the binary representation of the second primitive polynomial, $P2_{PNA}(B, A)$, to obtain $C_{PNA}(B, A)$. In this example, $C_{PNA}(A,B)$ will equal $C_{PNA}(B,A)$ when $C_{PNA}(A,B)=P1^{PNA}(A, B) \, P2_{PNA}(A, B)$ and $C_{PNA}(B, A)=P2_{PNA}(B, A)\|P1_{PNA}(B, A)$. In these example implementations, the correlation vectors used by Cohorts A and B for link hosting and link spawning are symmetrical. In other implementations, Cohort A and Cohort B may be configured to use asymmetrical correlation vectors for link spawning and link hosting. For instance, in some implementations, Cohort A may be configured to use the binary representation of the first binary primitive polynomial, $P1_{PNA}(A, B)$, as the correlation vector when spawning a link for Cohort B and use the binary representation of the second binary primitive polynomial, $P2_{PNA}(A, B)$, as the correlation vector when hosting a link from Cohort B. In these example implementations, Cohort B may be configured to use the binary representation of the second primitive polynomial, $P2_{PNA}(B, A)$, as the correlation vector when hosting the link from Cohort A and to use the binary representation of the first primitive polynomial, $P1_{PNA}(B, A)$, as the correlation vector when spawning the link for Cohort A.

Assuming the VDAXs of Cohort B and Cohort A are sufficiently configured and accurately representing themselves during the link exchange, then $C_{PNA}(B, A)$ will match $C_{PNA}(A, B)$ (e.g., $P1_{PNA}(A, B) \, P2_{PNA}(A, B)=P2_{PNA}(B, A)\|P1_{PNA}(B, A)$, $P1_{PNA}(A, B)=P2_{PNA}(B, A)$, or $P2_{PNA}(A, B)=P1_{PNA}(B, A)$). If, however, one of the link exchange participants (e.g., a malicious VDAX) is attempting to maliciously use the credentials and public polynomial of a cohort to maliciously exchange links, the malicious VDAX will not have access to the secret ratio of the cohort that the malicious VDAX is attempting to impersonate. As such, the malicious VDAX will be unable to accurately determine the correlation vector $C_{PNA}(B, A)$ without the secret ratio, even if the malicious VDAX is properly configured and has access to the public component, $PNA^P$, of the master PNA object and the engagement information of the cohort the malicious VDAX is attempting to impersonate.

The foregoing description provides example means for generating PNA-based correlation vectors. It is appreciated that other means for generating PNA-based correlation vectors may be developed in the future and used during the link exchange process.

VBLS Generation

In some implementations, a CG-ESP is configured to facilitate the generation and decoding of unique VBLS between two ecosystem members A and B (e.g., ecosystem-to-cohort, enclave-to-cohort, cohort-to-cohort, and/or the like). In these implementations, both community members use the same sequence (e.g., public sequence or private sequence), the same sequence mapping function, and the same GRI to generate a genomic engagement factor (GEF) that is used to transform (e.g. using disambiguation and/or encryption techniques) a digital object into a VBLS object and to decode the VBLS object to obtain the digital object. In these implementations, the sequence mapping functions of the engaging VDAXs map the sequence (which may be metadata of the digital object/VBLS object) into a genomic differentiation object (e.g., a modified or unmodified XNA object or ZNA object) to obtain the GEF. Examples of sequence mapping process are described above.

Figure 25:
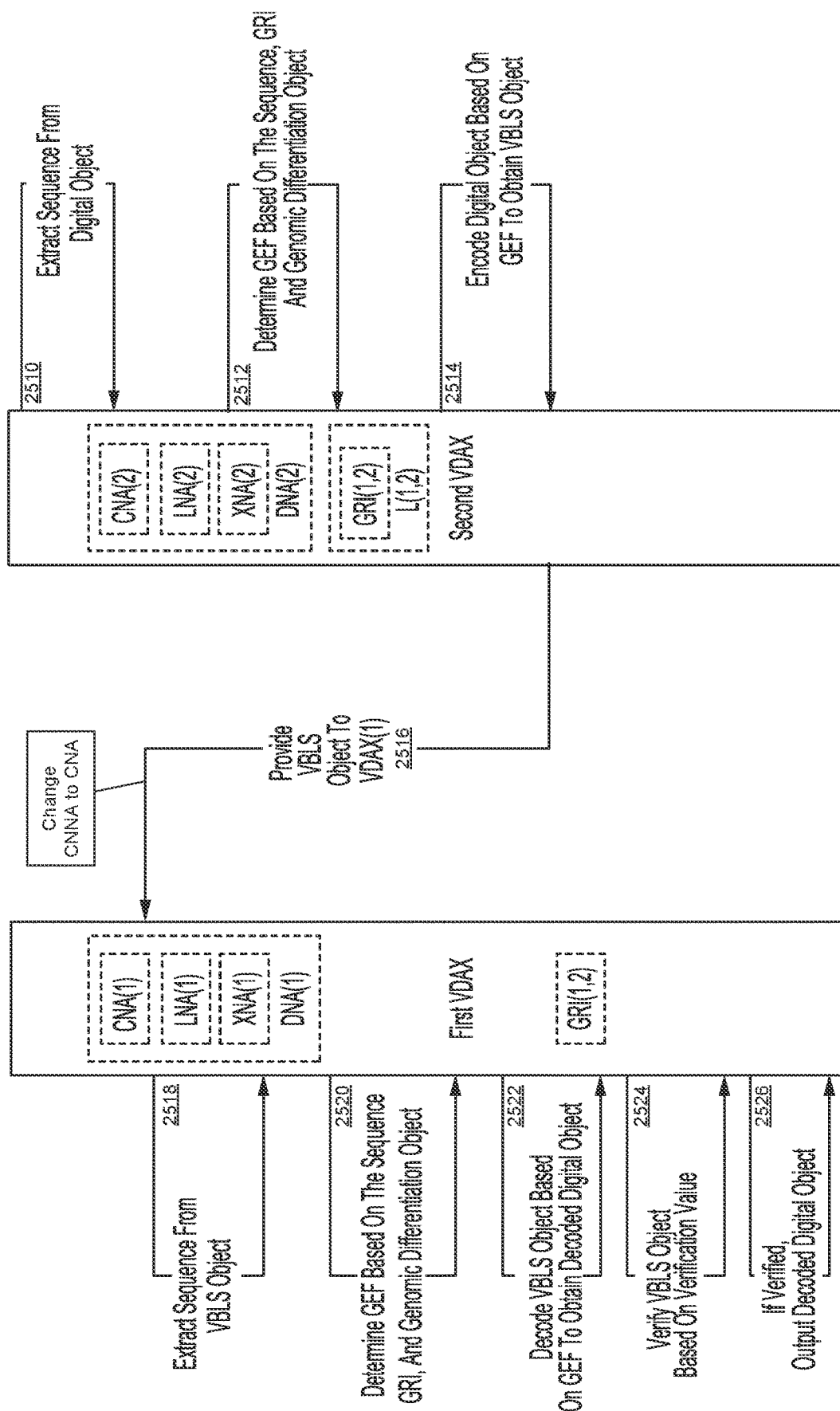
FIG. 25 illustrates an example process for generating Virtual Language Binary Script (VBLS) in accordance with some embodiments of the present disclosure.

FIG. 25 illustrates an example set of operations for a method for generating VBLS by a second VDAX 2504 that is decodable a first VDAX 2502 and decoding the VBLS by the first VDAX 2502. As previously discussed, in some implementations VBLS may be generated from digital objects. Digital objects evidence properties of intercellular engagement and digital session engagement enabled by the hyper-scalability properties of Cyphergenics that facilitate virtual session-less engagements. According to some implementations of the present disclosure, digital objects are transformed using a set of computational functions operating over information-theory facilitated genomic data constructions into VBLS. In some implementations, the relative entropy of the digital objects may be enhanced to $2^N$.

For purposes of explanation, the example implementations described with respect to FIG. 25 assume that the first VDAX 2502 and the second VDAX 2504 have exchanged links. For example, the disclosed method illustrates VBLS exchange in one direction. In this direction, the second VDAX 2504 (e.g., the link hosting VDAX 2404 of FIG. 24) uses GRI provided by (or otherwise corresponding to) the first VDAX 2502 (e.g., the link spawning VDAX 2402 of FIG. 24) during link exchange to generate VBLS that is decipherable by the first VDAX 2502. Example VBLS generation implementations are depicted on the right side of FIG. 25 and example VBLS decoding implementations are depicted on the left side of FIG. 25. It is appreciated that these example processes may also be applied when the first VDAX 2502 generates VBLS that is decipherable by the second VDAX 2504 using second GRI that is provided to the first VDAX 2502 by the second VDAX 2504 during link exchange.

In some implementations, the VBLS generation process may be performed when the second VDAX 2504 generates VBLS for the first VDAX 2502. In the example implementations of FIG. 25, the inputs to the VBLS generation process may be a series of digital objects, a genomic data object (e.g., a modified or unmodified XNA object) and GRI. In some of these implementations, the second VDAX 2504 may receive a series of digital objects that are to be provided the first VDAX 2502. In these implementations, the second VDAX 2504 may retrieve the GRI that was provided by the first VDAX 2502 and the genomic differentiation object (e.g., XNA object) that corresponds to the GRI. For example, the genomic data object may be an XNA object that corresponds to an enclave or ecosystem in which both the first VDAX 2502 and the second VDAX 2504 are members. In some implementations, the genomic data object may be a modified genomic data object that was previously modified using the GRI. Alternatively, the genomic data object may be an unmodified genomic data object. It is noted that the example processes of FIG. 25 illustrate the generation and decoding of a single VBLS object. As can be appreciated, the processes may be applied to each of the digital objects in the series of digital objects.

At 2510, the second VDAX 2504 extracts a sequence from a digital object. As discussed, the sequence may be a public sequence or a private sequence. In some implementations, the sequence may be extracted from a portion of the digital object that will not be transformed (which may be referred to as an "unencoded portion of the digital object"). In some of these implementations, the second VDAX 2504 may extract the sequence from the metadata of the digital object. For example, if the digital object is a networking packet where the payload is to be encrypted, the sequence may be extracted from the packet header (e.g., TCP/IP routing data). In another example, if the digital object is a MPEG transport stream packet, the sequence may be extracted from the transport packet header. It is appreciated that for other types of digital objects, the sequence may be extracted from other suitable metadata of the other types of digital objects. As previously discussed, the manner by which the sequence is extracted (e.g., the bit locations within the metadata, the size of the sequence, and/or the like) may be defined in the configuration of the CG-ESP corresponding to the digital ecosystem or may be indicated by the GRI, as discussed above.

At 2512, the second VDAX 2504 determines a GEF based on the extracted sequence. In some implementations, the sequence mapping module 440 of the second VDAX 2504 receives the extracted sequence, the GRI, and the genomic differentiation object (e.g., XNA object). As discussed, the genomic differentiation object may be modified or unmodified.

In implementations where an unmodified genomic differentiation object is input to the sequence mapping module 440, the sequence mapping module 440 may generate a GEF based on the sequence, the unmodified genomic differentiation object, and the GRI (e.g., as described with respect to FIG. 22). For example, in some of these implementations the sequence mapping module 440 may convert the sequence into a sequence conversion vector (SCV) and may map the CSV into the unmodified genomic differentiation object to obtain a mapped genomic object. The sequence mapping module 440 may then modify the mapped genomic differentiation object to obtain the modified genomic differentiation object. In these implementations, the sequence mapping module 440 may then determine the GEF based on the modified genomic differentiation object and the GRI (e.g., as described with respect to FIG. 22). It is appreciated that sequence mapping module 440 may be configured in accordance with other suitable manners. For example, the sequence mapping module 440 may modify the genomic differentiation object and then may map the SCV into the modified genomic differentiation object to obtain a mapped genomic differentiation object. In these example implementations, the sequence mapping module 440 may determine the GEF based on the mapped genomic differentiation object and the GRI.

In implementations where a modified genomic differentiation object is input to the sequence mapping module 440, the sequence mapping module 440 may generate a GEF based on the sequence, the modified genomic differentiation object, and the GRI (e.g., as described with respect to FIG. 23). In some of these implementations, the sequence mapping module 440 may convert the sequence into a CSV and may map the CSV into the modified genomic differentiation object to obtain a mapped genomic differentiation object. In these implementations, the sequence mapping module 440 may then determine the GEF based on the mapped genomic differentiation object and the GRI. It is noted that in these implementations, the modified genomic differentiation object may have been previously modified and stored in memory (e.g., persistent long-term storage or transient memory, such as RAM) and/or may have been modified prior to be being input to the sequence mapping module 440.

At 2514, the second VDAX 2504 transforms the digital object into a VBLS object using the GEF. In some implementations, the binary transformation module 450 receives the digital object to be transformed and the GEF and generates a VBLS object based thereon using a cipher-based function (e.g., encryption function or disambiguation function). It is noted that the function that is used to generate the VBLS object may be defined in a default configuration of the second VDAX 2504 or may be indicated in the GRI. As discussed, the resultant VBLS object may include an encoded portion (e.g., a payload of the digital object) and an unencoded portion (e.g., metadata of the digital object that is not encoded).

In some implementations, the binary transformation module 440 includes a disambiguation module 452 that transforms the digital object into the VBLS object using the GEF. In these implementations, the disambiguation module 452 may transform a digital object based on the GEF by XORing the GEF and a portion of digital object that is to be transformed to obtain the encoded digital object. In these implementations, the portion of the digital object that is XORed with the GEF may be the payload of the digital object. In implementations, the disambiguation module 452 may receive a different GEF for each digital object, as disambiguation techniques may be attackable with more efficient attacks if a same genomic engagement factor is used to encode two or more digital objects.

In some implementations, the binary transformation module 450 includes an encryption module 454 that transforms the digital object into the VBLS object. In these implementations, an encryption module 454 may be configured with one or more encryption functions that transform a digital object based on the GEF by encrypting a portion of digital object that is to be transformed using the GEF as an encryption key. The encryption module 454 may be configured with any suitable symmetric encryption functions (e.g., TDES, AES, Safer+, SAFER++, Twofish, or the like) that has a corresponding inverse encryption function (or decryption function) that may be used to decode an encoded digital object. In implementations, an encryption module 454 instance may be configured to receive a different genomic engagement factor for each digital object or may use the same transformation for two or more different digital objects. In implementations where a different GEF is generated for each respective digital object, the resultant encoded digital objects may be only subject to brute-force attack.

In some implementations, the second VDAX 2504 may generate an integrity value that provides to the first VDAX 2502 with the VBLS object. In some implementations, the second VDAX 2504 may determine the integrity value by transforming the entire digital object (including the unencoded portion) using the GEF determined at 2512. In these implementations, the entire digital object may be transformed using a computational function (e.g., a cipher-based, cipherless, or hybrid function) that receives the GEF as input. For example, in some implementations the second VDAX 2504 may input the digital object into a hash function that receives the GEF as input. In these implementations, the hash function outputs the integrity value, which the second VDAX 2504 may provide to the first VDAX 2502 with the VBLS object.

At 2516, the second VDAX 2504 provides the VBLS object to the first VDAX 2502 and the first VDAX 2502 receives the digital object. The second VDAX 2504 may provide the VBLS object to the first VDAX 2502 over any suitable medium. The first VDAX 2502 receives the VBLS object in a series of VBLS objects generated by the second VDAX 2504. In these implementations, the first VDAX 2502 may retrieve the GRI that it provided to the second VDAX 2504 and the genomic differentiation object (e.g., XNA object) that corresponds to the GRI. For example, the genomic differentiation object may be an XNA object that corresponds to an enclave or ecosystem in which both the first VDAX 2502 and the second VDAX 2504 are members.

At 2518, the first VDAX 2502 extracts the sequence from an unencoded portion of the VBLS object. As discussed, the sequence may be a public sequence or a private sequence. In some implementations, the sequence may be extracted from an unencoded portion of the VBLS object, such that the metadata contained therein may be the same metadata that was in the original digital object. In some of these implementations, the first VDAX 2502 may extract the sequence from the metadata of the VBLS object. For example, if the VBLS object is a networking packet where the encoded portion of the VBLS object contains an encoded payload, the sequence may be extracted from the packet header (e.g., TCP/IP routing data). In another example, if the digital object is a MPEG transport stream packet, the sequence may be extracted from the transport packet header. It is appreciated that for other types of digital objects, the sequence may be extracted from other suitable metadata of the other types of digital objects. As previously discussed, the manner by which the sequence is extracted (e.g., the bit locations within the metadata, the size of the sequence, and/or the like) may be defined in the configuration of the CG-ESP corresponding to the digital ecosystem or may be indicated by the GRI, as discussed above.

At 2520, the first VDAX 2502 generates the GEF based on the extracted sequence, a genomic differentiation object, and the GRI provided by the first VDAX 2502 to the second VDAX 2504. In some implementations, the sequence mapping module 440 of the first VDAX 2502 receives the extracted sequence, the GRI, and the genomic differentiation object (e.g., XNA object) and determines a GEF based thereon. It is noted in order to successfully decode the VBLS object, the sequence mapping module 440 of the first VDAX 2502 must perform a functionally equivalent sequence mapping process using the same inputs (e.g., sequence, genomic differentiation object, and GRI) as the sequence mapping module 440 of the second VDAX 2504.

In implementations where an unmodified genomic differentiation object is input to the sequence mapping module 440, the sequence mapping module 440 may generate a GEF based on the sequence, the unmodified genomic differentiation object, and the GRI (e.g., as described with respect to FIG. 22). As was discussed with respect to the second VSDAX, the sequence mapping module 440 may convert the sequence into a sequence conversion vector (SCV) and may map the CSV into the unmodified genomic differentiation object to obtain a mapped genomic object. The sequence mapping module 440 may then modify the mapped genomic differentiation object to obtain the modified genomic differentiation object. In these implementations, the sequence mapping module 440 may then determine the GEF based on the modified genomic differentiation object and the GRI. It is appreciated that sequence mapping module 440 may be configured in accordance with other suitable manners. For example, the sequence mapping module 440 may modify the genomic differentiation object and then may map the sequence into the modified genomic differentiation object to obtain a mapped genomic differentiation object. In these example implementations, the sequence mapping module 440 may determine the GEF based on the mapped genomic differentiation object and the GRI.

In implementations where a modified genomic differentiation object is input to the sequence mapping module 440, the sequence mapping module 440 may generate a GEF based on the sequence, the modified genomic differentiation object, and the GRI (e.g., as described with respect to FIG. 23). In some of these implementations, the sequence mapping module 440 may convert the sequence into a CSV and may map the CSV into the modified genomic differentiation object to obtain a mapped genomic differentiation object. In these implementations, the sequence mapping module 440 may then determine the GEF based on the mapped genomic differentiation object and the GRI. It is noted that in these implementations, the modified genomic differentiation object may have been previously modified and stored in memory (e.g., persistent long-term storage or transient memory, such as RAM) and/or may have been modified prior to be being input to the sequence mapping module 440. It is noted that the modified genomic differentiation object must be modified in the same manner as the modified genomic differentiation object of the second VDAX 2504 (e.g., as defined by the GRI).

At 2522, the first VDAX 2502 decodes the transformed portion of the VBLS object using the GEF to obtain the decoded portion of the digital object. In some implementations, the binary transformation module 440 performs an inverse transformation on the encoded portion of the VBLS object using the GEF as input to obtain a decoded digital object. It is noted that the inverse transformation function is the inverse function of the transformation function used by the second VDAX 2504 to encode the digital object.

In some implementations, the binary transformation module 440 of the first VDAX 2502 includes a disambiguation module 452 that transforms the VBLS object into a decoded digital object based on the GEF determined at 2520. In implementations, the disambiguation module 452 may be configured to decode an encoded portion of the digital object using an inverse disambiguation function and the GEF. In implementations, the inverse disambiguation function may include XORing the GEF and the encoded portion of the VBLS object. In these implementations, the XOR operation results in the decoded digital object, assuming that the GEF used to transform the encoded portion of the digital object matches the GEF that was determined by the sequence mapping module 540 of the first VDAX 2502.

In some implementations, the binary transformation module 450 includes an encryption module 454 that transforms the VBLS object into a decoded digital object based on the GEF. In implementations, an encryption module 454 instance may be configured to decode an encoded portion of the digital object using an inverse encryption function and the GEF determined at 2520. Assuming the GEF determined at 2520 matches the GEF that was used to encrypt the digital object, the inverse encryption function uses the GEF as a key to decrypt the encoded portion of the digital object to obtain the decoded digital object.

At 2524, the second VDAX 2504 verifies the integrity of the VBLS object based on the integrity value. In some implementations, the second VDAX 2504 may include an integrity value in the VBLS object. As discussed, in some implementations, the second VDAX 2504 may determine the integrity value by transforming the entire digital object (including the unencoded portion) using the GEF used to encode the encoded portion of the VBLS object. In these implementations, the entire digital object may be transformed using a computational function (e.g., a cipher-based, cipherless, or hybrid function) that receives the GEF as input. Upon decoding the VBLS object into the decoded digital object, the first VDAX 2502 may transform the decoded digital object using the same computational function and the GEF determined at 2518 as input to obtain the integrity value. If the generated integrity value matches the integrity value provided with the VBLS object, then the first VDAX 2502 may verify the integrity of the decoded digital object and may output the decoded digital object, as shown at 2526.

The foregoing processes are provided for example. It is appreciated that other processes for generating and decoding VBLS may be developed in accordance with the disclosure without departing from the scope of the disclosure.

CG-Enabled Processing Environments

Figure 26:
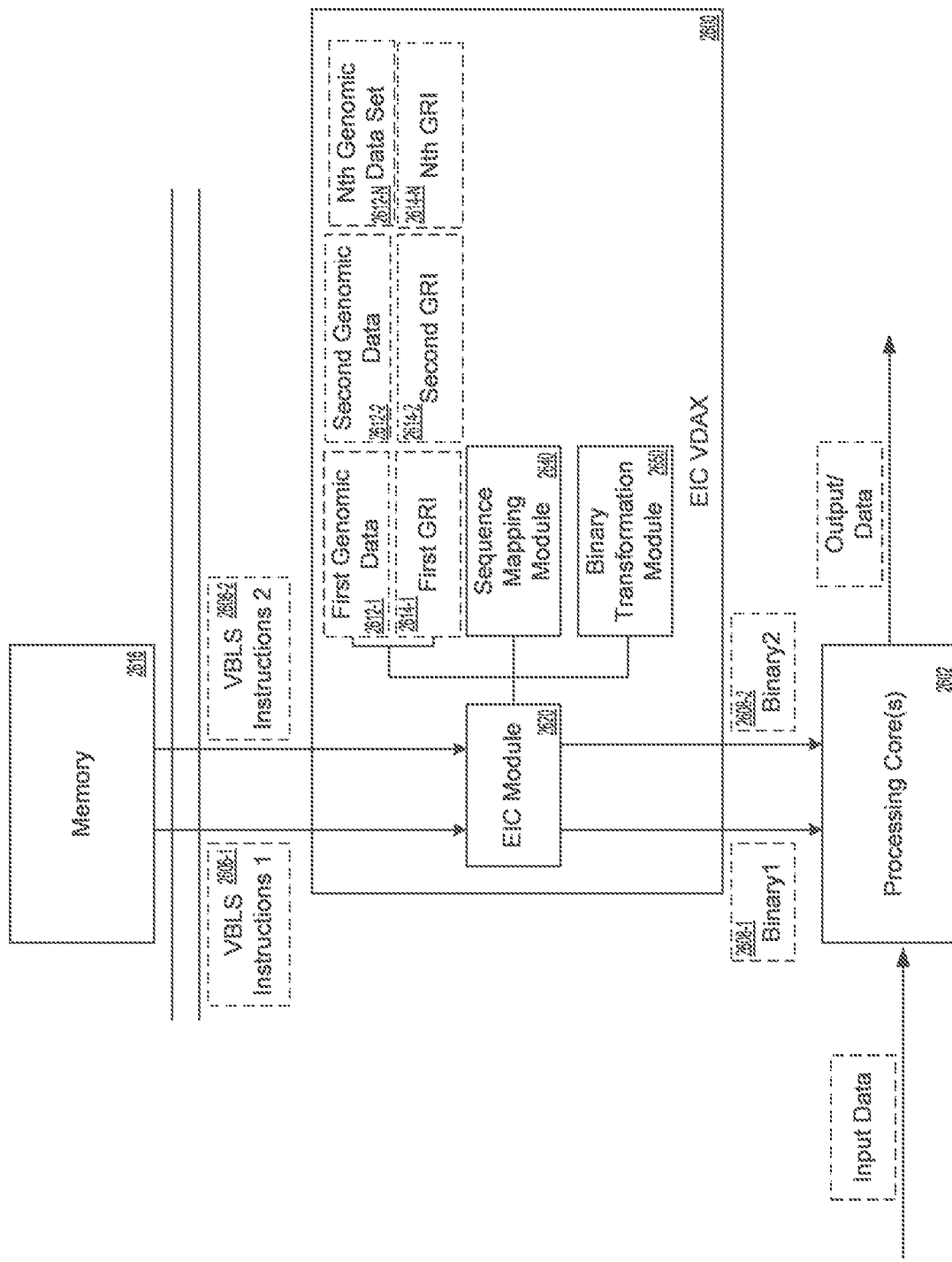
FIG. 26 illustrates an example VDAX that is configured to decode VBLS-encoded instructions into decoded executable instructions and/or to encode executable instructions into VBLS-encoded instructions according to some embodiments of the present disclosure.
Figure 27:
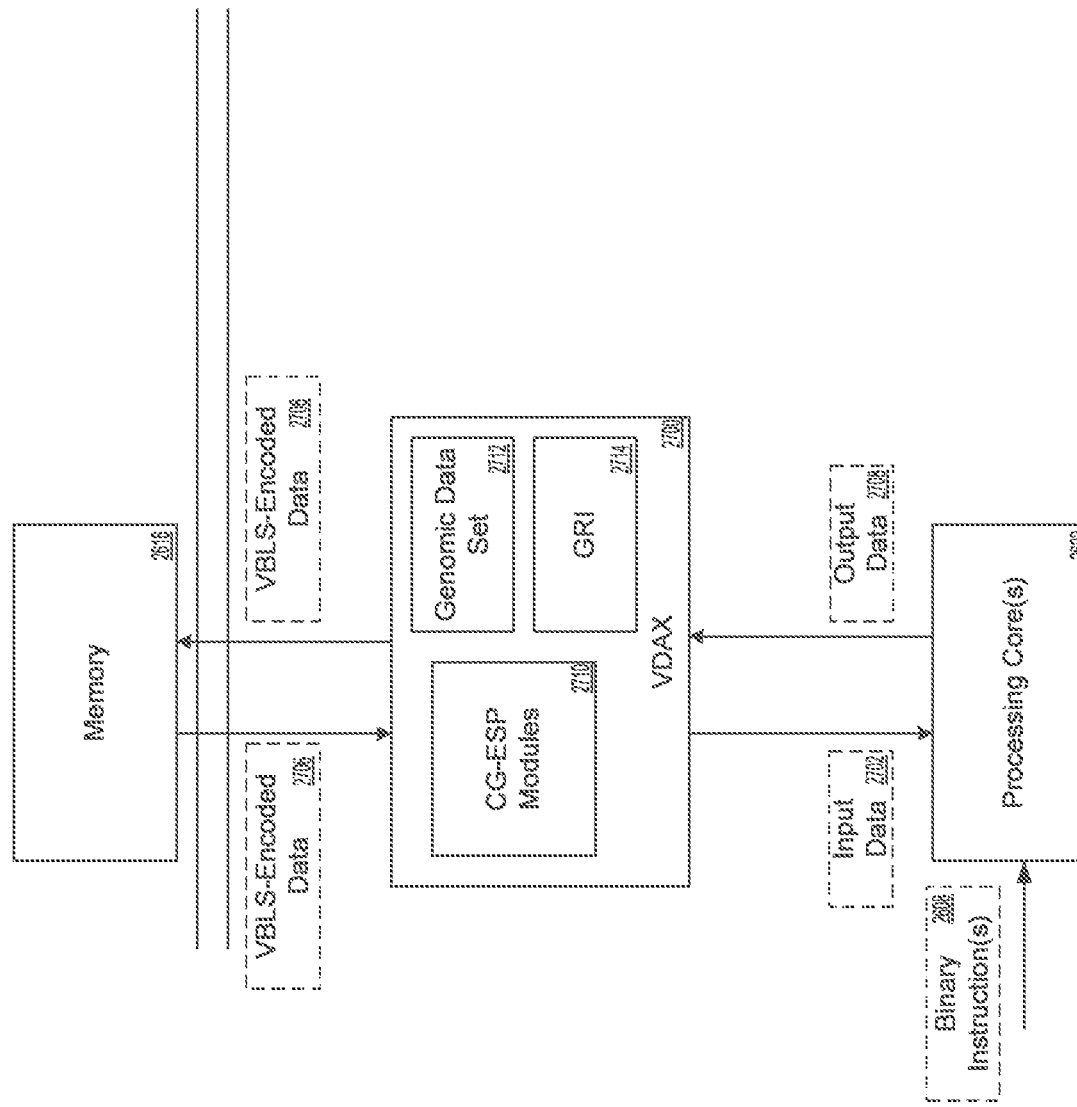
FIG. 27 illustrates an example VDAX that is configured to decode VBLS-encoded data into decoded data that is input to a processing core and/or to encode output data output by a processing core into VBLS-encoded data according to some embodiments of the present disclosure.

FIGS. 26 and 27 illustrate examples of CG-enabled processing environments that can be implemented in an example ephemeral architecture. FIG. 26 illustrates an example of a CG-enabled processing environment that enables virtual trusted execution domains, whereby the CG-enabled processing environment is configured to decode VBLS-encoded binary instructions 2606 into executable binary instructions 2608 that are thereafter executable by processing cores of the processing environment and/or encode binary instructions 2608 into VBLS-encoded binary instructions 2606 that are stored in memory for later decoding and execution. For purposes of explanation, FIG. 26 may be described as showing a CG-enabled instruction path. FIG. 27 illustrates an example VDAX that is configured to decode VBLS-encoded data into decoded data that is input to a processing core 2602 and/or to encode output data output by a processing core 2602 into VBLS-encoded data. For purposes of explanation, FIG. 27 may be described as showing a CG-enabled data path.

In some implementations, the VDAX of FIG. 26 and/or FIG. 27 is a hardware-based VDAX (e.g., a CG-enabled processing core, field programmable gate array, microprocessor, or the like). While a hardware-based VDAX may provide improved security features, the VDAX of FIG. 26 and/or FIG. 27 may be implemented as a software-based VDAX that is executed by a processing device, or a hybrid VDAX consisting of hardware and software elements. In some implementations, the term executable instruction components (EIC) VDAX may refer to a hardware-based VDAX that is configured with a CG-ESP that encodes and decodes VBLS-encoded instruction sets and/or VBLS-encoded program data. In some embodiments, the example VDAXs of FIGS. 26 and 27 may be the same VDAX, where the VDAX encodes and/or decodes both instruction sets and data. Alternatively, in some embodiments, a hardware-based EIC VDAX performs the instruction encoding/decoding, while a software or hybrid-based VDAX performs the data encoding/decoding (or vice-versa).

In the examples of FIG. 26 and FIG. 27, the digital objects that are being encoded and/or decoded are executable instructions and/or program data. The strategies that may be deployed with respect to sequence mapping may vary depending on the type of processing system, the operating system of the device, design choices and tradeoffs (e.g., higher levels of security v. more efficient execution), and the like. With respect to the design choice and the corresponding tradeoffs, generating a unique GEF for each respective instruction or instance of program data may provide improved security features, but may decrease performance of the execution environment as a result of having to determine a GEF for each respective instruction. In these implementations, the respective GEFs that are used to encode/decode respective digital object (e.g., single instructions or instances of program data) are generated based on respective sequences extracted from metadata that uniquely corresponds to the digital object. In other implementations, respective batches of digital objects (e.g., groups of instructions of a computer program or groupings of program data) may be encoded using respective GEFs, such that a first sequence extracted from metadata corresponding to a first batch may be used to generate a first GEF that is then used to encode/decode digital objects of the first batch, while a second sequence extracted from metadata corresponding to a second batch is used to generate a second GEF that is then used to encode/decode digital objects of the second batch. In other implementations, a single GEF may be used to encode/decode instructions and/or program data, whereby the single GEF is generated based on a sequence extracted from metadata associated with the computer program. In these implementations, the number of sequence mapping operations are greatly reduced but at the expense of a decreased level of security. As can be appreciated, the metadata from which a sequence extracted for sequence mapping may vary based on the type of metadata that is used to generate a GEF is extracted may vary depending on the type of metadata available, the desired security levels of the processing environment, and the like. Non-limiting examples of metadata from which a sequence can be extracted when decoding a set of one or more instructions of a computer program may include filesystem metadata, RAM metadata, OS-application specific metadata, executable application-specific metadata, and/or the like. Non-limiting examples of RAM metadata may be a memory location of a digital object or set of digital objects, such as a physical address, a logical address, a virtual address, a memory page, a page table, and/or the like. Non-limiting examples of filesystem metadata include a file path of the program, an inode corresponding to the program, FAT32 or FAT16 table components indicating locations where instruction sets are stored on an HDD or SSD, NTFS table components indicating locations where instruction sets are stored on the HDD or SSD, a hard disk partition on which an instruction or set of instructions is stored, a hard disk cluster on which an instruction or set of instructions is stored, and/or the like. Non-limiting examples of OS-application specific metadata may include process control metadata, thread control data, and/or the like. Application-specific metadata may include object file metadata, executable and link (ELF) metadata, ELF segments, common object format file (COFF) metadata, COFF segments, segment, segment offset, code segment, code segment offset, data segment, data segment offset, block starting symbol (BSS), BSS offset, heap segment, heap segment offset, stack segment, stack segment offset, and/or the like.

In the example implementations of FIG. 26, the CG-enabled processing environment may include a set of processing cores 2602 that execute computer program instruction sets (e.g., instruction sets of software applications, middleware applications, device drivers, operating system/kernel code, and/or the like) that are embodied as executable binary instructions 2608. It is noted that a computer program does not require that the instructions be executed by a computer (e.g., a desktop computer, a server computer, a mobile device, or the like). It is appreciated a computer program may include programs, routines, applications, and the like that are executed by any type of device, including but not limited to, a server computer, a desktop computer, a mobile device, a gaming device, a smart appliance, a robot or other autonomous device, an IoT device, a routing or other networking device, and/or the like. The processing cores 2602 of a processing environment may include general-purpose processing cores, special purpose processing cores (e.g., graphics processing cores, artificial intelligence processing cores, and/or the like), or other suitable processing devices that can execute executable instructions (Field Programmable Gate Arrays (FPGAs), microprocessors, or the like).

In some example embodiments, respective computer program instruction sets are stored as respective VBLS encoded instructions 2606. For example, in some implementations, each computer program instruction set may be encoded in a respective non-recurring "language", whereby each computer program instruction set is encoded using a specific genomic data set 2612 and specific GRI 2614. In some of these implementations, the genomic data sets 2612 used to encode different computer program instruction sets may be the same genomic data sets 2612 using different GRI 2614, such that each GRI 2614 corresponds to a respective computer program (e.g., first GRI 2614-1 for a first computer program, second GRI 2614-2 ... $N^{th}$ GRI 2614-N for an $N^{th}$ computer program). In some implementations, different computer program instruction sets may be encoded using different genomic data sets 2612 and different GRI 2614. For example, each computer program may be assigned its own genomic data set 2612 (e.g., a first genomic data set 2612-1 for a first computer program, a second genomic data set 2612-2 ... an $N^{th}$ genomic data set 2612-N for an $N^{th}$ computer program) that is used to decode and/or encode the instruction sets thereof. In some embodiments, different groups of computer programs may be assigned respective genomic data sets 2612. For example, a group of computer programs that are part of a suite or collection and/or provided by the same organization may be assigned the same genomic data set 2612. In this example, the respective computer programs may be encoded and decoded using the same GRI 2614 or different GRI 2614. It is appreciated that the community owner (e.g., chip provider, operator system provider, firmware provider, or the like) may configure a CG-enabled processing environment in any of these manners.

A computer program instruction set may be initially encoded into VBLS in any suitable manner. For example, in some embodiments, the computer program instruction set is initially received in an executable format, such that the computer program instruction set is not initially encoded. In this example, an EIC VDAX 2600 may assign genomic data (e.g., XNA) to the computer program during the installation process and may generate GRI 2614 for encoding the computer program instruction set. The EIC VDAX 2600 may then encode each instruction 2608 in the computer program instruction set into a respective VBLS-encoded instruction 2606 based on the gnomic data set 2612 assigned to the computer program and the corresponding GRI 2614. The VBLS-encoded instruction 2606 may then be stored in memory 2616 for later execution. As can be appreciated, "memory" may refer to one or more of read-only memory (ROM), random access memory (RAM), a cache, RAM, hard disk drive (HDD), a solid state drive (SDD), or the like.

In other example embodiments, a computer program may be provided (e.g., via download or a computer-readable medium such as a CD, DVD, removable flash memory drive, or the like) by the program provider in a VBLS-encoded format. In some example implementations, the program provider may also provide the requisite genomic data 2612 and GRI 2614 to decode the instructions 2608. In some implementations, the provider of the program and a VDAX representing the device to which the computer program is being installed (e.g., the EIC VDAX 2600 or a higher-level, software-based or hybrid VDAX) may undertake a link exchange process, such that the VDAX may provide GRI 2614 to the program provider, which a VDAX representing the program provider uses to encode the computer program instruction set. In some of these example embodiments, the encoded instructions 2606 may be stored in memory 2616, such that the EIC VDAX 2600 may decode the VBLS-encoded binary instructions 2606 at run time using the genomic data 2612 and the GRI 2614 corresponding to the computer program. In some implementations, the EIC VDAX 2600 may decode the entire VBLS-encoded computer program instruction set using a first set of genomic data 2612-1 and first GRI 2614-1 and then re-encode the computer program instruction. In these implementations, the EIC VDAX 2600 may use the second genomic data 2612-2 and/or second GRI 2614-2 to encode the computer program instruction sets and/or may use a different configuration to perform the CG-based encoding. For instance, the EIC VDAX 2600 may use a different sequence mapping technique and/or binary transformation technique to re-encode the computer program instruction set. In such implementations, the EIC VDAX 2600 would use these sequence mapping and/or binary transformation techniques, the different genomic data 2612-2 and/or the second GRI 2614-2 to decode the VBLS-encoded instructions at run-time. In this way, even the program provider would be unable to replicate VBLS-encoded instructions 2606.

In example embodiments, an EIC VDAX 2600 may be configured to read VBLS-encoded binary instructions 2606 of a computer program from memory 2616 and to decode the encoded binary instructions 2606 to obtain executable binary instructions 2608 based on the genomic data set 2612 assigned to the computer program and the GRI 2614 used to previously encode the instructions 2608. In some implementations, the decoded executable binary instructions 2608 are output to one or more processing cores 2602 of a CPU. In some implementations, the one or more processing cores 2602 receive the decoded binary instructions and execute the binary instructions 2608. In the case that the executed instructions result in output data 2708, the output data 2708 may also be encoded into VBLS-encoded data 2706 (see e.g., FIG. 27). Encoding output data 2708 may be performed at a different level, such as at the operating system-level and/or application-level. For example, the output data 2708 may be encoded into VBLS-encoded data 2706 by the operating system using a different genomic data set and GRI and the resultant VBLS-encoded data 2706 may be written into memory 2616. Additionally or alternatively, the EIC VDAX 2600 may be configured to encode the output data 2708 into VBLS-encoded data 2706.

In embodiments, the EIC VDAX 2600 may be embodied as a dedicated processing core that performs CG-based decoding and/or encoding of binary instruction sets. Additionally or alternatively, the EIC VDAX 2600 may be implemented as a field programmable gate array, a specialized chip, and/or a general processing core.

In the illustrated example, the EIC VDAX 2600 may include an EIC module 2620, a sequence mapping module 2640, and a binary transformation module 2650. As previously discussed, the EIC module 2620 may perform genomic operations on respective genomic data sets 2612 (e.g., ZNA generation and/or modification) that enable the EIC VDAX 2600 to decode VLBS, encode VBLS, and/or control a genomic topology of a virtual trusted execution domain. In embodiments, the sequence mapping module 2640 obtains sequences and performs sequence mapping operations on behalf of the EIC VDAX 2600, using specific genomic data (e.g., modified or unmodified DNA), specific GRI, and the obtained sequences to obtain genomic engagement factors (GEFs). In embodiments, the binary transformation module 2650 decodes VBLS-encoded binary instructions based on the genomic engagement factors obtained by the sequence mapping module 2640. For example, each instruction (or set of instructions) may be decoded using a different genomic engagement factor. Furthermore, in some embodiments, the binary transformation module 2650 can encode unencoded binary instructions into VBLS-encoded instructions using the genomic engagement factor and a set of computational functions, such that the resultant VBLS-encoded instructions may be stored in memory for future decoding and execution.

In some implementations, the EIC VDAX 2600 may include additional or alternative modules depending on the configuration thereof. For example, in some implementations the EIC VDAX 2600 may include a link module (not shown) that performs link exchange on behalf of the processing device when a new program is downloaded to and/or installed on the device which the processing device serves. Additionally or alternatively, the EIC VDAX 2600 may include a master integrity module that is configured to validate a computer program instruction set before it is installed onto the device. An EIC VDAX 2600 may include additional or alternative modules without departing from the scope of the disclosure.

In example embodiments depicted in FIG. 26, the EIC VDAX 2600 is decoding a first computer program instruction set 2606-1 of a first computer program and a second computer program instruction set 2606-2 of a second computer program. In the illustrated example, the EIC module 2620 is configured to fetch or otherwise obtain a first genomic object and first GRI corresponding to a first computer program instruction set that is to be decoded. As mentioned, the genomic objects in the example implementation may be ZNA objects. In the illustrated example, the EIC module 2620 modifies the first ZNA object based on the first GRI using a set of computational functions to obtain first modified ZNA. Similarly, the EIC module 2620 may modify a second ZNA object based on second GRI to obtain second modified ZNA. In some embodiments, the EIC module 2620 may be configured to execute the computational functions using a ZNA object and GRI as input to obtain the modified ZNA. As discussed throughout the disclosure, the modified ZNA may be used to encode a binary instruction set and/or to decode a VBLS-encoded instruction set.

In embodiments, the sequence mapping module 2640 is configured to perform sequence mapping operations on behalf of the EIC VDAX using the modified ZNA to obtain genomic engagement factors. In embodiments, the sequence mapping module 2640 may be configured to obtain a sequence (e.g., a public or private sequence) corresponding to an instruction (or a set of two or more instructions of an instruction set) that is to be executed and may map the sequence into the modified ZNA. In implementations, the sequence may be extracted from metadata associated with a set of one or more instructions of a computer program. The sequence mapping module 2640 may leverage other suitable public or private sequences without departing from the scope of the disclosure. As discussed, mapping a sequence into modified genomic data (e.g., modified ZNA) may include zero or more intermediate transformation steps where the obtained sequence is transformed using a set of computational functions (e.g., hash functions) to obtain an intermediate value, whereby the intermediate value and the modified ZNA value are input into a second set of computational functions to obtain a genomic engagement factor (GEF). In the illustrated example, the sequence mapping module 2640 may determine a first sequence (public or private sequence) corresponding to a first instruction (or set of first instructions) and may map the first sequence into the first modified ZNA to obtain a first GEF. Similarly, the sequence mapping module 2640 may determine a second sequence (public or private) corresponding to a second instruction (or set of second instructions) and may map the second sequence into the second modified ZNA to obtain a second GEF. As discussed throughout the disclosure, the GEFs may be used to encode binary instructions and/or to decode VBLS-encoded instructions. As discussed, the metadata from which a sequence is extracted may depend on the manner by which the instructions are encoded and decoded. For instance, if each instruction is encoded (and decoded) with a different GEF, then the metadata from which a sequence is extracted when decoding or encoding a respective instruction may be specific to the respective instruction (e.g., a value indicating a memory location of the respective instruction). If different subsets of the instructions of the computer program are respectively encoded (and decoded) with different GEFs, then the GEF corresponding to each respective subset may be determined based on metadata that corresponds to subset of instructions. In implementations where all of the instructions of a computer program are encoded using the same GEF, the metadata from which the sequence is extracted may correspond to the computer program.

In embodiments, the binary transformation module 2650 transforms a VBLS-encoded instruction into a decoded instruction based on the genomic engagement factor using a set of computational functions. In some embodiments, the binary transformation module 2650 decrypts each VBLS-encoded instruction (or set of instructions) based on a respective GEF. Alternatively, the binary transformation module 2650 may disambiguate the VBLS-encoded instruction using the respective GEF (e.g., using an XOR operation) to obtain the decoded instruction. The decoded instruction may then be output to a processing core 2602 that executes the instruction. For example, in the illustrated example, the binary transformation module 2650 may decode the first VBLS-encoded instruction (or set of first instructions) using the first GEF and may decode the second VBLS-encoded instruction (or set of second instructions) using the second GEF. It is noted that in embodiments, the binary transformation module 2650 may also transform unencoded binary instructions into VBLS based on respective GEFs determined by the sequence mapping module 2640. In these embodiments, the binary transformation module 2650 transforms the unencoded binary instructions into VBLS-encoded instructions and then the VBLS-encoded instructions are stored into memory for later execution.

Referring now to FIG. 27, a CG-enabled VDAX 2700 that is configured to decode VBLS-encoded data 2706 and to encode non-encoded data. In embodiments, the CG-enabled VDAX 2700 is implemented as a dedicated processing core (e.g., an EIC VDAX 2600, as shown in FIG. 26). Alternatively, the CG-enabled VDAX 2700 is a software-based VDAX that is executed by a processing device. For example, the CG-enabled VDAX 2700 may be implemented at the operating system level and may handle data encoding/decoding at run-time. In these embodiments, the CG-enabled VDAX 2700 protects data that is being used or is output by computer programs that are being executed by a processing device. In embodiments, the VDAX includes a set of CG-ESP modules 2710. For example, the CG-ESP modules 2710 may include a root DNA module (or a EIC module), a sequence mapping module, and/or a binary transformation module. In embodiments, the CG-ESP modules 2710 may further include other modules, such as a link exchange module, a master corroboration module, a master integrity controller, and/or the like.

In the illustrated example, the VDAX 2700 may obtain VBLS-encoded data 2706 from a memory device (e.g., RAM, ROM, solid state SSD, hard disk drive HHD, cache, hard disk, external memory device, or the like). In some embodiments, a root DNA module retrieves genomic data 2712 (e.g., XNA) that was used to encode the VLBS-encoded data 2706 and corresponding GRI 2714. In these embodiments, the VDAX 2700 (e.g., sequence mapping module) may obtain a sequence (e.g., private or public sequence) corresponding to the VBLS-encoded data 2706 and may generate a genomic engagement factor (GEF) based on the sequence, the genomic data 2712 (e.g., modified or unmodified XNA), and the GRI 2714 used to encode the VBLS-encoded data 2706. In these example embodiments, a binary transformation module may then decode (e.g., decrypt or disambiguate) the VBLS-encoded data 2706 using the GEF to obtain decoded data that may be provided as input data 2602 to a processing core 2602.

In some scenarios, a processing core 2602 may output data 2708 (which may be referred to as "output data" 2708) in response to executing one or more binary instructions. In some embodiments, the VDAX 2700 may be configured to encode the output data 2708 into VBLS-encoded data 2706 that is then stored in memory 2616. In embodiments, the VDAX 2700 may obtain genomic data and GRI corresponding to output data (e.g., modified or unmodified XNA of the computer program that is executing) and may generate a GEF based on the sequence, the genomic data 2712 (e.g., modified or unmodified XNA), and the GRI 2714 used to encode the VBLS-encoded data 2706. For example, in some embodiments the VDAX 2700 may extract a sequence from a value defining a memory space allocated for the output data 2708 and may provide the extracted sequence as input to a sequence mapping process to obtain a GEF that is then used to encode the output data 2708 into VBLS-encoded data 2706 that may then be stored in memory 2616 (e.g., RAM, ROM, HDD, SDD, a cache, and/or the like).

It is appreciated that the foregoing are examples of CG-enabled decoding and encoding processes. It is appreciated that further example configurations are considered. For example, in some embodiments, strategies for which a GEF is determined may be varied depending on the desired optimization (e.g., faster decoding versus higher levels of security).

CG-Facilitated Material Data Chains

As discussed with respect to FIG. 4, a Cyphergenics-enabled digital ecosystem may be configured with a CG-ESP that facilitates material data block chains (referred to as "MDCs") that are comprised of respective material data blocks (MDBs). For purposes of explanation, these digital ecosystems may be referred to as "ledger-based ecosystems". In embodiments, a material data block (MDB) may be any suitable data structure that stores data (referred to as "material data") and corresponding MDB metadata, such that the MDB is configured to be arranged in an MDC. AN MDC may refer to a digital ledger that may be collectively maintained by one or more cohorts (e.g., blockchain node devices) in a ledger-based ecosystem in accordance with a specific CG-ESP configuration. As will be appreciated from the following disclosure, the MDCs and the CG-ESP configurations that support those MDCs may provide for reduced resource consumption (e.g., less overall storage, less computational resources to verify blocks, and/or energy consumption across a set of participating node devices) when compared with current blockchain technologies, while maintaining or improving on the integrity and security of such blockchain technologies.

It is noted that the type, properties, and/or protocols of an MDC may vary depending on the application(s) of the MDC, the participants of in the digital ecosystem, the purpose of the digital ecosystem, and/or the interests of the ecosystem owner. For example, in some example embodiments, the protocol of an MDC may allow for non-redundant MDCs, such that each participating cohort stores the MDBs created by the respective cohort on its own MDC but does not require the respective cohort to store MDBs created by other cohorts in the digital ecosystem. In some of these example embodiments, each cohort maintains an MDC that is comprised of MDBs that were generated by the cohort, whereby each cohort provides an unverified portion of its MDC to one or more other cohorts that verify the unverified part of the MDC on behalf of the cohort that provided the unverified portion of the MDC. In these example embodiments, the cohorts that verify MDCs on behalf of other cohorts may maintain verification records that correspond to respective MDBs that were verified by the cohort when verifying a previously unverified portion of an MDC, as will be discussed in greater detail below. In some of these embodiments, one or more cohorts may be configured to verify and/or merge verified MDCs generated and maintained by other cohorts into a master MDC that is comprised of MDBs that were generated by the other cohorts. For example, in more trusted types of ecosystems (e.g., an enterprise setting, an industrial/manufacturing setting, or the like), a cohort that represents the entire ecosystem or an enclave thereof may receive verified portions of MDCs that were respectively generated and maintained by respective cohorts of the ecosystem/enclave and may verify the integrity of each cohort-specific MDC (e.g., that no MDBs have been altered, removed, or added to a respective cohort's verified portion of the MDC). In some of these embodiments, the verifying cohort may then generate or update a master MDC comprised of MDBs from one or more of the cohorts' respective verified MDCs. It is appreciated, however, that merging the MDBs from disparate MDCs into a master MDC is optional and not required.

In some example embodiments, the protocol(s) of the MDC or ledger-based application may require that at least a portion of MDBs in an MDC are notarized and maintained redundantly. For example, in some trustless (or less trustworthy) digital ecosystems (e.g., a set of competitors or adversaries collectively participating in the ledger-based digital ecosystem), MDBs containing certain types of data (e.g., transaction data, logistics data, sensor data, clinical testing data, or other types of data) are "notarized" by other cohorts in the ecosystem, whereby the notarized MDBs are redundantly stored in respective MDCs that are maintained by the respective cohorts that notarized the MDBs. In these embodiments, each cohort may store a complete copy of the MDC comprised of notarized MDBs or an incomplete version of the MDC that includes at least some overlapping set of notarized MDBs.

As can be appreciated from the foregoing, different members of a ledger-based ecosystem may perform one or more different roles with respect to the digital ecosystem. Non-limiting examples of different roles may include "MDB creator", "MDB verifier", and/or "MDB notary". For purposes of explanation, "MDB creator cohort" (or "creator cohort") may refer to a cohort in a digital community that is configured to create an MDB and/or store the MDB on a copy of its MDC. In embodiments, "verification cohort" may refer to a cohort in a ledger-based ecosystem that is configured to verify a portion of an MDC on behalf of one or more creator cohorts in the digital ecosystem, whereby verifying the portion of an MDC renders that portion of an MDC immutable. In embodiments, notary cohort may refer to a cohort in a digital community that notarizes MDBs created by MDB creators, whereby a notary cohort digitally notarizes a MDB to render the MDB immutable.

It is appreciated that within a ledger-based ecosystem, a cohort may serve in more than one role. For example, in some embodiments, an MDB creator cohort may also act as a verification cohort and/or a notary cohort. Similarly, in some embodiments, a verification cohort may also act as a notary cohort and/or as a creator cohort. In some embodiments, certain cohorts may serve only one role. For example, in some digital ecosystems, MDB creators may be configured to generate MDBs and maintain MDCs but not to verify or notarize MDCs of other cohorts. In embodiments, the roles that may be performed by respective cohorts in a digital ecosystem are a function of the CG-ESP configuration and genomic data sets of the respective cohorts. For example, in some example embodiments a cohort may verify an MDC on behalf of a creator cohort if a VDAX of the cohort is configured with the requisite set of Cyphergenics-based functions and a genomic data set that is sufficiently correlated with a genomic data set of the creator cohort that in combination allow the verification cohort and the creator cohort to independently generate identical CG-derived verification values given a set of MDBs. Similarly, in some example embodiments, a cohort may notarize an MDC on behalf of a creator cohort if a VDAX of the cohort is configured with the requisite set of Cyphergenics-based functions and a genomic data set that allow the notary cohort to generate a unique CG-derived notarization value for a given MDB created by a creator cohort, such that only the notary cohort can recreate the CG-derived notarization value.

It is noted that in some implementations, notarization of MDBs can be performed by non-correlated cohorts, such that the notary cohort may not belong to the same digital ecosystem (e.g., the notary cohort does not have "sufficiently correlated genomic data"). In such the case of notarizing cohorts can use the genomic data objects that were assigned to them to generate CG-derived notarization values despite not having geonic data that is correlated with that of the MDB creator cohort. MDCs that are maintained in such ecosystems may be referred to as "inter-ledger" MDCs and CG-ESP configurations that have functions to support such inter-ledger MDCs may be referred to as "inter-ledger" functions, while MDCs that are maintained in digital ecosystems where all of the cohorts share common genomic data may be referred to as "intra-ledger" MDCs and CG-ESP configurations that have functions to support such intra-ledger MDCs may be referred to as "intra-ledger" functions.

Furthermore, as used herein, the term "CG-derived values" (e.g., CG-derived verification values, CG-derived notary values, CG-derived creator values, CG-derived digital signatures, and the like) may refer to values that are generated by a VDAX using CG-based functions and/or input parameters that were determined using CG-based functions. For instance, (as will be discussed) a CG-derived verification value of a MDB may be determined using a genomic engagement factor (GEF) that results when a sequence from a MDB is mapped into a genomic differentiation object of a VDAX. The sequence mapping operation may be considered a CG-based function and the resultant GEF is an input parameter that was determined using a CG-based function (and a CG-derived value as well). While the VDAX may employ non-CG-based functions to generate the verification value corresponding to the MDB (e.g., hash function, CMAC, XOR, parameterized operations, and/or the like), the resultant verification value may still be referred to as "CG-derived verification value" because the GEF is provided as an input to the non-CG-based function. The foregoing applies to CG-derived notary values, CG-derived creator values, CG-derived digital signatures (which may be determined using a PNA object of a VDAX), and the like. Furthermore, CG-derived values are not specific to ledger-based ecosystems. CG-derived values may also refer to values that are generated in different types of CG-enabled digital ecosystems as well.

Figure 28:
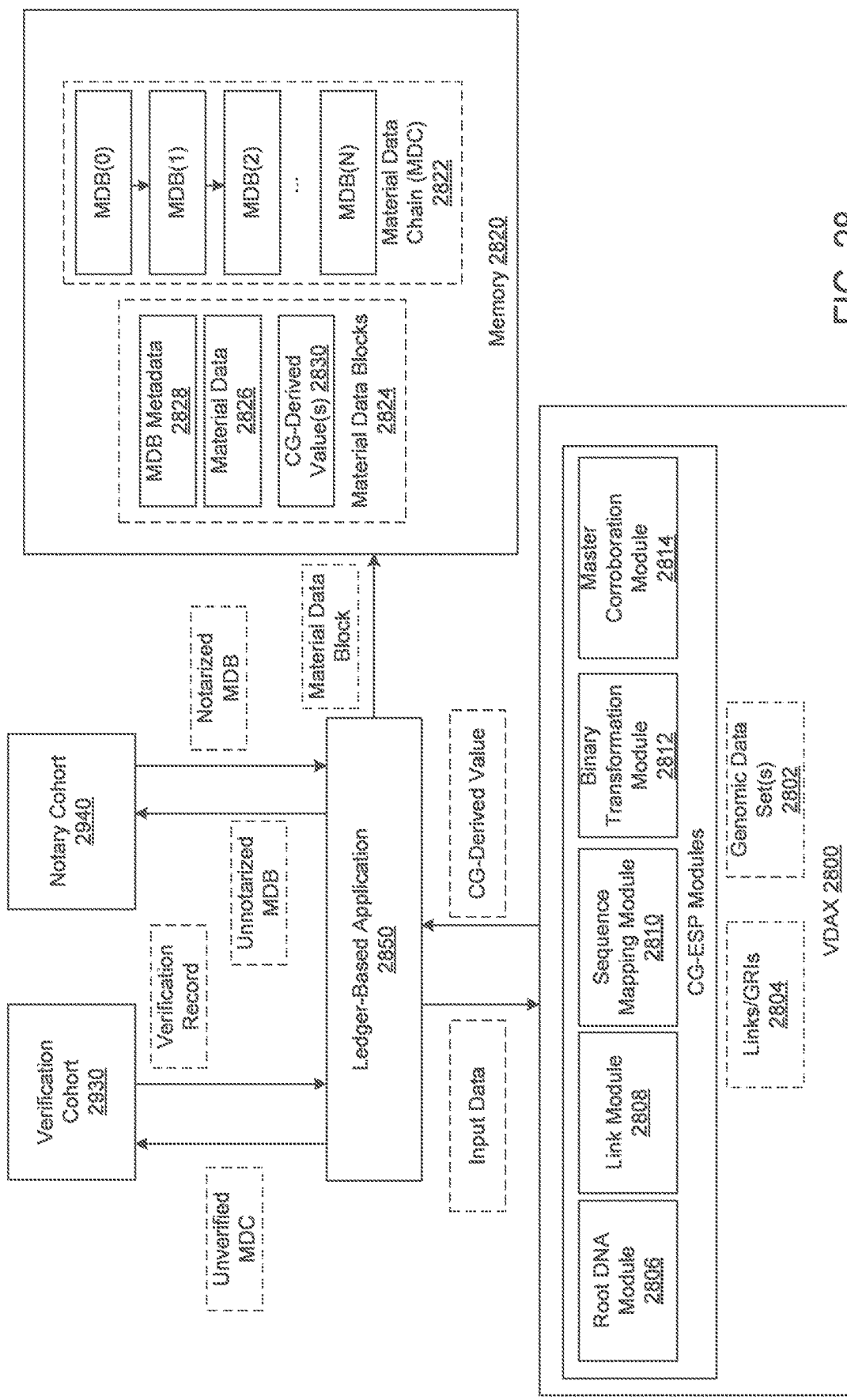
FIG. 28 illustrates example configurations of ledger-based ecosystems and underlying VDAXs according to some embodiments of the present disclosure.

Referring now to FIG. 28, example configurations of ledger-based ecosystems and underlying VDAXs are discussed. In FIG. 28, an example VDAX 2800 of an ecosystem participant (e.g., cohort) is configured with a CG-ESP and a genomic data set 2802. In embodiments, the VDAX 2800 interfaces with and/or is incorporated in a ledger-based application 2850. A ledger-based application 2850 may refer to any computing program that writes to, maintains, reads from, or otherwise interfaces with an MDC 2822 stored in memory 2820 (e.g., computer-readable medium(s)) accessible to the ledger-based application 2850. Ledger-based applications 2850 may include smart contracts, IOT applications (e.g., IOT sensors), commercial applications, system applications (e.g., operating system applications), server applications, and/or any other suitable types of applications that may interface with an MDC 2822.

In embodiments, a ledger-based application 2850 may communicate with other cohorts in a ledger-based digital ecosystem, such as verification cohorts 2930 and/or notary cohorts 2940. For example, in some example digital ecosystems, a ledger-based application 2850 may be configured to send verification data (e.g., an unverified portion of an MDC 2822 or data that is indicative thereof) to a verification cohort 2930. In some of these example embodiments, the verification cohort 2930 returns verification records for each respective MDB 2824 in the (previously) unverified portion of the MDC 2822 upon verifying the respective MDB 2824, whereby a verification record corresponding to a respective MDB includes a CG-derived verification value that was generated by the verification cohort 2930.

In some example digital ecosystems, a ledger-based application 2850 may be configured to send unnotarized MDBs to one or more notary cohorts 2940 for notarization by each notary cohort. In these embodiments, a notary cohort 2940 generates a CG-derived notarization value based on the MDB and returns a notarized version of the MDB that has been digitally notarized with the CG-derived notarization value to the ledger-based application 2850, which may in turn write the CG-derived notarization value in a corresponding MDB of the MDC maintained by the ledger-based application 2850. In some embodiments, the notary cohort 2940 may also store the notarized MDB on its own MDC (not shown). In these examples, the notary cohort(s) 2840 have a copy of a notarized MDB that include the CG-derived notarization value derived by the notary cohort and CG-derived creator value, such that if the integrity of the notarized MDB is called into question, a notary cohort 2940 can prove whether the contents (e.g., material data and/or MDB metadata) of the notarized MDB were altered by recalculating the CG-derived notarization value.

It is noted that in the foregoing example embodiments, each verification cohort 2930 and/or notary cohort 2940 also includes a respective VDAX (not shown in FIG. 28) that perform Cyphergenics-based functions on its behalf.

In different implementations of a ledger-based digital ecosystem, an MDC may be fully distributed (nodes redundantly store all MDBs created by other nodes), semi-distributed distributed (nodes store some but not all MDBs created by other nodes), or non-distributed ledgers (nodes do not store MDBs created by other nodes). In embodiments, an MDC 2822 may be comprised of MDBs 2824, wherein each MDB 2822 includes material data 2826, MDB metadata 2828, and a set of CG-derived values 2830. In embodiments, material data 2826 may refer to the substantive data that is being stored in an MDB 2824. For example, material data 2826 may be sensor readings, transaction records, logistics records, voting data, clinical data, health records, insurance records, enterprise data, betting data, access logs, contractual data, evidentiary data, and/or any other suitable data. In embodiments, the MDB metadata 2828 may include any suitable metadata that is maintained in a MDB 2824 by the ledger-based application 2850 and/or in accordance with the protocol(s) of the underlying digital ledger. For instance, non-limiting examples of MDB metadata 2828 may include a timestamp that indicates a date and/or time when the MDB 2824 was created, an originator attribute indicating the cohort that generated an MDB 2824, an MDB identifier that identifies the MDB 2824, a hash value of the MDB 2824 (e.g., a hash value that is generated by the ledger-based application based on the material data and one or more hash functions), a hash value of a preceding MDB 2824 in the MDC 2822, one or more verifier IDs that indicate one or more respective verification cohorts 2930 that verify the MDC 2822 that contain the MDB 2824, one or more notary IDs indicating one or more notary cohorts 2940 that notarize the MDC 2822, and/or other suitable information. It is noted that the exact types of MDB metadata 2828 that are maintained in an MDB 2824 can vary based on the ledger-based application and/or the protocols of the underlying digital ledger independent of the configuration of the CG-ESP(s) that facilitate a ledger-based digital ecosystem. Furthermore, while the CG-derived value(s) are shown as being stored in the MDB to which the CG-derived value(s) correspond, in some implementations the CG-derived values may be stored in separate MDBs and/or other suitable data structures.

In embodiments, CG-derived values 2830 are numerical values (e.g., bit vectors) generated by VDAXs in a digital ecosystem based on the genomic data of a respective VDAX (e.g., VDAX 2800) and at least a portion of an MDB 2824 using a set of Cyphergenics-based operations. The exact types of CG-derived values that are maintained in an MDB 2824 can vary depending on the purpose of the ledger-based digital ecosystem, the trustworthiness of the digital ecosystem, the owner of the digital ecosystem, and/or the types of participants in the digital ecosystem. As such, the types and properties of CG-derived values 2830 that are maintained for a specific digital ecosystem, the types of genomic data objects that are used to determine the CG-derived values 2830, and the computational functions that are used to determine the CG-derived values for a specific digital ecosystem are defined in the CG-ESPs of the community members of the specific digital ecosystem.

Examples of CG-derived values 2830 may include CG-derived verification values, CG-derived notarization values, CG-derived creator values, and/or the like. In embodiments, a CG-derived creator value may be a value that is generated by a creator of an MDB 2824 using at least a portion of the MDB 2824, a genomic data set of the MDB creator, and GRI (which may be secret GRI or GRI common to two or more cohorts). In this way, only the MDB creator can recreate a CG-derived creator value given an MDB created by the MDB creator. In some implementations, a CG-derived creator value is a value that is generated by the VDAX 2800 of an MDB creator using a set of one or more computational functions (e.g., cipher-based and/or cipherless) given a genomic engagement factor corresponding to the MDB. The CG-derived creator value may be determined using any number of suitable types of functions, such as: a hash function that receives the GEF and the MDB (or a hash value of the MDB) as input, an XOR function that receives the GEF and a hash value of the MDB as input, a CMAC function that receives the GEF and the MDB (or a hash value of the MDB) as input, and/or the like.

In embodiments, a CG-derived notarization value is a value corresponding to an MDB 2824 that is generated by a notary cohort in a digital ecosystem using at least a portion of the MDB 2824, a genomic data set of the notary cohort, and GRI (which may be secret GRI or GRI common to two or more cohorts). In this way, only the notary cohort that initially generated a respective MDB 2824 can recreate a CG-derived creator value given the MDB 2824 notarized by the cohort. In some embodiments, a CG-derived notarization value is a CG-derived hash value that is generated by the VDAX 2800 of an MDB creator using a set of one or more computational functions (e.g., cipher-based and/or cipherless) given a genomic engagement factor corresponding to the MDB. The CG-derived notarization value may be determined using any number of suitable types of functions, such as: a hash function that receives the GEF and the MDB (or a hash value of the MDB) as input, an XOR function that receives the GEF and a hash value of the MDB as input, a CMAC function that receives the GEF and the MDB (or a hash value of the MDB) as input, and/or the like.

In embodiments, a CG-derived verification value is a value that is generated by an MDB creator and/or one or more MDC verifiers based on at least a portion of an MDB, at least a portion of a preceding MDB, a genomic data object (e.g., XNA) of the MDB creator and/or MDC verifier(s), and GRI 2804 that is was exchanged between and secretly held by the MDB creator and the MDC verifier(s). In this way, only cohorts having sufficiently correlated genomic data and in possession of the GRI are able to recreate a verification value of an MDB based on the contents of the MDB and its preceding MDB. In some implementations, a CG-derived verification value is a value that is generated by the VDAXs of an MDB creator and/or a verifier using a set of computational functions (e.g., cipher-based and/or cipherless) given a GEF that was generated based on a sufficiently correlated genomic data set between the creator and verifier and commonly held GRI. The CG-derived verification value may be determined using any number of suitable types of functions, such as: a hash function, an XOR function, a CMAC function, and/or the like.

In embodiments, a ledger-based application 2850 that is executed by or with respect to a cohort is configured to provide one or more MDBs 2824 to a VDAX 2800 of the cohort and the VDAX 2800 determines one or more CG-derived values based on the received MDBs. In embodiments, a VDAX 2800 may include a root DNA module 2806, a link module 2808, a sequence mapping module 2810 (e.g., public and/or private sequence mapping module), a binary transformation module 2812, and/or a master corroboration module 2814. It is appreciated that the root DNA module 2806, link module 2808, sequence mapping module 2810, and the binary transformation module 2812 may operate in the manners described elsewhere throughout the application. In embodiments, a VDAX 2800 may perform link exchange with another members (e.g., cohorts) in a digital ecosystem to exchange GRI 2804 with those members in any suitable manner. While cohorts within a ledger-based digital ecosystem may use exchanged link information (e.g., GRI 2804) to securely exchange data (e.g., MDBs or other data) within an ecosystem, GRI 2804 that are exchanged with another cohort in a digital ecosystem may also be used by a VDAX of a cohort when generating certain types of CG-derived values (e.g., CG-derived verification values). It is appreciated that the GRI 2804 used to generate CG-derived verification values may be the same GRI 2804 that are used to facilitate VBLS encoding/decoding or may be different GRI 2804 that is exchanged between the cohorts. Furthermore, in some embodiments, a VDAX 2800 may be configured to generate and secretly hold GRI 2804 that are used to generate certain types of CG-derived values (e.g., CG-derived notarization values and/or CG-derived creator values).

CG-Based Verification of MDCs

Figure 29:
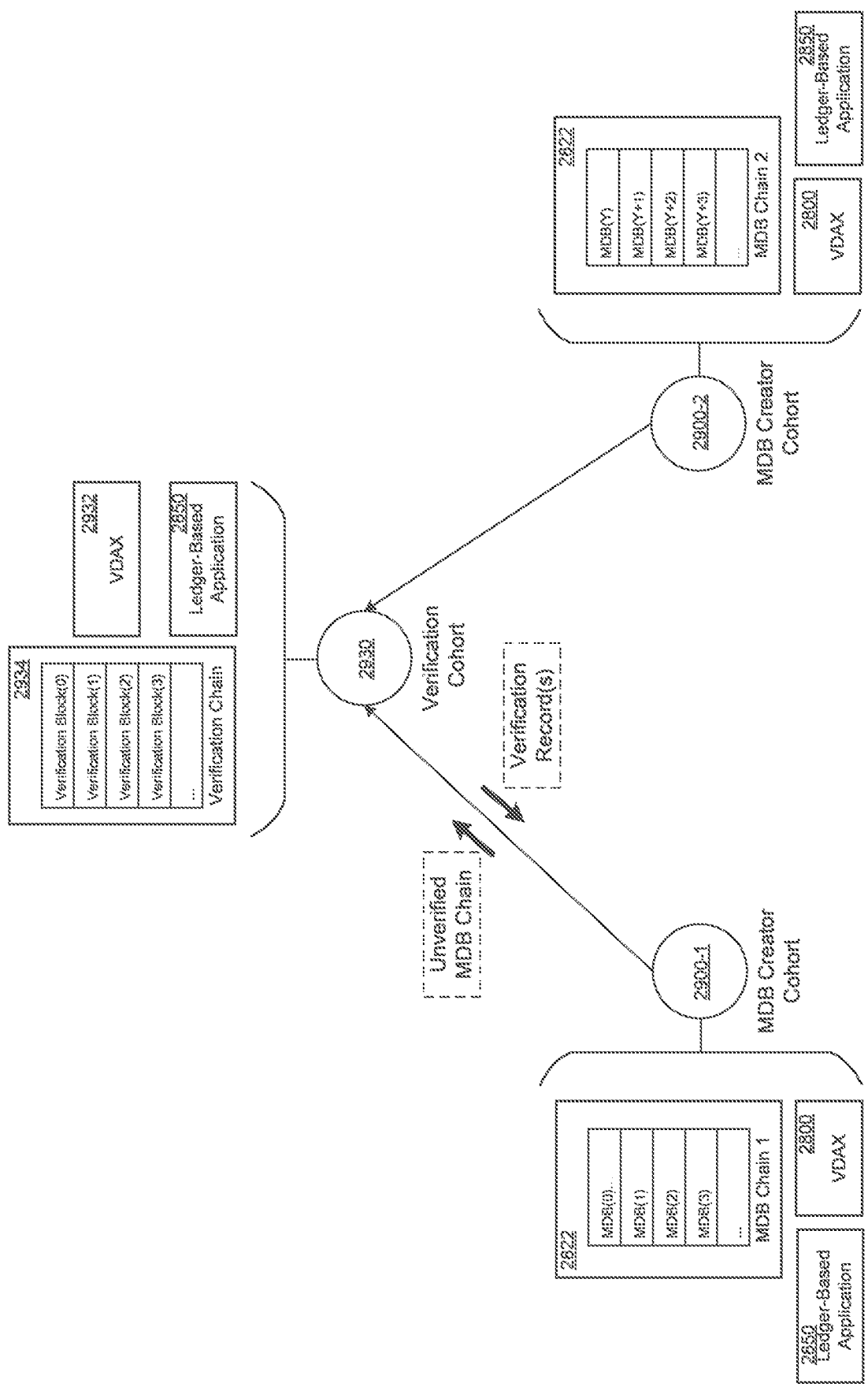
FIG. 29 illustrates an example ledger-based digital ecosystem that uses CG-based verification to maintain intra-ledger MDCs according to some embodiments of the present disclosure.

Referring to FIG. 29 and in continued reference to FIG. 28, an example ledger-based digital ecosystem that uses CG-based verification to maintain an intra-ledger MDC is disclosed. In some of these example digital ecosystems, each respective MDB creator cohort 2900 maintains a respective (and potentially non-redundant) MDC 2822 (e.g., MDC 2822-1 and MDC 2822-2) comprised of MDBs created by the respective MDB creator cohort 2900 (e.g., creator cohort 2900-1 and creator cohort 2900-2), such that each creator cohort 2900 may be at least responsible for maintaining its own portion of the MDC 2822. In embodiments, a MDB creator cohort 2900 may be configured to generate MDBs that each include respective material data, MDB metadata, and a set of CG-derived values (e.g., CG-derived verification values and any other required CG-derived values) that can be used to prove the validity, authenticity, source, and/or integrity of an MDC and its MDBs.

In some of these embodiments, a VDAX 2800 of a creator cohort 2900 may generate a CG-derived verification value corresponding to a MDB based on the MDB, the preceding MDB in the MDC 2822, a genomic data object of the creator cohort 2900 (e.g., a genomic differentiation object, such as XNA), and GRI exchanged with a VDAX of a verification cohort 2930 (which may be provided to the VDAX of the content creator by the VDAX 2800 or vice-versa). For instance, if a digital ecosystem includes one verification cohort 2930 (and/or verification is done at the enclave-level), each MDB may include one CG-derived verification value that is generated using GRI known by MDB creator cohort VDAX 2800 and the verification cohort 2930. In some implementations, when multiple verification cohorts 2930 verify MDBs generated by a MDB creator cohort 2900, the MDB creator VDAX 2800 may generate a respective CG-derived verification value corresponding to each respective verification cohort 2930 that verifies the portion of the MDC 2822 containing the MDB. For example, in the illustrated example, the VDAX 2800 may generate a verification value for a verification cohort 2930 based on GRI exchanged by the MDB creator cohort 2900 and the respective verification cohort 2930. If, however, there are additional verification cohorts (not shown), the VDAX 2800 may generate respective verification values for each additional verification cohort (not shown) based on the GRI exchanged with each respective verification cohort. In this way, each respective verification cohort 2930 may verify the MDC 2822 of the MDB creator independent of other verification cohorts based on the respective CG-derived verification value that is generated by the MDB creator cohort 2900 using the GRI that is shared between the respective verification cohort 2930 and the MDB creator cohort 2900. In some other implementations, each cohort VDAX of a participating node device in the ledger-based ecosystem, or in an enclave thereof, may perform link exchange with an ecosystem VDAX, or the enclave VDAX representing the specific enclave of the participating node devices, such that each cohort VDAX in the ledger-based ecosystem or enclave thereof may each receive the same ecosystem-specific or enclave-specific GRI from the ecosystem VDAX or enclave VDAX. In these implementations, each cohort VDAX in possession of ecosystem-specific or enclave-specific GRI can generate the same CG-enabled verification values for a particular set of MDBs. In this way, multiple verification cohorts 2930 may verify an MDB using the same verification value In some embodiments, each verification cohort 2930 in a respective digital ecosystem generates a verification record for each respective MDB in an MDC verified by the verification cohort 2930. In some example embodiments, a verification record may indicate the MDB that was verified (e.g., an MDB identifier that uniquely identifies the MDB), the CG-derived verification value corresponding to the MDB, and additional data relating to the verification. Example additional data of a verification record may include, but is not limited to, an identifier the MDB creator cohort that created the MDB, an identifier of the verification cohort that verified the MDB, an MDC identifier indicating an MDC in which the verified MDB is located, the MDB creator CG-derived value of the MDB, a timestamp of when the verification was made, other verification cohorts that verified the MDB, a hash value of the MDB (or a portion thereof), a hash value of the preceding MDB in the MDC (or a portion of the preceding MDB), and/or other suitable metadata. It is noted that the hash values of the MDB and the preceding MDB may be derived using traditional hashing techniques, such that the hash values are generated without the use of a CG-derived GEF. Put another way, the hash values of the MDB and/or the preceding MDB may be confirmed by an entity not in possession of the genomic data and/or GRI used to generate the CG-derived verification values.

In some embodiments, a verifying cohort 2930 may maintain a verification chain 2934, such that the verification chain 2934 may include verification blocks, where each verification block contains one or more verification records. For example, in some embodiments, each verification block may store a verification record that indicates a MDB that was verified by the verifying cohort 2930, the CG-derived verification value corresponding to the MDB, and any other suitable data. In some embodiments, each verification block in a verification chain 2934 may include a batch of verification records that indicates a batch of MDBs that were verified from an MDC 2822. For example, when a MDB creator cohort 2900 "commits" an unverified portion of its MDC 2822 to a verification cohort 2930, the verification cohort 2930 may verify each MDB in the unverified portion of an MDC and may include verification records for each verified MDB from the (previously) unverified portion of the MDC in a verification block that is then added to the verification chain maintained by the respective verification cohort 2930. It is noted that while shown as a dedicated chain, a verification chain may be stored in an MDC maintained by a respective verification cohort. In some of these implementations, the verification blocks may be stored as a side-chain of the MDC, such that the verification blocks do not need to be verified by another cohort of the ecosystem.

In some embodiments, the verification cohort 2930 may provide a verification notification to the MDB creator cohort 2900 indicating of a verification for a MDB or for the unverified portion of the MDC provided by the MDB creator. In embodiments, the verification notification may indicate whether a MDB or a batch of MDBs were verified as well as other suitable data (e.g., a CG-derived verification value of the MDB determined by the verification cohort, a time stamp, a CG-derived value to prove the source and/or authenticity of the notification, and/or the like). In some embodiments, the verification notification may contain one or more verification records generated by a respective verification cohort 2930. In some implementations, the MDB creator cohort 2900 may receive a verification notification and may store the verification notification (e.g., in the MDC, in a sidechain of the MDC, or elsewhere), such that if the veracity of the MDC and/or a MDB thereof are ever challenged, the MDB creator cohort 2900 may provide proof of verification by the verification cohorts (which can be used to prove the integrity of the MDC and its MDBs). In some embodiments, the creator cohort 2900 may maintain a verification chain as well. In these implementations, the creator cohort 2900 may store one or more verification blocks that contain the verification records provided by verification cohorts 2930 that verified the MDBs generated by the creator cohort 2900. In embodiments, the verification cohort 2930 may store the verification blocks in a separate verification chain (not shown) or in the MDC 2822 (e.g., in a side chain of the MDC or in the main chain of the MDC 2822).

Once a portion of an MDC 2822 has been verified by one or more verifying cohorts 2930, that portion of the MDC 2822 becomes immutable. The MDB creator cohort 2900 cannot change any of the material data and/or metadata in any MDB in a verified portion of an MDC 2822 and cannot remove or add an MDB from/to the verified portion of the MDC 2822 as the CG-derived verification values without changing the CG-derived verification values associated with the MDBs in the verified portion of the MDC 2822. In this way, each MDB creator cohort 2900 may store its own MDC 2822 without having to replicate the MDBs at any other cohort (node). In the event the integrity or authenticity of an MDC 2822 maintained by a specific cohort is ever challenged, the integrity or authenticity of the MDC 2822 may be easily verified by the one or more verification cohorts 2930 that verified the MDC 2822. For example, in some embodiments, each verification cohort 2930 may receive a portion of an MDC 2822 in question and for each MDB in the MDC 2822 may generate a CG-derived verification value based on the MDB and the MDB preceding the MDB. If the generated CG-derived verification value does not match the CG-derived verification value in the MDB and/or the CG-derived verification value maintained in the verification chain(s) maintained by the verification cohort(s) 2930, then the verification cohort 2930 determines that the MDC has been compromised. Furthermore, the verification cohort may also determine the specific MDB in the MDC where the first change occurred. If the generated CG-derived verification value matches the CG-derived verification value in the MDB and/or the CG-derived verification value maintained in the verification chain maintained by the verification cohort 2930, then the verification cohort 2930 determines that the MDC 2822 has not been compromised.

It is noted that a verification cohort 2930 may act as a MDB creator cohort 2900 and vice-versa. Furthermore, the foregoing may be applied to any type of ledger-based digital ecosystem when MDB creator cohorts 2900 and verification cohorts 2930 belong to the same genomic community (e.g., have sufficiently correlated genomic data sets). The configurations of such digital ecosystems may be defined by the community owners (e.g., the protocol of a distributed ledger, a platform provider, an enterprise, and/or other suitable community owners).

In some example implementations, a VDAX 2800 of a MDB creator cohort 2900 may receive input data relating to one or more consecutive MDBs (i.e., a portion of an MDC) from a ledger-based application 2850 and may determine a CG-derived verification value for each respective MDB 2824 based on the MDB 2824 and a preceding MDB 2824 in the MDC 2822. As mentioned, in some example implementations, a VDAX of a creator cohort 2900 may generate multiple CG-derived verification values if there are multiple verifying cohorts in the digital ecosystem that use different GRI to verify a block. In some of these example implementations, the root DNA module 2806 of the VDAX 2800 may modify a genomic differentiation object (e.g., XNA) assigned to the VDAX 2800 for participation in the digital ecosystem using GRI exchanged between the MDB creator cohort 2900 and a respective verifying cohort 2930 (e.g., GRI provided by the MDB creator cohort 2900 to the verifying cohort 2930 or vice versa) to obtain a modified genomic data object. In some of these implementations, the VDAX 2800 extracts a sequence from the MDB 2824 (e.g., from the MDB metadata of the MDB 2824 and/or other sequence sources) and inputs the modified genomic data object to the sequence mapping module 2810. In these implementations, the sequence mapping module 2810 may generate a genomic engagement factor (GEF) based on the extracted sequence and the modified genomic data object (e.g., as described above). Alternatively, the sequence mapping module 2810 may receive the sequence, GRI, and an unmodified genomic data object (XNA) and may determine the GEF based thereon (e.g., as described above). In embodiments, the master corroboration module 2814 receives the GEF corresponding to an MDB 2824 and generates a CG-derived verification value based on the GEF, the MDB, and a preceding MDB in the MDC. In some example configurations, the master corroboration module 2814 may be configured to determine a first hash value of the MDB 2824 and a second hash value of the preceding MDB in the MDC 2822. It is noted that the first and second hash value may be determined using a hash function (e.g., a non-CG-facilitated hash function) known to all the participants in the digital ecosystem, such that any properly configured cohort may be able to recreate the first and second hash values given the MDB and the preceding MDB, respectively. In some embodiments, the master corroboration value 2814 generates the first and second hash values. Alternatively, in some embodiments, the first and second hash values may be generated by the ledger-based application 2850 and provided to the VDAX (e.g., with the input data, in the MDB metadata of the MDB being verified, or the like). In example implementations, the master corroboration value may combine the first and second hash values (e.g., concatenate, append, interweave, add, multiply, or the like) in a specified manner to obtain a linking value that represents the combination of the MDB 2824 and the MDB preceding the MDB 2824 in the MDC 2822. In some of these embodiments, the master corroboration module 2814 may then generate the CG-derived verification value based on the GEF that was determined for the MDB 2824, the linking value, and a set of computational functions (e.g., cipher-based, cipherless, or hybrid functions). For example, in some embodiments, the master corroboration module 2814 may input the GEF and the linking value into a series of one or more of a cryptographic hash function, an encryption function, a binary transformation (or any other suitable computational function that may receive the linking value and GEF as input) to obtain a CG-derived verification value corresponding to the MDB 2824 vis-à-vis the preceding MDB. In this way, the resultant CG-derived verification value can only be validated by a verification cohort 2930 if the verification cohort 2930 possess the GRI that was used by the creator cohort 2900 to generate the verification value (e.g., via link exchange with the MDB creator cohort 2900 or an enclave VDAX) and a sufficiently correlated genomic data object (e.g., XNA). In embodiments, the CG-derived verification value of the MDB 2824 may then be written to the CG-derived values of the MDB 2824. In embodiments, the VDAX 2800 of a creator cohort 2900 may determine one or more CG-derived verification values for each respective MDB generated by the creator cohort as the MDB 2824 is added to the MDC 2822 of the creator cohort 2900. It is noted that the newly added MDBs remain unverified until the ledger-based application 2850 "commits" an unverified portion of the MDC 2822 containing the newly added MDBs by transmitting the unverified portion of the MDC to one or more verification cohorts 2930. Once a portion of the MDC 2822 is verified by the verifying cohort(s) 2930, that portion of the MDC 2822 becomes verified and immutable.

In some implementations, the MDB creator cohort 2900 (e.g., the ledger-based application 2850) may provide verification data corresponding to an unverified portion of an MDC 2822 to one or more verifying cohorts 2930. In some of these implementations, the verification data may be the entire unverified portion of the MDC. In other implementations, the verification data includes non-CG-derived value of each MDB 2824 (e.g., non-CG-derived values), and for each MDB 2824, any other suitable metadata from which a sequence may be extracted. In implementations, a verifying cohort 2930 may receive the verification data corresponding to the unverified portion of an MDC 2822 and may iteratively verify each MDB 2824 in the unverified portion of the MDC 2822 based on the verification data, its genomic data set, and the GRI commonly held by verification cohort 2930 and the MDB creator cohort 2900. A VDAX 2932 of the verification cohort 2930 may perform the same operations as the VDAX 2800 of the MDB creator cohort 2900. For example, in some implementations, the verification cohort VDAX 2932 may modify its genomic differentiation object (e.g., XNA object) corresponding to the digital ecosystem with the GRI corresponding to the MDB creator cohort 2900 to obtain a modified genomic differentiation object (e.g., a modified XNA object). For each MDB in the unverified portion of the MDC, the verification cohort VDAX 2932 may extract a sequence corresponding to the MDB (e.g., from the MDB metadata of an MDB) and may generate a GEF corresponding to the MDB based on the sequence, the commonly held GRI, and the modified genomic data object (e.g., as described above). Alternatively, in some implementations, the verification cohort VDAX 2932 may extract a sequence corresponding to the MDB (e.g., from the MDB metadata of an MDB) and may generate a GEF corresponding to the MDB based on the sequence, the commonly held GRI, and an unmodified genomic data object (e.g., as described above). It is noted that the configuration of the verification cohort's VDAX may be identical or otherwise functionally symmetric to that of the VDAX 2800 of the MDB creator cohort 2900, such that the same sequences are extracted and the same computational functions are executed to derive the GEF. In implementations, the verification cohort VDAX 2932 may, for each respective MDB, generate a CG-derived verification value based on the MDB, the preceding MDB that precedes the MDB in the MDC, and the GEF corresponding to the MDB. For example, in some embodiments, the verification cohort VDAX 2932 may determine the linking value corresponding to the MDB and the preceding MDB in the same manner as the master corroboration module 2814 of the MDB creator cohort 2900. In some embodiments, the verification cohort VDAX 2932 may then generate a CG-derived verification value by inputting the GEF and the linking value into the same set of computational functions that were used by master corroboration module 2814 of the creator cohort VDAX 2800. Assuming that the contents of the MDB and the preceding MDB have not been changed, the verification cohort VDAX 2932 may obtain the same CG-derived verification value as was determined by the creator cohort VDAX 2800. If the determined CG-derived verification value matches the CG-derived verification value in the MDB, the verification cohort VDAX 2932 verifies the MDB. In response to verifying the MDB, the verification cohort VDAX 2932 may generate a verification record corresponding to the verified MDB. As discussed, the verification record may be maintained in a verification block of a verification chain 2934 that is maintained by the verification cohort and/or may be provided to the MDB creator (or any other suitable cohort of the digital ecosystem). The verification record may indicate the MDB that is verified, the CG-derived verification value that was determined both by the verification cohort and the creator cohort, and any other suitable metadata. Later on, if the integrity of the MDC of the MDB creator cohort is ever audited or otherwise questioned, the verification records corresponding to the MDC may be used to prove whether the previously verified portions of the MDC were altered in any way.

CG-Based Notarization of MDCs

Figure 30:
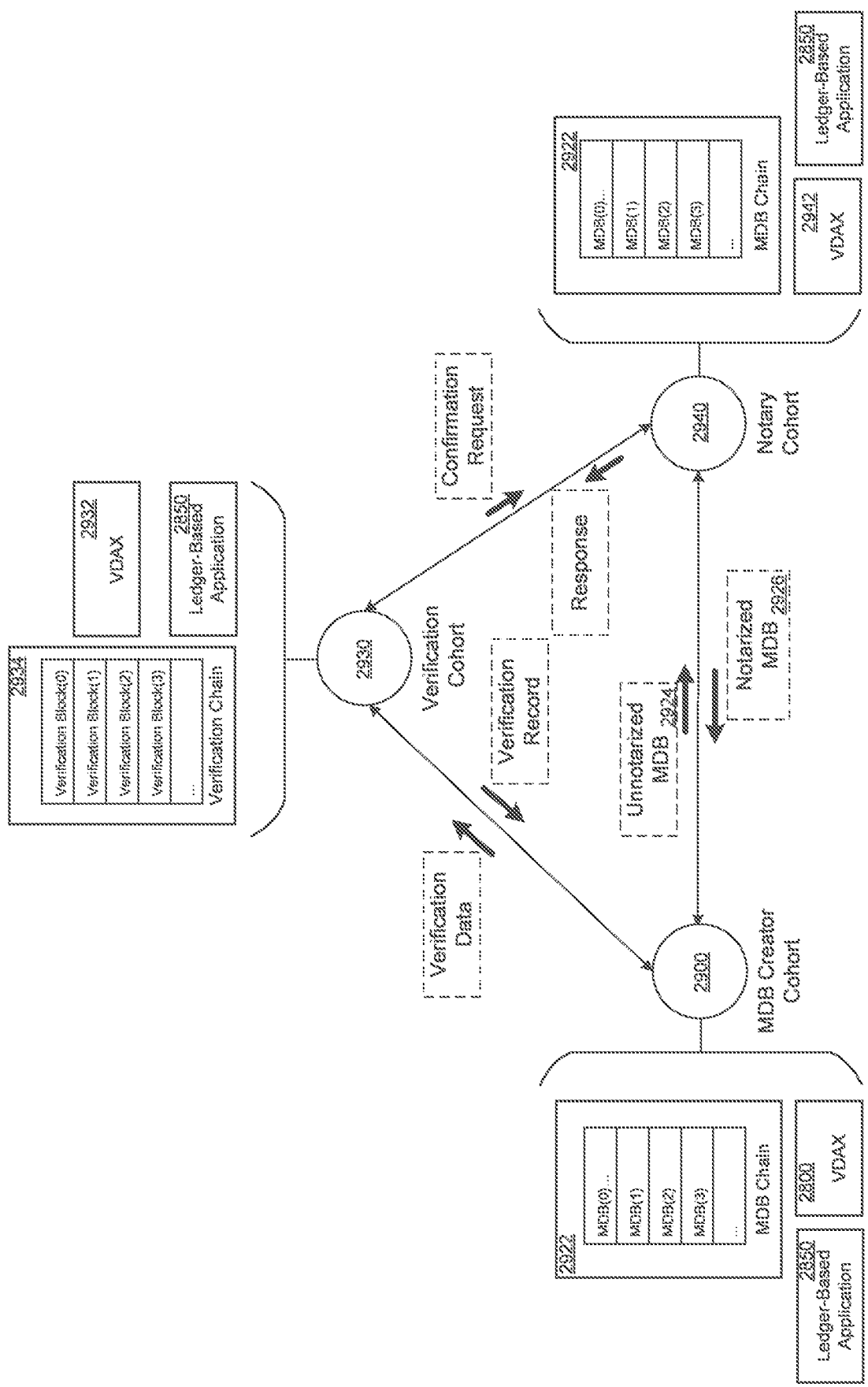
FIG. 30 illustrates an example ledger-based digital ecosystem that uses CG-based notarization to maintain inter-ledger MDCs according to some embodiments of the present disclosure.

With reference now to the VDAX of FIG. 28 in reference to FIG. 30, in some example implementations of a ledger-based ecosystem, VDAXs in the ledger-based ecosystem are configured to generate CG-derived values (e.g., CG-derived creator values and/or CG-derived notary values) given an MDB (or a portion of an MDB).

In some of these example implementations, a VDAX 2800 of a MDB creator cohort 2900 may receive input data relating to an MDB 2924 (e.g., the MDB 2924 itself or a portion thereof) from a ledger-based application 2850 and may determine a CG-derived creator value based on the input data, the genomic differentiation object of the creator cohort 2900, and GRI. In some implementations, the GRI may be secret GRI, such that the notary cohort has unique GRI with which it notarizes MDBs from other cohorts. In other implementations, the GRI may be used by multiple notary cohorts to notarize MDBs from other cohorts. In these implementations, the semi-secret GRI may be exchanged at the enclave level, such that the notary cohorts that participate in a certain enclave receive the GRI that is used to notarize the MDBs created by enclave cohorts.

In example implementations, a VDAX 2942 of a notary cohort 2940 may also receive input data relating to an MDB 2924 (e.g., the MDB 2924 itself or a portion thereof) from a ledger-based application 2850 and may determine a CG-derived notary value based on the input data, the genomic differentiation object of the notary cohort 2940, and GRI. In these implementations, a creator cohort 2900 can generate a CG-derived creator value given an MDB 2924 and one or more notary cohorts 2940 can generate respective notary values given the same MDB 2924 (which will not be matching values, unless both the creator cohorts and the notary cohorts use the same GRI and same genomic data). In some implementations, the CG-derived creator value and the one or more CG-derived notary values may be written into an MDB, thereby creating a notarized MDB. Unlike verification that ensures the integrity of a portion of an MDC, notarization can be used to ensure the integrity of individual MDBs. For example, each notary cohort 2940 may notarize an MDB 2924 and may store a copy of the notarized MDB 2926 with the CG-derived creator value and CG-derived notary value (generated by the notary cohort 2940) in the MDB 2926, such that if the integrity of the contents of the notarized MDB 2926 are ever called into question, the notary cohort(s) 2940 that notarized the MDB 2926 can prove whether or not the contents have been altered. For instance, if a MDB creator cohort 2900 and a set of two or more notary cohorts 2940 digitally notarize an MDB and later a party alleges that the contents of the MDB 2926 were changed, each of the creator cohort and the notary cohorts can recalculate the respective CG-derived values used to digitally notarize the notarized MDB and compare the recalculated values with the respective values in the notarized MDB 2926 to determine whether the contents of the MDB 2926 were altered.

As discussed, in some implementations, a VDAX 2800 of an MDB creator cohort 2900 and a VDAX 2942 of a notary cohort 2940 may be configured to obtain an unnotarized MDB 2924 generated by a MDB creator cohort and to generate a respective CG-derived value (e.g., creator value or notary value) based on the contents of the MDB. It is appreciated that the overall process for generating a CG-derived creator value or a CG-derived notarization value are substantially similar. As such, the following description is described with respect to a notary cohort 2940, but may also be applied to the VDAX 2800 of an MDB creator cohort 2900 to generate a CG-derived creator value. In embodiments, a VDAX 2942 of a notary cohort 2940 (referred to as the "notarizing VDAX 2942") may notarize an unnotarized MDB 2924 by generating a CG-derived notarization value based on the contents of the MDB 2924, a genomic differentiation object (e.g., XNA object) assigned to the notarizing VDAX 2942, and secret or semi-secret GRI held by the notarizing VDAX 2942. In these implementations, the notarizing VDAX 2942 generates a GEF based on a sequence extracted with respect to the unnotarized MDB 2924, the genomic differentiation object (e.g., XNA object) of the notarizing VDAX 2942, and the GRI held by the notarizing VDAX 2942. In implementations, the notarizing VDAX 2942 may extract the sequence from the metadata of the unnotarized MDB 2924 (e.g., a set of consecutive or non-consecutive bits or bytes from the metadata of the unnotarized MDB 2924). In some of these implementations, the notarizing VDAX 2942 may generate a GEF corresponding to an unnotarized MDB 2924 based on the sequence extracted therefrom, the secret or semi-secret GRI held by the VDAX 2942, and the genomic differentiation object of the VDAX 2942 (e.g., as was with respect to FIG. 22 or 23). In some of these implementations, the notarizing VDAX 2940 may modify its genomic differentiation object, and, for a respective unnotarized MDB 2924, may generate a respective GEF based on the sequence, the GRI, and the modified genomic differentiation of the notarizing VDAX 2942 (e.g., as described with respect to FIG. 23). In other implementations, the notarizing VDAX 2942 may generate a GEF corresponding to a respective unnotarized MDB 2924 based on the extracted sequence, the secret or semi-secret GRI, and the unmodified genomic differentiation of the notarizing VDAX 2942 (e.g., as described with respect to FIG. 22). It is appreciated that the notarizing VDAX 2942 may generate a GEF using other suitable sequence mapping techniques without departing from the scope of the disclosure.

In implementations, the notarizing VDAX 2942 (e.g., a master corroboration module thereof) may generate the notary value based on the GEF and the unnotarized MDB 2924 (e.g., the entire unnotarized MDB 2924 or specific portions thereof). In some of these implementations, the notarizing VDAX 2942 may apply one or more computational functions (e.g., cipher-based, cipherless, or hybrid function(s)) to the unnotarized MDB 2924 using the GEF corresponding to the unnotarized MDB 2924 as input to obtain the notary value for the unnotarized MDB 2924. In some of these implementations, the notarizing VDAX 2942 may apply the one or more computational functions to the unnotarized MDB 2924 by applying the computational functions to the portion of the MDB 2924 containing the "payload" of the MDB using the GEF as input to obtain the notary value. In these implementations, the notary value will not change as long as the material data (e.g., the payload) that is stored in the portion of the MDB 2924 is not subsequently changed. Alternatively, the notarizing VDAX 2942 may apply the one or more computational functions to the entire unnotarized MDB 2924 using the GEF as input to obtain the notary value. For purposes of explanation generating a notary value (or generating a creator value) based on the MDB 2924 may refer to generating a notary value using the substantive portion of the MDB 2924, the entirety of the unnotarized MDB 2924, a hash value of the MDB 2924, or the like. In some implementations, the notarizing VDAX 2942 may encrypt or disambiguate (e.g., XOR) at least a portion of the unnotarized MDB 2924 (e.g., the substantive portion of the MDB 2924 or the entire unnotarized MDB 2924) using the GEF as a key, whereby the resultant value is used as the notary value or notarizing VDAX 2942 further derives the notary value from the resultant value. In some implementations, the notarizing VDAX 2942 may hash at least a portion of the unnotarized MDB 2924 using the GEF as an input to the hash function, whereby the resultant hash value is used as the notary value. It is appreciated that the notarizing VDAX 2942 may determine the notary value of an unnotarized MDB 2924 based on a corresponding GEF in other suitable manners, including hybrid manners, without departing from the scope of the disclosure.

In some implementations, the notary cohort 2940 (e.g., the notarizing VDAX 2942 or the ledger-based application 2850) may digitally notarize the unnotarized MDB 2924 with the notary value, thereby notarizing the MDB 2926 with value that is unique and can only be recreated by the notarizing VDAX 2942. It is appreciated that the creator cohort 2900 may also digitally notarize the MDB 2924 in this same manner with a CG-derived creator value using GRI that is maintained by the creator VDAX 2800 and the genomic differentiation object of the creator VDAX 2800.

It is noted that in some implementations, the MDB creator cohort 2900 and the one or more notary cohorts may belong to different genomic communities and may not have correlated genomic data (e.g., correlated differentiation objects). Even in such scenarios, a notary cohort 2940 may notarize an MDB 2924, as the CG-derived notarization value is generated based on information that is secret or semi-secret held by the notary cohort 2940. In this way, a notary cohort 2940 may independently verify that the contents of a notarized MDB 2926 have not been changed, even in trustless ecosystems. For example, if the integrity of a notarized MDB 2926 is ever questioned, the notary cohort 2940 can determine whether the contents of the MDB 2926 were changed after notarization by redetermining the CG-notary value of the MDB 2926 and comparing the redetermined notary value to the notary value used to notarize the MDB 2926. I the CG-derived notary values match, then the notary cohort can verify the integrity of the MDB 2926.

In implementations, the notary cohort 2940 may provide the notarized MDB to the MDB creator cohort 2900 and the MDB creator cohort 2900 may add the notarized MDB to its copy of the MDC. In these embodiments, the MDB creator may store the CG-derived notarization value(s) for a particular MDB generated by the notary cohorts in the MDB or in relation to the MDB (e.g., in a side chain of the MDC or another MDB in the main chain of the MDC), such that the CG-derived notarization values provide verifiable proof that an MDB has not been changed or tampered with. For example, in some embodiments a notary cohort may receive a request to verify a notarization of an MDB. In these example embodiments, a notary cohort may receive the MDB (or certain contents thereof) and may attempt to recreate the CG-derived notarization value. If the notary cohort is able to recreate the CG-derived notarization value, the notary cohort may confirm that the MDB has not been changed or tampered with. If the notary cohort generates a value that does not match the CG-derived notarization value that was used to notarize the MDB, the notary cohort may confirm that the MDB has been altered.

In some embodiments, each notary cohort 2940 may also store the notarized MDB 2926 on their respective MDCs (e.g., inter-ledger chains). It is noted that in these embodiments, the MDCs maintained by each respective cohort in a digital ecosystem do not necessarily have to be congruent; however, each notarized MDB may be stored in a respective MDC maintained by the MDB creator cohort 2900 and each of the notary cohorts 2940 that notarized the MDB 2926. Furthermore, depending on the configuration of the digital ecosystem, the CG-derived notary values generated by different notary cohorts 2940 with respect to an MDB can be shared between notary cohorts 2940 and subsequently written to each notary cohort's respective copy of an MDB, further ensuring the integrity of the notarized MDB.

In some example embodiments, a ledger-based digital ecosystem may optionally support both notarization and verification, as shown in the example of FIG. 30. In these examples, a VDAX 2932 of a verification cohort 2930 (referred to as a "verification VDAX 2932") can verify portions of an MDC on behalf of cohorts, as was described with respect to FIG. 29. In these implementations, a verifying VDAX 2932 may be configured to verify unverified portions of an MDC that is maintained by another cohort within the ecosystem. In some of these implementations, the verifying VDAX 2932 may receive an unverified portion of an MDC from a cohort (e.g., creator cohort 2900) containing a series of sequential MDBs, where at least some of the MDBs in the unverified portion of the MDC have been notarized by one or more notary cohorts. In these implementations, the unverified portion of the MDC may include notarized MDBs 2926 and may further include unnotarized MDBs 2824 (e.g., MDBs that do not require notarization by a notary cohort). In these implementations, when a verification cohort 2930 receives the unverified portion of the MDC, the verification cohort may verify each sequential MDB in the unverified portion of the MDC using GRI that is known to both the creator cohort 2900 and the verification cohort 2930, as was described with respect to FIG. 29. In this way, notarized MDBs 2926 that are included in the MDC and subsequently verified by one or more verification cohorts 2930 become immutable. It is appreciated that in some implementations, a verification cohort 2930 may also be a notary cohort 2940, such that the verification VDAX 2392 can both verify MDCs (as described with respect to FIG. 29) and notarize MDBs. Alternatively, in some implementations a verification cohort 2930 may be configured to verify MDCs, while notary cohorts 2940 are configured to notarize MBDs.

In some example implementations, a verification cohort 2930 (or any other suitable cohort in the ledger-based digital ecosystem) may be configured to confirm the integrity of a notarized MDB 2926. In these implementations, the verification cohort 2930 may provide a confirmation request to the notary cohort(s) 2940 that notarized an MDB 2926. In these implementations, a confirmation request is sent to a notary cohort 2940 to confirm that an MDB 2926 has not been changed since it was notarized by the notary cohort. In some of these implementations, the notary cohort 2940 may receive a copy of the notarized MDB 2926 that the verification cohort 2930 is verifying (e.g., an MDB 2926 from the creator cohort 2900). In some implementations, the confirmation request may include the notarized MDB 2926 that is to be confirmed and may further include a notary value that was used to notarize the MDB 2926 by the notary cohort 2940. In these implementations, the notary VDAX 2942 may recalculate the notary value given the received MDB 2926 and may return a response to the confirmation request based on the recalculated notary value. In some implementations, the notary cohort 2940 may return the recalculated notary value to the verification cohort 2940 in the response. In these implementations, the verification cohort 2930 may receive the response and may determine if the recalculated notary value matches the notary value that was used to notarize the MDB 2926 by the notary cohort 2940. If so, the verification cohort 2930 may confirm the integrity of the MDB 2926. In some implementations, the notary cohort 2940 may be configured to determine if the recalculated notary value matches the notary value that was used to notarize the MDB 2926. If the recalculated notary value matches the notary value that was used to notarize the MDB 2926, the notary cohort 2940 can confirm the integrity of the MDB 2926 and may include the confirmation in the response. In the instance where the recalculated value does not match the notary value that was used to notarize the MDB 2926, the MDB 2926 can be further to determine if the MDB 2926 has been altered and by whom the block was altered. For example, if multiple notary cohorts 2940 determine that the recreated values do not match the notary values used to notarize the MBD 2926, then it can be determined that the MDB creator cohort 2900 (or a malicious actor) has altered the MDB 2926.

It is appreciated that the foregoing examples of FIGS. 28-30 are provided as example configurations of a ledger-based digital ecosystem. Within different ecosystems and implementations of a CG-ESP, the genomic data sets, the notarization mechanics, the verification mechanics, and/or the computational function of the CG-ESP may be varied by the community owner without departing from the scope of the disclosure.

Furthermore, while the examples of FIGS. 28-30 pertained to different implementations for maintaining MDCs, Cyphergenics may be applied to existing ledger-based ecosystems. For example, Cyphergenics may be applied to digital ledgers that comport to existing protocols (e.g., Ethereum blockchain, Hyperledger Fabric blockchain, R3 Corda blockchain, Ripple Blockchain, Quorum blockchain, later developed blockchains, or the like) or a set of layered protocols.

CONCLUSION

In view of the foregoing, it is noted that the techniques described throughout the disclosure may be adapted for implementation within existing cryptography frameworks. Furthermore, the modularity of the described frameworks provides an opportunity for further development of specific modules and CG-based techniques. As more configurations a developed, the modularity of a CG-ESP will provide for another layer of obfuscation, which further enhances the security features of the CG-ESP.

The background description is presented simply for context, and is not necessarily well-understood, routine, or conventional. Further, the background description is not an admission of what does or does not qualify as prior art. In fact, some or all of the background description may be work attributable to the named inventors that is otherwise unknown in the art.

Physical (such as spatial and/or electrical) and functional relationships between elements (for example, between modules, circuit elements, semiconductor layers, etc.) are described using various terms. Unless explicitly described as being "direct," when a relationship between first and second elements is described, that relationship encompasses both (i) a direct relationship where no other intervening elements are present between the first and second elements and (ii) an indirect relationship where one or more intervening elements are present between the first and second elements. Example relationship terms include "adjoining," "transmitting," "receiving," "connected," "engaged," "coupled," "adjacent," "next to," "on top of," "above," "below," "abutting," and "disposed."

The detailed description includes specific examples for illustration only, and not to limit the disclosure or its applicability. The examples are not intended to be an exhaustive list, but instead simply demonstrate possession by the inventors of the full scope of the currently presented and envisioned future claims. Variations, combinations, and equivalents of the examples are within the scope of the disclosure. No language in the specification should be construed as indicating that any non-claimed element is essential or critical to the practice of the disclosure.

The term "exemplary" simply means "example" and does not indicate a best or preferred example. The term "set" does not necessarily exclude the empty set—in other words, in some circumstances a "set" may have zero elements. The term "non-empty set" may be used to indicate exclusion of the empty set—that is, a non-empty set must have one or more elements. The term "subset" does not necessarily require a proper subset. In other words, a "subset" of a first set may be coextensive with (equal to) the first set. Further, the term "subset" does not necessarily exclude the empty set—in some circumstances a "subset" may have zero elements.

The phrase "at least one of A, B, and C" should be construed to mean a logical (A OR B OR C), using a non-exclusive logical OR, and should not be construed to mean "at least one of A, at least one of B, and at least one of C." The use of the terms "a," "an," "the," and similar referents in the context of describing the disclosure and claims encompasses both the singular and the plural, unless contradicted explicitly or by context. Unless otherwise specified, the terms "comprising," "having," "with," "including," and "containing," and their variants, are open-ended terms, meaning "including, but not limited to."

Each publication referenced in this disclosure, including foreign and domestic patent applications and patents, is hereby incorporated by reference in its entirety.

Although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of multiple embodiments remain within the scope of this disclosure.

One or more elements (for example, steps within a method, instructions, actions, or operations) may be executed in a different order (and/or concurrently) without altering the principles of the present disclosure. Unless technically infeasible, elements described as being in series may be implemented partially or fully in parallel. Similarly, unless technically infeasible, elements described as being in parallel may be implemented partially or fully in series.

While the disclosure describes structures corresponding to claimed elements, those elements do not necessarily invoke a means plus function interpretation unless they explicitly use the signifier "means for." Unless otherwise indicated, recitations of ranges of values are merely intended to serve as a shorthand way of referring individually to each separate value falling within the range, and each separate value is hereby incorporated into the specification as if it were individually recited.

While the drawings divide elements of the disclosure into different functional blocks or action blocks, these divisions are for illustration only. According to the principles of the present disclosure, functionality can be combined in other ways such that some or all functionality from multiple separately-depicted blocks can be implemented in a single functional block; similarly, functionality depicted in a single block may be separated into multiple blocks. Unless explicitly stated as mutually exclusive, features depicted in different drawings can be combined consistent with the principles of the present disclosure.

In the drawings, reference numbers may be reused to identify identical elements or may simply identify elements that implement similar functionality. Numbering or other labeling of instructions or method steps is done for convenient reference, not to indicate a fixed order. In the drawings, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. As just one example, for information sent from element A to element B, element B may send requests and/or acknowledgements to element A.

A special-purpose system includes hardware and/or software and may be described in terms of an apparatus, a method, or a computer-readable medium. In various embodiments, functionality may be apportioned differently between software and hardware. For example, some functionality may be implemented by hardware in one embodiment and by software in another embodiment. Further, software may be encoded by hardware structures, and hardware may be defined by software, such as in software-defined networking or software-defined radio.

In this application, including the claims, the term module refers to a special-purpose system. The module may be implemented by one or more special-purpose systems. The one or more special-purpose systems may also implement some or all of the other modules. In this application, including the claims, the term module may be replaced with the terms controller or circuit. In this application, including the claims, the term platform refers to one or more modules that offer a set of functions. In this application, including the claims, the term system may be used interchangeably with module or with the term special-purpose system.

The special-purpose system may be directed or controlled by an operator. The special-purpose system may be hosted by one or more of assets owned by the operator, assets leased by the operator, and third-party assets. The assets may be referred to as a private, community, or hybrid cloud computing network or cloud computing environment. For example, the special-purpose system may be partially or fully hosted by a third party offering software as a service (SaaS), platform as a service (PaaS), and/or infrastructure as a service (IaaS). The special-purpose system may be implemented using agile development and operations (DevOps) principles. In embodiments, some or all of the special-purpose system may be implemented in a multiple-environment architecture. For example, the multiple environments may include one or more production environments, one or more integration environments, one or more development environments, etc.

A special-purpose system may be partially or fully implemented using or by a mobile device. Examples of mobile devices include navigation devices, cell phones, smart phones, mobile phones, mobile personal digital assistants, palmtops, netbooks, pagers, electronic book readers, tablets, music players, etc. A special-purpose system may be partially or fully implemented using or by a network device. Examples of network devices include switches, routers, firewalls, gateways, hubs, base stations, access points, repeaters, head-ends, user equipment, cell sites, antennas, towers, etc.

A special-purpose system may be partially or fully implemented using a computer having a variety of form factors and other characteristics. For example, the computer may be characterized as a personal computer, as a server, etc. The computer may be portable, as in the case of a laptop, netbook, etc. The computer may or may not have any output device, such as a monitor, line printer, liquid crystal display (LCD), light emitting diodes (LEDs), etc. The computer may or may not have any input device, such as a keyboard, mouse, touchpad, trackpad, computer vision system, barcode scanner, button array, etc. The computer may run a general-purpose operating system, such as the WINDOWS operating system from Microsoft Corporation, the MACOS operating system from Apple, Inc., or a variant of the LINUX operating system. Examples of servers include a file server, print server, domain server, internet server, intranet server, cloud server, infrastructure-as-a-service server, platform-as-a-service server, web server, secondary server, host server, distributed server, failover server, and backup server.

The term hardware encompasses components such as processing hardware, storage hardware, networking hardware, and other general-purpose and special-purpose components. Note that these are not mutually-exclusive categories. For example, processing hardware may integrate storage hardware and vice versa.

Examples of a component are integrated circuits (ICs), application specific integrated circuit (ASICs), digital circuit elements, analog circuit elements, combinational logic circuits, gate arrays such as field programmable gate arrays (FPGAs), digital signal processors (DSPs), complex programmable logic devices (CPLDs), etc.

Multiple components of the hardware may be integrated, such as on a single die, in a single package, or on a single printed circuit board or logic board. For example, multiple components of the hardware may be implemented as a system-on-chip. A component, or a set of integrated components, may be referred to as a chip, chipset, chiplet, or chip stack. Examples of a system-on-chip include a radio frequency (RF) system-on-chip, an artificial intelligence (AI) system-on-chip, a video processing system-on-chip, an organ-on-chip, a quantum algorithm system-on-chip, etc.

The hardware may integrate and/or receive signals from sensors. The sensors may allow observation and measurement of conditions including temperature, pressure, wear, light, humidity, deformation, expansion, contraction, deflection, bending, stress, strain, load-bearing, shrinkage, power, energy, mass, location, temperature, humidity, pressure, viscosity, liquid flow, chemical/gas presence, sound, and air quality. A sensor may include image and/or video capture in visible and/or non-visible (such as thermal) wavelengths, such as a charge-coupled device (CCD) or complementary metal-oxide semiconductor (CMOS) sensor.

Examples of processing hardware include a central processing unit (CPU), a graphics processing unit (GPU), an approximate computing processor, a quantum computing processor, a parallel computing processor, a neural network processor, a signal processor, a digital processor, a data processor, an embedded processor, a microprocessor, and a co-processor. The co-processor may provide additional processing functions and/or optimizations, such as for speed or power consumption. Examples of a co-processor include a math co-processor, a graphics co-processor, a communication co-processor, a video co-processor, and an artificial intelligence (AI) co-processor.

The processor may enable execution of multiple threads. These multiple threads may correspond to different programs. In various embodiments, a single program may be implemented as multiple threads by the programmer or may be decomposed into multiple threads by the processing hardware. The threads may be executed simultaneously to enhance the performance of the processor and to facilitate simultaneous operations of the application. A processor may be implemented as a packaged semiconductor die. The die includes one or more processing cores and may include additional functional blocks, such as cache. In various embodiments, the processor may be implemented by multiple dies, which may be combined in a single package or packaged separately.

The networking hardware may include one or more interface circuits. In some examples, the interface circuit(s) may implement wired or wireless interfaces that connect, directly or indirectly, to one or more networks. Examples of networks include a cellular network, a local area network (LAN), a wireless personal area network (WPAN), a metropolitan area network (MAN), and/or a wide area network (WAN). The networks may include one or more of point-to-point and mesh technologies. Data transmitted or received by the networking components may traverse the same or different networks. Networks may be connected to each other over a WAN or point-to-point leased lines using technologies such as Multiprotocol Label Switching (MPLS) and virtual private networks (VPNs).

Examples of cellular networks include GSM, GPRS, 3G, 4G, 5G, LTE, and EVDO. The cellular network may be implemented using frequency division multiple access (FDMA) network or code division multiple access (CDMA) network. Examples of a LAN are Institute of Electrical and Electronics Engineers (IEEE) Standard 802.11-2020 (also known as the WIFI wireless networking standard) and IEEE Standard 802.3-2018 (also known as the ETHERNET wired networking standard). Examples of a WPAN include IEEE Standard 802.15.4, including the ZIGBEE standard from the ZigBee Alliance. Further examples of a WPAN include the BLUETOOTH wireless networking standard, including Core Specification versions 3.0, 4.0, 4.1, 4.2, 5.0, and 5.1 from the Bluetooth Special Interest Group (SIG). A WAN may also be referred to as a distributed communications system (DCS). One example of a WAN is the internet.

Storage hardware is or includes a computer-readable medium. The term computer-readable medium, as used in this disclosure, encompasses both nonvolatile storage and volatile storage, such as dynamic random access memory (DRAM). The term computer-readable medium only excludes transitory electrical or electromagnetic signals propagating through a medium (such as on a carrier wave). A computer-readable medium in this disclosure is therefore non-transitory, and may also be considered to be tangible.

Examples of storage implemented by the storage hardware include a database (such as a relational database or a NoSQL database), a data store, a data lake, a column store, a data warehouse. Example of storage hardware include nonvolatile memory devices, volatile memory devices, magnetic storage media, a storage area network (SAN), network-attached storage (NAS), optical storage media, printed media (such as bar codes and magnetic ink), and paper media (such as punch cards and paper tape). The storage hardware may include cache memory, which may be collocated with or integrated with processing hardware. Storage hardware may have read-only, write-once, or read/write properties. Storage hardware may be random access or sequential access. Storage hardware may be location-addressable, file-addressable, and/or content-addressable.

Example of nonvolatile memory devices include flash memory (including NAND and NOR technologies), solid state drives (SSDs), an erasable programmable read-only memory device such as an electrically erasable programmable read-only memory (EEPROM) device, and a mask read-only memory device (ROM). Example of volatile memory devices include processor registers and random access memory (RAM), such as static RAM (SRAM), dynamic RAM (DRAM), synchronous DRAM (SDRAM), synchronous graphics RAM (S GRAM), and video RAM (VRAM). Example of magnetic storage media include analog magnetic tape, digital magnetic tape, and rotating hard disk drive (HDDs). Examples of optical storage media include a CD (such as a CD-R, CD-RW, or CD-ROM), a DVD, a Blu-ray disc, and an Ultra HD Blu-ray disc.

Examples of storage implemented by the storage hardware include a distributed ledger, such as a permissioned or permissionless blockchain. Entities recording transactions, such as in a blockchain, may reach consensus using an algorithm such as proof-of-stake, proof-of-work, and proof-of-storage. Elements of the present disclosure may be represented by or encoded as non-fungible tokens (NFTs). Ownership rights related to the non-fungible tokens may be recorded in or referenced by a distributed ledger. Transactions initiated by or relevant to the present disclosure may use one or both of fiat currency and cryptocurrencies, examples of which include bitcoin and ether. Some or all features of hardware may be defined using a language for hardware description, such as IEEE Standard 1364-2005 (commonly called "Verilog") and IEEE Standard 1076-2008 (commonly called "VHDL"). The hardware description language may be used to manufacture and/or program hardware.

A special-purpose system may be distributed across multiple different software and hardware entities. Communication within a special-purpose system and between special-purpose systems may be performed using networking hardware. The distribution may vary across embodiments and may vary over time. For example, the distribution may vary based on demand, with additional hardware and/or software entities invoked to handle higher demand. In various embodiments, a load balancer may direct requests to one of multiple instantiations of the special purpose system. The hardware and/or software entities may be physically distinct and/or may share some hardware and/or software, such as in a virtualized environment. Multiple hardware entities may be referred to as a server rack, server farm, data center, etc.

Software includes instructions that are machine-readable and/or executable. Instructions may be logically grouped into programs, codes, methods, steps, actions, routines, functions, libraries, objects, classes, etc. Software may be stored by storage hardware or encoded in other hardware. Software encompasses (i) descriptive text to be parsed, such as HTML (hypertext markup language), XML (extensible markup language), and JSON (JavaScript Object Notation), (ii) assembly code, (iii) object code generated from source code by a compiler, (iv) source code for execution by an interpreter, (v) bytecode, (vi) source code for compilation and execution by a just-in-time compiler, etc. As examples only, source code may be written using syntax from languages including C, C++, JavaScript, Java, Python, R, etc.

Software also includes data. However, data and instructions are not mutually-exclusive categories. In various embodiments, the instructions may be used as data in one or more operations. As another example, instructions may be derived from data. The functional blocks and flowchart elements in this disclosure serve as software specifications, which can be translated into software by the routine work of a skilled technician or programmer. Software may include and/or rely on firmware, processor microcode, an operating system (OS), a basic input/output system (BIOS), application programming interfaces (APIs), libraries such as dynamic-link libraries (DLLs), device drivers, hypervisors, user applications, background services, background applications, etc. Software includes native applications and web applications. For example, a web application may be served to a device through a browser using hypertext markup language 5th revision (HTML5).

Software may include artificial intelligence systems, which may include machine learning or other computational intelligence. For example, artificial intelligence may include one or more models used for one or more problem domains. When presented with many data features, identification of a subset of features that are relevant to a problem domain may improve prediction accuracy, reduce storage space, and increase processing speed. This identification may be referred to as feature engineering. Feature engineering may be performed by users or may only be guided by users. In various implementations, a machine learning system may computationally identify relevant features, such as by performing singular value decomposition on the contributions of different features to outputs.

Examples of the models include recurrent neural networks (RNNs) such as long short-term memory (LSTM), deep learning models such as transformers, decision trees, support-vector machines, genetic algorithms, Bayesian networks, and regression analysis. Examples of systems based on a transformer model include bidirectional encoder representations from transformers (BERT) and generative pre-trained transformer (GPT). Training a machine-learning model may include supervised learning (for example, based on labelled input data), unsupervised learning, and reinforcement learning. In various embodiments, a machine-learning model may be pre-trained by their operator or by a third party. Problem domains include nearly any situation where structured data can be collected, and includes natural language processing (NLP), computer vision (CV), classification, image recognition, etc.

Some or all of the software may run in a virtual environment rather than directly on hardware. The virtual environment may include a hypervisor, emulator, sandbox, container engine, etc. The software may be built as a virtual machine, a container, etc. Virtualized resources may be controlled using, for example, a DOCKER container platform, a pivotal cloud foundry (PCF) platform, etc.

In a client-server model, some of the software executes on first hardware identified functionally as a server, while other of the software executes on second hardware identified functionally as a client. The identity of the client and server is not fixed: for some functionality, the first hardware may act as the server while for other functionality, the first hardware may act as the client. In different embodiments and in different scenarios, functionality may be shifted between the client and the server. In one dynamic example, some functionality normally performed by the second hardware is shifted to the first hardware when the second hardware has less capability. In various embodiments, the term "local" may be used in place of "client," and the term "remote" may be used in place of "server."

Some or all of the software may be logically partitioned into microservices. Each microservice offers a reduced subset of functionality. In various embodiments, each microservice may be scaled independently depending on load, either by devoting more resources to the microservice or by instantiating more instances of the microservice. In various embodiments, functionality offered by one or more microservices may be combined with each other and/or with other software not adhering to a microservices model.

Some or all of the software may be arranged logically into layers. In a layered architecture, a second layer may be logically placed between a first layer and a third layer. The first layer and the third layer would then generally interact with the second layer and not with each other. In various embodiments, this is not strictly enforced—that is, some direct communication may occur between the first and third layers.

The invention claimed is:

1. A method for executing computer programs in a trusted execution environment of a device comprising:
   retrieving a genomic differentiation object corresponding to a set of one or more computer programs including a computer program;
   modifying the genomic differentiation object based on genomic regulation instructions (GRI) to obtain a modified genomic differentiation object;
   executing a first executable instruction of the computer program, wherein executing the first executable instruction includes:
      retrieving first encoded data that is input to the first executable instruction;
      extracting a first sequence from first metadata associated with the first encoded data;
      generating a first genomic engagement factor (GEF) based on the first sequence, the GRI and, and the modified genomic differentiation object;
      decoding the first encoded data based on the first GEF to obtain first decoded data;
      executing the first executable instruction using the first decoded data; and
   executing a second executable instruction of the computer program, wherein executing the second executable instruction includes:
      retrieving second encoded data that is input to the second executable instruction;
      extracting a second sequence from second metadata associated with the second encoded data;
      generating a second GEF based on the second sequence, the GRI and, and the modified genomic differentiation object;
      decoding the second encoded data based on the second GEF to obtain second decoded data; and
      executing the second executable instruction using the second decoded data.

2. The method of claim 1, wherein executing the first executable instruction further includes:
   obtaining output data resulting from execution of the first executable instruction;
   generating a third GEF based on a third sequence corresponding to the output data, the GRI, and the modified genomic differentiation object; and
   transforming the output data into third encoded data based on the third GEF.

3. The method of claim 2, further comprising writing the third encoded data to memory.

4. The method of claim 3, wherein the third sequence is extracted from metadata corresponding to the output data, wherein the metadata includes one or more of random-access memory (RAM) metadata, application metadata, operating system-application metadata, and filesystem metadata.

5. The method of claim 4, further comprising executing a third executable instruction of the computer program by:
retrieving the third encoded data that is input to the third executable instruction;
extracting the third sequence from a value representing the metadata corresponding to the output data;
generating the third GEF based on the third sequence, the GRI and, and the modified genomic differentiation object;
decoding the third encoded data based on the third GEF to obtain the output data; and
executing the first executable instruction using the output data resulting from execution of the first executable instruction.

6. The method of claim 1, wherein the first metadata from which the first sequence is extracted and the second metadata from which the second sequence is extracted includes one or more of random-access memory (RAM) metadata, application metadata, operating system-application metadata, and filesystem metadata.

7. The method of claim 1, wherein generating the first GEF includes:
generating a sequence conversion vector (SCV) based on the first sequence and the first GRI;
mapping the modified genomic differentiation object based on the SCV to obtain a mapped modified genomic differentiation object; and
generating the first GEF based on the mapped modified genomic differentiation object.

8. The method of claim 7, wherein generating the SCV includes combining the first sequence and the GRI.

9. The method of claim 8, wherein generating the SCV further includes applying one or more computational functions to the combination of the first sequence and the GRI to obtain the SCV.

10. The method of claim 1, wherein decoding the first encoded data includes decrypting the first encoded data using the first GEF and decoding the second encoded data includes decrypting the second encoded data using the second GEF.

11. The method of claim 1, wherein decoding the first encoded data includes disambiguating the first encoded data using the first GEF and disambiguating the second encoded data includes decrypting the second encoded data using the second GEF.

12. The method of claim 1, wherein the genomic differentiation object is an ZNA object.

13. The method of claim 12, wherein the ZNA object is an N×M binary matrix.

14. The method of claim 12, wherein a VDAX of the device generates and assigns the ZNA object to the computer program.

15. The method of claim 1, wherein the device is a server computing device.

16. The method of claim 1, wherein the device is a mobile computing device.

17. The method of claim 1, wherein the device is a personal computing device.

18. The method of claim 1, wherein the device is a vehicle.

19. The method of claim 1, wherein the device is a gaming device.

20. The method of claim 1, wherein the device is an internet of things device.

21. The method of claim 1, wherein the device is a sensor device.

22. The method of claim 1, wherein the device is a video recording device.

23. The method of claim 1, wherein the device is a wearable computing device.

24. The method of claim 1, wherein the device is a smart appliance.

25. The method of claim 1, wherein the device is a network router.

26. The method of claim 1, wherein the computer program is a software application.

27. The method of claim 1, wherein the computer program is a middleware application.

28. The method of claim 1, wherein the computer program is a firmware application.

29. The method of claim 1, wherein the computer program is an operating system.

* * * * *